US012600719B2

(12) United States Patent
Wein et al.

(10) Patent No.: US 12,600,719 B2
(45) Date of Patent: Apr. 14, 2026

(54) SALT INDUCIBLE KINASE INHIBITORS

(71) Applicant: The General Hospital Corporation, Boston, MA (US)

(72) Inventors: Marc Nathan Wein, Wellesley, MA (US); William J. Greenlee, Teaneck, NJ (US)

(73) Assignee: The General Hospital Corporation, Boston, MA (US)

( * ) Notice: Subject to any disclaimer, the term of this patent is extended or adjusted under 35 U.S.C. 154(b) by 368 days.

(21) Appl. No.: 18/019,527

(22) PCT Filed: Aug. 5, 2021

(86) PCT No.: PCT/US2021/044673

§ 371 (c)(1),
(2) Date: Feb. 3, 2023

(87) PCT Pub. No.: WO2022/031928

PCT Pub. Date: Feb. 10, 2022

(65) Prior Publication Data

US 2024/0025892 A1 Jan. 25, 2024

Related U.S. Application Data

(60) Provisional application No. 63/061,515, filed on Aug. 5, 2020.

(51) Int. Cl.

| | |
|---|---|
| ***C07D 471/04*** | (2006.01) |
| ***C07D 401/12*** | (2006.01) |
| ***C07D 403/04*** | (2006.01) |
| ***C07D 403/12*** | (2006.01) |
| ***C07D 405/14*** | (2006.01) |
| ***C07D 409/14*** | (2006.01) |
| ***C07D 471/10*** | (2006.01) |
| ***C07D 487/10*** | (2006.01) |
| ***C07D 498/10*** | (2006.01) |
| ***C07D 519/00*** | (2006.01) |

(52) U.S. Cl.

CPC ......... *C07D 471/04* (2013.01); *C07D 401/12* (2013.01); *C07D 403/04* (2013.01); *C07D 403/12* (2013.01); *C07D 405/14* (2013.01); *C07D 409/14* (2013.01); *C07D 471/10* (2013.01); *C07D 487/10* (2013.01); *C07D 498/10* (2013.01); *C07D 519/00* (2013.01)

(58) Field of Classification Search

CPC .................................................... C07D 471/04

See application file for complete search history.

(56) References Cited

U.S. PATENT DOCUMENTS

| | | | |
|---|---|---|---|
| 5,990,146 A | 11/1999 | Boschelli et al. | |
| 6,162,804 A | 12/2000 | Bilodeau et al. | |
| 6,218,388 B1 | 4/2001 | Boschelli et al. | |
| 6,380,203 B1 | 4/2002 | Bilodeau et al. | |
| 7,071,337 B2 * | 7/2006 | Kath | A61P 43/00 546/159 |
| 11,998,540 B2 * | 6/2024 | Liau | A61K 31/5513 |
| 2004/0053942 A1 | 3/2004 | Alberti et al. | |
| 2005/0124599 A1 | 6/2005 | Kath et al. | |
| 2005/0176753 A1 | 8/2005 | Bilodeau et al. | |
| 2010/0016353 A1 | 1/2010 | Henne et al. | |
| 2010/0144751 A1 | 6/2010 | Marmsater et al. | |
| 2013/0165652 A1 | 6/2013 | Gwak et al. | |

FOREIGN PATENT DOCUMENTS

| | | |
|---|---|---|
| CN | 106565704 A | 4/2017 |
| CN | 107382983 | 11/2017 |
| CN | 111433200 | 7/2020 |
| CN | 115197208 | 10/2022 |
| CN | 115448881 | 12/2022 |
| EP | 1235825 | 9/2002 |
| EP | 2931722 | 10/2015 |
| JP | 2002501532 A | 1/2002 |
| JP | 2002523459 A | 7/2002 |
| JP | 2005530745 A | 10/2005 |
| JP | 2006501309 A | 1/2006 |
| JP | 2008515872 A | 5/2008 |
| WO | WO 2003/048132 A1 | 6/2003 |
| WO | WO 2004/113322 | 12/2004 |
| WO | WO 2008/078091 A1 | 7/2008 |
| WO | WO 2008/121687 A2 | 10/2008 |
| WO | WO 2008/124323 A1 | 10/2008 |
| WO | WO 2018/136634 A1 | 7/2018 |
| WO | WO 2019/081353 A1 | 5/2019 |
| WO | WO 2019/105886 | 6/2019 |
| WO | WO 2019/155456 | 8/2019 |
| WO | WO 2019/238424 | 12/2019 |
| WO | WO 2020/239658 | 12/2020 |
| WO | WO 2020/239660 | 12/2020 |

(Continued)

OTHER PUBLICATIONS

Xi et al. CAS: 159:577130, 2013.*

Barth et al. CAS: 135: 33479, 2001.*

Ardura et al., "Handling Parathormone Receptor Type 1 in Skeletal Diseases: Realities and Expectations of Abaloparatide," Trends Endocrinol. Metab., Oct. 2019, 30(10):756-766.

Arjun et al., "Design, Synthesis, and Biological Evaluation of (E)-N'4(1-Chloro-3,4-Dihydronaphthalen-2-yl)Methylene)Benzohydrazide Derivatives as Anti-prostate Cancer Agents," Frontiers in Chemistry, Jul. 2019, 7(474): 14 pages.

Compston et al., "Osteoporosis," Lancet, Jan. 2019, 393(10169):364-376.

(Continued)

*Primary Examiner* — Rei Tsang Shiao

(74) *Attorney, Agent, or Firm* — Fish & Richardson P.C.

(57) ABSTRACT

The present application provides compounds that modulate the activity of one or more salt inducible kinases (SIKs). Pharmaceutical composition and methods of treating diseases associated with abnormal expression and/or activity of one or more SIKs are also provided.

20 Claims, 37 Drawing Sheets

(56) References Cited

FOREIGN PATENT DOCUMENTS

| | | |
|---|---|---|
| WO | WO 2022/165529 | 8/2022 |
| WO | WO 2022/165530 | 8/2022 |

OTHER PUBLICATIONS

International Preliminary Report on Patentability in International Appln. No. PCT/US2021/044673, mailed Feb. 16, 2023, 12 pages.
International Search Report and Written Opinion in International Appln. No. PCT/US2021/044673, mailed Nov. 23, 2021, 15 pages.
Jagerschmidt et al., "Abstract 1015: Preclinical Investigation of the First-in-Class SIK2/SIK3 Inhibitor GLPG3970 in Models of Arthritis," Abstract, Presented at Proceedings of the ACR Convergence 2021, Virtual, Nov. 8, 2021, 3 pages.
Maxfield et al., "SIK2 Restricts Autophagic Flux to Support Triple-Negative Breast Cancer Survival," Mol. Cell Biol., Mar. 2016, 36(24):3048-3057.
Miranda et al., "Salt-Inducible Kinase 2 Couples Ovarian Cancer Cell Metabolism with Survival at the Adipocyte-Rich Metastatic Niche," Cancer Cell, Aug. 2016, 30(2):273-289.
Mujahid et al., "A UV-Independent Topical Small-Molecule Approach for Melanin Production in Human Skin," Cell Reports, Jun. 2017, 19(11):2177-2184.
Nishimori et al., "Salt-inducible kinases dictate parathyroid hormone 1 receptor action in bone development and remodeling," J Clin. Invest., Aug. 2019, 129(12):5187-5203.
Pubchem SID No. 370057738, "3-Phenylpyrazolo[1,5-a]pyrimidine-6-carboxamid," available May 25, 2018, retrieved on Oct. 19, 2021, 5 pages.
Sakamoto et al., "The Salt-Inducible Kinases: Emerging Metabolic Regulators," Trends Endocrinol. Metab., Dec. 2018, 29(12):827-840.
Sato et al., "A FAK/HDAC5 signaling axis controls osteocyte mechanotransduction," Nature Communications, Jul. 2020, 11(1):3282, 18 pages.
Sundberg et al., "Development of Chemical Probes for Investigation of Salt-Inducible Kinase Function in Vivo," ACS Chemical Biology, Aug. 2016, 11(8):2105-11, 17 pages.
Tarumoto et al., "LKB1, Salt-Inducible Kinases, and MEF2C are Linked Dependencies in Acute Myeloid Leukemia," Molecular Cell, Mar. 2018, 69(6):1017-1027.e6.
Tarumoto et al., "Salt-inducible kinase inhibition suppresses acute myeloid leukemia progression in vivo," Blood, Jan. 2020, 135(1):56-70.
Wang et al., "Design, Synthesis and Biological Evaluation of Benzohydrazide Derivatives Containing Dihydropyrazoles as Potential EGFR Kinase Inhibitors," Molecules, Aug. 2016, 21(8):1021, 21 pages.
Wein et al., "HDAC5 Controls MEF2C-Driven Sclerostin Expression in Osteocytes," Journal of Bone and Mineral Research, Mar. 2015, 30(3):400-11.
Wein et al., "Salt-Inducible Kinases: Physiology, Regulation by cAMP, and Therapeutic Potential," Trends Endocrinol Metab., Oct. 2018, 29(10):723-735, 13 pages.
Wein et al., "SIKs control osteocyte responses to parathyroid hormone," Nature Communications, Oct. 2016, 7:13176, 19 pages.
Zhou et al., "A novel compound ARN-3236 inhibits salt-inducible kinase 2 and sensitizes ovarian cancer cell lines and xenografts to paclitaxel," Clinical Cancer Research, Apr. 2017, 23(8):1945-1954.
Klaeger et al., "The target landscape of clinical kinase drugs," Science, Dec. 2017, 358(6367):eaan4368, 18 pages.
Office Action in Chinese Appln. No. 202180057654.6, dated Aug. 15, 2024, 20 pages (with English translation).
Partial European Search Report in European Appln. No. 21853415.4, dated Aug. 14, 2024, 18 pages.
Office Action in Chinese Appln. No. 202180057654.6, dated Mar. 22, 2024, 27 pages (with English translation).
Frett et al., "Computer aided drug discovery of highly ligand efficient, low molecular weight imidazopyridine analogs as FLT3 inhibitors," HHS Public Access Author Manuscript, doi: 10.1016/j.ejmech.2015.02.052, published online Dec. 1, 2015; published in final edited form as: Eur J Med Chem., Apr. 2015, 94:123-31, 27 pages.
Search Report and Written Opinion in Singaporean Appln. No. 11202300456V, mailed on Nov. 26, 2024, 12 pages.
Office Action in Chinese Appln. No. 202180057654.6, mailed on Apr. 18, 2025, 11 pages (with English translation).
Extended European Search Report in European Appln. No. 21853415.4, mailed on Nov. 5, 2024, 16 pages.
Office Action in Chinese Appln. No. 202180057654.6, mailed on Feb. 6, 2025, 16 pages (with English translation).
Office Action in Japanese Appln. No. 2023-507619, mailed on Mar. 11, 2025, 4 pages (with English translation).
Office Action in Japanese Appln. No. 2023-507619, mailed on Aug. 5, 2025, 15 pages (with English translation).
SID 370057738, "3-Phenylpyrazolo[1,5-a]pyrimidine-6-carboxamide," PubChem available May 25, 2025, retrieved on Aug. 13, 2025, retrieved from URL <https://pubchem.ncbi.nlm.nih.gov/substance/370057738>, 5 pages.
Extended European Search Report in European Appln. No. 25182598.0, mailed on Nov. 7, 2025, 12 pages.
Hicken et al., "Discovery of a novel class of imidazo [1, 2-a] pyridines with potent PDGFR activity and oral bioavailability," ACS Medicinal Chemistry Letters, Nov. 2013, 5(1):78-83.

* cited by examiner

Cmpd. SSA *in vitro* $IC_{50}$ values:
SIK2: <76 pM
c-Kit: 33.0 nM

SALT INDUCIBLE KINASE INHIBITORS

CLAIM OF PRIORITY

This application is a U.S. National Phase Application under 35 U.S.C. § 371 of International Patent Application No. PCT/US2021/044673, filed on Aug. 5, 2021, which claims priority to U.S. Patent Application Ser. No. 63/061,515, filed on Aug. 5, 2020, the entire contents of which are hereby incorporated by reference.

FEDERALLY SPONSORED RESEARCH OR DEVELOPMENT

This invention was made with Government support under Grant Nos. AR067285, DK116716, and AR072150, awarded by The National Institutes of Health. The Government has certain rights in the invention.

TECHNICAL FIELD

The present application provides compounds that modulate the activity of one or more salt inducible kinases (SIKs) and are useful in the treatment of diseases related to SIK.

BACKGROUND

Currently, analogs of parathyroid hormone (PTH) are the most commonly-used bone anabolic treatment options for high-risk patients with osteoporosis. While effective, widespread use of these agents is limited by the need for daily subcutaneous injections, and risks of hypercalcemia and osteosarcoma (see e.g., Compston et al, *Lancet,* 2019, 393 (10169):364-376; and Ardura et al, *Trends Endocrinol. Metab.* 2019, 30(10):756-766).

SUMMARY

The present invention provides, inter alia, compounds of Formula I:

I

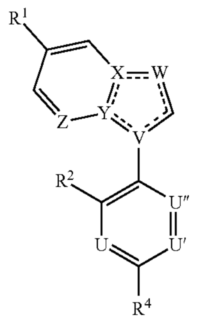

or pharmaceutically acceptable salts thereof, wherein:

V, W, X, Y, and Z are each independently C or N;

wherein at least two of V, W, X, Y, and Z are N, and the ring comprising V, W, X, Y, and Z forms a heteroaryl ring;

U is $CR^3$ or N;

U' is $CR^5$ or N;

U" is $CR^6$ or N;

$R^1$ is selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $OR^{a1}$, $C(O)R^{b1}$, $C(O)NR^{c1}R^{d1}$, $NR^{c1}C(O)R^{b1}$, $C(O)OR^{a1}$, $OC(O)R^{b1}$, $OC(O)NR^{c1}R^{d1}$, and $NR^{c1}C(O)OR^{a1}$, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- are each optionally substituted with 1, 2, 3, or 4 independently selected $R^{1A}$ substituents;

$R^{a1}$, $R^{b1}$, $R^{c1}$, and $R^{d1}$ are each independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 4-10 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, and (5-10 membered heteroaryl)-$C_{1-6}$ alkyl, wherein the $C_{1-6}$ alkyl, $C_{2-6}$ alkenyl, $C_{2-6}$ alkynyl, $C_{6-10}$ aryl, $C_{3-10}$ cycloalkyl, 4-10 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, and (5-10 membered heteroaryl)-$C_{1-6}$ alkyl are each optionally substituted with 1, 2, 3, or 4 independently selected $R^{1A}$ substituents;

or $R^{c1}$ and $R^{d1}$, together with the nitrogen to which they are attached, come together to form a 10-14 membered heterocycloalkyl or 10-14 membered heteroaryl group, wherein the 10-14 membered heterocycloalkyl and 10-14 membered heteroaryl group are each optionally substituted with 1, 2, 3, or 4 independently selected $R^{1A}$ substituents;

each $R^{1A}$ is independently selected from halo, $C_{1-6}$ alkyl, $C_{2-6}$ alkenyl, $C_{2-6}$ alkynyl, $C_{1-6}$ haloalkyl, $C_{1-6}$ alkoxy, $C_{6-10}$ aryl, $C_{3-10}$ cycloalkyl, 4-10 membered heterocycloalkyl, 5-10 membered heteroaryl, $NO_2$, CN, wherein the $C_{1-6}$ alkyl, $C_{2-6}$ alkenyl, and $C_{2-6}$ alkynyl are each optionally substituted with $C_{1-4}$ alkoxy;

$R^2$ is selected from H, halo, $C_{1-6}$ alkyl, $C_{2-6}$ alkenyl, $C_{2-6}$ alkynyl, $C_{1-6}$ haloalkyl, and $C_{1-6}$ alkoxy;

$R^3$ is selected from H, halo, $C_{1-6}$ alkyl, $C_{2-6}$ alkenyl, $C_{2-6}$ alkynyl, $C_{1-6}$ haloalkyl, and $C_{1-6}$ alkoxy;

$R^4$ is selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 4-10 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, (5-10 membered heteroaryl)-$C_{1-6}$ alkyl, $NO_2$, CN, $OR^{a4}$, $C(O)R^{b4}$, $C(O)NR^{c4}R^{d4}$, $C(O)N(R^{c4})NR^{c4}R^{d4}$, $NR^{c4}C(O)R^{b4}$, $C(O)OR^{a4}$, $OC(O)R^{b4}$, $OC(O)NR^{c4}R^{d4}$, and $NR^{c4}C(O)OR^{a4}$, wherein the $C_{6-10}$ aryl, $C_{3-10}$ cycloalkyl, 4-10 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, and (5-10 membered heteroaryl)-$C_{1-6}$ alkyl are each optionally substituted with 1, 2, 3, or 4 independently selected $R^{4A}$ substituents;

$R^{a4}$, $R^{b4}$, $R^{c4}$, and $R^{d4}$ are each independently selected from H, $C_{1-6}$ alkyl, $C_{2-6}$ alkenyl, $C_{2-6}$ alkynyl, $C_{1-6}$ haloalkyl, and $C_{1-6}$ alkoxy;

each $R^{4A}$ is independently selected from $C_{1-6}$ alkyl, $C_{2-6}$ alkenyl, $C_{2-6}$ alkynyl, $C_{1-6}$ haloalkyl, and $C_{1-6}$ alkoxy;

$R^5$ is selected from H, halo, $C_{1-6}$ alkyl, $C_{2-6}$ alkenyl, $C_{2-6}$ alkynyl, $C_{1-6}$ haloalkyl, and $C_{1-6}$ alkoxy;

or $R^4$ and $R^5$, together with the carbon atoms to which they are attached, come together to form a 5-6 membered aryl ring which is optionally substituted with 1, 2, 3, or 4 independently selected $R^7$ substituents;

$R^6$ is selected from H, $C_{1-6}$ alkyl, $C_{2-6}$ alkenyl, $C_{2-6}$ alkynyl, $C_{1-6}$ haloalkyl, and $C_{1-6}$ alkoxy;

each $R^7$ is independently selected from $C_{6-10}$ aryl, $C_{3-10}$ cycloalkyl, 4-14 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, (5-10 membered heteroaryl)-$C_{1-6}$ alkyl, $NO_2$, CN, and $OR^{a7}$, wherein the $C_{6-10}$ aryl, $C_{3-10}$ cycloalkyl, 4-14 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, (5-10 membered heteroaryl)-$C_{1-6}$ alkyl are each optionally substituted with 1, 2, 3, or 4 independently selected $R^{7A}$ substituents;

each $R^{a7}$ is independently selected from $C_{6-10}$ aryl, $C_{3-10}$ cycloalkyl, 4-10 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, and (5-10 membered heteroaryl)-$C_{1-6}$ alkyl; and each $R^{7A}$ is independently selected from $C_{1-6}$ alkyl, $C_{2-6}$ alkenyl, $C_{2-6}$ alkynyl, $C_{1-6}$ haloalkyl, $C_{1-6}$ alkoxy, amino, $C_{1-6}$ alkylamino, di($C_{1-6}$ alkyl)amino, phenyl, $C_{3-6}$ cycloalkyl, 4-6 membered heterocycloalkyl, 5-6 membered heteroaryl, and wherein the $C_{1-6}$ alkyl, $C_{2-6}$ alkenyl, and $C_{2-6}$ alkynyl are each optionally substituted with amino or $C_{1-4}$ alkoxy.

In some aspects of the above embodiments, $R^4$ is selected from H, halo, $C_{1-6}$ alkyl, $C_2$-6 alkenyl, $C_{2-6}$ alkynyl, $C_{1-6}$ haloalkyl, $C_{6-10}$ aryl, $C_{3-10}$ cycloalkyl, 4-10 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, (5-10 membered heteroaryl)-$C_{1-6}$ alkyl, $NO_2$, CN, $OR^{a4}$, $C(O)R^{b4}$, $C(O)NR^{c4}R^{d4}$, $NR^{c4}C(O)R^{b4}$, $C(O)OR^{a4}$, $OC(O)R^{b4}$, $OC(O)NR^{c4}R^{d4}$, and $NR^{c4}C(O)OR^{a4}$, wherein the $C_{6-10}$ aryl, $C_{3-10}$ cycloalkyl, 4-10 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, and (5-10 membered heteroaryl)-$C_{1-6}$ alkyl are each optionally substituted with 1, 2, 3, or 4 independently selected $R^{4A}$ substituents;

In some embodiments, V, X, and Z are each C, and W and Y are each N.

In some embodiments, X, Y, and Z are each C, and V and W are each N.

In some embodiments, V, Y, and Z are each C, and W and X are each N.

In some embodiments, V and Y are each C, and W, X, and Z are each N.

In some embodiments, $R^1$ is selected from 5-10 membered heteroaryl, $OR^{a1}$, $C(O)NR^{c1}R^{d1}$, and $NR^{c1}C(O)R^{b1}$, wherein the 5-10 membered heteroaryl is optionally substituted with 1, 2, 3, or 4 independently selected $R^{1A}$ substituents. In some embodiments, $R^1$ is selected from 5-6 membered heteroaryl, $OR^{a1}$, $C(O)NR^{c1}R^{d1}$, and $NR^{c1}C(O)R^{b1}$ wherein the 5-6 membered heteroaryl is optionally substituted with 1 or 2 independently selected $R^{1A}$ substituents.

In some embodiments, $R^{a1}$, $R^{b1}$, $R^{c1}$, and $R^{d1}$ are each independently selected from H, 4-10 membered heterocycloalkyl, (4-10 membered heterocycloalkyl)-$C_{1-6}$ alkyl, and (5-10 membered heteroaryl)-$C_{1-6}$ alkyl, wherein the 4-10 membered heterocycloalkyl, (4-10 membered heterocycloalkyl)-$C_{1-6}$ alkyl, and (5-10 membered heteroaryl)-$C_{1-6}$ alkyl are each optionally substituted with 1 or 2 independently selected $R^{1A}$ substituents;

or $R^{c1}$ and $R^{d1}$, together with the nitrogen to which they are attached, come together to form a 10-14 membered heterocycloalkyl or 10-14 membered heteroaryl group.

In some embodiments, $R^{a1}$, $R^{b1}$, $R^{c1}$, and $R^{d1}$ are each independently selected from H, methyl, pyrazolyl, pyridinylmethyl, pyridinylethyl, imidazo[1,2-a]pyridinylmethyl, benzoimidazolylmethyl, imidazo[4,5-c]pyridinylmethyl, benzoxazolylmethyl, oxetanylmethyl, oxetanylethyl, thietanyl-(1,1-dioxide)methyl, 2-oxaspiro[3.3]heptanyl, and 2-oxaspiro[3.5]nonanyl, wherein the methyl, pyrazolyl, pyridinylmethyl, pyridinylethyl, imidazo[1,2-a]pyridinylmethyl, benzoimidazolylmethyl, imidazo[4,5-c]pyridinylmethyl, benzoxazolylmethyl, oxetanylmethyl, oxetanylethyl, thietanyl-(1,1-dioxide)methyl, 2-oxaspiro[3.3]heptanyl, and 2-oxaspiro[3.5]nonanyl are each optionally substituted with 1 or 2 independently selected $R^{1A}$ substituents;

or $R^{c1}$ and $R^{d1}$, together with the nitrogen to which they are attached, come together to form 1,2,3,4-tetrahydrobenzo[4,5]imidazo[1,2-a]pyrazinyl.

In some embodiments, each $R^{1A}$ is independently selected from $C_{1-6}$ alkyl, $C_{3-10}$ cycloalkyl, 4-10 membered heterocycloalkyl, and CN, wherein each $C_{1-6}$ alkyl is optionally substituted with $C_{1-4}$ alkoxy. In some embodiments, each $R^{1A}$ is independently selected from methyl, ethyl, methoxymethyl, cyclopropyl, oxetanyl, and CN.

In some embodiments, $R^2$ is selected from H and $C_{1-6}$ alkoxy. In some embodiments, $R^2$ is selected from H and methoxy.

In some embodiments, U is $CR^3$. In some embodiments, $R^3$ is selected from H, halo, and $C_{1-6}$ alkoxy. In some embodiments, $R^3$ is selected from H, fluoro, chloro, and methoxy.

In some embodiments, U is N.

In some embodiments, U" is $CR^6$. In some embodiments, $R^6$ is selected from H and $C_{1-6}$ alkoxy. In some embodiments, $R^6$ is H.

In some embodiments, U" is N.

In some embodiments, $R^4$ is selected from H, 5-10 membered heteroaryl, CN, and $C(O)NR^{c4}R^{d4}$, wherein the 5-10 membered heteroaryl is optionally substituted with 1, 2, 3, or 4 independently selected $R^{4A}$ substituents.

In some embodiments, $R^4$ is selected from H, 5-6 membered heteroaryl, CN, and $C(O)NR^{c4}R^{d4}$, wherein the 5-6 membered heteroaryl is optionally substituted with 1 or 2 independently selected $R^{4A}$ substituents.

In some embodiments, $R^{c4}$ and $R^{d4}$ are each independently selected from H, $C_{1-6}$ alkyl, and $C_{1-6}$ haloalkyl.

In some embodiments, $R^{c4}$ and $R^{d4}$ are each independently selected from H, ethyl, and trifluoroethyl.

In some embodiments, $R^4$ is selected from H, CN, oxadiazolyl, and $C(O)NHCH_2CF_3$, wherein the oxadiazolyl is optionally substituted with 1 or 2 $R^{4A}$ substituents.

In some embodiments, each $R^{4A}$ is an independently selected $C_{1-6}$ alkyl group. In some embodiments, each $R^{4A}$ is ethyl.

In some embodiments, U' is $CR^5$. In some embodiments, $R^5$ is selected from H, halo, $C_{1-6}$ alkyl, and $C_{1-6}$ alkoxy. In some embodiments, $R^5$ is selected from H, fluoro, chloro, methyl, and methoxy.

In some embodiments, U' is N.

In some embodiments, $R^4$ and $R^5$ together with the carbon atoms to which they are attached, come together to form a 5-6 membered aryl ring which is optionally substituted with 1, 2, 3, or 4 independently selected $R^7$ substituents. In some embodiments, $R^4$ and $R^5$ together with the carbon atoms to which they are attached, come together to form a 6-membered aryl ring which is optionally substituted with 1 or 2 independently selected $R^7$ substituents.

In some embodiments, each $R^7$ is independently selected from $C_{3-10}$ cycloalkyl, 4-14 membered heterocycloalkyl, 5-10 membered heteroaryl, and $OR^{a7}$, wherein the $C_{3-10}$ cycloalkyl, 4-14 membered heterocycloalkyl, and 5-10 membered heteroaryl are each optionally substituted with 1 or 2 independently selected $R^{7A}$ substituents.

In some embodiments, each $R^{a7}$ is an independently selected 4-10 membered heterocycloalkyl group. In some embodiments, each $R^{a7}$ is azetidinyl.

In some embodiments, each $R^7$ is independently selected from bicyclo[1.1.1]pentanyl, azetidinyl, pyrrolidinyl, piperidinyl, morpholinyl, imidazolyl, azaspiro[3.3]heptanyl, diazaspiro[3.5]nonanyl, oxadiazaspiro[5.5]undecanyl, diazaspiro[4.4]nonanyl, and azetidinyloxy, wherein the bicyclo[1.1.1]pentanyl, azetidinyl, pyrrolidinyl, piperidinyl, morpholinyl, imidazolyl, azaspiro[3.3]heptanyl, diazaspiro[3.5]nonanyl, oxadiazaspiro[5.5]undecanyl, and diazaspiro[4.4]nonanyl are each optionally substituted with 1 or 2 $R^{7A}$ substituents.

In some embodiments, each $R^{7A}$ is independently selected from $C_{1-6}$ alkyl, amino, $C_{3-6}$ cyclopropyl and 4-6 membered heterocycloalkyl, wherein each $C_{1-6}$ alkyl is optionally substituted with amino or $C_{1-4}$ alkoxy. In some embodiments, each $R^{7A}$ is independently selected from methyl, methoxyethyl, aminomethyl, amino, cyclopropyl, and oxetanyl.

In some embodiments:

V, X, and Z are each C, and W and Y are each N; or
X, Y, and Z are each C, and V and W are each N; or
V, Y, and Z are each C, and W and X are each N; or
V and Y are each C, and W, X, and Z are each N;

$R^1$ is selected from 5-10 membered heteroaryl, $OR^{a1}$, $C(O)NR^{c1}R^{d1}$, and $NR^{c1}C(O)R^{b1}$, wherein the 5-10 membered heteroaryl is optionally substituted with 1, 2, 3, or 4 independently selected $R^{1A}$ substituents;

$R^{a1}$, $R^{b1}$, $R^{c1}$, and $R^{d1}$ are each independently selected from H, 4-10 membered heterocycloalkyl, (4-10 membered heterocycloalkyl)-$C_{1-6}$ alkyl, and (5-10 membered heteroaryl)-$C_{1-6}$ alkyl, wherein the 4-10 membered heterocycloalkyl, (4-10 membered heterocycloalkyl)-$C_{1-6}$ alkyl, and (5-10 membered heteroaryl)-$C_{1-6}$ alkyl are each optionally substituted with 1 or 2 independently selected $R^{1A}$ substituents;

or $R^{c1}$ and $R^{d1}$, together with the nitrogen to which they are attached, come together to form a 10-14 membered heterocycloalkyl or 10-14 membered heteroaryl group;

each $R^{1A}$ is independently selected from $C_{1-6}$ alkyl, $C_{3-10}$ cycloalkyl, 4-10 membered heterocycloalkyl, and CN, wherein each $C_{1-6}$ alkyl is optionally substituted with $C_{1-4}$ alkoxy;

$R^2$ is H or $C_{1-6}$ alkoxy;

U is $CR^3$ or N;

U' is $CR^5$ or N;

U" is $CR^6$ or N;

$R^3$ is selected from H, halo, and $C_{1-6}$ alkoxy;

$R^4$ is selected from H, 5-10 membered heteroaryl, CN, and $C(O)NR^{c4}R^{d4}$, wherein the 5-10 membered heteroaryl is optionally substituted with 1, 2, 3, or 4 independently selected $R^{4A}$ substituents;

$R^{c4}$ and $R^{d4}$ are each independently selected from H, $C_{1-6}$ alkyl, and $C_{1-6}$ haloalkyl;

each $R^{4A}$ is an independently selected $C_{1-6}$ alkyl group;

$R^5$ is selected from H, halo, $C_{1-6}$ alkyl, and $C_{1-6}$ alkoxy;

or $R^4$ and $R^5$ together with the carbon atoms to which they are attached, come together to form a 5-6 membered aryl ring which is optionally substituted with 1, 2, 3, or 4 independently selected $R^7$ substituents;

$R^6$ is selected from H and $C_{1-6}$ alkoxy;

each $R^7$ is independently selected from $C_{3-10}$ cycloalkyl, 4-14 membered heterocycloalkyl, 5-10 membered heteroaryl, and $OR^{a7}$, wherein the $C_{3-10}$ cycloalkyl, 4-14 membered heterocycloalkyl, and 5-10 membered heteroaryl are each optionally substituted with 1 or 2 independently selected $R^{7A}$ substituents;

each $R^{a7}$ is an independently selected 4-10 membered heterocycloalkyl group; and each $R^{7A}$ is independently selected from $C_{1-6}$ alkyl, amino, $C_{3-6}$ cyclopropyl and 4-6 membered heterocycloalkyl, wherein each $C_{1-6}$ alkyl is optionally substituted with amino or $C_{1-4}$ alkoxy.

In some embodiments:

V, X, and Z are each C, and W and Y are each N; or
X, Y, and Z are each C, and V and W are each N; or
V, Y, and Z are each C, and W and X are each N; or
V and Y are each C, and W, X, and Z are each N;

$R^1$ is selected from 5-6 membered heteroaryl, $OR^{a1}$, $C(O)NR^{c1}R^{d1}$, and $NR^{c1}C(O)R^b$, wherein the 5-6 membered heteroaryl is optionally substituted with 1 or 2 independently selected $R^{1A}$ substituents;

$R^{a1}$, $R^{b1}$, $R^{c1}$, and $R^{d1}$ are each independently selected from H, 4-10 membered heterocycloalkyl, (4-10 membered heterocycloalkyl)-$C_{1-6}$ alkyl, and (5-10 membered heteroaryl)-$C_{1-6}$ alkyl, wherein the 4-10 membered heterocycloalkyl, (4-10 membered heterocycloalkyl)-$C_{1-6}$ alkyl, and (5-10 membered heteroaryl)-$C_{1-6}$ alkyl are each optionally substituted with 1 or 2 independently selected $R^{1A}$ substituents;

or $R^{c1}$ and $R^{d1}$, together with the nitrogen to which they are attached, come together to form a 10-14 membered heterocycloalkyl or 10-14 membered heteroaryl group;

each $R^{1A}$ is independently selected from $C_{1-6}$ alkyl, $C_{3-6}$ cycloalkyl, 4-6 membered heterocycloalkyl, and CN, wherein each $C_{1-6}$ alkyl is optionally substituted with $C_{1-4}$ alkoxy;

$R^2$ is H or $C_{1-6}$ alkoxy;

U is $CR^3$ or N;

U' is $CR^5$ or N;

U" is $CR^6$ or N;

$R^3$ is selected from H, halo, and $C_{1-6}$ alkoxy;

$R^4$ is selected from H, 5-6 membered heteroaryl, CN, and $C(O)NR^{c4}R^{d4}$, wherein the 5-6 membered heteroaryl is optionally substituted with 1 or 2 independently selected $R^{4A}$ substituents;

$R^{c4}$ and $R^{d4}$ are each independently selected from H, $C_{1-6}$ alkyl, and $C_{1-6}$ haloalkyl; each $R^{4A}$ is an independently selected $C_{1-6}$ alkyl group;

$R^5$ is selected from H, halo, $C_{1-6}$ alkyl, and $C_{1-6}$ alkoxy;

or $R^4$ and $R^5$ together with the carbon atoms to which they are attached, come together to form a 6-membered aryl ring which is optionally substituted with 1 or 2 independently selected $R^7$ substituents;

each $R^7$ is independently selected from $C_{3-10}$ cycloalkyl, 4-14 membered heterocycloalkyl, 5-10 membered heteroaryl, and $OR^{a7}$, wherein the $C_{3-10}$ cycloalkyl, 4-14 membered heterocycloalkyl, and 5-10 membered heteroaryl are each optionally substituted with 1 or 2 independently selected $R^{7A}$ substituents;

each $R^{a7}$ is an independently selected 4-10 membered heterocycloalkyl group; and each $R^{7A}$ is independently selected from $C_{1-6}$ alkyl, amino, $C_{3-6}$ cyclopropyl and 4-6 membered heterocycloalkyl, wherein each $C_{1-6}$ alkyl is optionally substituted with amino or $C_{1-4}$ alkoxy.

In some embodiments:

V, X, and Z are each C, and W and Y are each N; or

X, Y, and Z are each C, and V and W are each N; or

V, Y, and Z are each C, and W and X are each N; or

V and Y are each C, and W, X, and Z are each N;

$R^1$ is selected from 5-6 membered heteroaryl, $OR^{a1}$, $C(O)NR^{c1}R^{d1}$, and $NR^{c1}C(O)R^{b1}$, wherein the 5-6 membered heteroaryl is optionally substituted with 1 or 2 independently selected $R^{1A}$ substituents;

$R^{a1}$, $R^{b1}$, $R^{c1}$, and $R^{d1}$ are each independently selected from H, methyl, pyrazolyl, pyridinylmethyl, pyridinylethyl, imidazo[1,2-a]pyridinylmethyl, benzoimidazolylmethyl, imidazo[4,5-c]pyridinylmethyl, benzoxazolylmethyl, oxetanylmethyl, oxetanylethyl, thietanyl-(1,1-dioxide)methyl, 2-oxaspiro[3.3]heptanyl, and 2-oxaspiro[3.5]nonanyl, wherein the methyl, pyrazolyl, pyridinylmethyl, pyridinylethyl, imidazo[1,2-a]pyridinylmethyl, benzoimidazolylmethyl, imidazo[4,5-c]pyridinylmethyl, benzoxazolylmethyl, oxetanylmethyl, oxetanylethyl, thietanyl-(1,1-dioxide)methyl, 2-oxaspiro[3.3]heptanyl, and 2-oxaspiro[3.5]nonanyl are each optionally substituted with 1 or 2 independently selected $R^{1A}$ substituents;

or $R^{c1}$ and $R^{d1}$, together with the nitrogen to which they are attached, come together to form 1,2,3,4-tetrahydrobenzo[4,5]imidazo[1,2-a]pyrazinyl;

each $R^{1A}$ is independently selected from methyl, ethyl, methoxymethyl, and CN;

$R^2$ is H or $C_{1-6}$ alkoxy;

U is $CR^3$ or N;

U' is $CR^5$ or N;

U" is $CR^6$ or N;

$R^3$ is selected from H, halo, and $C_{1-6}$ alkoxy;

$R^4$ is selected from H, 5-6 membered heteroaryl, CN, and $C(O)NR^{c4}R^{d4}$, wherein the 5-6 membered heteroaryl is optionally substituted with 1 or 2 independently selected $R^{4A}$ substituents;

$R^{c4}$ and $R^{d4}$ are each independently selected from H, $C_{1-6}$ alkyl, and $C_{1-6}$ haloalkyl;

each $R^{4A}$ is an independently selected $C_{1-6}$ alkyl group;

$R^5$ is selected from H, halo, $C_{1-6}$ alkyl, and $C_{1-6}$ alkoxy;

or $R^4$ and $R^5$ together with the carbon atoms to which they are attached, come together to form a 6-membered aryl ring which is optionally substituted with 1 or 2 independently selected $R^7$ substituents;

each $R^7$ is independently selected from bicyclo[1.1.1]pentanyl, azetidinyl, pyrrolidinyl, piperidinyl, morpholinyl, imidazolyl, azaspiro[3.3]heptanyl, diazaspiro[3.5]nonanyl, oxadiazaspiro[5.5]undecanyl, diazaspiro[4.4]nonanyl, and azetidinyloxy, wherein the bicyclo[1.1.1]pentanyl, azetidinyl, pyrrolidinyl, piperidinyl, morpholinyl, imidazolyl, azaspiro[3.3]heptanyl, diazaspiro[3.5]nonanyl, oxadiazaspiro[5.5]undecanyl, and diazaspiro[4.4]nonanyl are each optionally substituted with 1 or 2 $R^{7A}$ substituents; and each $R^{7A}$ is independently selected from methyl, methoxyethyl, aminomethyl, amino, cyclopropyl, and oxetanyl.

In some embodiments, the compound of Formula I is a compound of Formula II.

II

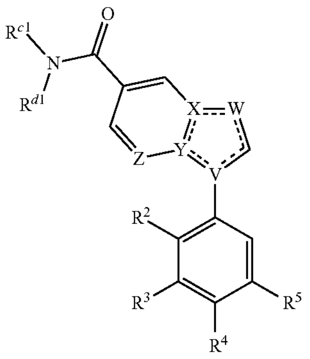

or a pharmaceutically acceptable salt thereof.

In some embodiments, the compound of Formula I is a compound of Formula III:

III

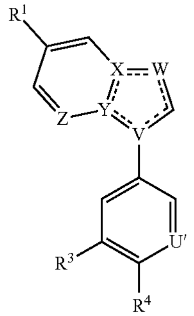

or a pharmaceutically acceptable salt thereof.

In some embodiments, the compound of Formula I is a compound of Formula IV:

IV

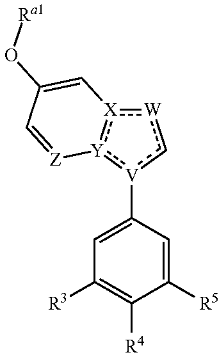

or a pharmaceutically acceptable salt thereof.

In some embodiments, the compound of Formula I is a compound of Formula V:
V
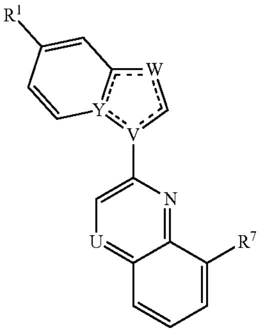
or a pharmaceutically acceptable salt thereof.
In some embodiments, the compound provided herein is selected from:
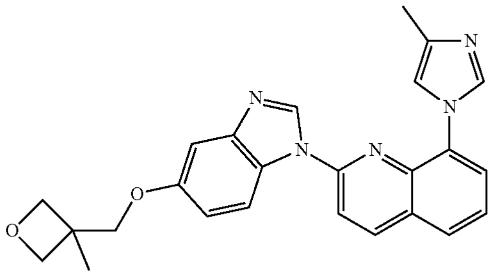
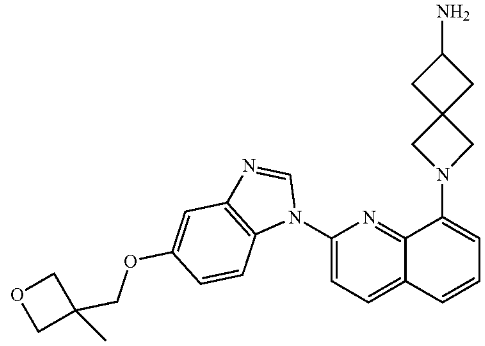
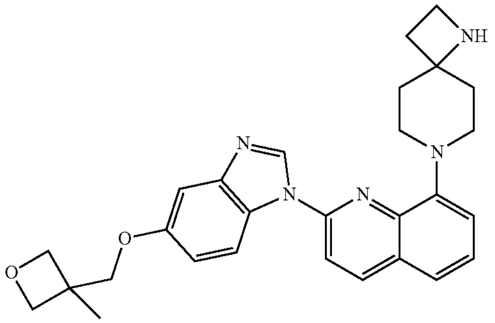
-continued
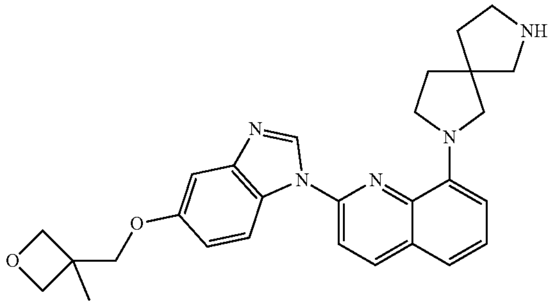
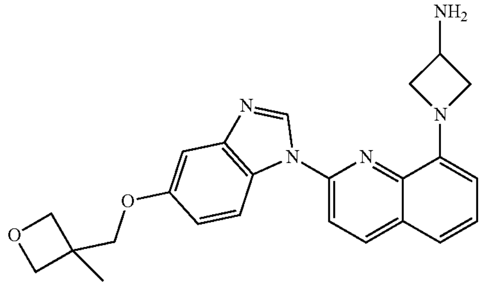
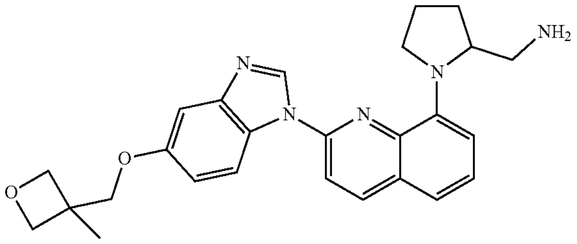
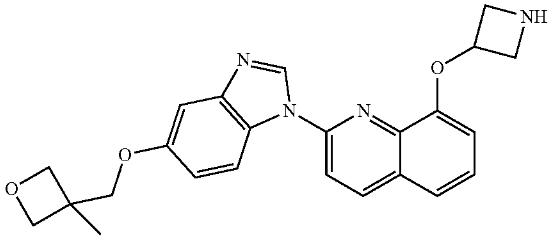
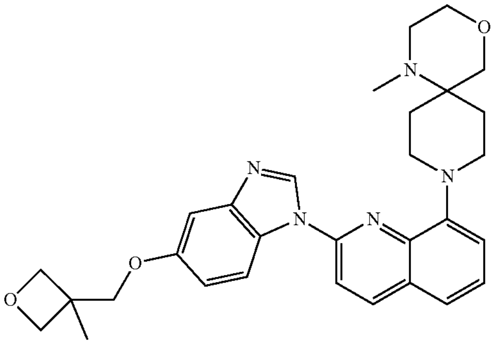
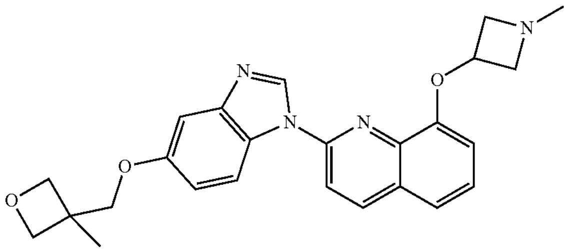

-continued
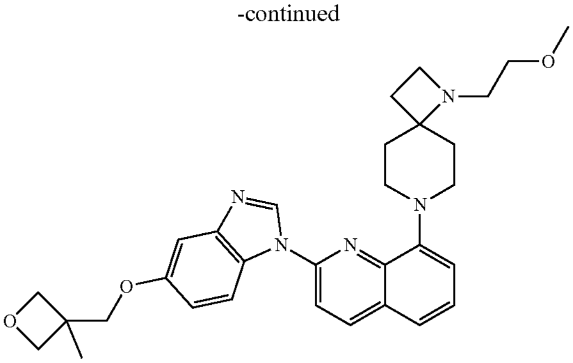
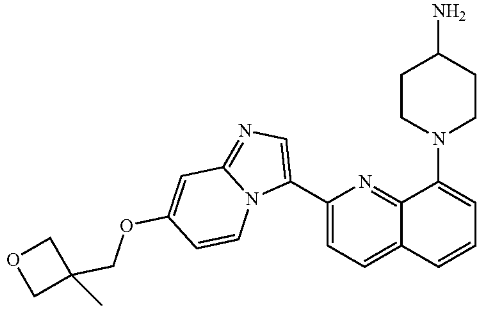
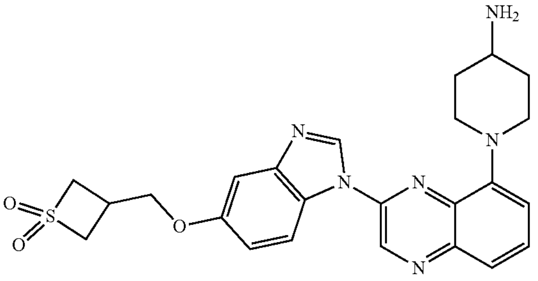
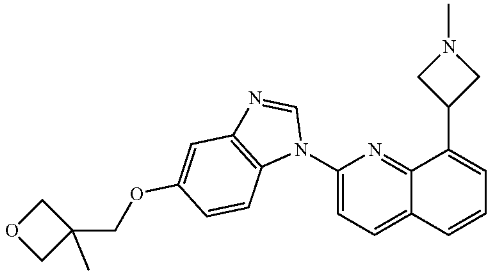
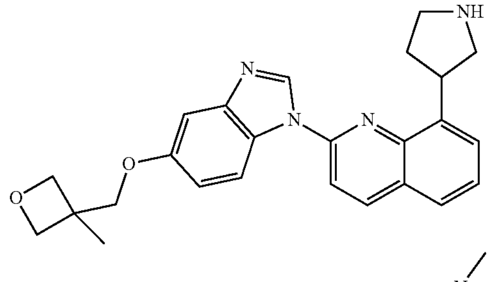
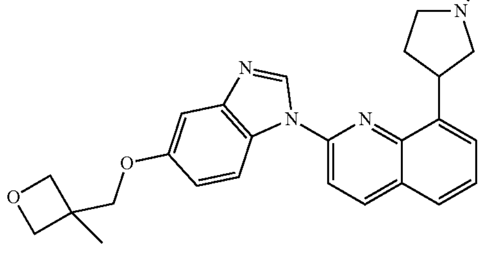
-continued
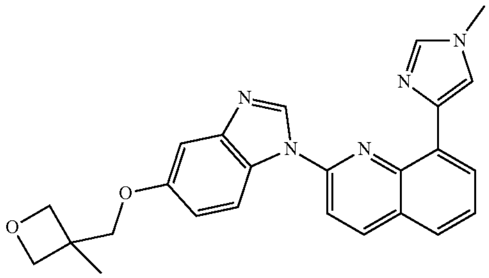
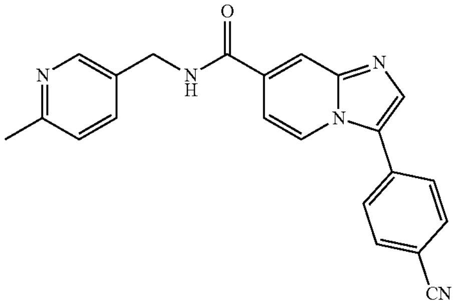
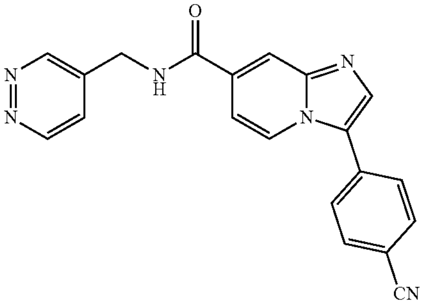
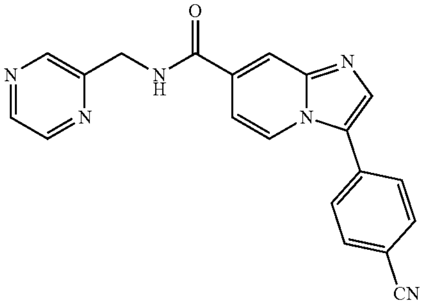
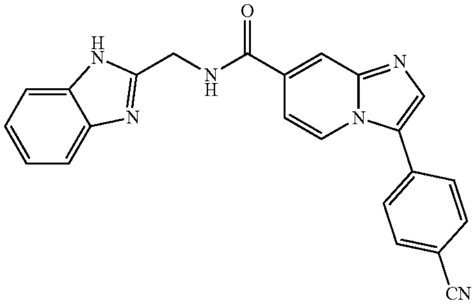

-continued
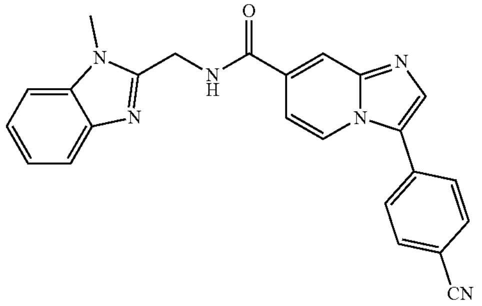
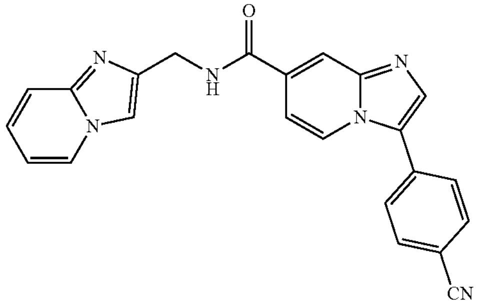
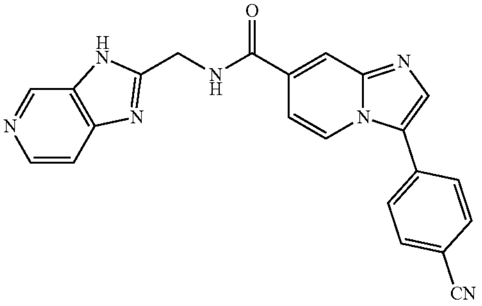
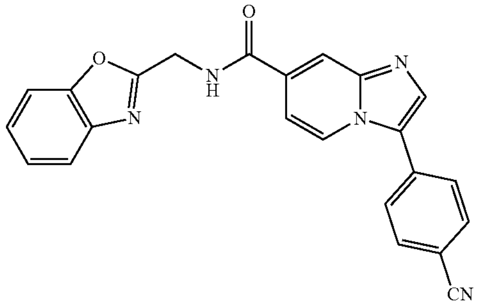
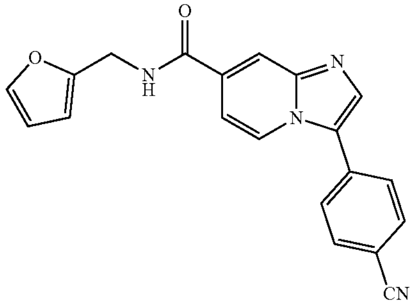
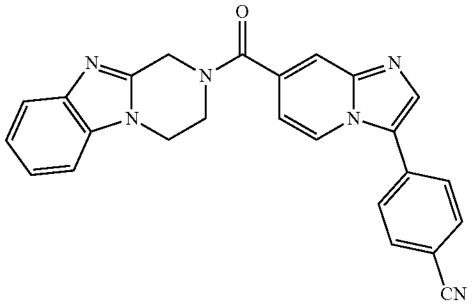
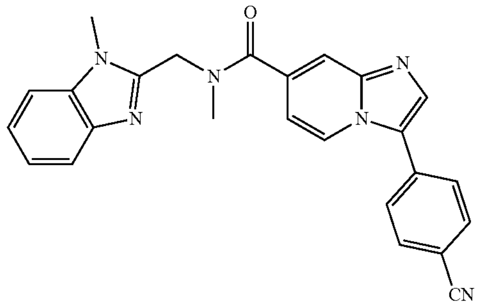
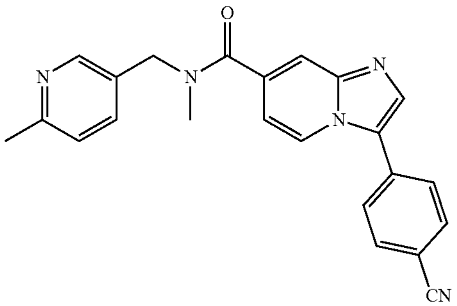
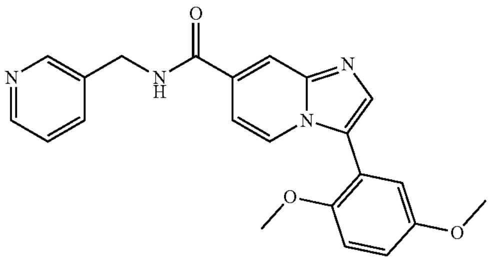
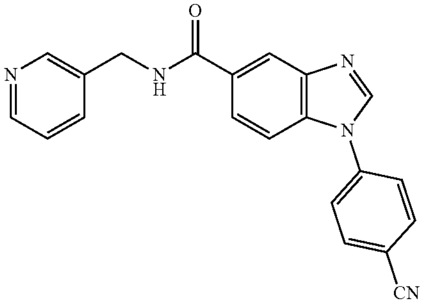
-continued -continued
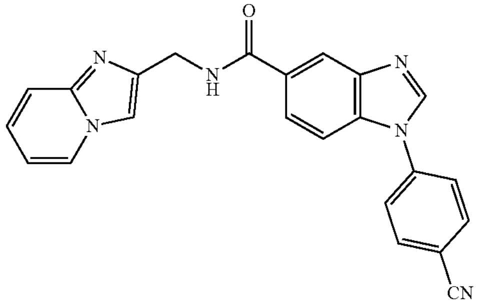
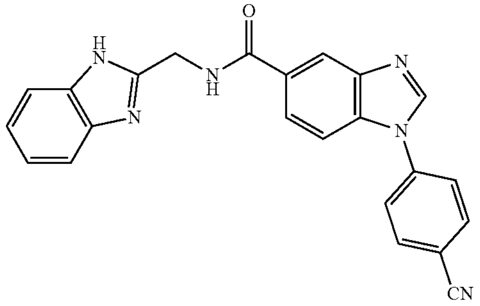
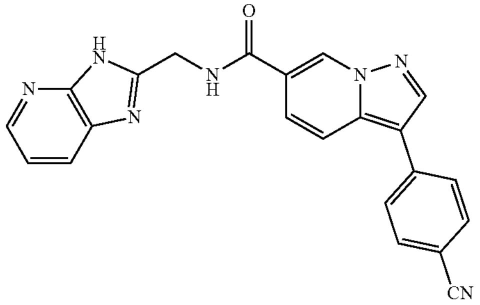
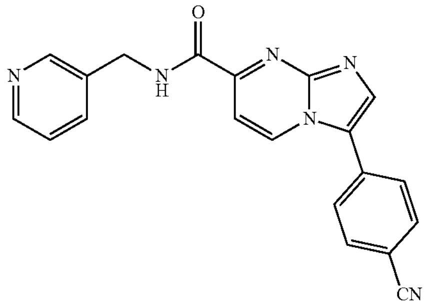
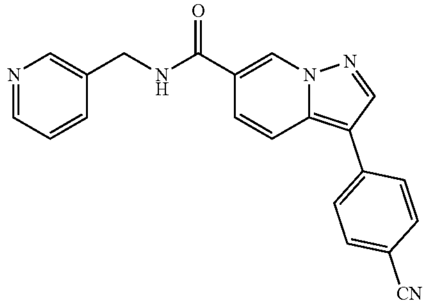
-continued
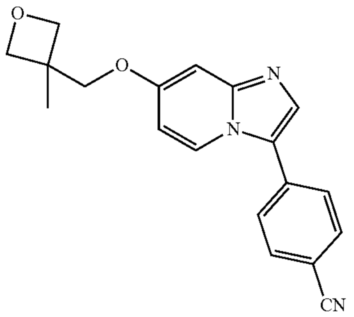
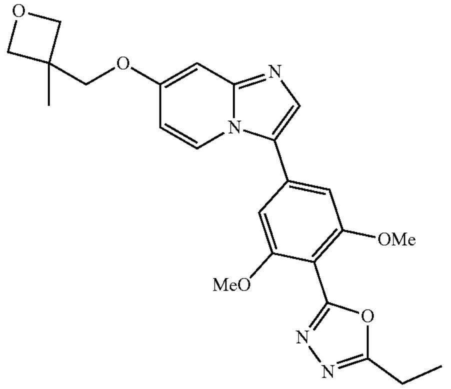
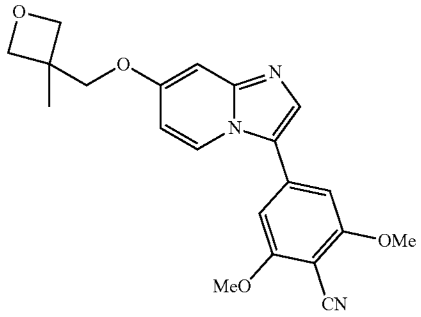
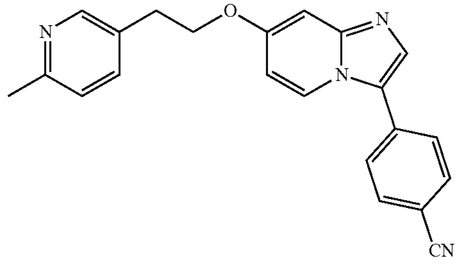
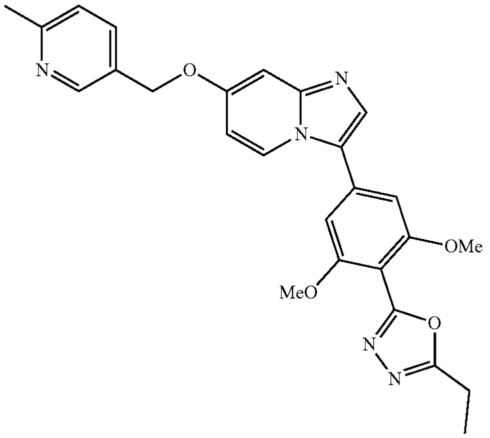

-continued
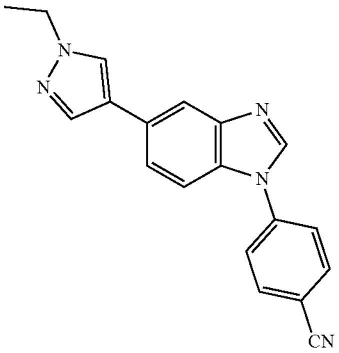
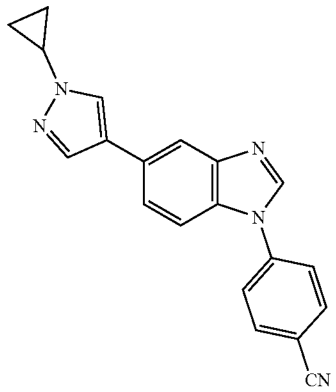
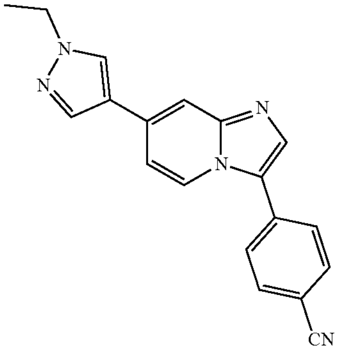
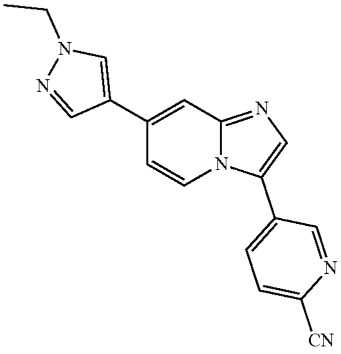
-continued
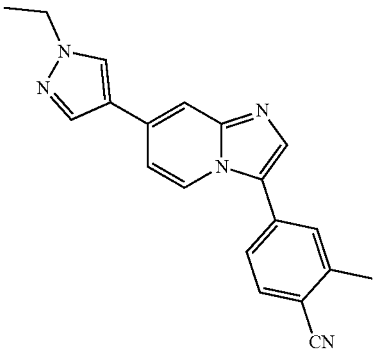
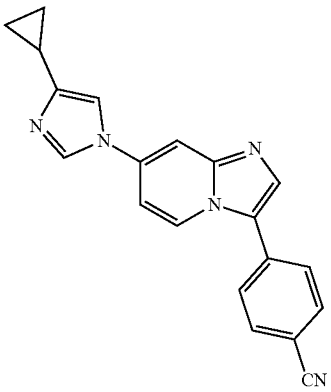
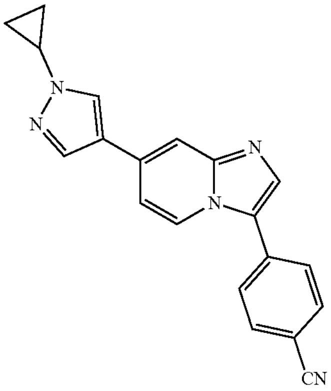
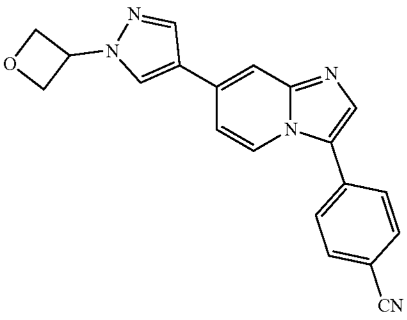

-continued
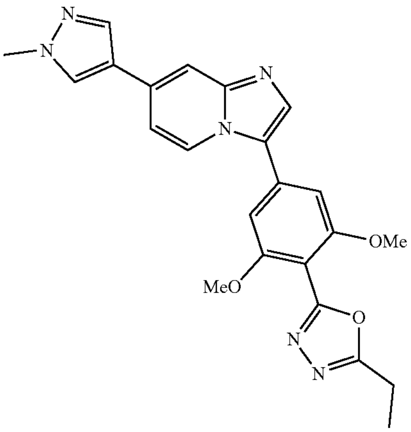
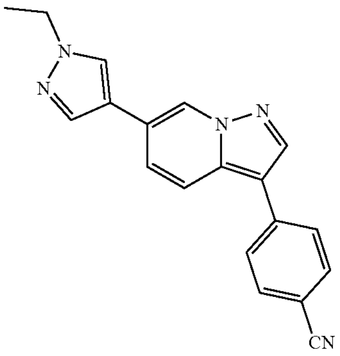
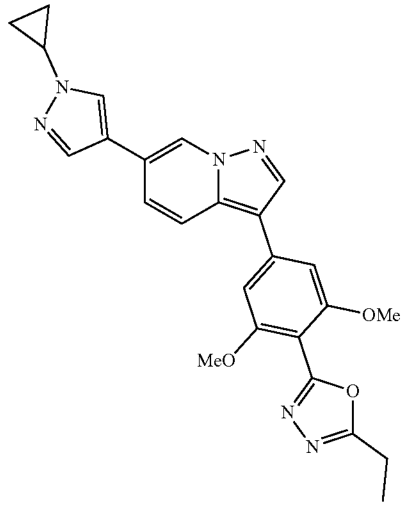
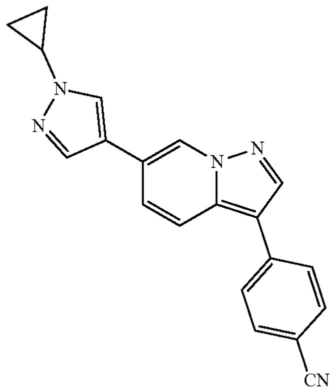
-continued
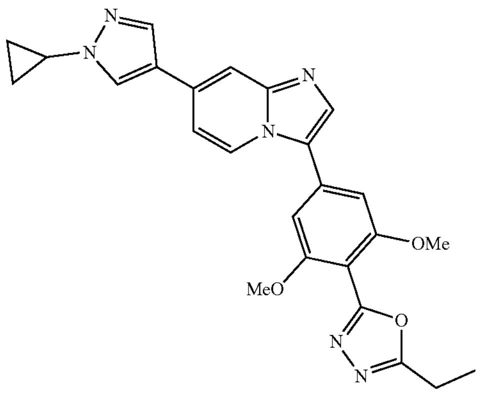
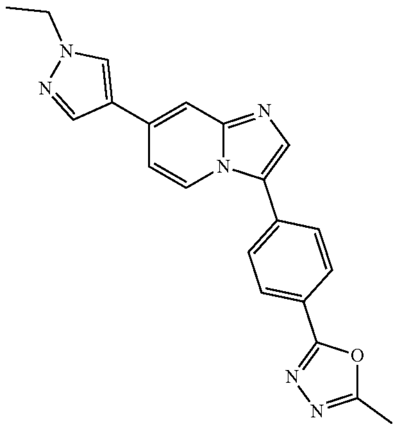
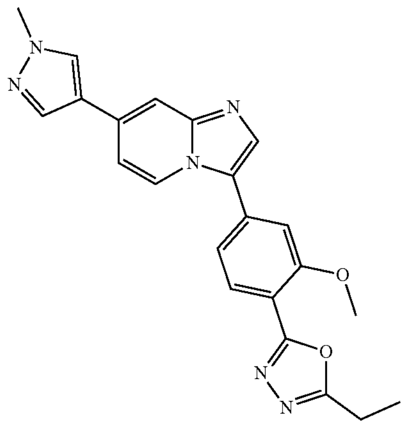
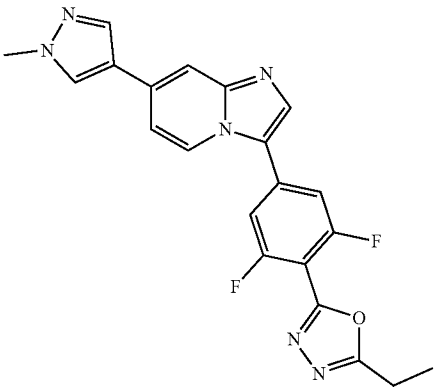

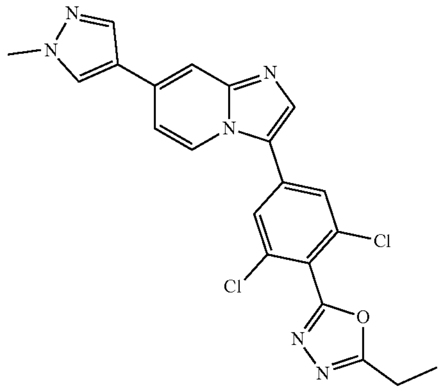
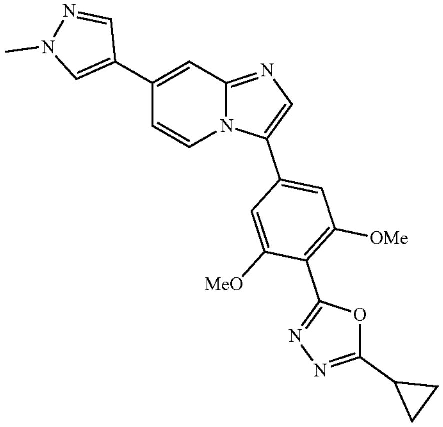
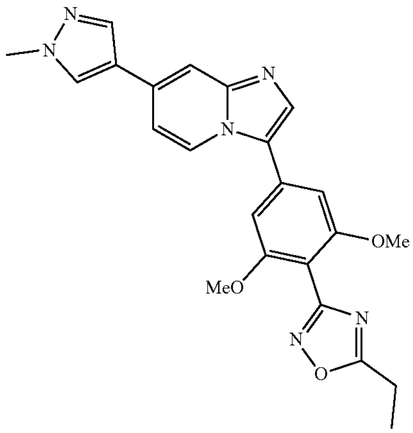
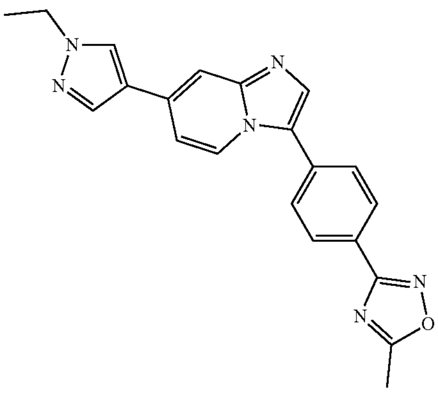
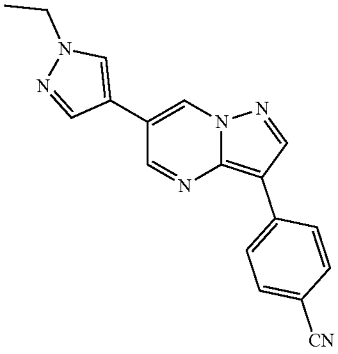
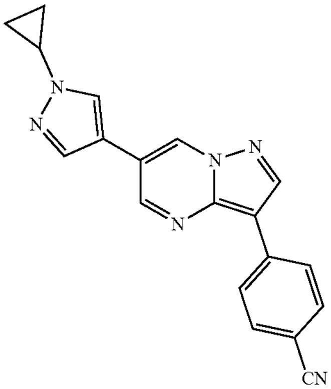
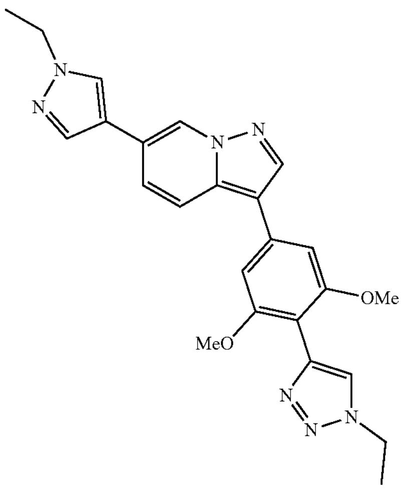
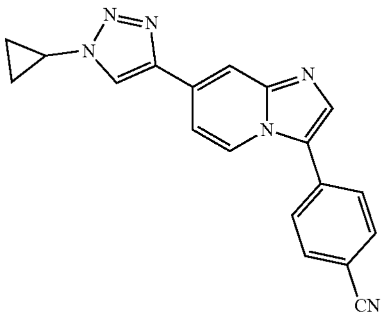

-continued

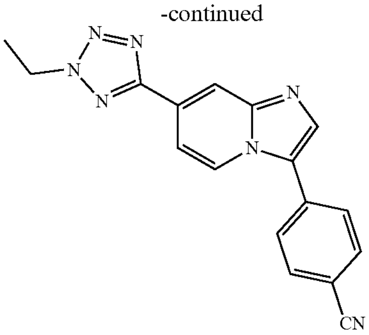

and

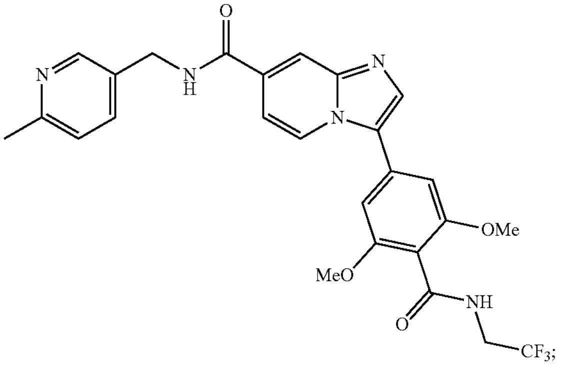

or a pharmaceutically acceptable salt thereof.

In some embodiments the compound of Formula (I) has formula:

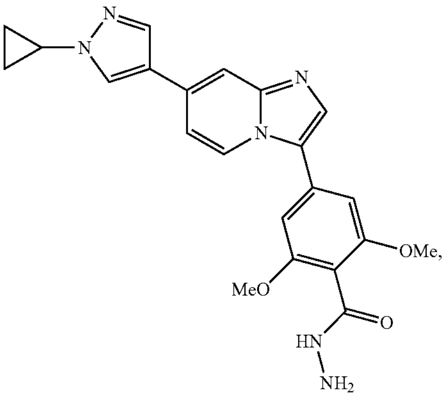 [SMILES: COc1cc(-c2cnc3cc(-c4cnn(C5CC5)c4)ccn23)cc(OC)c1C(=O)NN]

or a pharmaceutically acceptable salt thereof.

The present application further provides pharmaceutical compositions, comprising a compound provided herein, or a pharmaceutically acceptable salt thereof, and a pharmaceutically acceptable carrier.

The present application further provides methods of inhibiting an activity of a salt inducible kinase (SIK), comprising contacting the kinase with a compound provided herein, or a pharmaceutically acceptable salt thereof.

In some embodiments, the compound provided herein is a selective inhibitor of salt inducible kinase 2 (SIK2) and salt inducible kinase 3 (SIK3), over one salt inducible kinase 1 (SIK1).

The present application further provides methods of treating a disease in a patient, wherein the disease is associated with abnormal expression or activity of a salt inducible kinase, comprising administering to the patient a therapeutically effective amount of a compound provided herein, or a pharmaceutically acceptable salt thereof.

In some embodiments, the salt inducible kinase is one or more of salt inducible kinase 2 (SIK2) and salt inducible kinase 3 (SIK3).

In some embodiments, the disease is selected from cancer, inflammatory bowel disease, diabetes, a skin pigmentation disease, osteoporosis, and a musculoskeletal disease.

In some embodiments, the disease is cancer. In some embodiments, the cancer is selected from ovarian cancer, breast cancer, acute myeloid leukemia, and multiple myeloma.

In some embodiments, the disease is inflammatory bowel disease.

In some embodiments, the disease is diabetes.

In some embodiments, the disease is a skin pigmentation disease.

In some embodiments, the disease is osteoporosis.

In some embodiments, the disease is osteoarthritis.

In some embodiments, the disease is a musculoskeletal disease.

In some embodiments, the disease is inflammatory arthritide. In some embodiments, the inflammatory arthritide is rheumatoid arthritis.

In some embodiments, the treating comprises one or more of increasing bone formation, increasing bone anabolism, and increasing bone mass in the patient.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DETAILED DESCRIPTION

Figure 1A:
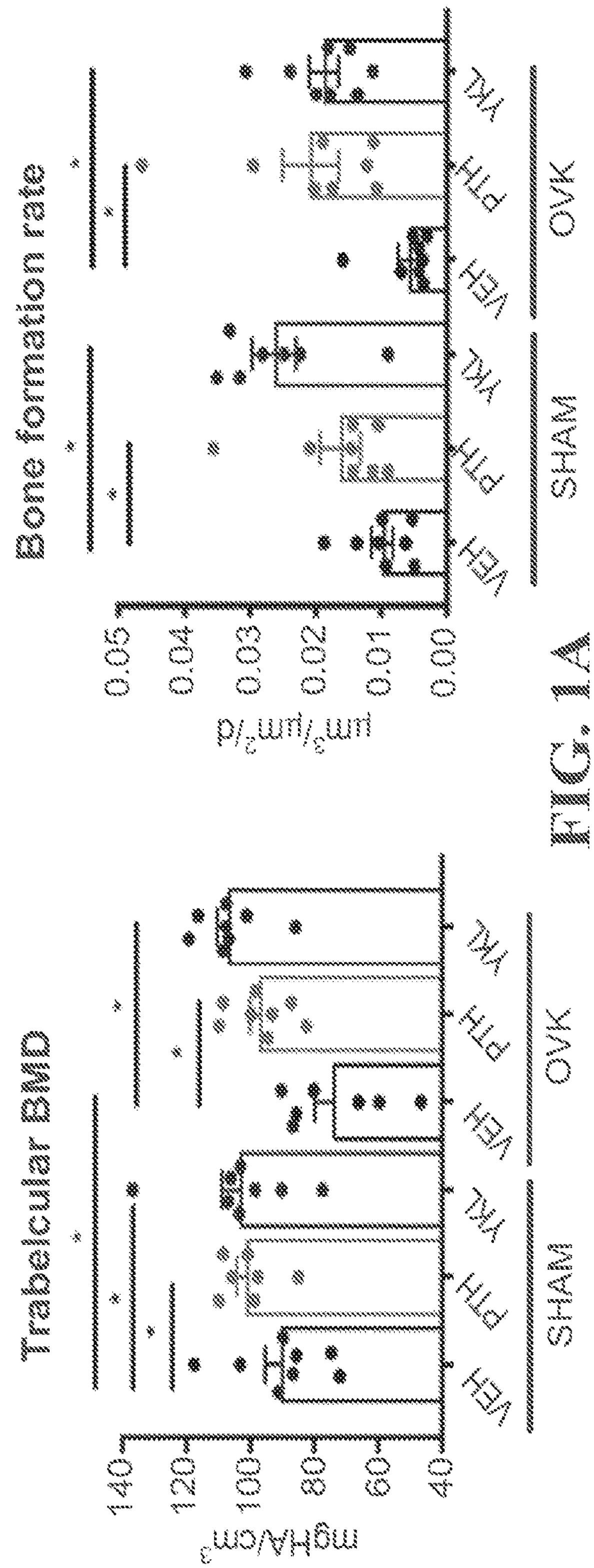
FIG. 1A shows that PTH and SIKi treatment increase bone density and bone formation rate. 12 week old female C57B6 mice were subjected to sham or ovariectomy (OVX) surgery. 5 weeks later, mice were treated with vehicle, PTH (100 mcg/d), or YKL-05-099 (18 mg/kg) once daily for 4 weeks.
Figure 1B:
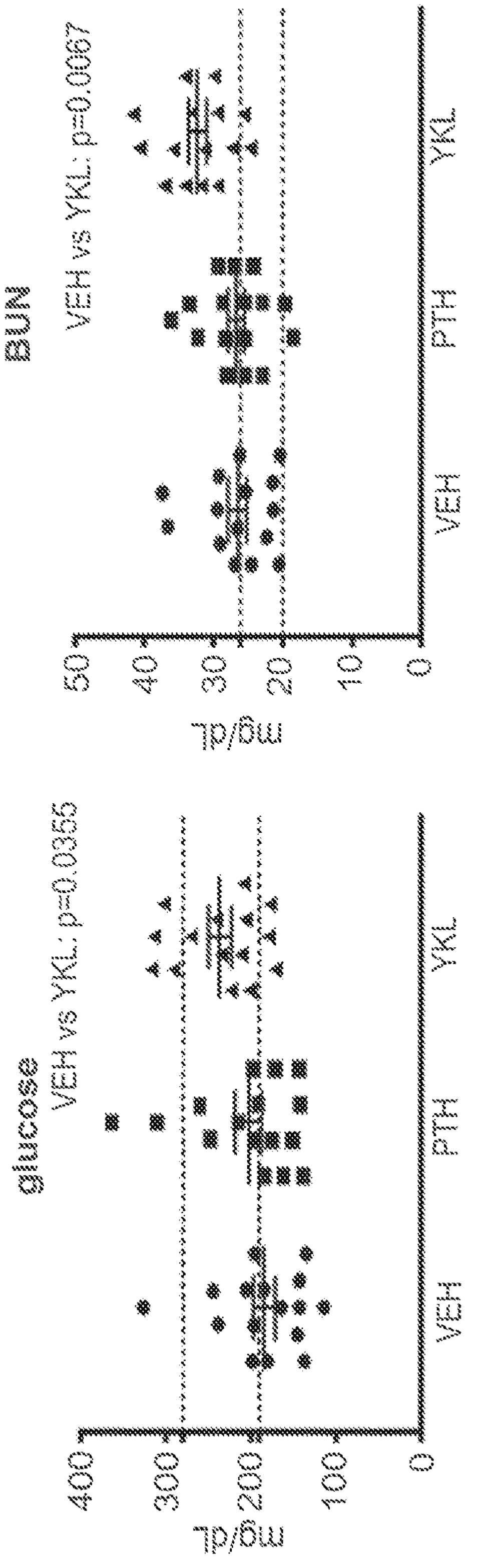
FIG. 1B shows that fasting glucose and BUN levels were increased in response to 4 weeks of YKL-05-099 treatment in mice. 12 week old female C57B6 mice were subjected to sham or ovariectomy (OVX) surgery. 5 weeks later, mice were treated with vehicle, PTH (100 mcg/d), or YKL-05-099 (18 mg/kg) once daily for 4 weeks.
Figure 2A:
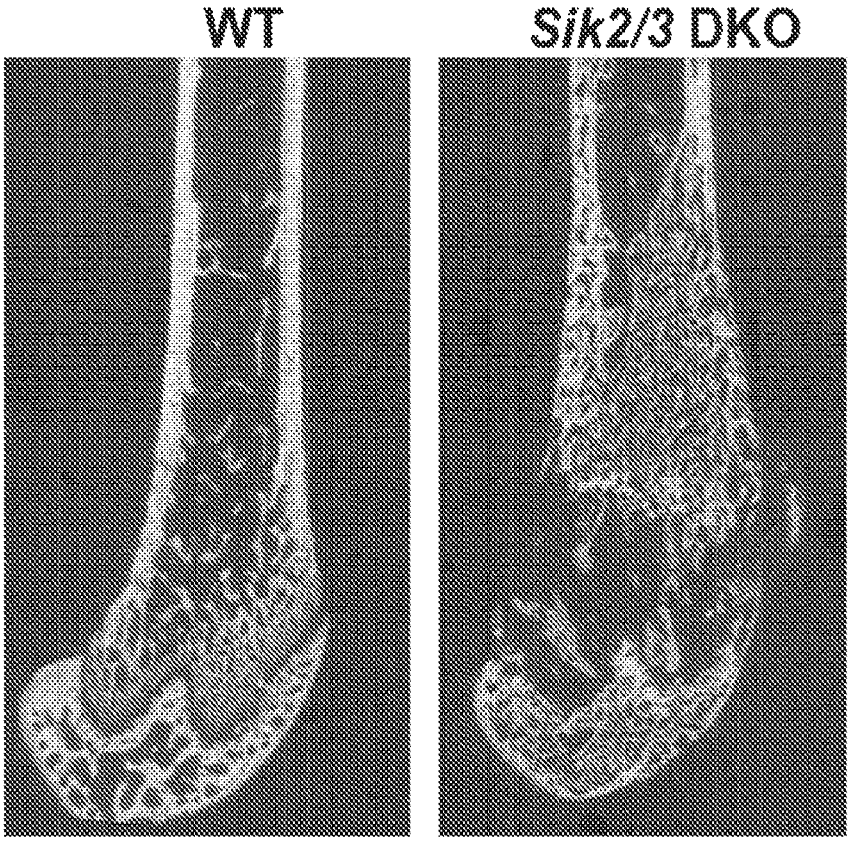
FIG. 2A shows femur micro-CT showing increased bone mass following global/inducible SIK2/3 deletion. SIK2/3 floxed mice were crossed to ubiquitin-Cre$^{ERt2}$ animals. 6 week old mice were treated with tamoxifen and then analyzed 3 weeks later. Controls (SIK2/3 floxed but negative for ubiquitin-Cre$^{ERt2}$ transgene) were also treated with tamoxifen.
Figure 2B:
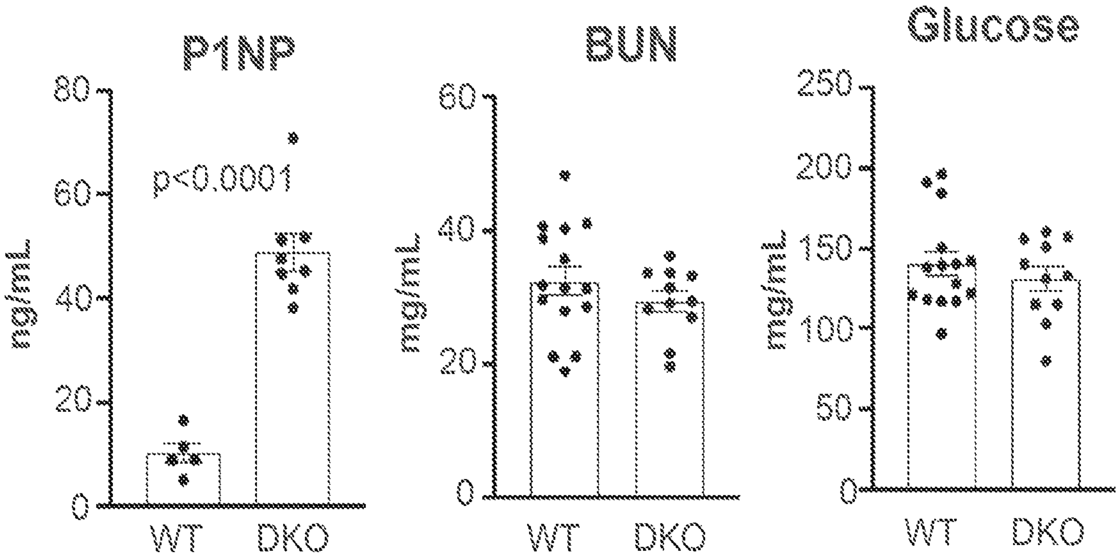
FIG. 2B shows serum markers showing increased bone formation (P1NP) but unchanged BUN and glucose in SIK2/3 mutants. SIK2/3 floxed mice were crossed to ubiquitin-Cre$^{ERt2}$ animals. 6 week old mice were treated with tamoxifen and then analyzed 3 weeks later. Controls (SIK2/3 floxed but negative for ubiquitin-Cre$^{ERt2}$ transgene) were also treated with tamoxifen.

Recent reports have described the signaling pathway used by PTH in target cells in bone (see e.g., Wein et al, *Nature Communications,* 2016, 7:13176; Wein et al, *Trends Endocrinol Metab.* 2018; and Nishimori et al, *J. Clin. Invest.* 2019). One step in this cascade is that PTH signaling leads to PKA-dependent inhibition of salt inducible kinases (SIKs). Small molecule SIK inhibitors, such as YKL-05-099 (see e.g., Sundberg et al, *ACS chemical biology,* 2016; and Tarumoto et al, *Blood,* 2019), a tool compound that inhibits all 3 SIK isoforms, mimic the actions of PTH (see e.g., Wein et al, *Nature Communications,* 2016, 7:13176). The efficacy of YKL-05-099 has been tested in mice rendered hypogonadal by surgical removal of the ovaries, a model of post-menopausal osteoporosis. Compared with once daily PTH injections, YKL-05-099 showed comparable/superior efficacy with respect to boosting bone formation and bone mass, as shown in FIG. 1A. However, hyper-glycemia and impaired renal function was observed in mice treated with this non-specific tool SIK inhibitor, as shown in FIG. 1B. The mouse genetics suggested that specific SIK2/3 inhibitors may be sufficient to boost bone formation and bone mass (see e.g., Nishimori et al, *J. Clin. Invest.* 2019). Therefore, mice were generated where SIK2/3 can be deleted ubiquitously in a tamoxifen-dependent manner to assess the safety and skeletal efficacy of selective SIK2/3 deletion in adult animals. It was found that inducible SIK2/3 deletion led to increased bone anabolism without effects on blood glucose or BUN, as shown in FIG. 2.

Figure 3:
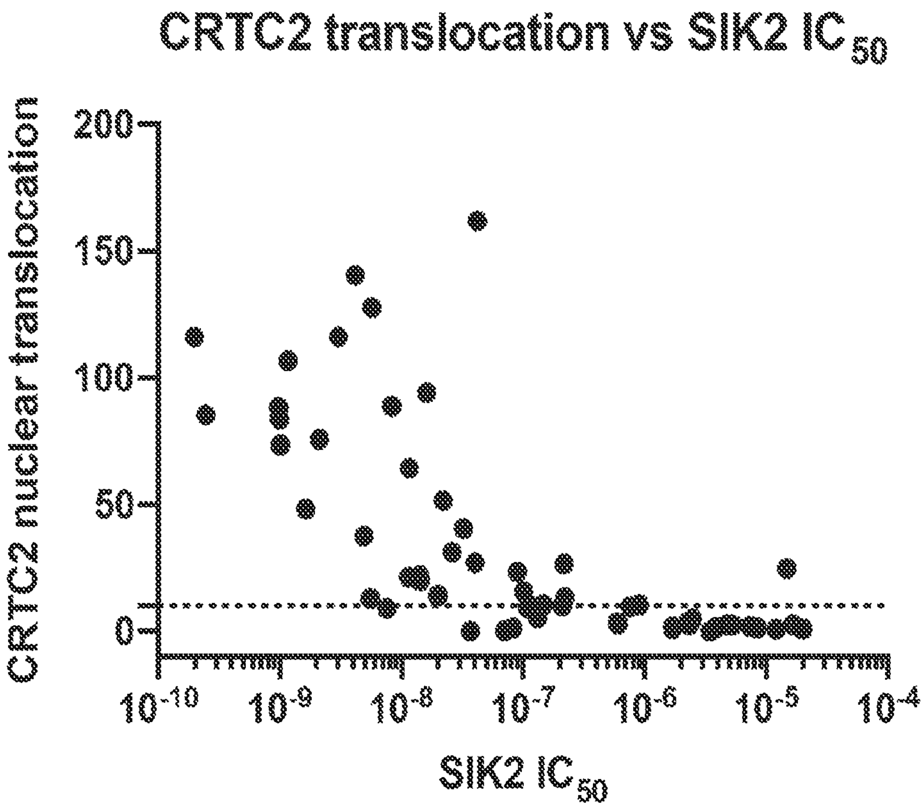
FIG. 3 shows the relationship between SIK2 inhibition in vitro and cellular activity across 80 representative compounds. CRTC2 is a SIK2/3 substrate that translocates to the nucleus upon de-phosphorylation. A relationship was observed in which potent SIK2 inhibitors also stimulated CRTC2 translocation in cells.

The present application provides new SIK2/3 inhibitors with improved potency, selectivity, and drug-like properties. The compounds have been tested for SIK inhibition, stimulation of CRTC2 nuclear translocation, and regulation of osteoblast gene expression and differentiation, as shown in FIG. 3. Selected compounds with cellular efficacy that inhibit SIK2/3 to a greater extent than SIK1 have been tested for kinome selectivity, microsome stability, CYP isoform inhibition, kinetic solubility, plasma protein binding, Caco2 efflux, and single dose mouse PK, with largely favorable results observed (e.g., sub-nM potency against SIK2/3, and favorable kinome selectivity).

In addition to osteoporosis, SIK inhibitors have been studied as research tools and potential therapeutic agents for cancer (see e.g., Miranda et al, *Cancer Cell,* 2016, 30(2): 273-289; Zhou et al, *Clinical Cancer Research: An Official Journal of the American Association for Cancer Research,* 2016; Tarumoto et al, *Molecular Cell,* 2018, 69(6):1017-1027 e6; and Maxfield et al, *Mol. Cell Biol.* 2016, 36(24): 3048-3057), inflammatory bowel disease (see e.g., Sundberg et al, *ACS chemical biology,* 2016), diabetes (see e.g., Sakamoto et al, *Trends Endocrinol. Metab.* 2018, 29(12): 827-840), and skin pigmentation (see e.g., Mujahid et al, *Cell Reports,* 2017, 19(11):2177-2184). Accordingly, the compounds provided herein may be useful in the treatment of said indications and other indications associated with one or more SIKs (e.g., SIK2 and/or SIK3).

Compounds

The present application provides compounds of Formula I:

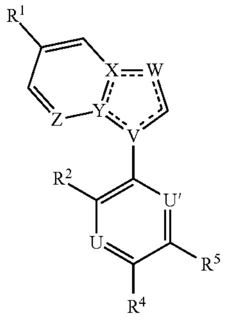

I or a pharmaceutically acceptable salt thereof, wherein:

V, W, X, Y, and Z are each independently C or N;

wherein at least two of V, W, X, Y, and Z are N, and the ring comprising V, W, X, Y, and Z forms a heteroaryl ring;

U is $CR^3$ or N;

U' is $CR^5$ or N;

U" is $CR^6$ or N;

$R^1$ is selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $OR^{a1}$, $C(O)R^{b1}$, $C(O)NR^{c1}R^{d1}$, $NR^{c1}C(O)R^{b1}$, $C(O)OR^{a1}$, $OC(O)R^{b1}$, $OC(O)NR^{c1}R^{d1}$, and $NR^{c1}C(O)OR^{a1}$, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- are each optionally substituted with 1, 2, 3, or 4 independently selected $R^{1A}$ substituents;

$R^{a1}$, $R^{b1}$, $R^{c1}$, and $R^{d1}$ are each independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 4-10 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, and (5-10 membered heteroaryl)-$C_{1-6}$ alkyl, wherein the $C_{1-6}$ alkyl, $C_{2-6}$ alkenyl, $C_{2-6}$ alkynyl, $C_{6-10}$ aryl, $C_{3-10}$ cycloalkyl, 4-10 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, and (5-10 membered heteroaryl)-$C_{1-6}$ alkyl are each optionally substituted with 1, 2, 3, or 4 independently selected $R^{1A}$ substituents;

or $R^{c1}$ and $R^{d1}$, together with the nitrogen to which they are attached, come together to form a 10-14 membered heterocycloalkyl or 10-14 membered heteroaryl group, wherein the 10-14 membered heterocycloalkyl and 10-14 membered heteroaryl group are each optionally substituted with 1, 2, 3, or 4 independently selected $R^{1A}$ substituents;

each $R^{1A}$ is independently selected from halo, $C_{1-6}$ alkyl, $C_{2-6}$ alkenyl, $C_{2-6}$ alkynyl, $C_{1-6}$ haloalkyl, $C_{1-6}$ alkoxy, $C_{6-10}$ aryl, $C_{3-10}$ cycloalkyl, 4-10 membered heterocycloalkyl, 5-10 membered heteroaryl, $NO_2$, CN, wherein the $C_{1-6}$ alkyl, $C_{2-6}$ alkenyl, and $C_{2-6}$ alkynyl are each optionally substituted with $C_{1-4}$ alkoxy;

$R^2$ is selected from H, halo, $C_{1-6}$ alkyl, $C_{2-6}$ alkenyl, $C_{2-6}$ alkynyl, $C_{1-6}$ haloalkyl, and $C_{1-6}$ alkoxy;

$R^3$ is selected from H, halo, $C_{1-6}$ alkyl, $C_{2-6}$ alkenyl, $C_{2-6}$ alkynyl, $C_{1-6}$ haloalkyl, and $C_{1-6}$ alkoxy;

$R^4$ is selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 4-10 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, (5-10 membered heteroaryl)-$C_{1-6}$ alkyl, $NO_2$, CN, $OR^{a4}$, $C(O)R^{b4}$, $C(O)NR^{c4}R^{d4}$, $NR^{c4}C(O)R^{b4}$, $C(O)OR^{a4}$, $OC(O)R^{b4}$, $OC(O)NR^{c4}R^{d4}$, and $NR^{c4}C(O)OR^{a4}$, wherein the $C_{6-10}$ aryl, $C_{3-10}$ cycloalkyl, 4-10 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, and (5-10 membered heteroaryl)-$C_{1-6}$ alkyl are each optionally substituted with 1, 2, 3, or 4 independently selected $R^{4A}$ substituents;

$R^{a4}$, $R^{b4}$, $R^{c4}$, and $R^{d4}$ are each independently selected from H, $C_{1-6}$ alkyl, $C_{2-6}$ alkenyl, $C_{2-6}$ alkynyl, $C_{1-6}$ haloalkyl, and $C_{1-6}$ alkoxy;

each $R^{4A}$ is independently selected from $C_{1-6}$ alkyl, $C_{2-6}$ alkenyl, $C_{2-6}$ alkynyl, $C_{1-6}$ haloalkyl, and $C_{1-6}$ alkoxy;

$R^5$ is selected from H, halo, $C_{1-6}$ alkyl, $C_{2-6}$ alkenyl, $C_{2-6}$ alkynyl, $C_{1-6}$ haloalkyl, and $C_{1-6}$ alkoxy;

or $R^4$ and $R^5$, together with the carbon atoms to which they are attached, come together to form a 5-6 membered aryl ring which is optionally substituted with 1, 2, 3, or 4 independently selected $R^7$ substituents;

$R^6$ is selected from H, $C_{1-6}$ alkyl, $C_{2-6}$ alkenyl, $C_{2-6}$ alkynyl, $C_{1-6}$ haloalkyl, and $C_{1-6}$ alkoxy;

each $R^7$ is independently selected from $C_{6-10}$ aryl, $C_{3-10}$ cycloalkyl, 4-14 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, (5-10 membered heteroaryl)-$C_{1-6}$ alkyl, $NO_2$, CN, and $OR^{a7}$, wherein the $C_{6-10}$ aryl, $C_{3-10}$ cycloalkyl, 4-14 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, (5-10 membered heteroaryl)-$C_{1-6}$ alkyl are each optionally substituted with 1, 2, 3, or 4 independently selected $R^{7A}$ substituents;

each $R^{a7}$ is independently selected from $C_{6-10}$ aryl, $C_{3-10}$ cycloalkyl, 4-10 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, and (5-10 membered heteroaryl)-$C_{1-6}$ alkyl; and each $R^{7A}$ is independently selected from $C_{1-6}$ alkyl, $C_{2-6}$ alkenyl, $C_{2-6}$ alkynyl, $C_{1-6}$ haloalkyl, $C_{1-6}$ alkoxy, amino, $C_{1-6}$ alkylamino, di($C_{1-6}$ alkyl)amino, phenyl, $C_{3-6}$ cycloalkyl, 4-6 membered heterocycloalkyl, 5-6 membered heteroaryl, and wherein the $C_{1-6}$ alkyl, $C_{2-6}$ alkenyl, and $C_{2-6}$ alkynyl are each optionally substituted with amino or $C_{1-4}$ alkoxy.

In some embodiments, two of V, W, X, Y, and Z are N.

In some embodiments, three of V, W, X, Y, and Z are N.

In some embodiments, four of V, W, X, Y, and Z are N.

In some embodiments, V, X, and Z are each C, and W and Y are each N.

In some embodiments, X, Y, and Z are each C, and V and W are each N.

In some embodiments, V, Y, and Z are each C, and W and X are each N.

In some embodiments, V and Y are each C, and W, X, and Z are each N.

In some embodiments, $R^1$ is selected from phenyl, $C_{3-6}$ cycloalkyl, 5-6 membered heteroaryl, 4-6 membered heterocycloalkyl, $OR^{a1}$, $C(O)NR^{c1}R^{d1}$, and $NR^{c1}C(O)R^{b}$, $C(O)OR^{a1}$, $OC(O)R^{b1}$, $OC(O)NR^{c1}R^{d1}$, and $NR^{c1}C(O)OR^{a1}$, wherein the phenyl, $C_{3-6}$ cycloalkyl, 5-10 membered heteroaryl, and 4-6 membered heterocycloalkyl, are each optionally substituted with 1, 2, 3, or 4 independently selected $R^{1A}$ substituents.

In some embodiments, $R^1$ is selected from 5-10 membered heteroaryl, $OR^{a1}$, $C(O)NR^{c1}R^{d1}$, and $NR^{c1}C(O)R^{b1}$, wherein the 5-10 membered heteroaryl is optionally substituted with 1, 2, 3, or 4 independently selected $R^{1A}$ substituents.

In some embodiments, $R^1$ is selected from 5-6 membered heteroaryl, $OR^{a1}$, $C(O)NR^{c1}R^{d1}$, and $NR^{c1}C(O)R^{b1}$, wherein the 5-6 membered heteroaryl is optionally substituted with 1, 2, 3, or 4 independently selected $R^{1A}$ substituents.

In some embodiments, $R^1$ is selected from 5-6 membered heteroaryl, $OR^{a1}$, $C(O)NR^{c1}R^{d1}$, and $NR^{c1}C(O)R^{b1}$, wherein the 5-6 membered heteroaryl is optionally substituted with 1 or 2 independently selected $R^{1A}$ substituents.

In some embodiments, $R^{a1}$, $R^{b1}$, $R^{c1}$, and $R^{d1}$ are each independently selected from H, 4-10 membered heterocycloalkyl, (4-10 membered heterocycloalkyl)-$C_{1-6}$ alkyl, and (5-10 membered heteroaryl)-$C_{1-6}$ alkyl, wherein the 4-10 membered heterocycloalkyl, (4-10 membered heterocycloalkyl)-$C_{1-6}$ alkyl, and (5-10 membered heteroaryl)-$C_{1-6}$ alkyl are each optionally substituted with 1 or 2 independently selected $R^{1A}$ substituents;

or $R^{c1}$ and $R^{d1}$, together with the nitrogen to which they are attached, come together to form a 10-14 membered heterocycloalkyl or 10-14 membered heteroaryl group.

In some embodiments, $R^{a1}$, $R^{b1}$, $R^{c1}$, and $R^{d1}$ are each independently selected from H, 4-10 membered heterocycloalkyl, (4-10 membered heterocycloalkyl)-$C_{1-6}$ alkyl, and (5-10 membered heteroaryl)-$C_{1-6}$ alkyl, wherein the 4-10 membered heterocycloalkyl, (4-10 membered heterocycloalkyl)-$C_{1-6}$ alkyl, and (5-10 membered heteroaryl)-$C_{1-6}$ alkyl are each optionally substituted with 1, 2, 3, or 4 independently selected $R^{1A}$ substituents.

In some embodiments, $R^{a1}$, $R^{b1}$, $R^{c1}$, and $R^{d1}$ are each independently selected from H, 4-10 membered heterocycloalkyl, (4-10 membered heterocycloalkyl)-$C_{1-6}$ alkyl, and (5-10 membered heteroaryl)-$C_{1-6}$ alkyl, wherein the 4-10 membered heterocycloalkyl, (4-10 membered heterocycloalkyl)-$C_{1-6}$ alkyl, and (5-10 membered heteroaryl)-$C_{1-6}$ alkyl are each optionally substituted with 1 or 2 independently selected RA substituents.

In some embodiments, $R^{c1}$ and $R^{d1}$ together with the nitrogen to which they are attached, come together to form a 10-14 membered heterocycloalkyl or 10-14 membered heteroaryl group.

In some embodiments, $R^{c1}$ and $R^{d1}$ together with the nitrogen to which they are attached, come together to form a 10-14 membered heterocycloalkyl group.

In some embodiments, $R^{c1}$ and $R^{d1}$ together with the nitrogen to which they are attached, come together to form a 10-14 membered heteroaryl group.

In some embodiments, $R^{a1}$, $R^{b1}$, $R^{c1}$, and $R^{d1}$ are each independently selected from H, methyl, pyrazolyl, pyridinylmethyl, pyridinylethyl, imidazo[1,2-a]pyridinylmethyl, benzoimidazolylmethyl, imidazo[4,5-c]pyridinylmethyl, benzoxazolylmethyl, oxetanylmethyl, oxetanylethyl, thietanyl-(1,1-dioxide)methyl, 2-oxaspiro[3.3]heptanyl, and 2-oxaspiro[3.5]nonanyl, wherein the methyl, pyrazolyl, pyridinylmethyl, pyridinylethyl, imidazo[1,2-a]pyridinylmethyl, benzoimidazolylmethyl, imidazo[4,5-c]pyridinylmethyl, benzoxazolylmethyl, oxetanylmethyl, oxetanylethyl, thietanyl-(1,1-dioxide)methyl, 2-oxaspiro[3.3]heptanyl, and 2-oxaspiro[3.5]nonanyl are each optionally substituted with 1 or 2 independently selected $R^{1A}$ substituents;

or $R^{c1}$ and $R^{d1}$, together with the nitrogen to which they are attached, come together to form 1,2,3,4-tetrahydrobenzo[4,5]imidazo[1,2-a]pyrazinyl.

In some embodiments, each $R^{1A}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, and CN, wherein the $C_{1-6}$ alkyl, $C_{2-6}$ alkenyl, and $C_{2-6}$ alkynyl are each optionally substituted with $C_{1-4}$ alkoxy.

In some embodiments, each $R^{1A}$ is independently selected from $C_{1-6}$ alkyl, $C_{1-6}$ haloalkyl, $C_{3-10}$ cycloalkyl, 4-10 membered heterocycloalkyl and CN, wherein the $C_{1-6}$ alkyl is optionally substituted with $C_{1-4}$ alkoxy.

In some embodiments, each $R^{1A}$ is independently selected from $C_{1-6}$ alkyl, $C_{1-6}$ haloalkyl, $C_{3-6}$ cycloalkyl, 4-6 membered heterocycloalkyl, and CN, wherein the $C_{1-6}$ alkyl is optionally substituted with $C_{1-4}$ alkoxy.

In some embodiments, each RA is independently selected from $C_{1-6}$ alkyl and CN, wherein each $C_{1-6}$ alkyl is optionally substituted with $C_{1-4}$ alkoxy.

In some embodiments, each $R^{1A}$ is independently selected from $C_{1-4}$ alkyl, $C_{3-6}$ cycloalkyl, 4-6 membered heterocycloalkyl, and CN, wherein each $C_{1-4}$ alkyl is optionally substituted with methoxy.

In some embodiments, each $R^{1A}$ is independently selected from $C_{1-4}$ alkyl and CN, wherein each $C_{1-4}$ alkyl is optionally substituted with methoxy.

In some embodiments, each $R^{1A}$ is independently selected from methyl, ethyl, methoxymethyl, cyclopropyl, oxetanyl, and CN.

In some embodiments, $R^2$ is selected from H, $C_{1-6}$ alkyl, $C_{1-6}$ haloalkyl, and $C_{1-6}$ alkoxy.

In some embodiments, $R^2$ is selected from H, $C_{1-6}$ alkyl, and $C_{1-6}$ alkoxy.

In some embodiments, $R^2$ is selected from H and $C_{1-6}$ alkoxy.

In some embodiments, $R^2$ is selected from H and $C_{1-4}$ alkoxy.

In some embodiments, $R^2$ is selected from H and methoxy.

In some embodiments, $R^2$ is H.

In some embodiments, $R^2$ is methoxy.

In some embodiments, U is $CR^3$.

In some embodiments, $R^3$ is selected from H, halo, $C_{1-6}$ alkyl, $C_{1-6}$ haloalkyl, and $C_{1-6}$ alkoxy.

In some embodiments, $R^3$ is selected from H, halo, $C_{1-6}$ alkyl, and $C_{1-6}$ alkoxy.

In some embodiments, $R^3$ is selected from H, halo, and $C_{1-6}$ alkoxy.

In some embodiments, $R^3$ is selected from H, halo, and $C_{1-4}$ alkoxy.

In some embodiments, $R^3$ is selected from H, fluoro, chloro, and methoxy.

In some embodiments, $R^3$ is H.

In some embodiments, $R^3$ fluoro.

In some embodiments, $R^3$ is chloro.

In some embodiments, $R^3$ is methoxy.

In some embodiments, U is N.

In some embodiments, U" is $CR^6$.

In some embodiments, $R^6$ is selected from H, $C_{1-6}$ alkyl, and $C_{1-6}$ alkoxy.

In some embodiments, $R^6$ is selected from H and $C_{1-6}$ alkoxy.

In some embodiments, $R^6$ is selected from H and $C_{1-4}$ alkoxy.

In some embodiments, $R^6$ is selected from H and methoxy.

In some embodiments, $R^6$ is H.

In some embodiments, U" is N.

In some embodiments, U is $CR^3$ and U" is $CR^6$.

In some embodiments, U is N and U" is $CR^6$.

In some embodiments, U is $CR^3$ and U" is N.

In some embodiments, U is N and U" is N.

In some embodiments, $R^4$ is selected from H, $C_{6-10}$ aryl, $C_{3-10}$ cycloalkyl, 4-10 membered heterocycloalkyl, 5-10 membered heteroaryl, CN, $OR^{a4}$, $C(O)R^{b4}$, $C(O)NR^{c4}R^{d4}$, $NR^{c4}C(O)R^{b4}$, $C(O)OR^{a4}$, $OC(O)R^{b4}$, $OC(O)NR^{c4}R^{d4}$, and $NR^{c4}C(O)OR^{a4}$, wherein the $C_{6-10}$ aryl, $C_{3-10}$ cycloalkyl, 4-10 membered heterocycloalkyl, and 5-10 membered heteroaryl are each optionally substituted with 1, 2, 3, or 4 independently selected $R^{4A}$ substituents.

In some embodiments, $R^4$ is selected from H, phenyl, $C_{3-6}$ cycloalkyl, 4-6 membered heterocycloalkyl, 5-6 membered heteroaryl, CN, and $C(O)NR^{c4}R^{d4}$, wherein the phenyl, $C_{3-6}$ cycloalkyl, 4-6 membered heterocycloalkyl, and 5-6 membered heteroaryl are each optionally substituted with 1 or 2 independently selected $R^{4A}$ substituents.

In some embodiments, $R^4$ is selected from H, 5-10 membered heteroaryl, CN, and $C(O)NR^{c4}R^{d4}$, wherein the 5-10 membered heteroaryl is optionally substituted with 1, 2, 3, or 4 independently selected $R^{4A}$ substituents.

In some embodiments, $R^4$ is selected from H, 5-6 membered heteroaryl, CN, and $C(O)NR^{c4}R^{d4}$, wherein the 5-6 membered heteroaryl is optionally substituted with 1, 2, 3, or 4 independently selected $R^{4A}$ substituents.

In some embodiments, $R^4$ is selected from H, 5-6 membered heteroaryl, CN, $C(O)NR^{c4}R^{d4}$, and $C(O)N(R^4)NR^{c4}R^{d4}$, wherein the 5-6 membered heteroaryl is optionally substituted with 1 or 2 independently selected $R^{4A}$ substituents.

In some embodiments, $R^4$ is selected from H, 5-6 membered heteroaryl, CN, and $C(O)NR^{c4}R^{d4}$, wherein the 5-6 membered heteroaryl is optionally substituted with 1 or 2 independently selected $R^{4A}$ substituents.

In some embodiments, $R^4$ is $C(O)N(R^4)NR^{c4}R^{d4}$.

In some embodiments, $R^{a4}$, $R^{b4}$, $R^{c4}$, and $R^{d4}$ are each independently selected from H, $C_{1-6}$ alkyl, and $C_{1-6}$ haloalkyl.

In some embodiments, $R^{c4}$ and $R^{d4}$ are each independently selected from H, $C_{1-6}$ alkyl, and $C_{1-6}$ haloalkyl.

In some embodiments, $R^{a4}$, $R^{b4}$, $R^{c4}$, and $R^{d4}$ are each independently selected from H, $C_{1-4}$ alkyl, and $C_{1-4}$ haloalkyl.

In some embodiments, $R^{c4}$ and $R^{d4}$ are each independently selected from H, $C_{1-4}$ alkyl, and $C_{1-4}$ haloalkyl.

In some embodiments, $R^{a4}$, $R^{b4}$, $R^{c4}$, and $R^{d4}$ are each independently selected from H, ethyl, and trifluoroethyl.

In some embodiments, $R^{c4}$ and $R^{d4}$ are each independently selected from H, ethyl, and trifluoroethyl.

In some embodiments, $R^4$ is selected from H, CN, oxadiazolyl, and $C(O)NR^{c4}R^{d4}$, wherein the oxadiazolyl is optionally substituted with 1, 2, 3, or 4 independently selected $R^{4A}$ substituents; and $R^{c4}$ and $R^{d4}$ are each independently selected from H, $C_{1-4}$ alkyl, and $C_{1-4}$ haloalkyl.

In some embodiments, $R^4$ is selected from H, CN, oxadiazolyl, and $C(O)NR^{c4}R^{d4}$, wherein the oxadiazolyl is optionally substituted with 1 or 2 independently selected $R^{4A}$ substituents; and $R^{c4}$ and $R^{d4}$ are each independently selected from H, $C_{1-4}$ alkyl, and $C_{1-4}$ haloalkyl.

In some embodiments, $R^4$ is selected from H, CN, oxadiazolyl, and $C(O)NHCH_2CF_3$, wherein the oxadiazolyl is optionally substituted with 1, 2, 3, or 4 independently selected $R^{4A}$ substituents.

In some embodiments, $R^4$ is selected from H, CN, oxadiazolyl, and $C(O)NHCH_2CF_3$, wherein the oxadiazolyl is optionally substituted with 1 or 2 independently selected $R^{4A}$ substituents.

In some embodiments, each $R^{4A}$ is independently selected from $C_{1-6}$ alkyl, $C_{1-6}$ haloalkyl, and $C_{1-6}$ alkoxy.

In some embodiments, each $R^{4A}$ is independently selected from $C_{1-6}$ alkyl and $C_{1-6}$ haloalkyl.

In some embodiments, each $R^{4A}$ is independently selected from $C_{1-4}$ alkyl and $C_{1-4}$ haloalkyl.

In some embodiments, each $R^{4A}$ is an independently selected $C_{1-6}$ alkyl group.

In some embodiments, each $R^{4A}$ is an independently selected $C_{1-6}$ haloalkyl group.

In some embodiments, each $R^{4A}$ is an independently selected $C_{1-4}$ alkyl group.

In some embodiments, each $R^{4A}$ is an independently selected $C_{1-4}$ haloalkyl group.

In some embodiments, each $R^{4A}$ is ethyl.

In some embodiments, U' is N.

In some embodiments, U' is $CR^5$.

In some embodiments, one of U, U', and U" is N.

In some embodiments, two of U, U', and U" are N.

In some embodiments, $R^5$ is selected from H, halo, $C_{1-6}$ alkyl, $C_{1-6}$ haloalkyl, and $C_{1-6}$ alkoxy.

In some embodiments, $R^5$ is selected from H, halo, $C_{1-6}$ alkyl, and $C_{1-6}$ alkoxy.

In some embodiments, $R^5$ is selected from H, halo, and $C_{1-6}$ alkoxy.

In some embodiments, $R^5$ is selected from H, halo, $C_{1-4}$ alkyl, and $C_{1-4}$ alkoxy.

In some embodiments, $R^5$ is selected from H, halo, and $C_{1-4}$ alkoxy.

In some embodiments, $R^5$ is selected from H, fluoro, chloro, and methoxy.

In some embodiments, $R^5$ is H.

In some embodiments, $R^5$ is fluoro.

In some embodiments, $R^5$ is chloro.

In some embodiments, $R^5$ is methoxy.

In some embodiments, $R^3$ and $R^5$ are each an independently selected halo.

In some embodiments, $R^3$ and $R^5$ are each fluoro. In some embodiments, $R^3$ and $R^5$ are each chloro.

In some embodiments, $R^3$ and $R^5$ are each an independently selected $C_{1-6}$ alkoxy.

In some embodiments, $R^3$ and $R^5$ are each methoxy.

In some embodiments, $R^4$ and $R^5$ together with the carbon atoms to which they are attached, come together to form a 5-6 membered aryl ring which is optionally substituted with 1, 2, 3, or 4 independently selected $R^7$ substituents.

In some embodiments, $R^4$ and $R^5$ together with the carbon atoms to which they are attached, come together to form a 5-6 membered aryl ring which is optionally substituted with 1 or 2 independently selected $R^7$ substituents.

In some embodiments, $R^4$ and $R^5$ together with the carbon atoms to which they are attached, come together to form a 5-membered aryl ring which is optionally substituted with 1 or 2 independently selected $R^7$ substituents.

In some embodiments, $R^4$ and $R^5$ together with the carbon atoms to which they are attached, come together to form a 6-membered aryl ring which is optionally substituted with 1 or 2 independently selected $R^7$ substituents.

In some embodiments, each $R^7$ is independently selected from phenyl, $C_{3-10}$ cycloalkyl, 4-14 membered heterocycloalkyl, 5-10 membered heteroaryl, phenyl-$C_{1-6}$ alkyl-, $C_{3-10}$ cycloalkyl-$C_{1-6}$ alkyl-, (4-10 membered heterocycloalkyl)-$C_{1-6}$ alkyl, (5-10 membered heteroaryl)-$C_{1-6}$ alkyl, and $OR^{a7}$, wherein the phenyl, $C_{3-10}$ cycloalkyl, 4-14 membered heterocycloalkyl, 5-10 membered heteroaryl, phenyl-$C_{1-6}$ alkyl-, $C_{3-10}$ cycloalkyl-$C_{1-6}$ alkyl-, (4-10 membered heterocycloalkyl)-$C_{1-6}$ alkyl, (5-10 membered heteroaryl)-$C_{1-6}$ alkyl are each optionally substituted with 1, 2, 3, or 4 independently selected $R^{7A}$ substituents.

In some embodiments, each $R^7$ is independently selected from phenyl, $C_{3-10}$ cycloalkyl, 4-14 membered heterocycloalkyl, 5-10 membered heteroaryl, phenyl-$C_{1-6}$ alkyl-, $C_{3-10}$ cycloalkyl-$C_{1-6}$ alkyl-, (4-10 membered heterocycloalkyl)-$C_{1-6}$ alkyl, (5-10 membered heteroaryl)-$C_{1-6}$ alkyl, and $OR^{a7}$, wherein the phenyl, $C_{3-10}$ cycloalkyl, 4-14 membered heterocycloalkyl, 5-10 membered heteroaryl, phenyl-$C_{1-6}$ alkyl-, $C_{3-10}$ cycloalkyl-$C_{1-6}$ alkyl-, (4-10 membered heterocycloalkyl)-$C_{1-6}$ alkyl, (5-10 membered heteroaryl)-$C_{1-6}$ alkyl are each optionally substituted with 1 or 2 independently selected $R^{7A}$ substituents.

In some embodiments, each $R^7$ is independently selected from $C_{3-10}$ cycloalkyl, 4-14 membered heterocycloalkyl, 5-10 membered heteroaryl, and $OR^{a7}$, wherein the $C_{3-10}$ cycloalkyl, 4-14 membered heterocycloalkyl, and 5-10 membered heteroaryl are each optionally substituted with 1, 2, 3, or 4 independently selected $R^{7A}$ substituents.

In some embodiments, each $R^7$ is independently selected from $C_{3-10}$ cycloalkyl, 4-14 membered heterocycloalkyl, 5-10 membered heteroaryl, and $OR^{a7}$, wherein the $C_{3-10}$ cycloalkyl, 4-14 membered heterocycloalkyl, and 5-10 membered heteroaryl are each optionally substituted with 1 or 2 independently selected $R^{7A}$ substituents.

In some embodiments, each $R^{a7}$ is independently selected from phenyl, $C_{3-6}$ cycloalkyl, 4-6 membered heterocycloalkyl, 5-6 membered heteroaryl, phenyl-$C_{1-6}$ alkyl-, $C_{3-6}$ cycloalkyl-$C_{1-6}$ alkyl-, (4-6 membered heterocycloalkyl)-$C_{1-6}$ alkyl, and (5-6 membered heteroaryl)-$C_{1-6}$ alkyl.

In some embodiments, each $R^{a7}$ is independently selected from 4-10 membered heterocycloalkyl and 5-10 membered heteroaryl.

In some embodiments, each $R^{a7}$ is independently selected from 4-6 membered heterocycloalkyl and 5-6 membered heteroaryl.

In some embodiments, each $R^{a7}$ is an independently selected 4-10 membered heterocycloalkyl group.

In some embodiments, each $R^{a7}$ is an independently selected 4-6 membered heterocycloalkyl group.

In some embodiments, each $R^{a7}$ is azetidinyl.

In some embodiments, each $R^7$ is independently selected from bicyclo[1.1.1]pentanyl, azetidinyl, pyrrolidinyl, piperidinyl, morpholinyl, imidazolyl, azaspiro[3.3]heptanyl, diazaspiro[3.5]nonanyl, oxadiazaspiro[5.5]undecanyl, diazaspiro[4.4]nonanyl, and azetidinyloxy, wherein the bicyclo[1.1.1]pentanyl, azetidinyl, pyrrolidinyl, piperidinyl, morpholinyl, imidazolyl, azaspiro[3.3]heptanyl, diazaspiro[3.5]nonanyl, oxadiazaspiro[5.5]undecanyl, and diazaspiro[4.4]nonanyl are each optionally substituted with 1, 2, 3, or 4 independently selected $R^{7A}$ substituents.

In some embodiments, each $R^7$ is independently selected from bicyclo[1.1.1]pentanyl, azetidinyl, pyrrolidinyl, piperidinyl, morpholinyl, imidazolyl, azaspiro[3.3]heptanyl, diazaspiro[3.5]nonanyl, oxadiazaspiro[5.5]undecanyl, diazaspiro[4.4]nonanyl, and azetidinyloxy, wherein the bicyclo[1.1.1]pentanyl, azetidinyl, pyrrolidinyl, piperidinyl, morpholinyl, imidazolyl, azaspiro[3.3]heptanyl, diazaspiro[3.5]nonanyl, oxadiazaspiro[5.5]undecanyl, and diazaspiro[4.4]nonanyl are each optionally substituted with 1 or 2 independently selected $R^{7A}$ substituents.

In some embodiments, each $R^{7A}$ is independently selected from $C_{1-6}$ alkyl, amino, $C_{1-6}$ alkylamino, di($C_{1-6}$ alkyl)amino, $C_{3-6}$ cyclopropyl, and 4-6 membered heterocycloalkyl, wherein each $C_{1-6}$ alkyl is optionally substituted with amino or $C_{1-4}$ alkoxy.

In some embodiments, each $R^{7A}$ is independently selected from $C_{1-6}$ alkyl, amino, $C_{3-6}$ cyclopropyl and 4-6 membered heterocycloalkyl, wherein each $C_{1-6}$ alkyl is optionally substituted with amino or $C_{1-4}$ alkoxy.

In some embodiments, each $R^{7A}$ is independently selected from $C_{1-6}$ alkyl, amino, $C_{3-6}$ cyclopropyl and 4-6 membered heterocycloalkyl, wherein each $C_{1-6}$ alkyl is optionally substituted with amino or methoxy.

In some embodiments, each $R^{7A}$ is independently selected from methyl, ethyl, amino, cyclopropyl, and oxetanyl, wherein each methyl and ethyl is optionally substituted with amino or methoxy.

In some embodiments, each $R^{7A}$ is independently selected from methyl, methoxyethyl, aminomethyl, amino, cyclopropyl, and oxetanyl.

In some embodiments:

V, X, and Z are each C, and W and Y are each N; or

X, Y, and Z are each C, and V and W are each N; or

V, Y, and Z are each C, and W and X are each N; or

V and Y are each C, and W, X, and Z are each N;

$R^1$ is selected from 5-10 membered heteroaryl, $OR^{a1}$, $C(O)NR^{c1}R^{d1}$, and $NR^{c1}C(O)R^{b1}$, wherein the 5-10 membered heteroaryl is optionally substituted with 1, 2, 3, or 4 independently selected $R^{1A}$ substituents;

$R^{a1}$, $R^{b1}$, $R^{c1}$, and $R^{d1}$ are each independently selected from H, 4-10 membered heterocycloalkyl, (4-10 membered heterocycloalkyl)-$C_{1-6}$ alkyl, and (5-10 membered heteroaryl)-$C_{1-6}$ alkyl, wherein the 4-10 membered heterocycloalkyl, (4-10 membered heterocycloalkyl)-$C_{1-6}$ alkyl, and (5-10 membered heteroaryl)-$C_{1-6}$ alkyl are each optionally substituted with 1 or 2 independently selected $R^{1A}$ substituents;

or $R^{c1}$ and $R^{d1}$, together with the nitrogen to which they are attached, come together to form a 10-14 membered heterocycloalkyl or 10-14 membered heteroaryl group;

each $R^{1A}$ is independently selected from $C_{1-6}$ alkyl, $C_{3-10}$ cycloalkyl, 4-10 membered heterocycloalkyl, and CN, wherein each $C_{1-6}$ alkyl is optionally substituted with $C_{1-4}$ alkoxy;

$R^2$ is H or $C_{1-6}$ alkoxy;

U is $CR^3$ or N;

U' is $CR^5$ or N;

U" is $CR^6$ or N;

$R^3$ is selected from H, halo, and $C_{1-6}$ alkoxy;

$R^4$ is selected from H, 5-10 membered heteroaryl, CN, and $C(O)NR^{c4}R^{d4}$, wherein the 5-10 membered heteroaryl is optionally substituted with 1, 2, 3, or 4 independently selected $R^{4A}$ substituents;

$R^{c4}$ and $R^{d4}$ are each independently selected from H, $C_{1-6}$ alkyl, and $C_{1-6}$ haloalkyl;

each $R^{4A}$ is an independently selected $C_{1-6}$ alkyl group;

$R^5$ is selected from H, halo, $C_{1-6}$ alkyl, and $C_{1-6}$ alkoxy;

or $R^4$ and $R^5$ together with the carbon atoms to which they are attached, come together to form a 5-6 membered aryl ring which is optionally substituted with 1, 2, 3, or 4 independently selected $R^7$ substituents;

$R^6$ is selected from H and $C_{1-6}$ alkoxy;

each $R^7$ is independently selected from $C_{3-10}$ cycloalkyl, 4-14 membered heterocycloalkyl, 5-10 membered heteroaryl, and $OR^{a7}$, wherein the $C_{3-10}$ cycloalkyl, 4-14 membered heterocycloalkyl, and 5-10 membered heteroaryl are each optionally substituted with 1 or 2 independently selected $R^{7A}$ substituents;

each $R^{a7}$ is an independently selected 4-10 membered heterocycloalkyl group; and each $R^{7A}$ is independently selected from $C_{1-6}$ alkyl, amino, $C_{3-6}$ cyclopropyl and 4-6 membered heterocycloalkyl, wherein each $C_{1-6}$ alkyl is optionally substituted with amino or $C_{1-4}$ alkoxy.

In some embodiments:

V, X, and Z are each C, and W and Y are each N; or

X, Y, and Z are each C, and V and W are each N; or

V, Y, and Z are each C, and W and X are each N; or

V and Y are each C, and W, X, and Z are each N;

$R^1$ is selected from 5-6 membered heteroaryl, $OR^{a1}$, $C(O)NR^{c1}R^{d1}$, and $NR^{c1}C(O)R^{b1}$, wherein the 5-6 membered heteroaryl is optionally substituted with 1 or 2 independently selected $R^{1A}$ substituents;

$R^{a1}$, $R^{b1}$, $R^{c1}$, and $R^{d1}$ are each independently selected from H, 4-10 membered heterocycloalkyl, (4-10 membered heterocycloalkyl)-$C_{1-6}$ alkyl, and (5-10 membered heteroaryl)-$C_{1-6}$ alkyl, wherein the 4-10 membered heterocycloalkyl, (4-10 membered heterocycloalkyl)-$C_{1-6}$ alkyl, and (5-10 membered heteroaryl)-$C_{1-6}$ alkyl are each optionally substituted with 1 or 2 independently selected $R^{1A}$ substituents;

or $R^{c1}$ and $R^{d1}$, together with the nitrogen to which they are attached, come together to form a 10-14 membered heterocycloalkyl or 10-14 membered heteroaryl group;

each $R^{1A}$ is independently selected from $C_{1-6}$ alkyl, $C_{3-6}$ cycloalkyl, 4-6 membered heterocycloalkyl, and CN, wherein each $C_{1-6}$ alkyl is optionally substituted with $C_{1-4}$ alkoxy;

$R^2$ is H or $C_{1-6}$ alkoxy;

U is $CR^3$ or N;

U' is $CR^5$ or N;

U" is $CR^6$ or N;

$R^3$ is selected from H, halo, and $C_{1-6}$ alkoxy;

$R^4$ is selected from H, 5-6 membered heteroaryl, CN, and $C(O)NR^{c4}R^{d4}$, wherein the 5-6 membered heteroaryl is optionally substituted with 1 or 2 independently selected $R^{4A}$ substituents;

$R^{c4}$ and $R^{d4}$ are each independently selected from H, $C_{1-6}$ alkyl, and $C_{1-6}$ haloalkyl;

each $R^{4A}$ is an independently selected $C_{1-6}$ alkyl group;

$R^5$ is selected from H, halo, $C_{1-6}$ alkyl, and $C_{1-6}$ alkoxy;

or $R^4$ and $R^5$ together with the carbon atoms to which they are attached, come together to form a 6-membered aryl ring which is optionally substituted with 1 or 2 independently selected $R^7$ substituents;

each $R^7$ is independently selected from $C_{3-10}$ cycloalkyl, 4-14 membered heterocycloalkyl, 5-10 membered heteroaryl, and $OR^{a7}$, wherein the $C_{3-10}$ cycloalkyl, 4-14 membered heterocycloalkyl, and 5-10 membered heteroaryl are each optionally substituted with 1 or 2 independently selected $R^{7A}$ substituents;

each $R^{a7}$ is an independently selected 4-10 membered heterocycloalkyl group; and each $R^{7A}$ is independently selected from $C_{1-6}$ alkyl, amino, $C_{3-6}$ cyclopropyl and 4-6 membered heterocycloalkyl, wherein each $C_{1-6}$ alkyl is optionally substituted with amino or $C_{1-4}$ alkoxy.

In some embodiments:

V, X, and Z are each C, and W and Y are each N; or

X, Y, and Z are each C, and V and W are each N; or

V, Y, and Z are each C, and W and X are each N; or

V and Y are each C, and W, X, and Z are each N;

$R^1$ is selected from 5-6 membered heteroaryl, $OR^{a1}$, $C(O)NR^{c1}R^{d1}$, and $NR^{c1}C(O)R^{b1}$, wherein the 5-6 membered heteroaryl is optionally substituted with 1 or 2 independently selected $R^{1A}$ substituents;

$R^{a1}$, $R^{b1}$, $R^{c1}$, and $R^{d1}$ are each independently selected from H, methyl, pyrazolyl, pyridinylmethyl, pyridinylethyl, imidazo[1,2-a]pyridinylmethyl, benzoimidazolylmethyl, imidazo[4,5-c]pyridinylmethyl, benzoxazolylmethyl, oxetanylmethyl, oxetanylethyl, thietanyl-(1,1-dioxide)methyl, 2-oxaspiro[3.3]heptanyl, and 2-oxaspiro[3.5]nonanyl, wherein the methyl, pyrazolyl, pyridinylmethyl, pyridinylethyl, imidazo[1,2-a]pyridinylmethyl, benzoimidazolylmethyl, imidazo[4,5-c]pyridinylmethyl, benzoxazolylmethyl, oxetanylmethyl, oxetanylethyl, thietanyl-(1,1-dioxide)methyl, 2-oxaspiro[3.3]heptanyl, and 2-oxaspiro[3.5]nonanyl are each optionally substituted with 1 or 2 independently selected $R^{1A}$ substituents;

or $R^{c1}$ and $R^{d1}$, together with the nitrogen to which they are attached, come together to form 1,2,3,4-tetrahydrobenzo[4,5]imidazo[1,2-a]pyrazinyl;

each $R^{1A}$ is independently selected from methyl, ethyl, methoxymethyl, and CN;

$R^2$ is H or $C_{1-6}$ alkoxy;

U is $CR^3$ or N;

U' is $CR^5$ or N;

U" is $CR^6$ or N;

$R^3$ is selected from H, halo, and $C_{1-6}$ alkoxy;

$R^4$ is selected from H, 5-6 membered heteroaryl, CN, and $C(O)NR^{c4}R^{d4}$, wherein the 5-6 membered heteroaryl is optionally substituted with 1 or 2 independently selected $R^{4A}$ substituents;

$R^{c4}$ and $R^{d4}$ are each independently selected from H, $C_{1-6}$ alkyl, and $C_{1-6}$ haloalkyl;

each $R^{4A}$ is an independently selected $C_{1-6}$ alkyl group;

$R^5$ is selected from H, halo, $C_{1-6}$ alkyl, and $C_{1-6}$ alkoxy;

or $R^4$ and $R^5$ together with the carbon atoms to which they are attached, come together to form a 6-membered aryl ring which is optionally substituted with 1 or 2 independently selected $R^7$ substituents;

each $R^7$ is independently selected from bicyclo[1.1.1]pentanyl, azetidinyl, pyrrolidinyl, piperidinyl, morpholinyl, imidazolyl, azaspiro[3.3]heptanyl, diazaspiro[3.5]nonanyl, oxadiazaspiro[5.5]undecanyl, diazaspiro[4.4]nonanyl, and azetidinyloxy, wherein the bicyclo[1.1.1]pentanyl, azetidinyl, pyrrolidinyl, piperidinyl, morpholinyl, imidazolyl, azaspiro[3.3]heptanyl, diazaspiro[3.5]nonanyl, oxadiazaspiro[5.5]undecanyl, and diazaspiro[4.4]nonanyl are each optionally substituted with 1 or 2 $R^{7A}$ substituents; and each $R^{7A}$ is independently selected from methyl, methoxyethyl, aminomethyl, amino, cyclopropyl, and oxetanyl.

In some embodiments, the compound of Formula I is a compound of Formula II.

II

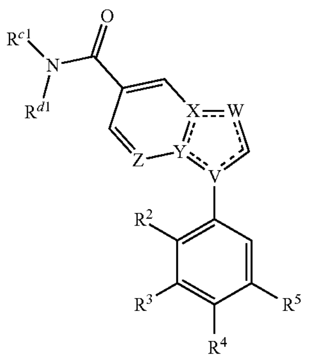

or a pharmaceutically acceptable salt thereof, wherein variables V, W, X, Y, Z, $R^{c1}$, $R^{d1}$, $R^2$, $R^3$, $R^4$, and $R^5$ are defined according to the definitions provided herein for compounds of Formula I.

In some embodiments, the compound of Formula I is a compound of Formula III:

III

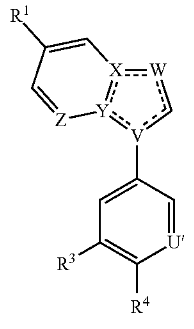

or a pharmaceutically acceptable salt thereof, wherein $R^1$ is a 5-10 membered heteroaryl which is optionally with 1, 2, 3, or 4 $R^{1A}$ substituents, wherein variables U', V, W, X, Y, Z, $R^{1A}$, $R^3$, $R^4$, and $R^5$ are defined according to the definitions provided herein for compounds of Formula I.

In some embodiments, the compound of Formula I is a compound of Formula IIIa:

IIIa

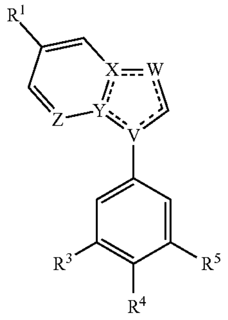

or a pharmaceutically acceptable salt thereof, wherein $R^1$ is a 5-10 membered heteroaryl which is optionally with 1, 2, 3, or 4 $R^{1A}$ substituents, wherein variables V, W, X, Y, Z, $R^{1A}R^3$, $R^4$, and $R^5$ are defined according to the definitions provided herein for compounds of Formula I.

In some embodiments, the compound of Formula I is a compound of Formula IV:

IV

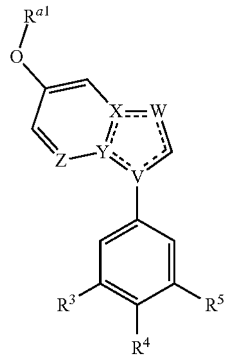

or a pharmaceutically acceptable salt thereof, wherein variables V, W, X, Y, Z, $R^{a1}$, $R^3$, $R^4$, and $R^5$ are defined according to the definitions provided herein for compounds of Formula I.

In some embodiments, the compound of Formula I is a compound of Formula V:

V

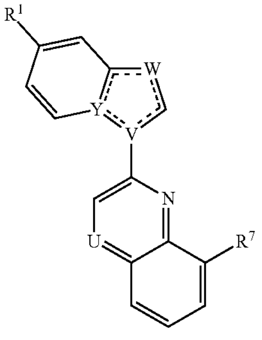

or a pharmaceutically acceptable salt thereof, wherein variables U, V, W, Y, $R^1$, and $R^7$ are defined according to the definitions provided herein for compounds of Formula I.

In some embodiments, the compound provided herein (e.g., the compound of any one of Formulas I-V), or a pharmaceutically acceptable salt thereof, is selected from:

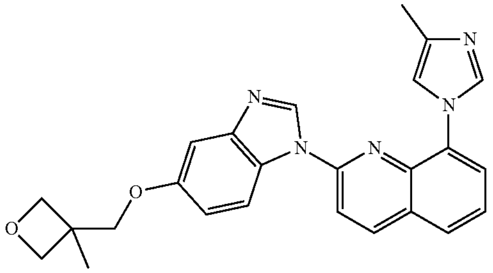

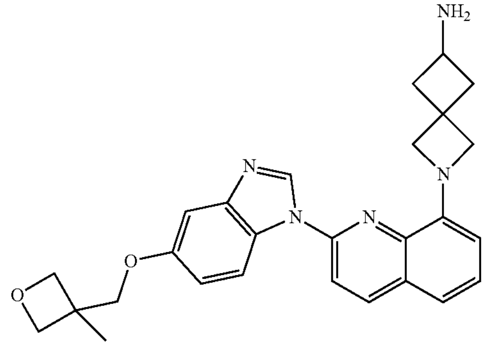

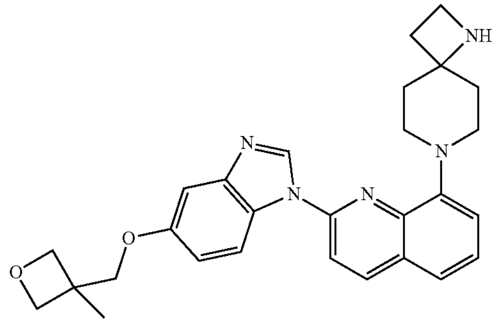

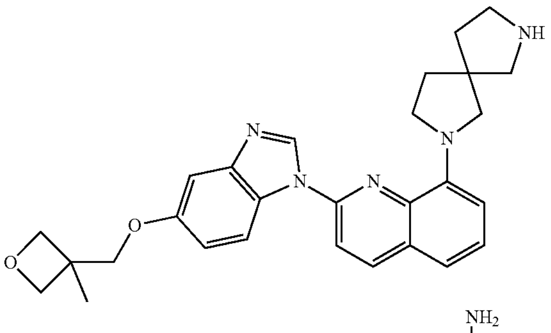

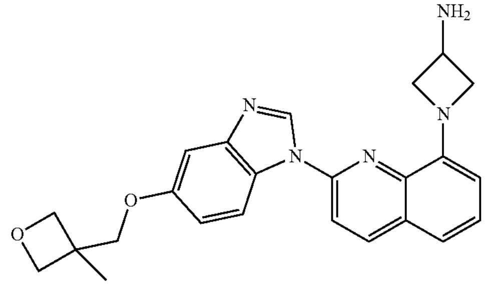

-continued
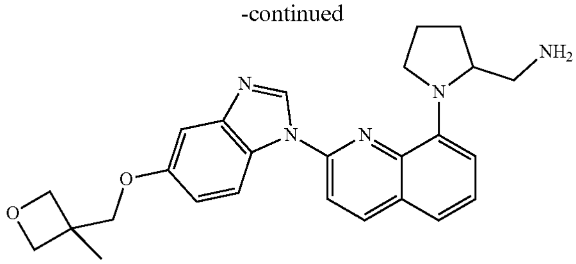
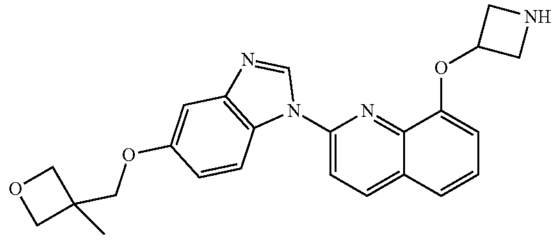
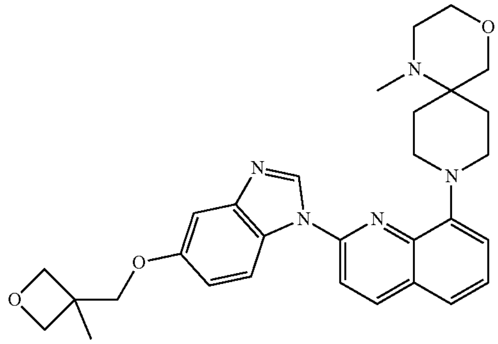
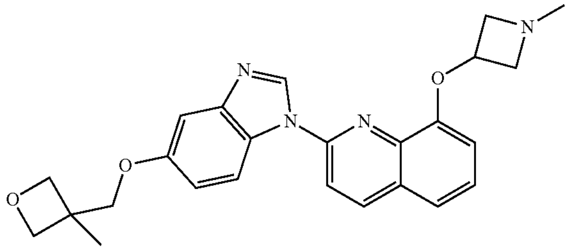
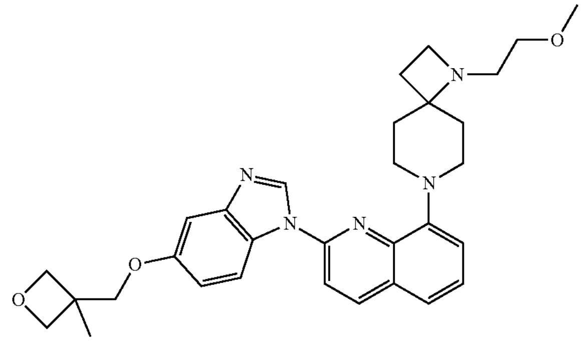
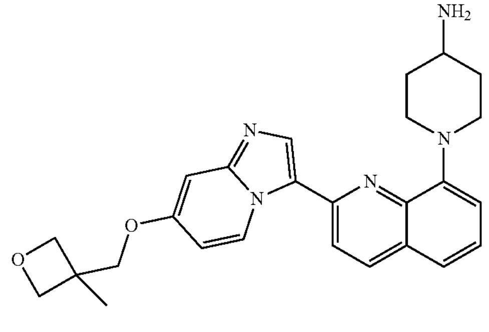
-continued
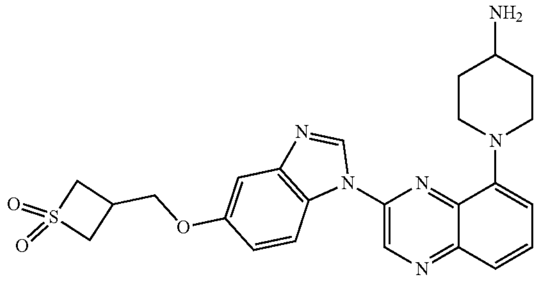
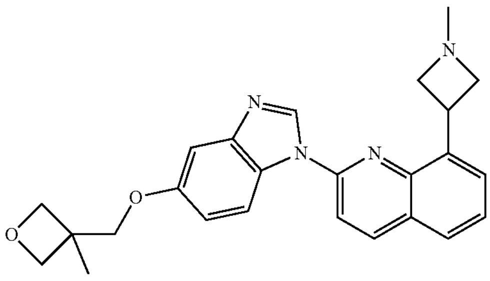
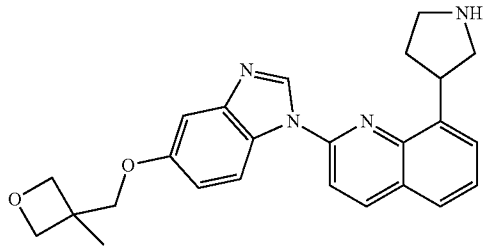
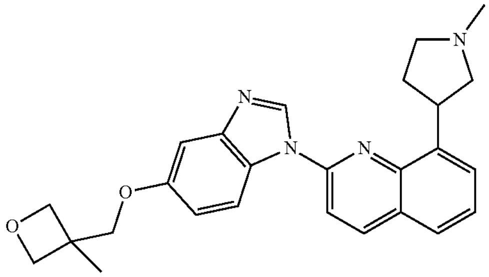
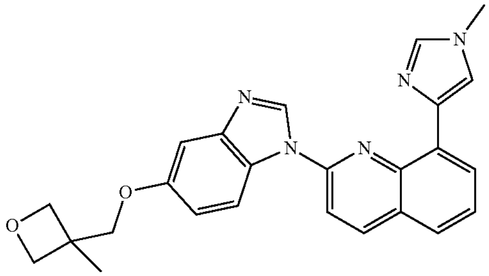
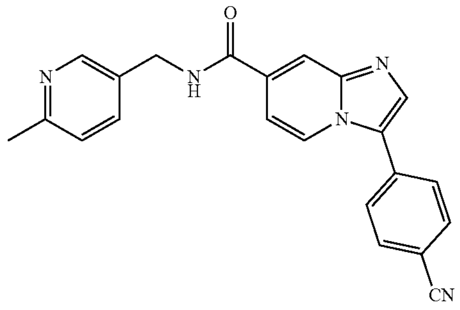

-continued
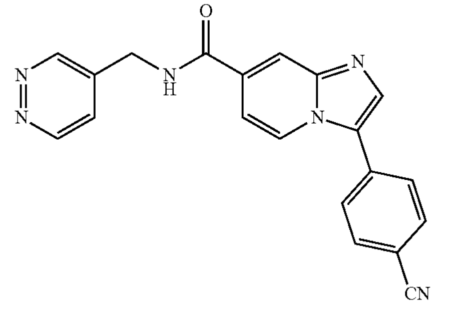
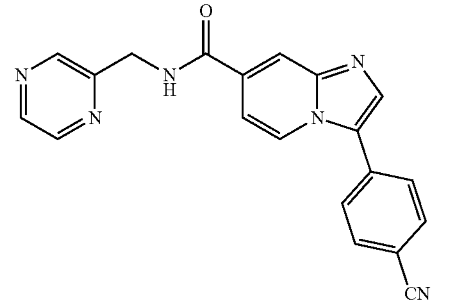
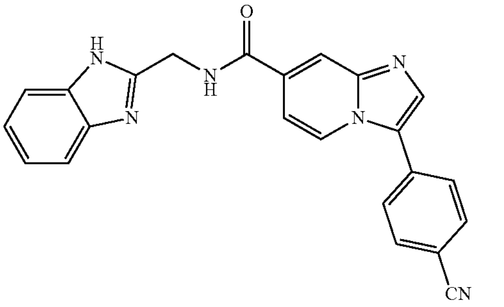
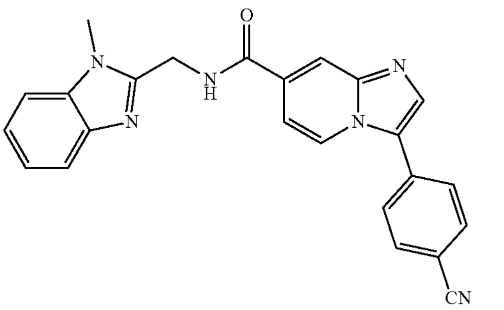
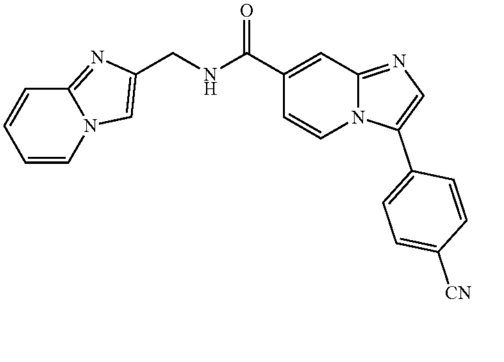
-continued
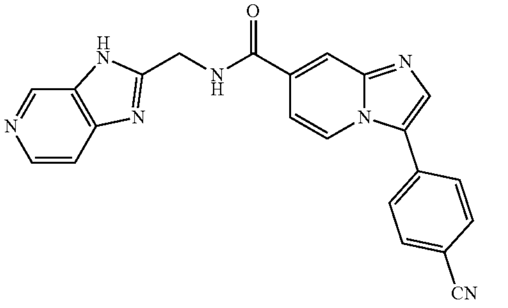
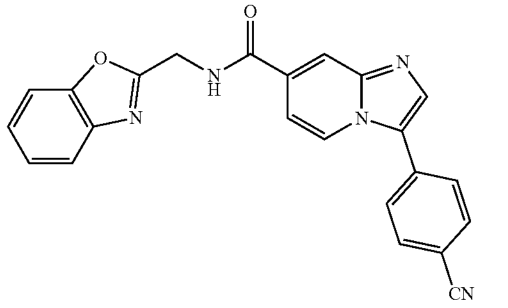
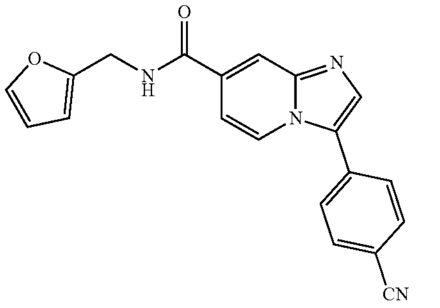
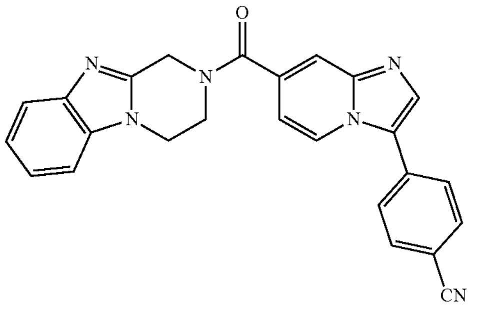
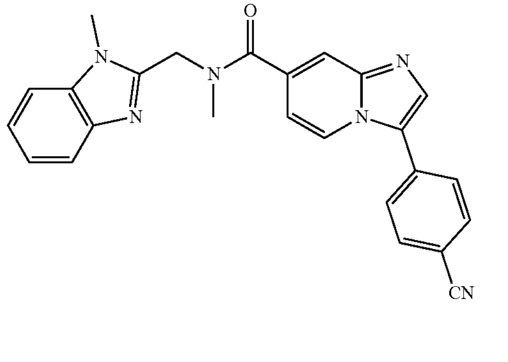

-continued
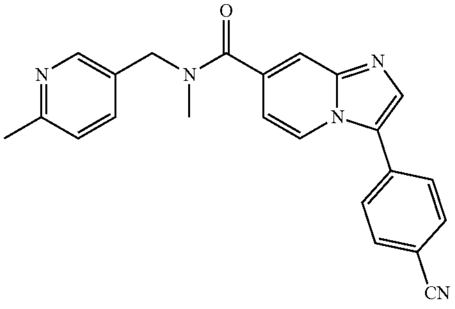
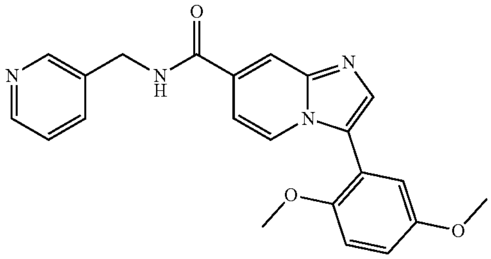
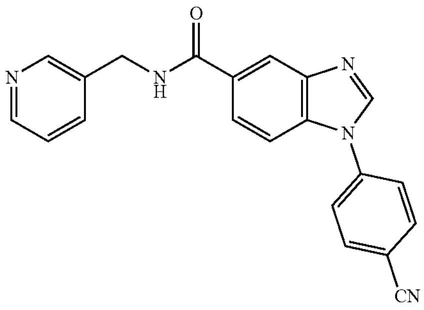
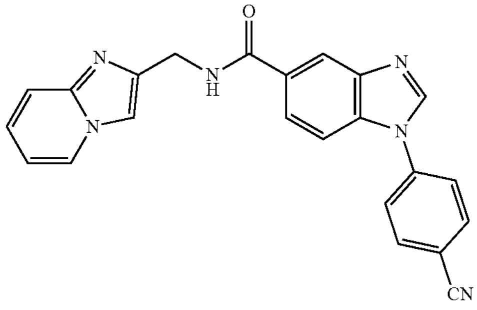
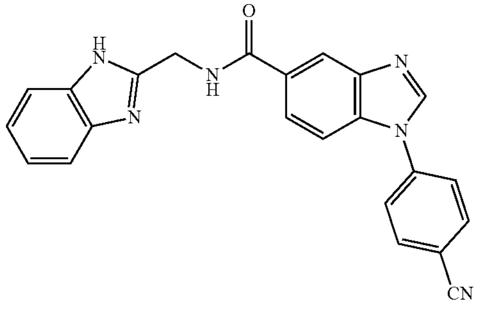
-continued
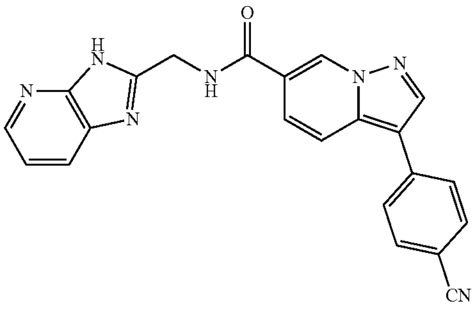
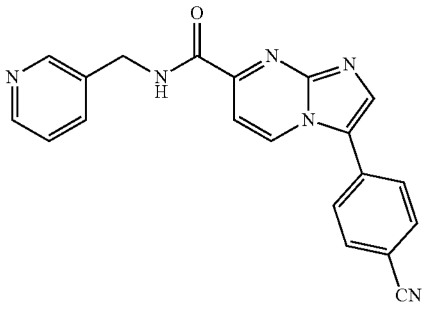
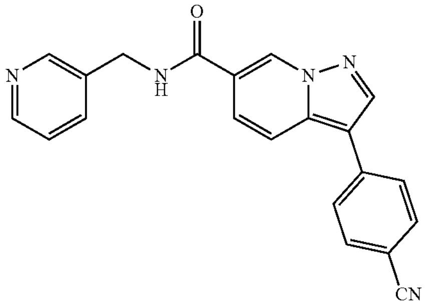
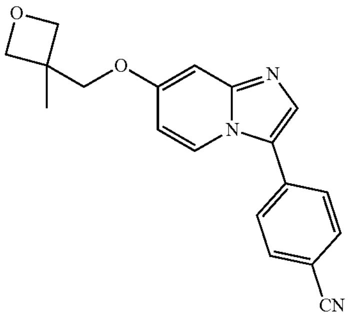
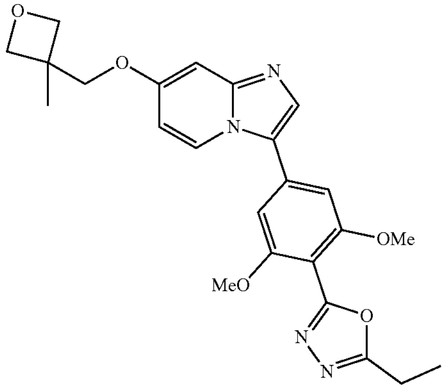

-continued
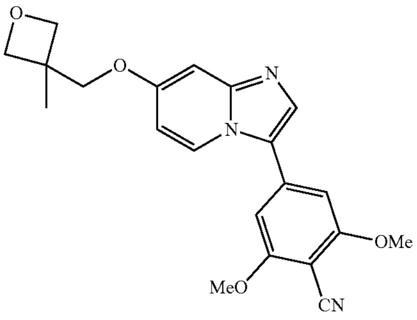
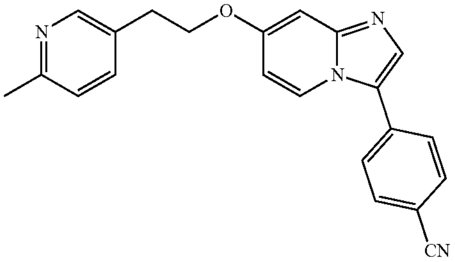
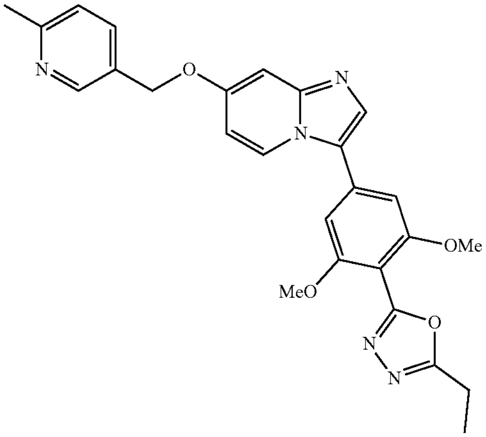
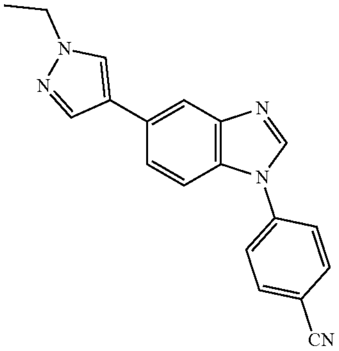
-continued
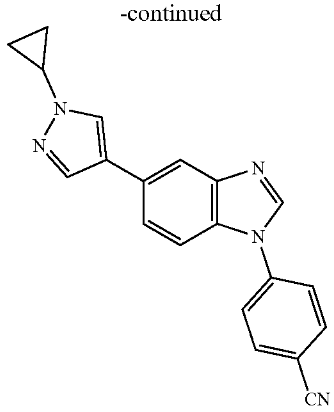
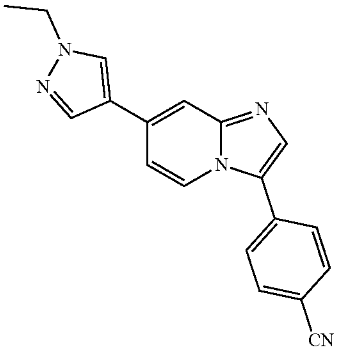
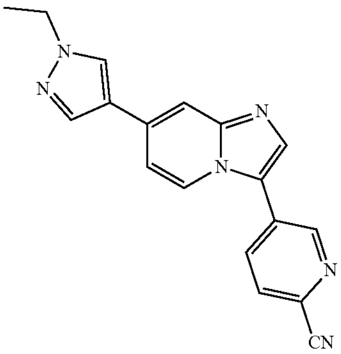
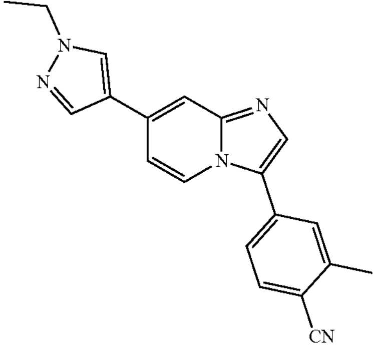

-continued
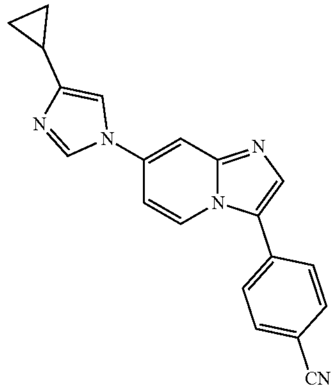
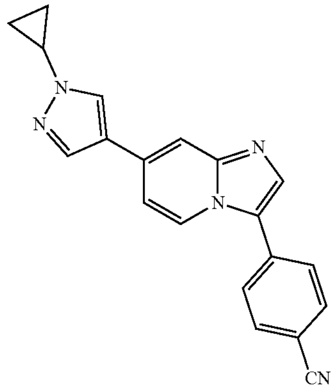
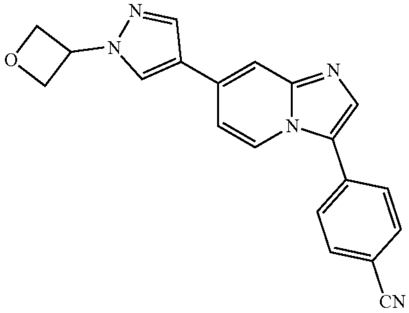
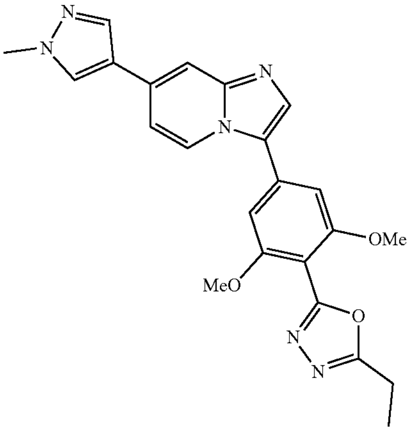
-continued
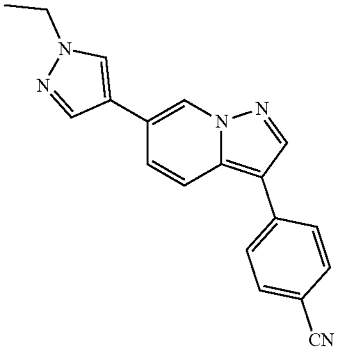
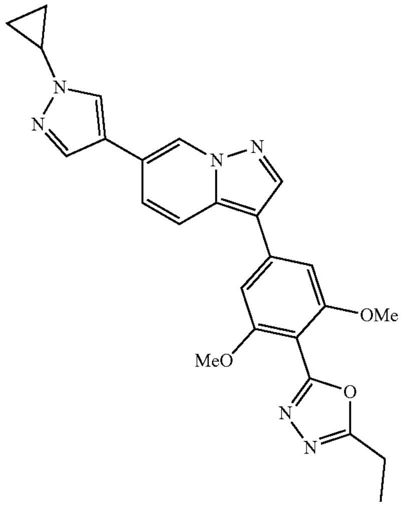
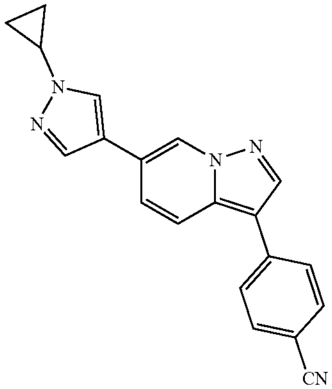
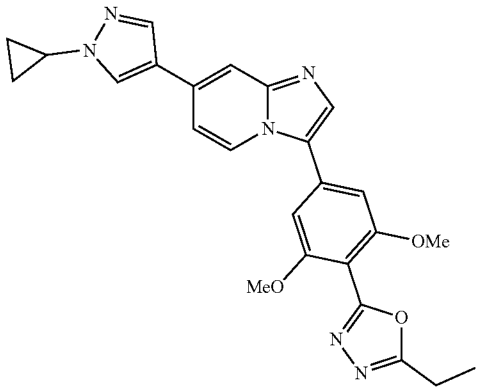

-continued
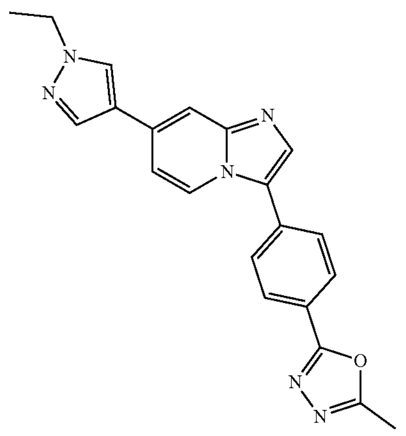
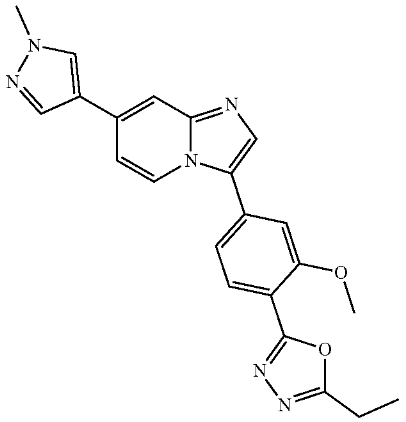
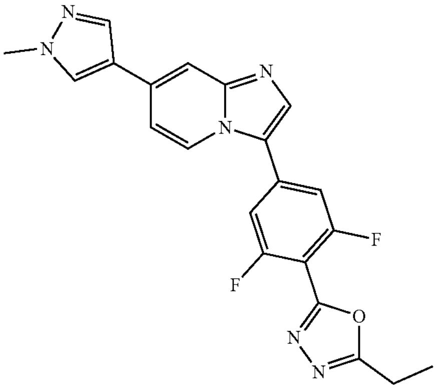
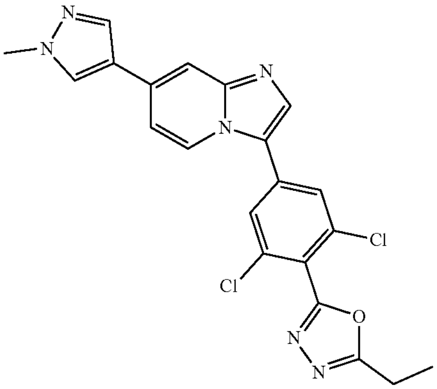
-continued
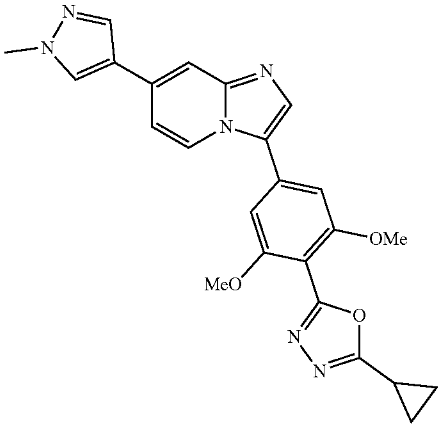
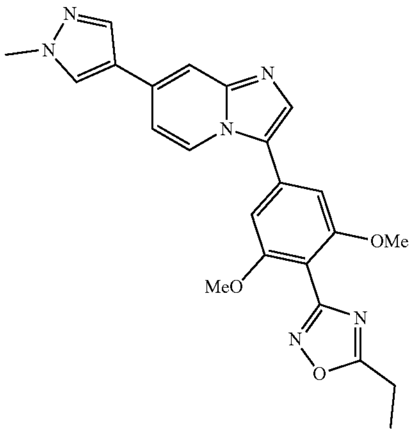
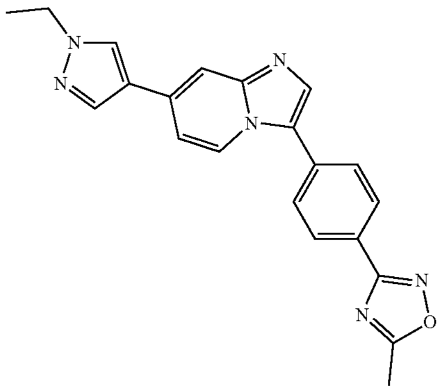
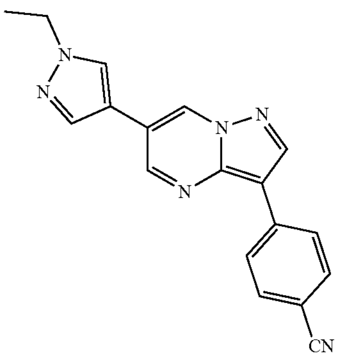

-continued

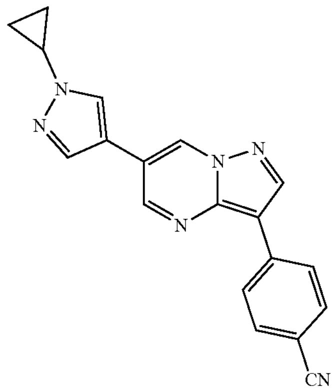

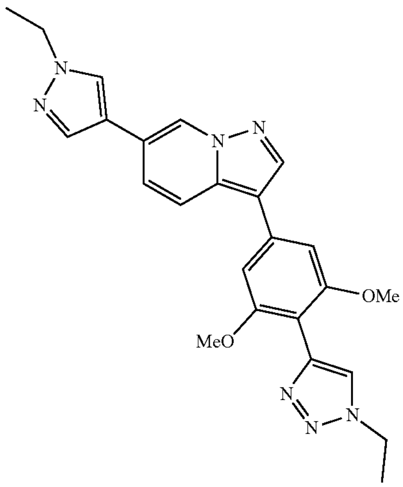

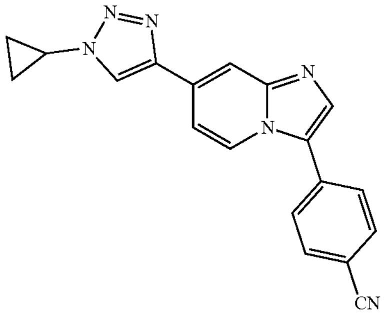

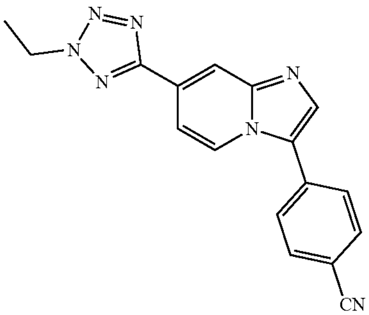

and

-continued

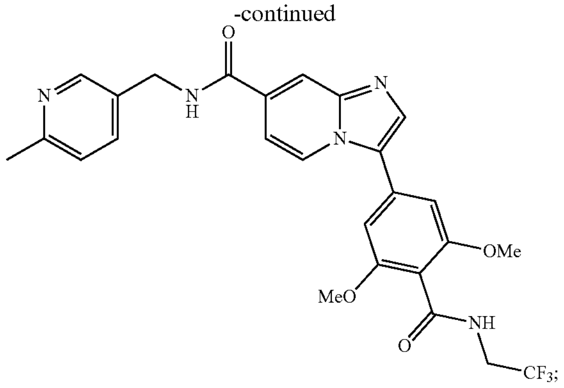

or a pharmaceutically acceptable salt thereof.

In some embodiments, the compound has formula:

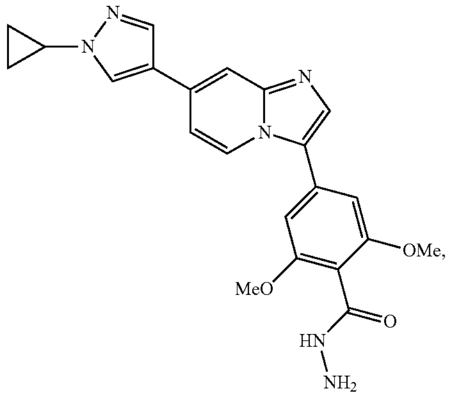 [SMILES: COc1cc(-c2cnc3cc(-c4cnn(C5CC5)c4)ccn23)cc(OC)c1C(=O)NN]

or a pharmaceutically acceptable salt thereof.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

As used herein, the phrase "each 'variable' is independently selected from" means substantially the same as wherein "at each occurrence 'variable' is selected from."

Throughout the definitions, the term "$C_{n-m}$" indicates a range which includes the endpoints, wherein n and m are integers and indicate the number of carbons. Examples include $C_{1-3}$, $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "amino" refers to a group of formula —$NH_2$.

As used herein, the term "aryl" refers to an aromatic hydrocarbon group, which may be monocyclic or polycyclic (e.g., having 2 or more fused rings). The term "$C_{n-m}$ aryl" refers to an aryl group having from n to m ring carbon atoms. Aryl groups include, but are not limited to, phenyl, naphthyl, and the like. In some embodiments, aryl groups have from 6 to 14 carbon atoms (i.e., $C_{6-14}$ aryl). In some embodiments, aryl groups have from 6 to 10 carbon atoms (i.e., $C_{6-10}$ aryl). In some embodiments, the aryl is phenyl.

As used herein, "halo" refers to F, Cl, Br, or I. In some embodiments, a halo is F or Cl. In some embodiments, a halo is F.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. In some embodiments, the haloalkyl group is trifluoromethyl or trifluoroethyl.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)amino" refers to a group of formula —N(alkyl)$_2$, wherein each alkyl group independently has n to m carbon atoms. In some embodiments, each alkyl group independently has 1 to 6, 1 to 4, or 1 to 3 carbon atoms.

As used herein, "cycloalkyl" refers to non-aromatic cyclic hydrocarbons including cyclized alkyl and alkenyl groups. Cycloalkyl groups can include mono- or polycyclic (e.g., having 2 or more fused rings) groups, spirocycles, and bridged rings (e.g., a bridged bicycloalkyl group). Ring-forming carbon atoms of a cycloalkyl group can be optionally substituted by oxo (i.e., =O). Also included in the definition of cycloalkyl are moieties that have one or more aromatic rings fused (i.e., having a bond in common with) to the cycloalkyl ring, for example, benzo or thienyl derivatives of cyclobutane, cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, 10, 11, 12, 13, or 14 ring-forming carbons (i.e., $C_{3-14}$). In some embodiments, the cycloalkyl is a $C_{3-14}$ monocyclic or bicyclic cycloalkyl. In some embodiments, the cycloalkyl is a $C_{3-10}$ monocyclic or bicyclic cycloalkyl. In some embodiments, the cycloalkyl is a $C_{3-7}$ monocyclic cycloalkyl. In some embodiments, the cycloalkyl is a $C_{4-7}$ monocyclic cycloalkyl. In some embodiments, the cycloalkyl is a $C_{4-14}$ spirocycle or bridged cycloalkyl (e.g., a bridged bicycloalkyl group). In some embodiments, the cycloalkyl is a $C_{4-10}$ spirocycle or bridged cycloalkyl (e.g., a bridged bicycloalkyl group). Example cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, adamantanyl, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like.

As used herein, "heteroaryl" refers to a monocyclic or polycyclic (e.g., having 2 or more fused rings) aromatic heterocycle having at least one heteroatom ring member selected from N, O, and S. In some embodiments, the heteroaryl ring has 1, 2, 3, or 4 heteroatom ring members independently selected from N, O, and S. In some embodiments, the heteroaryl ring has 1, 2, 3, or 4 heteroatom ring members independently selected from N and O. In some embodiments, the heteroaryl is a 5-14 membered monocyclic or bicyclic heteroaryl having 1, 2, 3, or 4 heteroatom ring members independently selected from N, O, and S. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-14 membered monocyclic or bicyclic heteroaryl having 1, 2, 3, or 4 heteroatom ring members independently selected from N and O. In some embodiments, the heteroaryl is a 5-10 membered monocyclic or bicyclic heteroaryl having 1, 2, 3, or 4 heteroatom ring members independently selected from N and O. In some embodiments, the heteroaryl is a 5-6 membered monocyclic heteroaryl having 1 or 2 heteroatom ring members independently selected from N, O, and S. In some embodiments, the heteroaryl is a 5-6 membered monocyclic heteroaryl having 1 or 2 heteroatom ring members independently selected from N and O. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, thienyl (or thiophenyl), furyl (or furanyl), pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl and 1,2-dihydro-1,2-azaborine, pyridinyl, pyrimidinyl, pyrazinyl, pyridazinyl, azolyl, triazolyl, thiadiazolyl, quinolinyl, isoquinolinyl, indolyl, benzothiophenyl, benzofuranyl, benzisoxazolyl, imidazo[1,2-b]thiazolyl, purinyl, triazinyl, thieno[3,2-b]pyridinyl, imidazo[1,2-a]pyridinyl, 1,5-naphthyridinyl, 1H-pyrazolo[4,3-b]pyridinyl, triazolo[4,3-a]pyridinyl, 1H-pyrrolo[3,2-b]pyridinyl, 1H-pyrrolo[2,3-b]pyridinyl, pyrazolo[1,5-a]pyridinyl, indazolyl, and the like.

As used herein, "heterocycloalkyl" refers to monocyclic or polycyclic heterocycles having at least one non-aromatic ring (i.e., a saturated or partially unsaturated ring), wherein one or more of the ring-forming carbon atoms of the heterocycloalkyl is replaced by a heteroatom selected from N, O, and S, and wherein the ring-forming carbon atoms and heteroatoms of a heterocycloalkyl group can be optionally substituted by one or more oxo groups (i.e., substituted by one or more =O groups, such as S(O), C(O), $S(O)_2$, and the like), etc.). When a ring-forming carbon atom or heteroatom of a heterocycloalkyl group is optionally substituted by one or more oxo groups, the O of said group is in addition to the number of ring-forming atoms specified herein. Heterocycloalkyl groups include monocyclic and polycyclic (e.g., having 2 or more fused rings) systems. Heterocycloalkyl groups provided include monocyclic and polycyclic 3 to 14 membered, 3 to 10 membered, 4 to 14 membered, 4 to 10 membered, 5 to 14 membered, 5 to 10 membered, 4 to 7 membered, 5 to 7 membered, or 5 to 6 membered heterocycloalkyl groups. Heterocycloalkyl groups can also include spirocycles and bridged rings (e.g., a 5 to 14 membered bridged biheterocycloalkyl ring having one or more of the ring-forming carbon atoms replaced by a heteroatom independently selected from N, O, and S). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 double bonds. In some embodiments, the heterocycloalkyl group contains 1, 2, or 3 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azetidine, and the like. A heterocycloalkyl group containing a fused aromatic ring can be attached through any ring-forming atom including a ring-forming atom of the fused aromatic ring.

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

As used herein, an "alkylene group" is a bivalent straight chain or branched alkyl linking group. For example, "$C_{o-p}$ cycloalkyl-$C_{n-m}$ alkyl-", "$C_{o-p}$ aryl-$C_{n-m}$ alkyl-", "phenyl-$C_{n-m}$ alkyl-", "heteroaryl-$C_{n-m}$ alkyl-", and "heterocycloalkyl-$C_{n-m}$ alkyl-" contain alkyl linking groups. Examples of "alkyl linking groups" or "alkylene groups" include methylene, ethan-1,1-diyl, ethan-1,2-diyl, propan-1,3-diyl, propan-1,2-diyl, propan-1,1-diyl and the like.

As used herein, the term "oxo" refers to an oxygen atom (i.e., =O) as a divalent substituent, forming a carbonyl group when attached to a carbon (i.e., C=O or C(O)), or attached to a nitrogen or sulfur heteroatom forming a nitroso, sulfinyl, or sulfonyl group.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "independently selected from" means that each occurrence of a variable or substituent (e.g., "each $R^{1A}$"), are independently selected at each occurrence from the applicable list.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula I, Formula Ia, etc.) provided herein include stereoisomers of the compounds.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

As used herein, the terms "room temperature" or "RT" are understood in the art, and refer generally to a temperature (e.g., a reaction temperature) that is about the temperature of the room in which the reaction is carried out, for example, a temperature from about 20° C. to about 30° C.

In some embodiments, the compounds provided herein, or salts thereof, are substantially isolated. By "substantially isolated" is meant that the compound is at least partially or substantially separated from the environment in which it was formed or detected.

Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes.

The compounds provided herein, or intermediates useful in the preparation of the compounds provided herein can be prepared, for example, according to the procedures described in one or more of Schemes 1-7, using appropriately substituted starting materials.

Scheme 1.

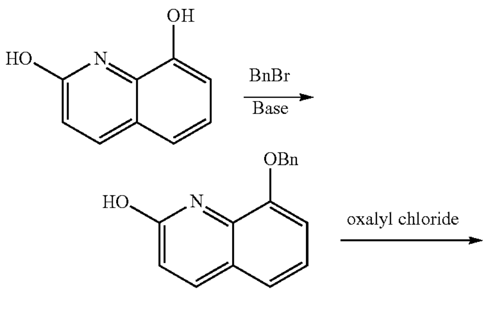

-continued
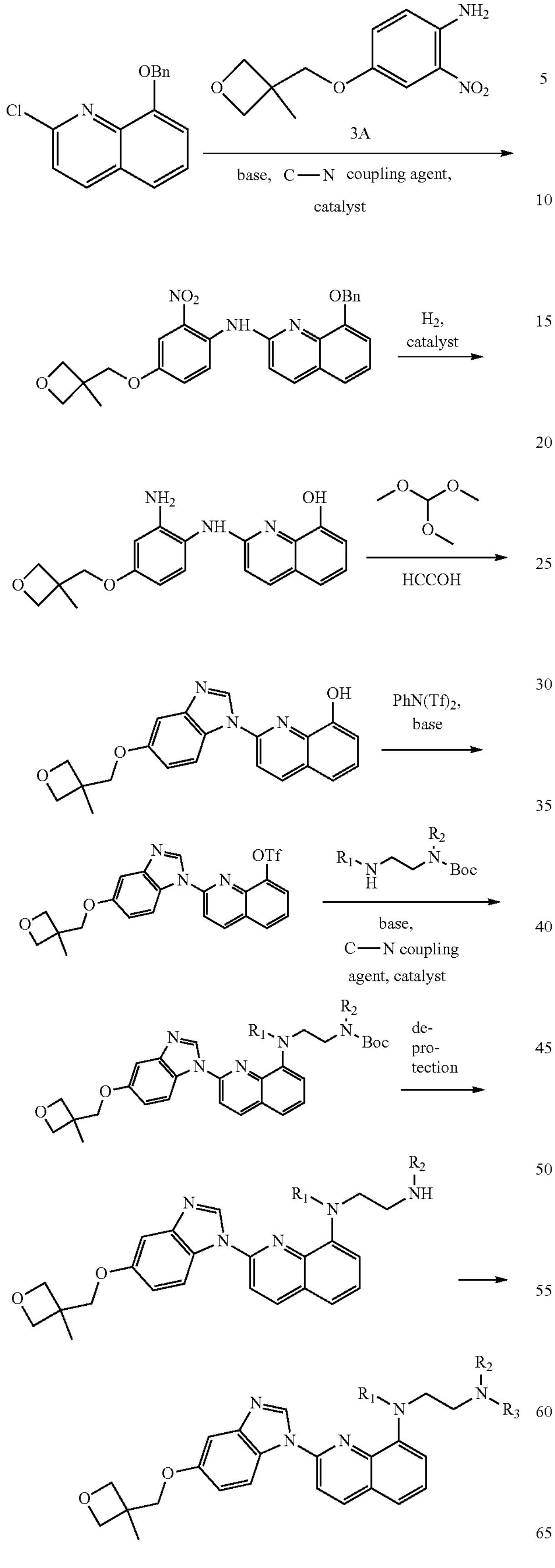
Scheme 2.
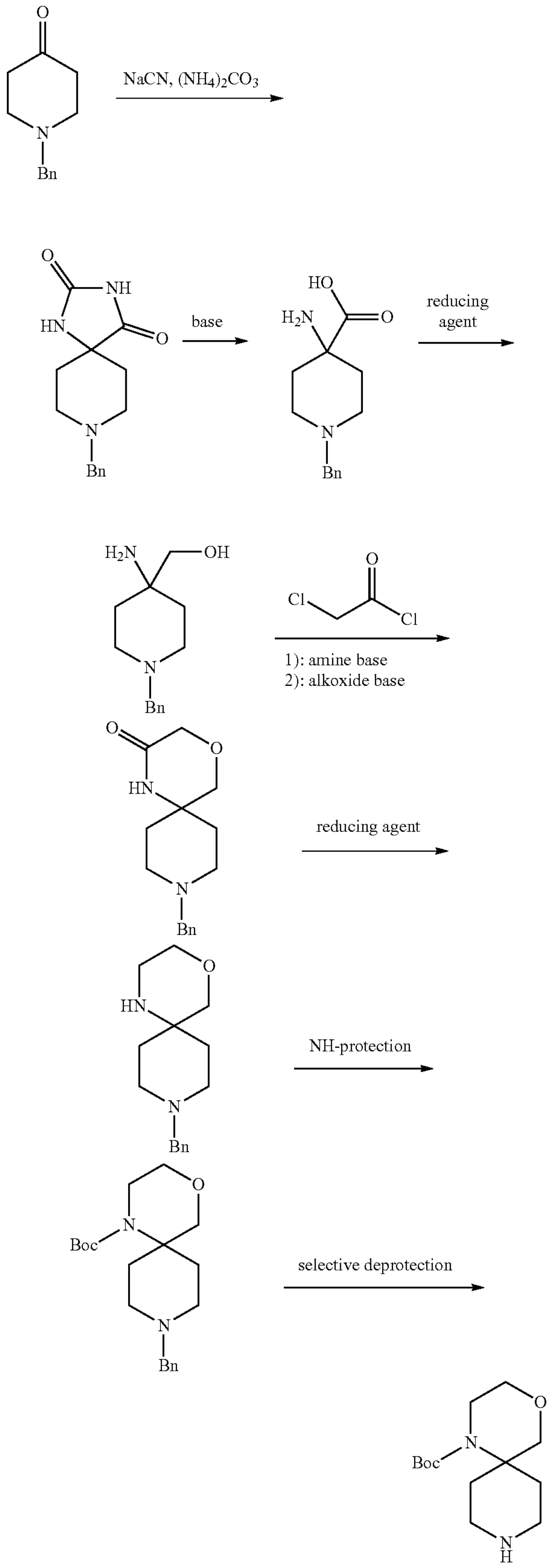

Scheme 3.
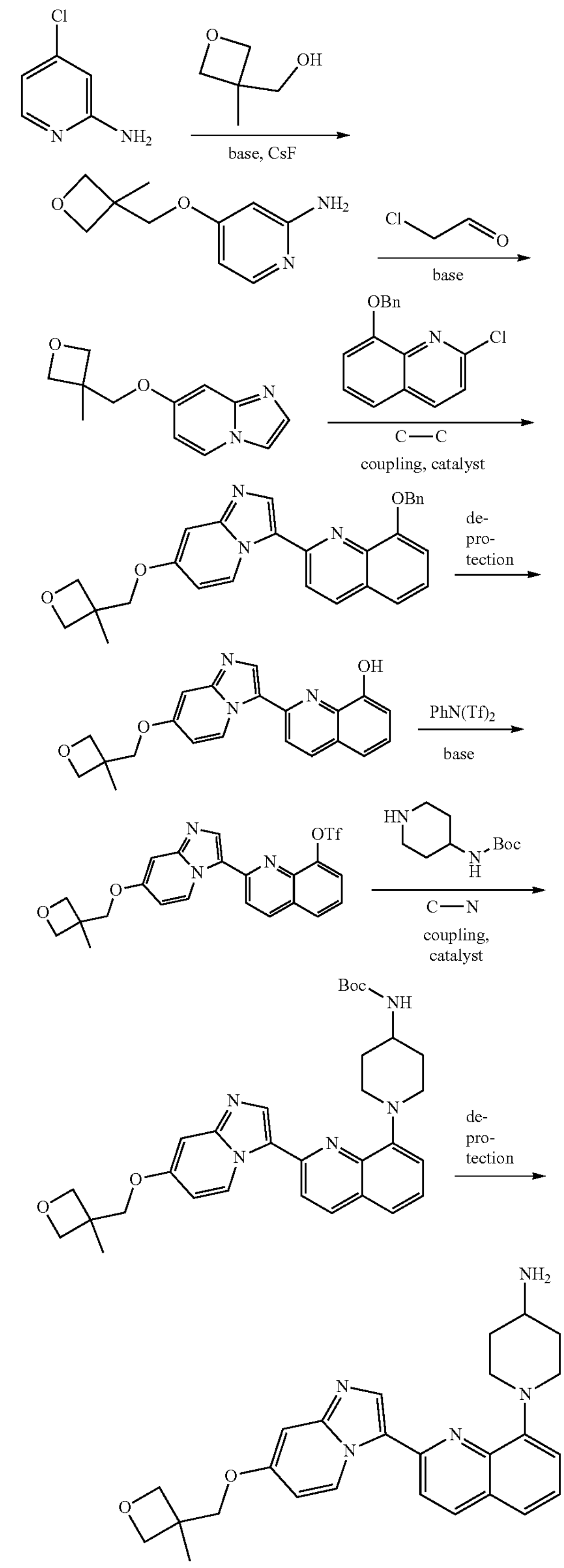
Scheme 4.
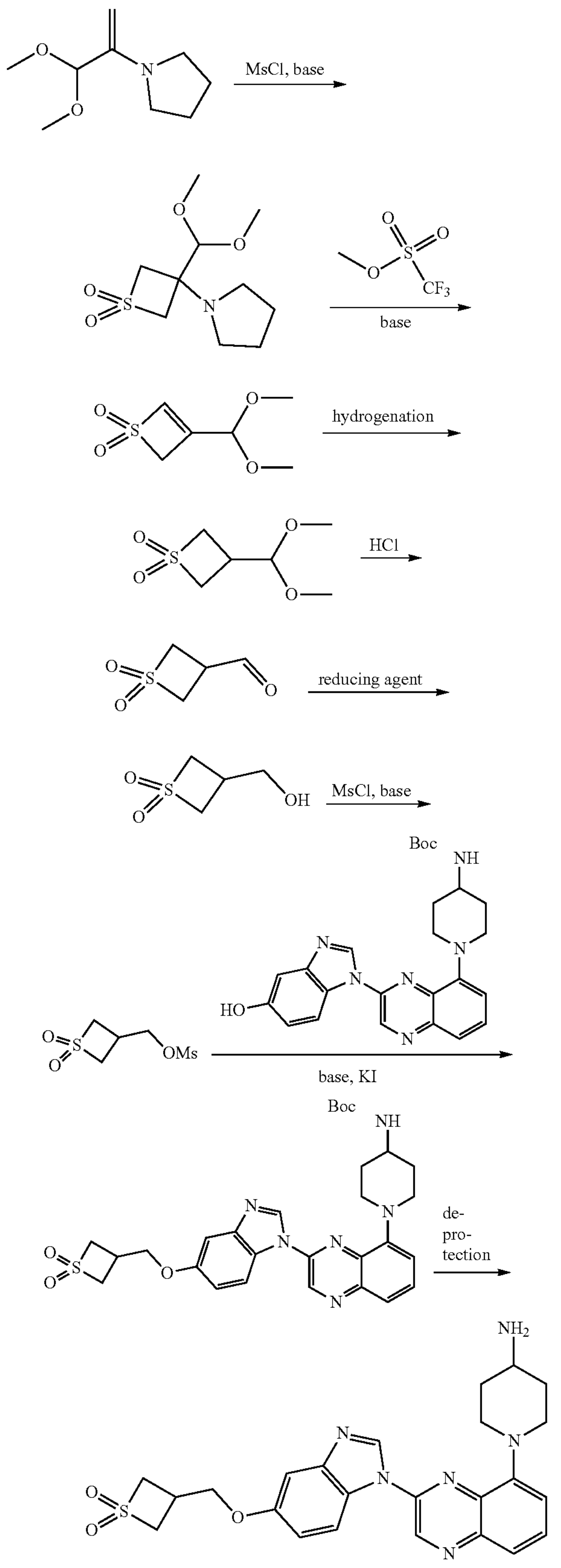

Scheme 5.
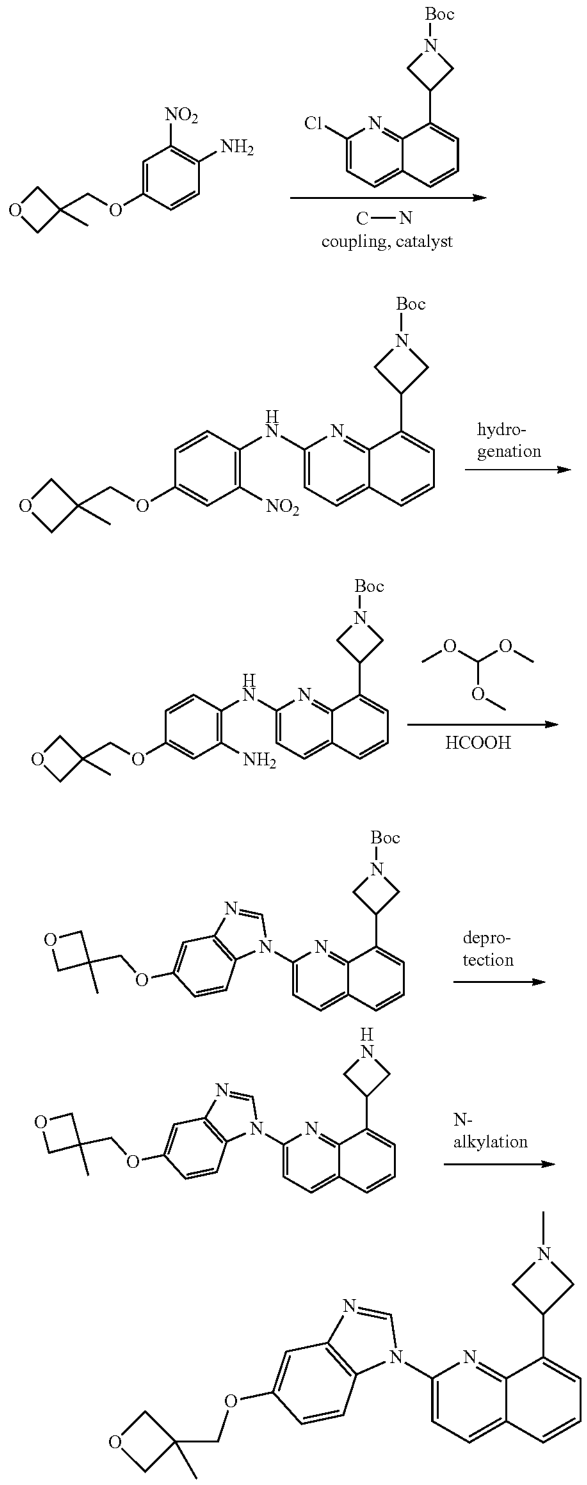
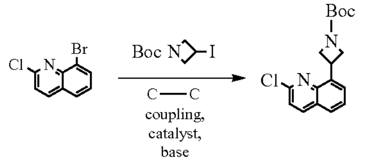
Scheme 6.
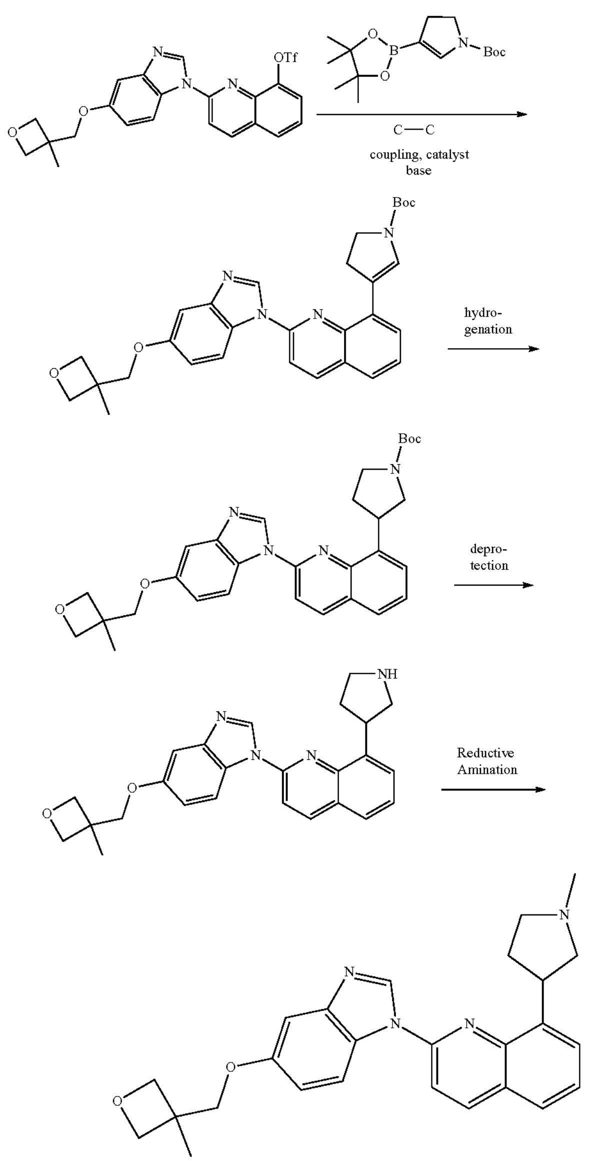
Scheme 7.
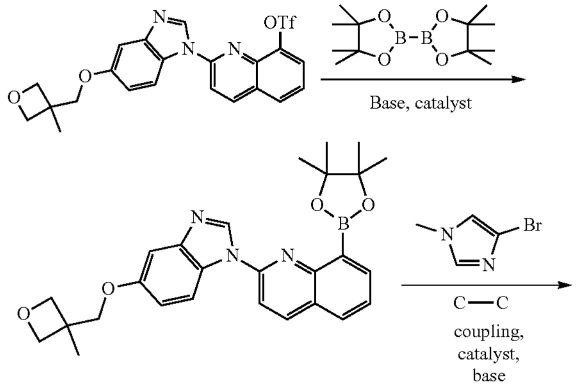

-continued

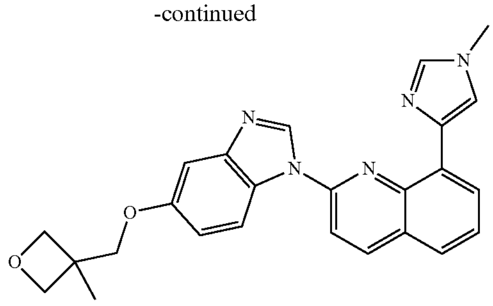

A skilled artisan will appreciate that the processes described above are not the exclusive means by which compounds provided herein may be synthesized and that a broad repertoire of synthetic organic reactions is available to be potentially employed in synthesizing compounds provided herein. A skilled artisan knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, $3^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (IPLC) and normal phase silica chromatography.

Methods of Use

The compounds provided herein can inhibit the activity of a salt inducible kinase (SIK), e.g., SIK2 and/or SIK3. In some embodiments, the present application provides methods of inhibiting an activity of one or more salt inducible kinases (SIKs), comprising contacting the kinase with a compound provide herein (e.g., a compound of any one of Formulas I-V), or a pharmaceutically acceptable salt thereof.

In some embodiments, the method is an in vitro method. In some embodiments, the method is an ex vivo method. In some embodiments, the method is an in vivo method.

As used herein, the term "contacting" refers to the bringing together of indicated moieties in an in vitro system or an in vivo system. For example, "contacting" a salt inducible kinase with a compound provided herein includes the administration of a compound provided herein, or a pharmaceutically acceptable salt thereof, to an individual or patient (e.g., a human patient), having a salt inducible kinase, as well as, for example, introducing a compound described herein into a sample containing a cellular or purified preparation containing the salt inducible kinase.

In some embodiments, the compounds provided herein are selective inhibitors of one or more SIKs. In some embodiments, the compounds provided herein are selective inhibitors of salt inducible kinase 2 (SIK2) over salt inducible kinase 1 (SIK1). In some embodiments, the compounds provided herein are selective inhibitors of salt inducible kinase 3 (SIK3) over salt inducible kinase 1 (SIK1). In some embodiments, the compounds provided herein are selective inhibitors of salt inducible kinase 2 (SIK2) and salt inducible kinase 3 (SIK3), over salt inducible kinase 1 (SIK1).

The present application further provides methods of treating a disease in a patient (e.g., in a patient in need thereof), wherein the disease is associated with abnormal expression and/or activity of a salt inducible kinase (e.g., SIK2 and/or SIK3). In some embodiments, the method comprises administering to the patient a therapeutically effective amount of a compound provided herein, or a pharmaceutically acceptable salt thereof.

As used herein, the term "patient," refers to any animal, including mammals such as mice, rats, other rodents, rabbits, dogs, cats, swine, cattle, sheep, horses, primates, and humans. In some embodiments, the patient is a human patient.

In some embodiments, the disease is associated with abnormal expression and/or activity of SIK2. In some embodiments, the disease is associated with abnormal expression and/or activity of SIK3. In some embodiments, the disease is associated with abnormal expression and/or activity of SIK2 and SIK3. In some embodiments, the methods provided herein further comprise identifying a patient who has been diagnosed as having abnormal expression and/or activity of one or more SIKs (e.g., SIK2 and/or SIK3).

In some embodiments, the disease is associated with elevated expression (i.e., overexpression) and/or activity of SIK2. In some embodiments, the disease is associated with elevated expression and/or activity of SIK3. In some embodiments, the disease is associated with elevated expression and/or activity of SIK2 and SIK3. In some embodiments, the methods provided herein further comprise identifying a patient who has been diagnosed as having elevated expression and/or activity of one or more SIKs (e.g., SIK2 and/or SIK3).

In some embodiments, the disease is selected from cancer, inflammatory bowel disease, diabetes, a skin pigmentation disease, osteoporosis, osteoarthritis, an inflammatory arthritide, and a musculoskeletal disease.

In some embodiments, the disease is cancer.

In some embodiments, the cancer is selected from ovarian cancer, breast cancer (e.g., triple negative breast cancer), acute myeloid leukemia (AML), and multiple myeloma.

In some embodiments, the disease is inflammatory bowel disease.

In some embodiments, the disease is diabetes.

In some embodiments, the disease is a skin pigmentation disease.

In some embodiments, the disease is osteoporosis.

In some embodiments, the disease is osteoarthritis.

In some embodiments, the disease is an inflammatory arthritide.

In some embodiments, the inflammatory arthritide is rheumatoid arthritis.

In some embodiments, the disease is a musculoskeletal disease.

In some embodiments, the treating comprises one or more of increasing bone formation, increasing bone anabolism, and increasing bone mass in the patient.

As used herein, the phrase "therapeutically effective amount" refers to the amount of active compound or pharmaceutical composition (e.g., an amount of any solid form or salt thereof as provided herein) that elicits the biological or medicinal response in a tissue, system, animal, individual or human that is being sought by a researcher, veterinarian, medical doctor, or other clinician. An appropriate "effective" amount in any individual case may be determined using techniques known to a skilled artisan.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In some embodiments, each component is "pharmaceutically acceptable" as defined herein (see e.g., *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009).

As used herein, the term "treating" or "treatment" refer to inhibiting the disease; for example, inhibiting a disease, condition, or disorder in a patient who is experiencing or displaying the pathology or symptomatology of the disease, condition, or disorder (i.e., arresting further development of the pathology and/or symptomatology) or ameliorating the disease; for example, ameliorating a disease, condition, or disorder in a patient who is experiencing or displaying the pathology or symptomatology of the disease, condition, or disorder (i.e., reversing the pathology and/or symptomatology) such as decreasing the severity of disease.

In some embodiments, the compounds provided herein, and pharmaceutically acceptable salts thereof, may be useful in preventing or reducing the risk of developing any of the diseases referred to herein; e.g., preventing or reducing the risk of developing a disease, condition, or disorder in a patient who may be predisposed to the disease, condition, or disorder but does not yet experience or display the pathology or symptomatology of the disease.

Combination Therapies

One or more additional therapeutic agents such as, for example, anti-inflammatory agents, steroids, immunosuppressants, anesthetics (e.g., for use in combination with a surgical procedure) or other agents useful for treating one or more of the diseases described herein can be used in combination with the compounds and salts provided herein.

Example anti-inflammatory agents include, but are not limited to, aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

Example steroids include, but are not limited to, corticosteroids such as cortisone, dexamethasone, hydrocortisone, methylprednisolone, prednisolone, and prednisone.

Example immunosuppressants include, but are not limited to, azathioprine, chlorambucil, cyclophosphamide, cyclosporine, daclizumab, infliximab, methotrexate, and tacrolimus.

Example anesthetics include, but are not limited, to local anesthetics (e.g., lidocaine, procain, ropivacaine) and general anesthetics (e.g., desflurane, enflurane, halothane, isoflurane, methoxyflurane, nitrous oxide, sevoflurane, mmobarbital, methohexital, thiamylal, thiopental, diazepam, lorazepam, midazolam, etomidate, ketamine, propofol, alfentanil, fentanyl, remifentanil, buprenorphine, butorphanol, hydromorphone levorphanol, meperidine, methadone, morphine, nalbuphine, oxymorphone, pentazocine).

Additional therapeutic agents that can be used in combination with the compounds provided herein include, but are not limited to therapeutic agents useful for the treatment of one or more of the diseases provided herein. For example, the compounds provided herein can be used in combination with one or more additional therapeutic agents useful for the treatment of osteoporosis, including, but not limited to, bisphosphonate agents, denosumab, raloxifene, teriparatide, abaloparatide, romosozumab, and the like.

In some embodiments, the additional therapeutic agent is administered simultaneously with a compound or salt provided herein. In some embodiments, the additional therapeutic agent is administered after administration of the compound or salt provided herein. In some embodiments, the additional therapeutic agent is administered prior to administration of the compound or salt provided herein. In some embodiments, the compound or salt provided herein is administered during a surgical procedure. In some embodiments, the compound or salt provided herein is administered in combination with an additional therapeutic agent during a surgical procedure.

Pharmaceutical Compositions and Formulations

When employed as pharmaceuticals, the compounds and salts provided herein can be administered in the form of pharmaceutical compositions. These compositions can be prepared as described herein or elsewhere, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. In some embodiments, the compounds, salts, and pharmaceutical compositions provided herein are suitable for parenteral administration. In some embodiments, the compounds, salts, and pharmaceutical compositions provided herein are suitable for intravenous administration.

In some embodiments, the compounds, salts, and pharmaceutical compositions provided herein are suitable for oral administration.

Also provided are pharmaceutical compositions which contain, as the active ingredient, a compound provided herein, or a pharmaceutically acceptable salt thereof, in combination with one or more pharmaceutically acceptable carriers (e.g., excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active ingredient can be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

It is appreciated that certain features of the disclosure, which are, for clarity, described in the context of separate embodiments, can also be provided in combination in a single embodiment (while the embodiments are intended to be combined as if written in multiply dependent form). Conversely, various features of the disclosure which are, for brevity, described in the context of a single embodiment, can also be provided separately or in any suitable subcombination.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Intermediate 1. tert-Butyl N-[2-[2-[5-[(3-methyloxetan-3-yl)methoxy]benzimidazol-1-yl]-8-quinolyl]-2-azaspiro[3.3]heptan-6-yl]carbamate

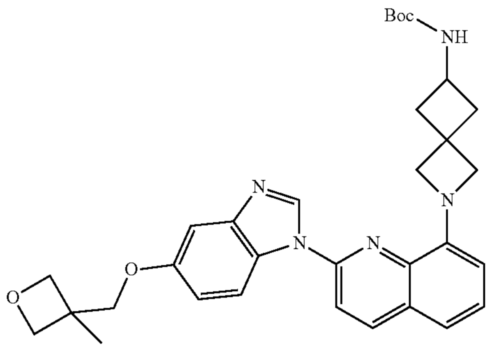 [SMILES: CC1(COc2ccc3c(c2)ncn3-c2ccc3cccc(N4CC5(CC(NC(=O)OC(C)(C)C)C5)C4)c3n2)COC1]

Step 1. 8-Benzyloxyquinolin-2-ol

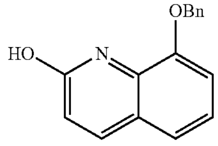 [SMILES: Oc1ccc2cccc(OCc3ccccc3)c2n1]

To a mixture of quinoline-2,8-diol (10 g, 62.05 mmol, 1 eq) in DMF (100 mL) was added $K_2CO_3$ (17.15 g, 124.10 mmol, 2 eq) and BnBr (11.14 g, 65.15 mmol, 7.74 mL, 1.05 eq) at 20° C., then the reaction mixture was heated at 60° C. for 12 h. The reaction mixture was poured into water (700 mL), then the mixture was filtered and the filter cake was dried in vacuum. The title compound was obtained as a white solid (14 g, crude).

Step 2. 8-Benzyloxy-2-chloro-quinoline

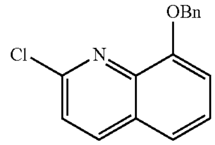 [SMILES: Clc1ccc2cccc(OCc3ccccc3)c2n1]

To a mixture of 8-benzyloxyquinolin-2-ol (14 g, 55.71 mmol, 1 eq) in DCE (200 mL) was added oxalyl chloride (17.68 g, 139.29 mmol, 12.19 mL, 2.5 eq) and DMF (4.07 g, 55.71 mmol, 4.29 mL, 1 eq), the resulting mixture was heated at 80° C. for 12 h. The reaction mixture was then washed with saturated aqueous $NaHCO_3$ (500 mL) and the water layer was extracted with DCM (200 mL, 3×). The combined organic layer was dried over $Na_2SO_4$ and concentrated to afford the title compound as a yellow solid (14 g, crude).

Step 3. 8-Benzyloxy-N-[4-[(3-methyloxetan-3-yl)methoxy]-2-nitro-phenyl]quinolin-2-amine

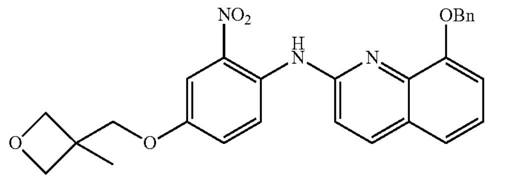 [SMILES: CC1(COc2ccc(Nc3ccc4cccc(OCc5ccccc5)c4n3)c([N+](=O)[O-])c2)COC1]

To a mixture of 8-benzyloxy-2-chloro-quinoline (10 g, 37.07 mmol, 1 eq) and 4-[(3-methyloxetan-3-yl)methoxy]-2-nitro-aniline (8.83 g, 37.07 mmol, 1 eq) in dioxane (200 mL) was added $Cs_2CO_3$ (24.16 g, 74.15 mmol, 2 eq), BINAP (2.31 g, 3.71 mmol, 0.1 eq), and $Pd_2(dba)_3$ (1.70 g, 1.85 mmol, 0.05 eq) at 20° C. The mixture was then stirred at 110° C. for 12 h under $N_2$. The reaction mixture was then concentrated to afford the crude product, which was washed with petroleum ether:ethyl acetate (300 mL, 5:1) and dried in vacuum. The title compound was obtained as red solid (15 g, 31.81 mmol, 85.81% yield). $^1$H NMR (400 MHz, DMSO-$d_6$) δ: 1.42 (s, 3H) 4.15 (s, 2H) 4.36 (d, J=5.88 Hz, 2H) 4.55 (d, J=5.75 Hz, 2H) 5.22 (s, 2H) 7.18-7.23 (m, 2H) 7.24-7.30 (m, 3H) 7.33-7.39 (m, 2H) 7.42 (t, J=7.44 Hz, 2H) 7.58 (d, J=7.38 Hz, 2H) 7.67 (d, J=3.00 Hz, 1H) 8.14 (d, J=8.88 Hz, 1H) 8.76 (d, J=9.26 Hz, 1H) 9.79 (s, 1H)

Step 4. 2-[2-Amino-4-[(3-methyloxetan-3-yl)methoxy]anilino]quinolin-8-ol

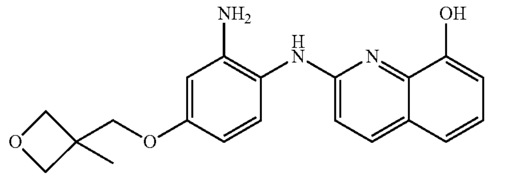 [SMILES: CC1(COc2ccc(Nc3ccc4cccc(O)c4n3)c(N)c2)COC1]

To a mixture of 8-benzyloxy-N-[4-[(3-methyloxetan-3-yl)methoxy]-2-nitro-phenyl]quinolin-2-amine (10 g, 21.21 mmol, 1 eq) in MeOH (300 mL) was added Pd/C (5 g, 10% purity) then the reaction mixture was stirred at 55° C. for 12 h under $H_2$ (15 psi). The reaction mixture was filtered and the filtrate was concentrated to afford the title compound as a red solid (6 g, crude).

Step 5. 2-[5-[(3-Methyloxetan-3-yl)methoxy]benzimidazol-1-yl]quinolin-8-ol

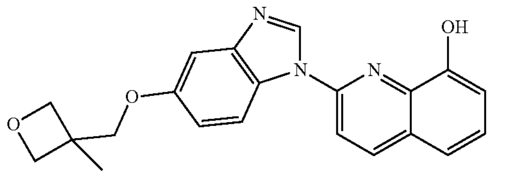 [SMILES: CC1(COc2ccc3c(c2)ncn3-c2ccc3cccc(O)c3n2)COC1]

To a mixture of 2-[2-amino-4-[(3-methyloxetan-3-yl)methoxy]anilino]quinolin-8-ol (4.5 g, 12.81 mmol, 1 eq) in trimethoxymethane (40 mL) was added HCOOH (1.85 g, 38.42 mmol, 3 eq) then the reaction mixture was stirred at 100° C. for 1 h. The reaction mixture was then cooled to 20° C., petroleum ether (PE) (50 mL) was added, then the mixture was filtered and the filter cake was dried in vacuum to afford the title compound as a red solid (3.2 g, 8.85 mmol, 69.14% yield). $^1$H NMR (400 MHz, DMSO-$d_6$) δ: 1.42 (s, 3H) 4.16 (s, 2H) 4.35 (d, J=5.75 Hz, 2H) 4.56 (d, J=5.75 Hz, 2H) 7.11 (dd, J=8.94, 2.44 Hz, 1H) 7.22 (dd, J=7.19, 1.56 Hz, 1H) 7.39 (d, J=2.38 Hz, 1H) 7.41-7.50 (m, 2H) 8.14 (d, J=8.88 Hz, 1H) 8.55 (d, J=9.00 Hz, 1H) 8.64 (d, J=8.88 Hz, 1H) 9.28 (s, 1H)

Step 6. [2-[5-[(3-Methyloxetan-3-yl)methoxy]benzimidazol-1-yl]-8-quinolyl]trifluoromethanesulfonate

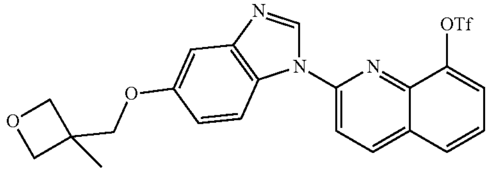 [SMILES: CC1(COc2ccc3c(c2)ncn3-c2ccc3cccc(OS(=O)(=O)C(F)(F)F)c3n2)COC1]

To a mixture of 2-[5-[(3-methyloxetan-3-yl)methoxy]benzimidazol-1-yl]quinolin-8-ol (1.5 g, 4.15 mmol, 1 eq) in DMF (10 mL) was added $Et_3N$ (840.00 mg, 8.30 mmol, 1.16 mL, 2 eq) and 1,1,1-trifluoro-N-phenyl-N-(trifluoromethylsulfonyl)methanesulfonamide (1.63 g, 4.57 mmol, 1.1 eq) at 20° C., and the reaction mixture was stirred at 20° C. for 1 h. The reaction mixture was poured into ice-water (100 mL) and extracted with EtOAc (50 mL, 4×). The combined organic layer was dried over $Na_2SO_4$ and concentrated to afford the title compound as a red solid (1.0 g, crude).

Step 8. N-[2-[2-[5-[(3-Methyloxetan-3-yl)methoxy]benzimidazol-1-yl]-8-quinolyl]-2-azaspiro[3.3]heptan-6-yl]carbamate

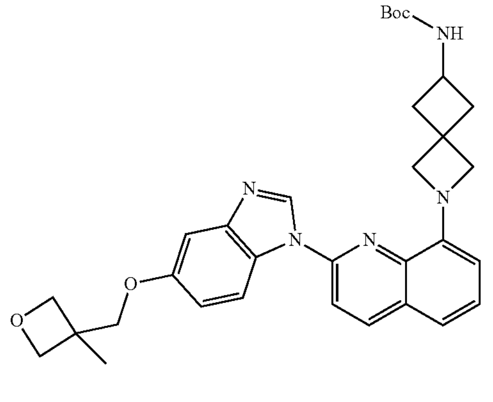 [SMILES: CC1(COc2ccc3c(c2)ncn3-c2ccc3cccc(N4CC5(CC(NC(=O)OC(C)(C)C)C5)C4)c3n2)COC1]

To a mixture of [2-[5-[(3-methyloxetan-3-yl)methoxy]benzimidazol-1-yl]-8-quinolyl]trifluoromethanesulfonate (200 mg, 405.31 μmol, 1 eq) and tert-butyl N-(2-azaspiro[3.3]heptan-6-yl)carbamate (86.04 mg, 405.31 μmol, 1 eq) in toluene (10 mL) was added $Cs_2CO_3$ (264.11 mg, 810.61 μmol, 2 eq), BINAP (50.47 mg, 81.06 μmol, 0.2 eq), and $Pd_2(dba)_3$ (37.11 mg, 40.53 μmol, 0.1 eq), and the reaction mixture was stirred at 100° C. for 12 h under $N_2$. The reaction mixture was then filtered, the filtrate was concentrated then purified by prep-TLC (ethyl acetate:methanol=10:1) to afford the title compound as a yellow oil (170 mg, 305.94 μmol, 75.48% yield).

Intermediates 2-7

Intermediates 2-7 were prepared according to the procedures described for Intermediate 1, using appropriately substituted starting materials.

TABLE 1

| Int. No. | Chemical Name | Structure | Amount (mg) | Purity (%) |
|---|---|---|---|---|
| 2 | tert-butyl 7-(2-(5-((3-methyloxetan-3-yl)methoxy)-1H-benzo[d]imidazol-1-yl)quinolin-8-yl)-1,7-diazaspiro[3.5]nonane-1-carboxylate | 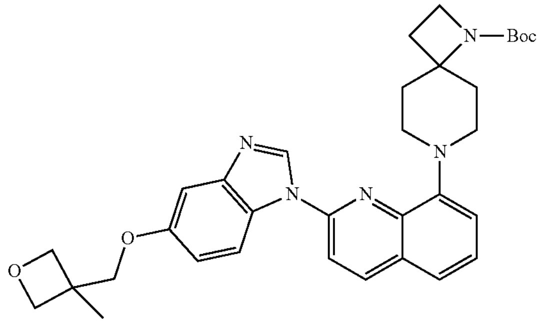 [SMILES: CC1(COc2ccc3c(c2)ncn3-c2ccc3cccc(N4CCC5(CC4)CCN5C(=O)OC(C)(C)C)c3n2)COC1] | 25.9 | 95.88 |
| 3 | tert-butyl 9-(2-(5-((3-methyloxetan-3-yl)methoxy)-1H-benzo[d]imidazol-1-yl)quinolin-8-yl)-4-oxa-1,9-diazaspiro[5.5]undecane-1-carboxylate | 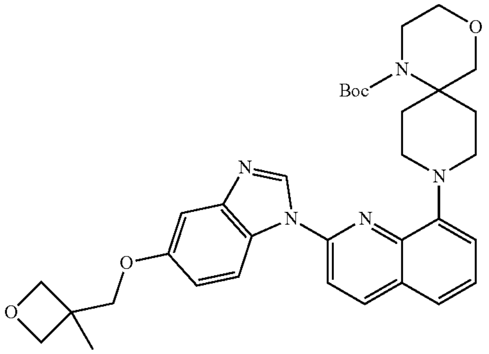 [SMILES: CC1(COc2ccc3c(c2)ncn3-c2ccc3cccc(N4CCC5(CC4)COCCN5C(=O)OC(C)(C)C)c3n2)COC1] | 85 | Crude |
| 4 | tert-butyl 7-(2-(5-((3-methyloxetan-3-yl)methoxy)-1H-benzo[d]imidazol-1-yl)quinolin-8-yl)-1,7-diazaspiro[3.5]nonane-1-carboxylate | 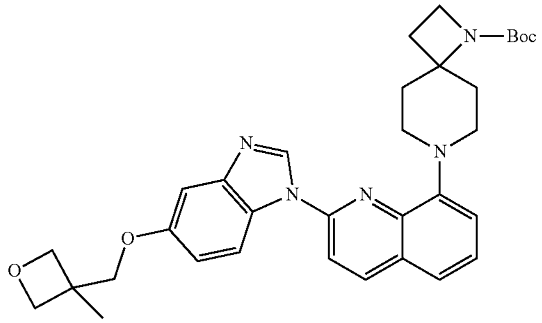 [SMILES: CC1(COc2ccc3c(c2)ncn3-c2ccc3cccc(N4CCC5(CC4)CCN5C(=O)OC(C)(C)C)c3n2)COC1] | 90 | Crude |
| 5 | tert-butyl 7-(2-(5-((3-methyloxetan-3-yl)methoxy)-1H-benzo[d]imidazol-1-yl)quinolin-8-yl)-2,7-diazaspiro[4.4]nonane-2-carboxylate | 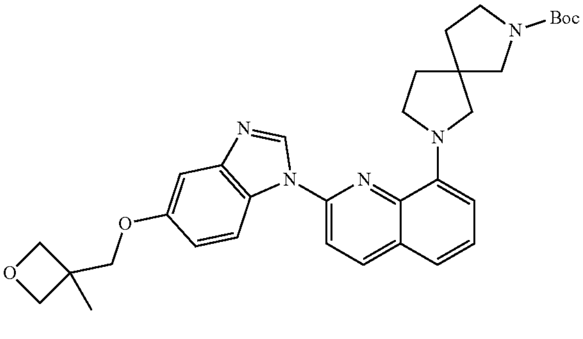 [SMILES: CC1(COc2ccc3c(c2)ncn3-c2ccc3cccc(N4CCC5(CCN(C(=O)OC(C)(C)C)C5)C4)c3n2)COC1] | 11.4 | 95.3 |

TABLE 1-continued

| Int. No. | Chemical Name | Structure | Amount (mg) | Purity (%) |
|---|---|---|---|---|
| 6 | tert-butyl (1-(2-(5-((3-methyloxetan-3-yl)methoxy)-1H-benzo[d]imidazol-1-yl)quinolin-8-yl)azetidin-3-yl)carbamate | 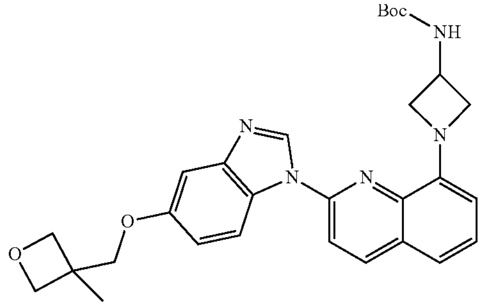 [SMILES: CC1(COc2ccc3c(c2)ncn3-c2ccc3cccc(N4CC(NC(=O)OC(C)(C)C)C4)c3n2)COC1] | 28.2 | 97.6 |
| 7 | tert-butyl ((1-(2-(5-((3-methyloxetan-3-yl)methoxy)-1H-benzo[d]imidazol-1-yl)quinolin-8-yl)pyrrolidin-2-yl)methyl)carbamate | 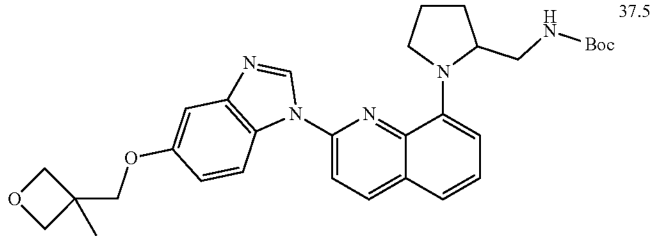 | 37.5 | Crude |

Intermediate 8. tert-Butyl 3-[[2-[5-[(3-methyloxetan-3-yl) methoxy]benzimidazol-1-yl]-8-quinolyl]oxy]azetidine-1-carboxylate

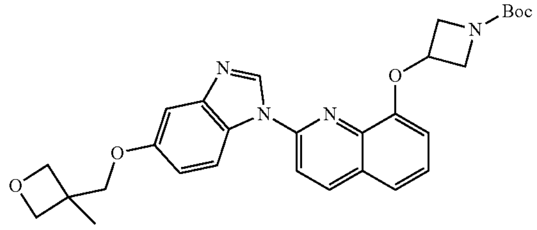 [SMILES: CC1(COc2ccc3c(c2)ncn3-c2ccc3cccc(OC4CN(C(=O)OC(C)(C)C)C4)c3n2)COC1]

A mixture of 2-[5-[(3-methyloxetan-3-yl)methoxy]benzimidazol-1-yl]quinolin-8-ol (200 mg, 553.41 μmol, 1 eq), tert-butyl 3-hydroxyazetidine-1-carboxylate (124.61 mg, 719.44 μmol, 1.3 eq), and 2-(tributyl-phosphanylidene)acetonitrile (200.35 mg, 830.12 μmol, 1.5 eq) in toluene (3 mL) was degassed and purged with $N_2$ (3×), and then the mixture was stirred at 100° C. for 12 h under $N_2$. The reaction mixture was then concentrated to afford the title compound, which was purified by prep-TLC ($SiO_2$, ethyl acetate:methanol, 10:1) as a yellow solid (100 mg, 193.58 μmol, 34.98% yield).

Intermediate 9. tert-Butyl 4-oxa-1,9-diazaspiro[5.5] undecane-1-carboxylate

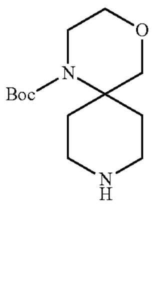

Step 1. 8-Benzyl-1,3,8-triazaspiro[4.5]decane-2,4-dione

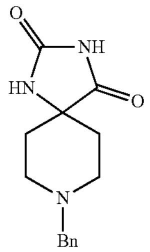 [SMILES: O=C1NC(=O)C2(CCN(Cc3ccccc3)CC2)N1]

N A solution of 1-benzylpiperidin-4-one (29.4 g, 155.4 mmol, 28.8 mL, 1 eq) in MeOH (210 mL) was added to a solution of ammoniacarbonic acid (45.4 g, 574.8 mmol, 47.3 mL, 3.7 eq) in $H_2O$ (210 mL). The mixture was cooled to 0° C. and a solution of NaCN (7.7 g, 157.1 mmol, 1.0 eq) in $H_2O$ (20 mL) was added drop-wise over 10 min, and the reaction mixture was stirred at 25° C. for 20 h. The reaction mixture was then filtered and the filter cake was concentrated under reduced pressure to afford the title compound as a white solid (42 g, crude).

Step 2. 4-Amino-1-benzyl-piperidine-4-carboxylic acid

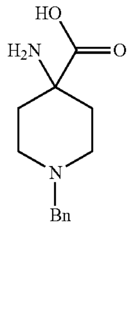

A mixture of 8-benzyl-1,3,8-triazaspiro[4.5]decane-2,4-dione (42 g, 161.9 mmol, 1 eq), $LiOH{\cdot}H_2O$ (33.9 g, 809.9 mmol, 5 eq) in $H_2O$ (500 mL), was stirred at 100° C. for 12 h. The reaction mixture was filtered and HCl (12N) was added to the solution until to pH ~2. The mixture was filtered and the filter cake was concentrated under reduced pressure to afford the title compound as a white solid (21 g, crude).

Step 3. (4-Amino-1-benzyl-4-piperidyl)methanol

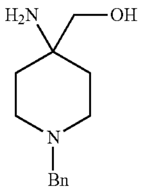 [SMILES: NC1(CO)CCN(Cc2ccccc2)CC1]

$LiAlH_4$ (3.2 g, 85.4 mmol, 2 eq) was added portionwise to a mixture of 4-amino-1-benzyl-piperidine-4-carboxylic acid (10 g, 42.68 mmol, 1 eq) in THE (200 mL) at 0° C. After addition, the reaction mixture was stirred at 70° C. for 3 h under $N_2$. The mixture was then cooled to 20° C., 10 mL water was added, followed by addition of NaOH (15 mL, 1M). The resulting mixture was stirred at 20° C. for 10 min and filtered. The filtrate was concentrated to afford the title compound as a yellow oil.

Step 4. 9-Benzyl-4-oxa-1,9-diazaspiro[5.5]undecan-2-one

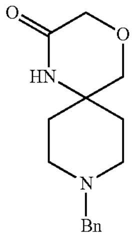 [SMILES: O=C1COCC2(CCN(Cc3ccccc3)CC2)N1]

A solution of 2-chloroacetyl chloride (974.0 mg, 8.6 mmol, 685.9 μL, 0.9 eq) in DCM (20 mL) was added dropwise to a mixture of (4-amino-1-benzyl-4-piperidyl) methanol (2.0 g, 9.1 mmol, 1 eq) and $Et_3N$ (918.6 mg, 9.1 mmol, 1.3 mL, 1 eq) in DCM (10 mL) at 0° C., then the resulting mixture was stirred at 20° C. for 12 h. The reaction mixture was concentrated and the resulting residue was dissolved in THE (20 mL), t-BuOK (3.1 g, 27.2 mmol, 3 eq) was added, and the reaction mixture was stirred at 20° C. for 1 h. The reaction mixture was concentrated and the crude product was purified by column chromatography on silica gel (ethyl acetate:methanol=1:0 to 10:1) to afford the title compound as a yellow solid (1.3 g, 4.9 mmol, 55.0% yield).

Step 5. 9-Benzyl-4-oxa-1,9-diazaspiro[5.5]undecane

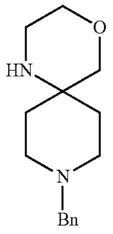

$LiAlH_4$ (947.7 mg, 24.9 mmol, 5 eq) was added portionwise to a mixture of 9-benzyl-4-oxa-1,9-diazaspiro[5.5]undecan-2-one (1.3 g, 5.0 mmol, 1 eq) in THE (50 mL) at 0° C. After addition, the reaction mixture was stirred at 70° C. for 4 h. The reaction mixture was cooled to 0° C. and water (1 mL) was added, followed by addition of NaOH (1 mL, aqueous, 1 M). After addition, the reaction mixture was stirred at 20° C. for 10 min and then filtered. The filtrate was dried over $Na_2SO_4$ and concentrated to afford the title compound as a yellow oil (1.2 g, crude).

Step 6. tert-Butyl 9-benzyl-4-oxa-1,9-diazaspiro[5.5]undecane-1-carboxylate

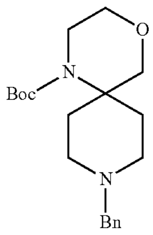

To a mixture of 9-benzyl-4-oxa-1,9-diazaspiro[5.5]undecane (500 mg, 2.03 mmol, 1 eq) in DCM (10 mL) was added $Boc_2O$ (442.9 mg, 2.0 mmol, 466.3 μL, 1 eq), then the reaction mixture was stirred at 20° C. for 12 h. The reaction mixture was concentrated and the crude product was purified by flash column chromatography on silica gel (petroleum ether:ethyl acetate=2:1) to afford the title compound as a yellow oil (500 mg, 1.4 mmol, 71.1% yield).

Step 7. tert-Butyl 4-oxa-1,9-diazaspiro[5.5]undecane-1-carboxylate

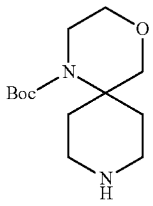

To a mixture of tert-butyl 9-benzyl-4-oxa-1,9-diazaspiro[5.5]undecane-1-carboxylate (200 mg, 577.3 μmol, 1 eq) in MeOH (5 mL) was added Pd/C (100 mg, 10% purity) and ammonia, formic acid (182.0 mg, 2.9 mmol, 5 eq) at 25° C., then the reaction mixture was stirred at 70° C. for 1 h. The reaction mixture was filtered and the filtrate was concentrated to afford the title compounds as a yellow oil (150 mg, crude).

Intermediate 10. Benzo[d]oxazol-2-ylmethanamine

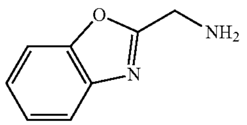 [SMILES: NCc1nc2ccccc2o1]

Step 1. Benzyl N-[2-(2-hydroxyanilino)-2-oxo-ethyl]carbamate

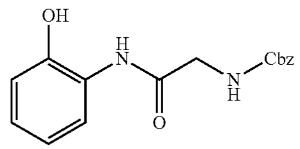 [SMILES: O=C(CNC(=O)OCc1ccccc1)Nc1ccccc1O]

To a solution of 2-(benzyloxycarbonylamino)acetic acid (6.33 g, 30.2 mmol, 1.1 eq) 2-aminophenol (3 g, 27.5 mmol, 1 eq) in DMF (20 mL) was added DIEA (7.11 g, 55.0 mmol, 9.58 mL, 2 eq), HATU (12.5 g, 33.0 mmol, 1.2 eq) in one portion at 25° C. The mixture was stirred at 25° C. for 12 h. The reaction mixture was quenched by addition water 100 mL, extracted with EtOAc 200 mL. The combined organic layers were washed with brine 100 mL, dried over $Na_2SO_4$, filtered, and concentrated under reduced pressure to give a residue. The crude product was triturated with EtOAc (30 mL) at 25° C. for 10 min, filtered and concentrated under reduced pressure to afford the title compound (3.6 g, crude) as a yellow solid.

Step 2. Benzyl N-(1,3-benzoxazol-2-ylmethyl)carbamate

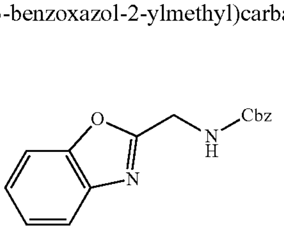

A mixture of benzyl N-[2-(2-hydroxyanilino)-2-oxo-ethyl]carbamate (3.6 g, 12.0 mmol, 1 eq) in propionic acid (19.9 g, 268 mmol, 20 mL, 22.4 eq) and then the mixture was stirred at 130° C. for 12 h. The reaction mixture was concentrated under reduced pressure to give a residue. The residue was purified by column ($SiO_2$, Petroleum ether/Ethyl acetate=50:1 to 3:1) to afford the title compound (2.1 g, crude) as a yellow solid.

Step 3. 1,3-Benzoxazol-2-ylmethanamine

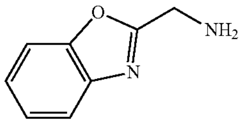 [SMILES: NCc1nc2ccccc2o1]

A mixture of benzyl N-(1,3-benzoxazol-2-ylmethyl)carbamate (0.5 g, 1.77 mmol, 1 eq), Pd/C (500 mg, 10% purity) in MeOH (50 mL), $NH_3{\cdot}H_2O$ (2 mL) was degassed and purged with $H_2$ (3×), and then the mixture was stirred at 25° C. for 2 h under $H_2$ (15 psi) atmosphere. The resulting mixture was then filtered and the filtrate was concentrated to afford the title compound (235 mg, crude) as a red solid.

Intermediate 11. 1,2,3,4-Tetrahydrobenzo[4,5]imidazo[1,2-a]pyrazine

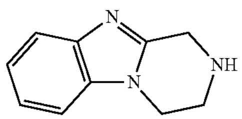 [SMILES: c1ccc2c(c1)nc1n2CCNC1]

To a mixture of NaOH (3 g, 75.0 mmol, 21.2 eq) in $H_2O$ (3 mL), was added 1H-benzimidazol-2-ylmethanamine (0.52 g, 3.53 mmol, 1 eq), tetrabutylammonium, bromide (45.6 mg, 141 μmol, 0.04 eq) was added the mixture, then the mixture was stirred at 25° C. for 1 h. Next, 1,2-dibromoethane (1.33 g, 7.07 mmol, 533 μL, 2 eq) dissolved in 10 mL of DMF was added drop-wise and the reaction mixture was stirred at 25° C. for 2 h. The mixture was then filtered and the filtrate was concentrated to give a crude product. The resulting residue was purified by prep-HPLC (basic condition, column: Waters Xbridge Prep OBD C18 150*40 mm*10 um; mobile phase: [water(0.040% $NH_3H_2O$+10 mM $NH_4HCO_3$)-ACN]; B %: 5%-30%, 8 min) to afford the title compound (30 mg, crude) as a white solid.

Example 1. 8-(4-Methylimidazol-1-yl)-2-[5-[(3-methyloxetan-3-yl)methoxy]benzimidazol-1-yl]quinoline

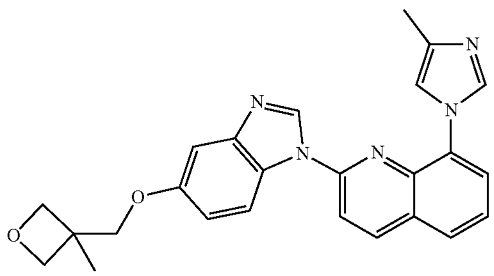 [SMILES: Cc1cn(-c2cccc3ccc(-n4cnc5cc(OCC6(C)COC6)ccc54)nc23)cn1]

A mixture of [2-[5-[(3-methyloxetan-3-yl)methoxy]benzimidazol-1-yl]-8-quinolyl]trifluoromethanesulfonate (Intermediate 1, Step 7, 0.1 g, 202.65 μmol, 1 eq), 4-methyl-1H-imidazole (24.96 mg, 303.98 μmol, 1.5 eq), $K_3PO_4$ (86.03 mg, 405.31 μmol, 2 eq), $Pd_2(dba)_3$ (92.79 mg, 101.33 μmol, 0.5 eq) and ditert-butyl-[2-(2,4,6-triisopropylphenyl)

phenyl]phosphane (43.03 mg, 101.33 μmol, 0.5 eq) in toluene (3 mL) and dioxane (0.6 mL) was degassed and purged with $N_2$ (3×), and then the mixture was stirred at 120° C. for 12 h under $N_2$ atmosphere. The reaction mixture was filtered, concentrated under reduced pressure, and purified by prep-HPLC (basic condition; column: Waters Xbridge Prep OBD C18 150*40 mm*10 m; mobile phase: [water (0.05% $NH_3H_2O$+10 mM $NH_4HCO_3$)-ACN]; B %: 35%-50%, 6 min) to afford the title compound as a white solid (4 mg, 9.38 μmol, 4.63% yield, 99.766% purity). $^1$H NMR (400 MHz, MeOD-$d_4$) δ=8.93-8.88 (m, 1H), 8.49 (d, J=9.0 Hz, 1H), 8.04-7.84 (m, 4H), 7.79 (dd, J=1.2, 7.4 Hz, 1H), 7.65-7.52 (m, 1H), 7.28-7.10 (m, 2H), 6.86 (dd, J=2.4, 9.0 Hz, 1H), 4.63-4.57 (m, 2H), 4.40-4.36 (m, 2H), 4.04-3.95 (m, 2H), 5.22-3.55 (m, 1H), 5.22-3.55 (m, 1H), 2.32-2.23 (m, 3H), 1.39-1.35 (m, 3H).

Example 2. 2-[2-[5-[(3-Methyloxetan-3-yl)methoxy]benzimidazol-1-yl]-8-quinolyl]-2-azaspiro[3.3]heptan-6-amine

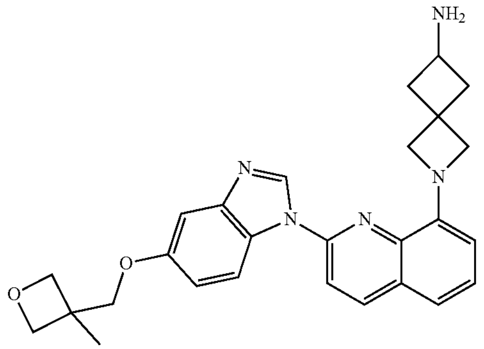 [SMILES: CC1(COc2ccc3c(c2)ncn3-c2ccc3cccc(N4CC5(CC(N)C5)C4)c3n2)COC1]

A mixture of tert-butyl N-[2-[2-[5-[(3-methyloxetan-3-yl)methoxy]benzimidazol-1-yl]-8-quinolyl]-2-azaspiro[3.3]heptan-6-yl]carbamate (Intermediate 1, 50 mg, 89.98 μmol, 1 eq) in trifluoroacetic acid (TFA, 1 mL) and DCM (5 mL) was stirred at 20° C. for 16 h. The reaction mixture was concentrated, and $NH_3 \cdot H_2O$ was added to pH=7. The crude product was purified by prep-HPLC (Waters Xbridge BEH C18 100×30 mm×10 μm; mobile phase: [water (10 mM $NH_4HCO_3$)-ACN]; B %: 40%-65%, 10 min) to afford the title compound as a yellow solid (14.7 mg, 29.49 μmol, 32.77% yield, 91.393% purity). $^1$H NMR (400 MHz, DMSO-$d_6$) δ: 1.42 (s, 3H) 1.84-1.93 (m, 2H) 2.36-2.41 (m, 2H) 3.20-3.24 (m, 1H) 4.08-4.25 (m, 6H) 4.35 (d, J=5.75 Hz, 2H) 4.56 (d, J=5.75 Hz, 2H) 6.65 (br d, J=6.63 Hz, 1H) 7.11 (br d, J=8.76 Hz, 1H) 7.32 (d, J=7.75 Hz, 1H) 7.39-7.45 (m, 2H) 7.97 (d, J=8.88 Hz, 1H) 8.14 (d, J=9.01 Hz, 1H) 8.49 (d, J=8.88 Hz, 1H) 8.95 (s, 1H).

Examples 3-9

Examples 3-9 were prepared according to the procedures described in Example 1, beginning with the appropriate Intermediate compound described above. NMR data for the compounds of Examples 3 and 6-9 are shown in Table 2B.

TABLE 2A

| Ex. No. | Compound Name | Structure | Amount (mg) | Purity (%) |
|---|---|---|---|---|
| 3 | 2-(5-((3-methyloxetan-3-yl)methoxy)-1H-benzo[d]imidazol-1-yl)-8-(1,7-diazaspiro[3.5]nonan-7-yl)quinoline | 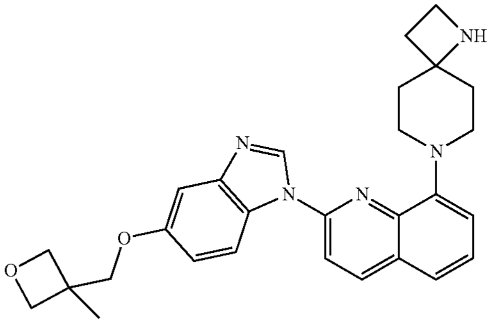 [SMILES: CC1(COc2ccc3c(c2)ncn3-c2ccc3cccc(N4CCC5(CCN5)CC4)c3n2)COC1] | 25.9 | 95.88 |
| 6 | 2-(5-((3-methyloxetan-3-yl)methoxy)-1H-benzo[d]imidazol-1-yl)-8-(2,7-diazaspiro[4.4]nonan-2-yl)quinoline | 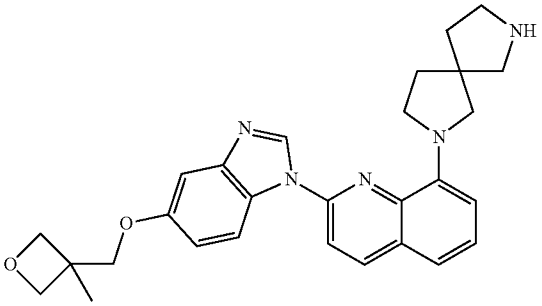 [SMILES: CC1(COc2ccc3c(c2)ncn3-c2ccc3cccc(N4CCC5(CCNC5)C4)c3n2)COC1] | 11.4 | 95.3 |

TABLE 2A-continued

| Ex. No. | Compound Name | Structure | Amount (mg) | Purity (%) |
|---|---|---|---|---|
| 7 | 1-(2-(5-((3-methyloxetan-3-yl)methoxy)-1H-benzo[d]imidazol-1-yl)quinolin-8-yl)azetidin-3-amine | 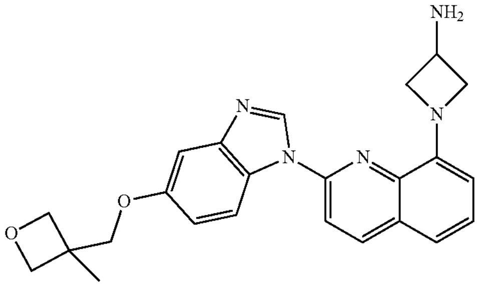 [SMILES: CC1(COc2ccc3c(c2)ncn3-c2ccc3cccc(N4CC(N)C4)c3n2)COC1] | 28.2 | 97.6 |
| 8 | (1-(2-(5-((3-methyloxetan-3-yl)methoxy)-1H-benzo[d]imidazol-1-yl)quinolin-8-yl)pyrrolidin-2-yl)methanamine | 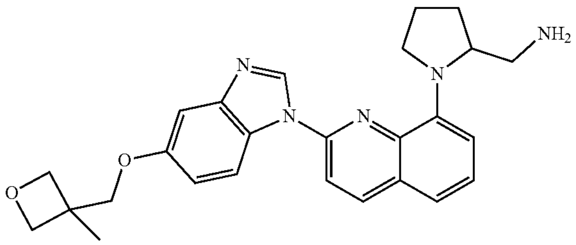 [SMILES: CC1(COc2ccc3c(c2)ncn3-c2ccc3cccc(N4CCCC4CN)c3n2)COC1] | 37.5 | Crude |
| 9 | 8-(azetidin-3-yloxy)-2-(5-((3-methyloxetan-3-yl)methoxy)-1H-benzo[d]imidazol-1-yl)quinoline | 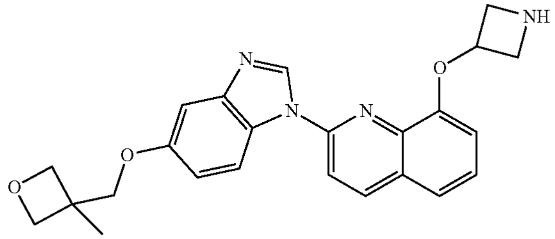 [SMILES: CC1(COc2ccc3c(c2)ncn3-c2ccc3cccc(OC4CNC4)c3n2)COC1] | 9.3 | 99.1 |

TABLE 2B

| Ex. No. | 1H-NMR Data |
|---|---|
| 3 | 400 MHz, DMSO-$d_6$, δ: 1.43 (s, 3 H) 1.85-2.18 (m, 6 H) 2.64-2.78 (m, 2 H) 3.06 (br s, 2 H) 3.76 (br d, J = 7.75 Hz, 2 H) 4.16 (br s, 2 H) 4.35 (d, J = 5.75 Hz, 2 H) 4.56 (d, J = 5.75 Hz, 2 H) 7.08-7.19 (m, 1 H) 7.28-7.34 (m, 1 H) 7.40 (br s, 1 H) 7.50 (br t, J = 7.69 Hz, 1 H) 7.59-7.66 (m, 1 H) 8.13-8.24 (m, 1 H) 8.55 (d, J = 8.88 Hz, 1 H) 8.83-9.01 (m, 1 H) 9.16-9.23 (m, 1 H) |
| 6 | 400 MHz, DMSO-$d_6$, δ: 1.34-1.47 (m, 3 H) 1.88-2.13 (m, 4 H) 3.15-3.25 (m, 4 H) 3.66-3.68 (m, 1 H) 3.67 (br s, 1 H) 3.79-3.85 (m, 2 H) 4.11-4.17 (m, 2 H) 4.30-4.37 (m, 2 H) 4.50-4.59 (m, 2 H) 6.91-6.97 (m, 1 H) 7.08-7.13 (m, 1 H) 7.35-7.49 (m, 3 H) 7.97-8.02 (m, 1 H) 8.13-8.18 (m, 1 H) 8.35-8.41 (m, 1 H) 8.48-8.53 (m, 1 H) 8.95-9.03 (m, 1 H) |
| 7 | 400 MHz, DMSO-$d_6$, δ: 1.41 (s, 3 H) 3.69-3.75 (m, 2 H) 3.80-3.89 (m, 1 H) 4.13-4.17 (m, 2 H) 4.31-4.36 (m, 2 H) 4.46-4.57 (m, 4 H) 6.66 (d, J = 7.63 Hz, 1 H) 7.12 (dd, J = 8.82, 2.06 Hz, 1 H) 7.31 (d, J = 8.00 Hz, 1 H) 7.37-7.47 (m, 2 H) 7.96 (d, J = 8.76 Hz, 1 H) 8.07-8.16 (m, 1 H) 8.49 (d, J = 8.75 Hz, 1 H) 8.92 (s, 1 H) |
| 8 | 400 MHz, DMSO-$d_6$, δ: 9.06 (s, 1H), 8.51 (d, J = 9.0 Hz, 1H), 8.34-8.27 (m, 1H), 8.03 (d, J = 8.9 Hz, 1H), 7.51-7.36 (m, 3H), 7.16-7.04 (m, 2H), 4.56 (d, J = 5.6 Hz, 2H), 4.47 (br s, 1H), 4.34 (d, J = 5.7 Hz, 2H), 4.15 (s, 2H), 4.13-4.05 (m, 1H), 3.43 (br d, J = 4.4 Hz, 1H), 3.28-3.24 (m, 1H), 2.63-2.57 (m, 1H), 2.46-2.42 (m, 1H), 2.16 (br d, J = 7.5 Hz, 1H), 2.04-1.83 (m, 3H), 1.42 (s, 3H) |
| 9 | 400 MHz, MeOD-$d_4$, δ: 9.03 (s, 1H), 8.91 (d, J = 9.0 Hz, 1H), 8.47 (d, J = 8.9 Hz, 1H), 8.03 (d, J = 8.9 Hz, 1H), 7.61-7.55 (m, 1H), 7.50 (t, J = 7.9 Hz, 1H), 7.34 (d, J = 2.1 Hz, 1H), 7.19 (dd, J = 2.2, 8.9 Hz, 1H), 7.01 (d, J = 7.6 Hz, 1H), 5.35 (br t, J = 5.9 Hz, 1H), 4.75 (br d, J = 5.9 Hz, 2H), 4.51 (d, J = 5.9 Hz, 2H), 4.23-4.13 (m, 4H), 4.03-3.96 (m, 2H), 1.51 (s, 3H) |

Example 10. 1-Methyl-9-[2-[5-[(3-methyloxetan-3-yl)methoxy]benzimidazol-1-yl]-8-quinolyl]-4-oxa-1,9-diazaspiro[5.5]undecane

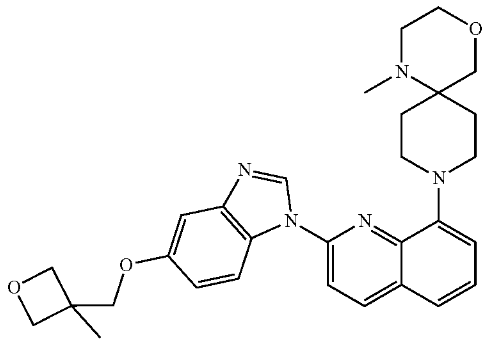 [SMILES: CN1CCOCC12CCN(c1cccc3ccc(-n4cnc5cc(OCC6(C)COC6)ccc54)nc13)CC2]

To a solution of 9-[2-[5-[(3-methyloxetan-3-yl)methoxy]benzimidazol-1-yl]-8-quinolyl]-4-oxa-1,9-diazaspiro[5.5]undecane (Example 4, 85 mg, 170.1 μmol, 1 eq) in MeOH (4 mL) was added AcOH (10.2 mg, 170.1 μmol, 1 eq) to pH ~5, then HCHO (25.5 mg, 850.7 mol, 5 eq) was added at 0° C. The mixture was then stirred at 25° C. for 0.5 h. Next, $NaBH_3CN$ (32.1 mg, 510.4 μmol, 3 eq) was added and the mixture was stirred at 25° C. for 12 h. The reaction mixture was filtered and concentrated under reduced pressure and the resulting residue was purified by prep-HPLC (basic condition, column: Waters Xbridge Prep OBD C18 150*40 mm*10 m; mobile phase: [water(0.04% $NH_3H_2O$+10 mM $NH_4HCO_3$)-ACN]; B %: 30%-55%, 10 min) to afford the title compound as a light yellow solid (32.1 mg, 62.3 μmol, 36.6% yield, 99.6% purity). $^1$H NMR (400 MHz, DMSO-$d_6$) δ: 9.15 (s, 1H), 8.86 (d, J=8.8 Hz, 1H), 8.53 (d, J=9.3 Hz, 1H), 8.12 (d, J=9.0 Hz, 1H), 7.60 (d, J=7.7 Hz, 1H), 7.48 (t, J=7.9 Hz, 1H), 7.40 (d, J=2.2 Hz, 1H), 7.32 (d, J=8.2 Hz, 1H), 7.07-6.98 (m, 1H), 4.52 (d, J=5.7 Hz, 2H), 4.32 (d, J=5.7 Hz, 2H), 4.13 (s, 2H), 3.62 (br d, J=8.6 Hz, 6H), 2.91 (br t, J=11.1 Hz, 2H), 2.59 (br s, 2H), 2.40 (s, 3H), 2.25-2.10 (m, 2H), 1.64 (br d, J=13.0 Hz, 2H), 1.39 (s, 3H).

Example 11. 8-((1-Methylazetidin-3-yl)oxy)-2-(5-((3-methyloxetan-3-yl)methoxy)-1H-benzo[d]imidazol-1-yl)quinoline

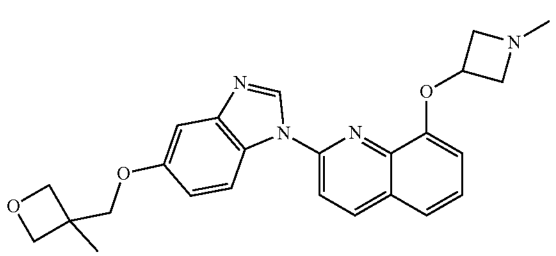 [SMILES: CN1CC(Oc2cccc3ccc(-n4cnc5cc(OCC6(C)COC6)ccc54)nc23)C1]

The title compound was prepared according to the procedures described for Example 10, substituting 8-(azetidin-3-yloxy)-2-(5-((3-methyloxetan-3-yl)methoxy)-1H-benzo[d]imidazol-1-yl)quinoline for 9-[2-[5-[(3-methyloxetan-3-yl)methoxy]benzimidazol-1-yl]-8-quinolyl]-4-oxa-1,9-diazaspiro[5.5]undecane. $^1$H NMR (400 MHz, MeOD-$d_4$) δ: 9.00 (s, 1H), 8.89 (d, J=9.0 Hz, 1H), 8.42 (d, J=8.9 Hz, 1H), 7.98 (d, J=8.9 Hz, 1H), 7.58-7.43 (m, 2H), 7.32 (d, J=2.3 Hz, 1H), 7.17 (dd, J=2.3, 9.0 Hz, 1H), 7.02 (d, J=7.4 Hz, 1H), 5.09 (br t, J=5.6 Hz, 1H), 4.75 (d, J=5.9 Hz, 2H), 4.51 (d, J=5.9 Hz, 2H), 4.15 (s, 2H), 4.05-3.96 (m, 2H), 3.49 (br dd, J=5.1, 9.3 Hz, 2H), 2.51 (s, 3H), 1.51 (s, 3H)

Example 12. 8-[1-(2-Methoxyethyl)-1,7-diazaspiro[3.5]nonan-7-yl]-2-[5-[(3-methyloxetan-3-yl)methoxy]benzimidazol-1-yl]quinoline

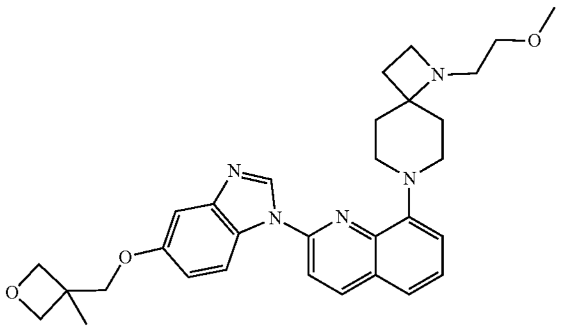 [SMILES: COCCN1CCC12CCN(c1cccc3ccc(-n4cnc5cc(OCC6(C)COC6)ccc54)nc13)CC2]

To a solution of 8-(1,7-diazaspiro[3.5]nonan-7-yl)-2-[5-[(3-methyloxetan-3-yl)methoxy]benzimidazol-1-yl]quinoline (Example 5, 75 mg, 160 μmol, 1 eq) and 1-bromo-2-methoxy-ethane (88.8 mg, 639 μmol, 60.0 uL, 4 eq) in MeCN (5 mL) was added diisopropylethylamine (DIEA, 61.9 mg, 479 μmol, 83.5 μL, 3 eq) at 25° C. The reaction mixture was then stirred at 60° C. for 12 h. The mixture was concentrated and the resulting residue was purified by prep-HPLC (basic condition column: Waters Xbridge Prep OBD C18 150*40 mm*10 μm; mobile phase: [water (0.040% $NH_3H_2O$+10 mM $NH_4HCO_3$)-ACN]; B %: 25%-55%, 10 min) to afford the title compound as a yellow solid (20.3 mg, 37.12 μmol, 23.24% yield, 96.481% purity). $^1$H NMR (400 MHz, DMSO-$d_6$) δ: 1.34-1.45 (m, 3H) 1.81-1.95 (m, 4H) 1.99-2.11 (m, 2H) 2.66-2.75 (m, 4H) 3.14-3.21 (m, 2H) 3.26-3.29 (m, 3H) 3.37-3.39 (m, 2H) 3.68-3.77 (m, 2H) 4.12-4.16 (m, 2H) 4.31-4.36 (m, 2H) 4.51-4.56 (m, 2H) 7.06-7.11 (m, 1H) 7.27-7.32 (m, 1H) 7.37-7.41 (m, 1H) 7.45-7.51 (m, 1H) 7.59-7.64 (m, 1H) 8.13-8.17 (m, 1H) 8.52-8.57 (m, 1H) 8.92-8.97 (m, 1H) 9.14-9.21 (m, 1H).

Example 13. 1-(2-(7-((3-Methyloxetan-3-yl)methoxy)imidazo[1,2-a]pyridin-3-yl)quinolin-8-yl)piperidin-4-amine

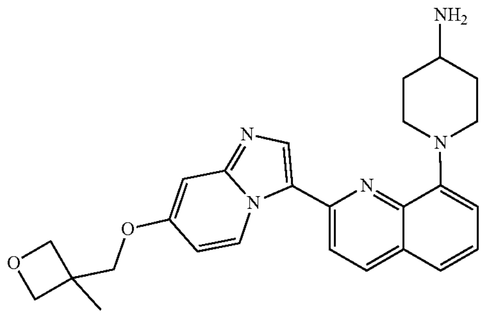 [SMILES: CC1(COc2ccn3c(-c4ccc5cccc(N6CCC(N)CC6)c5n4)cnc3c2)COC1]

Step 1. 4-[(3-Methyloxetan-3-yl)methoxy]pyridin-2-amine

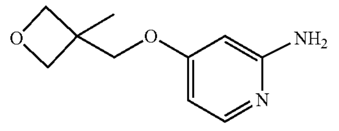

To a mixture of 4-chloropyridin-2-amine (5 g, 38.9 mmol, 1 eq) and (3-methyloxetan-3-yl)methanol (4.37 g, 42.8 mmol, 4.24 mL, 1.1 eq) in DMSO (150 mL) was added CsF (5.91 g, 38.9 mmol, 1.43 mL, 1 eq) and t-BuOK (8.73 g, 77.8 mmol, 2 eq) at 20° C. The mixture was then stirred at 85° C. for 12 h, followed by stirring at 90° C. for 12 h. The reaction mixture was added into $H_2O$ (100 mL), then extracted with EtOAc (100 mL, 3×). The combined organic phase was washed with $H_2O$ (100 mL), saturated aqueous $NH_4Cl$ (100 mL), and brine (50 mL), then dried over $Na_2SO_4$, filtered, and the filtrate was concentrated under reduced pressure. The resulting residue was purified by column chromatography ($SiO_2$, petroleum ether:ethyl acetate=10:1 to 0:1) to afford the title compound as a brown oil (3.19 g, crude).

Step 2. 7-[(3-Methyloxetan-3-yl)methoxy]imidazo[1,2-a]pyridine

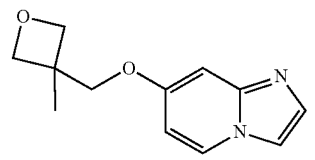 [SMILES: CC1(COc2ccn3ccnc3c2)COC1]

To a mixture of 4-[(3-methyloxetan-3-yl)methoxy]pyridin-2-amine (3.19 g, 16.4 mmol, 1 eq) in EtOH (150 mL) was added $NaHCO_3$ (5.52 g, 65.7 mmol, 2.56 mL, 4 eq) and 2-chloroacetaldehyde (4.83 g, 24.6 mmol, 3.96 mL, 1.5 eq) at 20° C. The mixture was then stirred at 80° C. for 3 h. The reaction mixture was concentrated under reduced pressure to remove EtOH, then extracted with EtOAc (100 mL, 3×). The combined organic phase was washed with saturated aqueous $NH_4Cl$ (50 mL) and brine (50 mL), then dried over $Na_2SO_4$ and filtered. The filtrate was concentrated under reduced pressure to afford the title compound as a brown oil (3.58 g, crude).

Step 3. 8-Benzyloxy-2-[7-[(3-methyloxetan-3-yl)methoxy]imidazo[1,2-a]pyridin-3-yl]quinoline

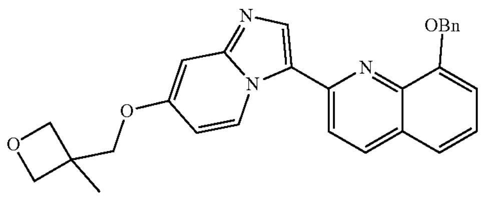 [SMILES: CC1(COc2ccn3c(-c4ccc5cccc(OCc6ccccc6)c5n4)cnc3c2)COC1]

To a solution of 7-[(3-methyloxetan-3-yl)methoxy]imidazo[1,2-a]pyridine (1 g, 4.58 mmol, 1 eq), 8-benzyloxy-2-chloro-quinoline (1.36 g, 5.04 mmol, 1.1 eq) and $K_2CO_3$ (1.27 g, 9.16 mmol, 2 eq) in dioxane (30 mL) was added water (0.5 mL), $Pd(OAc)_2$ (103 mg, 458 μmol, 0.1 eq), and $Pd(PPh_3)_4$ (529 mg, 458 μmol, 0.1 eq) at 15° C. under $N_2$. The mixture was then stirred at 100° C. for 12 h. The mixture was filtered, concentrated, and the resulting residue was purified by column chromatography ($SiO_2$, petroleum ether/ethyl acetate/methanol=3:1:0 to 0:5:1) to afford the title compound as a yellow oil (940 mg, crude).

Step 4. 2-[7-[(3-Methyloxetan-3-yl)methoxy]imidazo[1,2-a]pyridin-3-yl]quinolin-8-ol

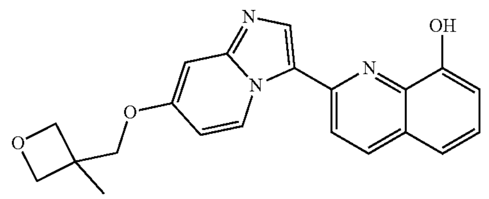 [SMILES: CC1(COc2ccn3c(-c4ccc5cccc(O)c5n4)cnc3c2)COC1]

A mixture of 8-benzyloxy-2-[7-[(3-methyloxetan-3-yl)methoxy]imidazo[1,2-a]pyridin-3-yl]quinoline (900 mg, 1.99 mmol, 1 eq) and Pd/C (900 mg, 10% purity) in MeOH (150 mL) was degassed and purged with $H_2$ (3×) then the mixture was stirred at 40° C. for 12 h under $H_2$ atmosphere (15 psi), followed by stirring at 45° C. for an additional 4 h under $H_2$ atmosphere (15 psi). The mixture was filtered and concentrated to afford the title compound as a yellow oil (395 mg, crude).

Step 5. [2-[7-[(3-Methyloxetan-3-yl)methoxy]imidazo[1,2-a]pyridin-3-yl]-8-quinolyl]trifluoromethanesulfonate

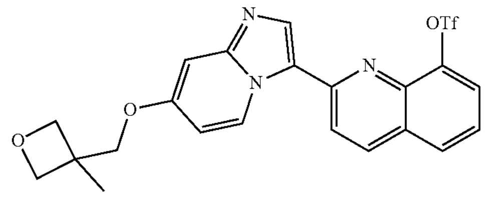 [SMILES: CC1(COc2ccn3c(-c4ccc5cccc(OS(=O)(=O)C(F)(F)F)c5n4)cnc3c2)COC1]

To a solution of 2-[7-[(3-methyloxetan-3-yl)methoxy]imidazo[1,2-a]pyridin-3-yl]quinolin-8-ol (180 mg, 498 μmol, 1 eq) and $Et_3N$ (101 mg, 996 μmol, 139 μL, 2 eq) in DMF (3 mL) was added 1,1,1-trifluoro-N-phenyl-N-(trifluoromethylsulfonyl)methanesulfonamide (196 mg, 548 μmol, 1.1 eq) at 20° C., and the mixture was stirred at 20° C. for 1 h. The mixture was filtered and the filter cake was dried to afford the title compound as a yellow solid (85 mg, crude).

Step 6. tert-Butyl N-[1-[2-[7-[(3-methyloxetan-3-yl)methoxy]imidazo[1,2-a]pyridin-3-yl]-8-quinolyl]-4-piperidyl]carbamate

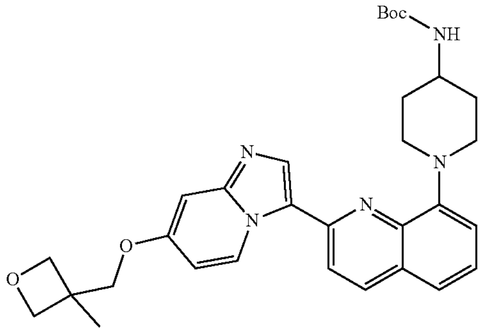 [SMILES: CC1(COc2ccn3c(-c4ccc5cccc(N6CCC(NC(=O)OC(C)(C)C)CC6)c5n4)cnc3c2)COC1]

A mixture of [2-[7-[(3-methyloxetan-3-yl)methoxy]imidazo[1,2-a]pyridin-3-yl]-8-quinolyl]trifluoromethanesulfonate (85 mg, 172 μmol, 1 eq), tert-butyl N-(4-piperidyl)carbamate (40.0 mg, 189 μmol, 1.1 eq), $Cs_2CO_3$ (112 mg, 345 μmol, 2 eq), BINAP (21.5 mg, 34.5 μmol, 0.2 eq) and $Pd_2(dba)_3$ (15.8 mg, 17.2 μmol, 0.1 eq) in toluene (4 mL) was degassed and purged with $N_2$ (3×), then the mixture was stirred at 100° C. for 16 h under $N_2$ atmosphere. The mixture was filtered, concentrated, and the resulting residue was purified by prep-TLC (ethyl acetate:methanol=5:1) to afford the title compound as a yellow oil (50 mg, crude).

Step 7. 1-[2-[7-[(3-Methyloxetan-3-yl)methoxy]imidazo[1,2-a]pyridin-3-yl]-8-quinolyl]piperidin-4-amine

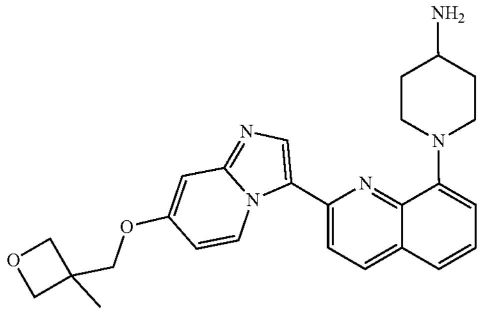 [SMILES: CC1(COc2ccn3c(-c4ccc5cccc(N6CCC(N)CC6)c5n4)cnc3c2)COC1]

A mixture of tert-butyl N-[1-[2-[7-[(3-methyloxetan-3-yl)methoxy]imidazo[1,2-a]pyridin-3-yl]-8-quinolyl]-4-piperidyl]carbamate (50 mg, 92.0 μmol, 1 eq) in DCM (2 mL) and TFA (0.2 mL) was stirred at 20° C. for 5 h. The DCM was removed under $N_2$, and MeOH (2 mL) was added. $NaHCO_3$ was added to the mixture to pH 7. The mixture was filtered, concentrated, and the resulting residue was purified by prep-HPLC (FA condition; column: Phenomenex Luna C18 100*30 mm*5 μm; mobile phase: [water(0.2% FA)-ACN]; B %: 5%-35%, 10 min) to afford the title compound as a yellow solid (4.3 mg, 8.23 μmol, 8.95% yield, 93.715% purity, FA). $^1$H NMR (400 MHz, DMSO-$d_6$) δ: 1.41-1.44 (m, 3H) 1.80-1.93 (m, 2H) 2.03-2.12 (m, 2H) 2.72-2.82 (m, 2H) 3.08 (br d, J=2.81 Hz, 1H) 3.76-3.80 (m, 2H) 4.22-4.26 (m, 2H) 4.33-4.38 (m, 2H) 4.53-4.58 (m, 2H) 7.24-7.31 (m, 3H) 7.42-7.47 (m, 1H) 7.53-7.57 (m, 1H) 8.11-8.14 (m, 1H) 8.28-8.32 (m, 1H) 8.36-8.48 (m, 2H) 8.52-8.56 (m, 1H) 10.39-10.46 (m, 1H).

Example 14. 3-(((1-(8-(4-Aminopiperidin-1-yl)quinoxalin-2-yl)-1H-benzo[d]imidazol-5-yl)oxy)methyl)thietane 1,1-dioxide

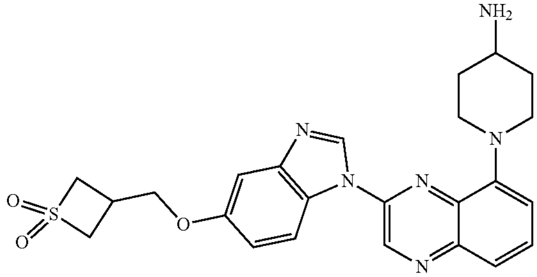 [SMILES: NC1CCN(c2cccc3ncc(-n4cnc5cc(OCC6CS(=O)(=O)C6)ccc54)nc23)CC1]

Step 1. 3-(Dimethoxymethyl)-3-pyrrolidin-1-yl-thietane 1,1-dioxide

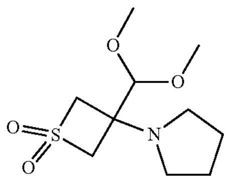 [SMILES: COC(OC)C1(N2CCCC2)CS(=O)(=O)C1]

A solution of methanesulfonyl chloride 7.36 g, 64.2 mmol, 4.97 mL, 1.1 eq) in diethyl ether (15 mL) was added to a mixture of 1-[1-(dimethoxymethyl)vinyl]pyrrolidine (10 g, 58.4 mmol, 1 eq) and $Et_3N$ (6.50 g, 64.2 mmol, 8.94 mL, 1.1 eq) in diethyl ether (30 mL) at 0° C., and the reaction mixture was then stirred at 20° C. for 1 h. The reaction mixture was poured into water (60 mL) and the water layer was extracted with DCM. The combined organic layer was dried over $Na_2SO_4$ and concentrated to afford the title compound as a yellow oil (13 g, crude). $^1$H NMR (400 MHz, $CDCl_3$) δ: 1.82 (br s, 4H) 2.78-2.86 (m, 4H) 3.56 (s, 6H) 4.09 (br d, J=14.38 Hz, 2H) 4.28 (br d, J=14.63 Hz, 2H) 4.44-4.55 (m, 1H).

Step 2: 3-(Dimethoxymethyl)-2H-thiete 1,1-dioxide

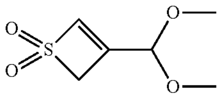

To a solution of methyl trifluoromethanesulfonate (11.3 g, 68.8 mmol, 7.53 mL, 1.1 eq) in DCM (20 mL) was added 3-(dimethoxymethyl)-3-pyrrolidin-1-yl-thietane 1,1-dioxide (15.6 g, 62.6 mmol, 1 eq) in DCM (100 mL) at 0° C., and the reaction mixture was then stirred at 20° C. for 18 h. $Et_3N$ (6.96 g, 68.8 mmol, 9.58 mL, 1.1 eq) in DCM (30 mL) was added and the resulting mixture was stirred at 45° C. for 1 h. The reaction mixture was poured into a mixture of $H_2O$ (60 mL) and HCl (15 mL, 1N), extracted with DCM (50 mL, 3×), dried over $Na_2SO_4$, filtered, and concentrated under reduced pressure. The resulting residue was purified by column chromatography ($SiO_2$, petroleum ether:ethyl acetate=10:1 to 0:1) to afford the title compound as a yellow solid (5.7 g, crude). $^1$H NMR (400 MHz, $CDCl_3$) δ: 3.37 (s, 6H) 4.39-4.52 (m, 2H) 5.16 (s, 1H) 6.77 (s, 1H)

Step 3. 3-(Dimethoxymethyl)thietane 1,1-dioxide

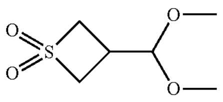

To a mixture of 3-(dimethoxymethyl)-2H-thiete 1,1-dioxide (5.6 g, 31.4 mmol, 1 eq) in EtOH (200 mL) was added Pd/C (3 g, 10% purity), then the reaction mixture was stirred at 50° C. for 24 h under $H_2$ atmosphere (50 psi). The mixture was filtered and concentrated to afford the title compound as a yellow oil (4.95 g, crude). $^1$H NMR (400 MHz, $CDCl_3$) δ: 2.72-2.88 (m, 1H) 3.30-3.48 (m, 6H) 3.95-4.16 (m, 4H) 4.52 (d, J=6.17 Hz, 1H).

Step 4. 1,1-Dioxothietane-3-carbaldehyde

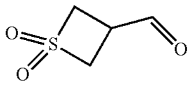

A mixture of 3-(dimethoxymethyl)thietane 1,1-dioxide (1.37 g, 7.60 mmol, 1 eq) in HCl (20 mL, 1N) was stirred at 80° C. for 1 h. The reaction mixture was then extracted with EtOAc (50 mL, 3×), and the combined organic phase was dried over $Na_2SO_4$, filtered, and concentrated under reduced pressure to afford the title compound as a yellow oil (434 mg, 3.24 mmol, 42.56% yield).

Step 5. (1,1-Dioxothietan-3-yl)methanol

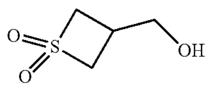

To a mixture 1,1-dioxothietane-3-carbaldehyde (150 mg, 1.12 mmol, 1 eq) in MeOH (3 mL) was added $NaBH_4$ (63.5 mg, 1.68 mmol, 1.5 eq) at 0° C., and the resulting mixture was stirred at 15° C. for 1 h. $H_2O$ (0.5 mL) was added the mixture, then the mixture was concentrated under reduced pressure. DCM was added to the resulting residue, then the mixture was filtered and concentrated to afford the title compound as a yellow oil (86 mg, crude). $^1$H NMR (400 MHz, $CDCl_3$) δ: 2.68-2.81 (m, 1H) 3.82-3.88 (m, 2H) 3.93-4.04 (m, 2H) 4.13-4.24 (m, 2H).

Step 6. (1,1-Dioxothietan-3-yl)methyl methanesulfonate

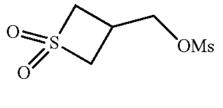 [SMILES: CS(=O)(=O)OCC1CS(=O)(=O)C1]

To a solution of (1,1-dioxothietan-3-yl)methanol (86 mg, 631.57 μmol, 1 eq) and $Et_3N$ (128 mg, 1.26 mmol, 176 μL, 2 eq) in DCM (3 mL) was added MsCl (109 mg, 947 μmol, 73.3 μL, 1.5 eq) at 0° C., and the mixture was then stirred at 20° C. for 1 h. The reaction mixture was added into $H_2O$ (2 mL), then extracted with DCM (3 mL, 3×). The combined organic phase was washed with brine (2 mL), then dried over $Na_2SO_4$, filtered, and concentrated under reduced pressure. The resulting residue was purified by prep-TLC (petroleum ether/ethyl acetate=1:2) afford the title compound as a yellow oil (10 mg, crude). $^1$H NMR (400 MHz, $CDCl_3$) δ: 2.95-3.05 (m, 1H) 3.07-3.13 (m, 3H) 3.96-4.04 (m, 2H) 4.23-4.35 (m, 2H) 4.39-4.46 (m, 2H).

Step 7. tert-Butyl N-[1-[3-[5-[(1,1-dioxothietan-3-yl)methoxy]benzimidazol-1-yl]quinoxalin-5-yl]-4-piperidyl]carbamate

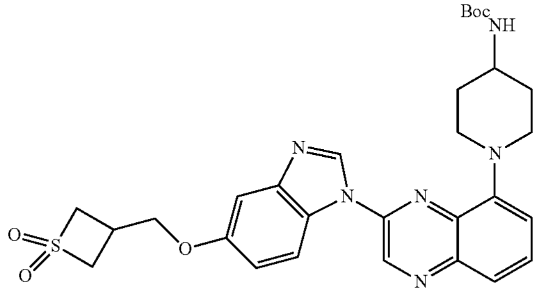 [SMILES: NC1CCN(c2cccc3ncc(-n4cnc5cc(OCC6CS(=O)(=O)C6)ccc54)nc23)CC1]

A mixture of tert-butyl N-[1-[3-(5-hydroxybenzimidazol-1-yl)quinoxalin-5-yl]-4-piperidyl]carbamate (24 mg, 52.1 μmol, 1 eq), (1,1-dioxothietan-3-yl)methyl methanesulfonate (10 mg, 46.7 μmol), $Cs_2CO_3$ (34.0 mg, 104 μmol, 2 eq) and KI (8.65 mg, 52.1 μmol, 1 eq) in DMF (2 mL) was stirred at 70° C. for 36 h. The reaction mixture was poured into a saturated aqueous $NH_4Cl$ solution (10 mL), then extracted with EtOAc (10 mL, 3×). The combined organic phase was washed with brine (10 mL), then dried over $Na_2SO_4$, filtered, and concentrated under reduced pressure to afford the title compound as a yellow oil (50 mg, crude).

Step 8. 1-[3-[5-[(1,1-Dioxothietan-3-yl)methoxy]benzimidazol-1-yl]quinoxalin-5-yl]piperidin-4-amine

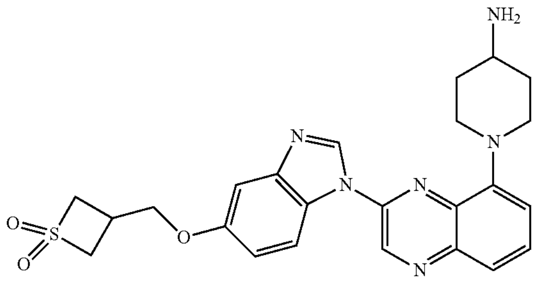 [SMILES: NC1CCN(c2cccc3ncc(-n4cnc5cc(OCC6CS(=O)(=O)C6)ccc54)nc23)CC1]

A mixture of tert-butyl N-[1-[3-[5-[(1,1-dioxothietan-3-yl)methoxy]benzimidazol-1-yl]quinoxalin-5-yl]-4-piperidyl]carbamate (50 mg, 86.4 μmol, 1 eq) in EtOAc(HCl 2M) (2 mL) was stirred at 20° C. for 1 h. The mixture was concentrated and the resulting residue was purified by prep-HPLC (basic condition, column: Waters Xbridge 150*25 mm*5 μm; mobile phase: [water(0.04% $NH_3H_2O$+ 10 mM $NH_4HCO_3$)-ACN]; B %: 22%-42%, 10 min) to afford the title compound as a yellow solid (4.3 mg, 8.77 μmol, 10.15% yield, 97.629% purity). $^1$H NMR (400 MHz, DMSO-$d_6$) δ: 1.65-1.76 (m, 2H) 1.93-2.00 (m, 2H) 2.74-2.94 (m, 4H) 2.97-3.12 (m, 2H) 3.71-3.81 (m, 2H) 4.06-4.15 (m, 2H) 4.24-4.30 (m, 2H) 4.31-4.41 (m, 2H) 7.18-7.24 (m, 1H) 7.32-7.37 (m, 1H) 7.40-7.45 (m, 1H) 7.67-7.73 (m, 2H) 8.74-8.80 (m, 1H) 9.34-9.38 (m, 1H) 9.62-9.65 (m, 1H).

Example 15. 8-(1-Methylazetidin-3-yl)-2-(5-((3-methyloxetan-3-yl)methoxy)-1H-benzo[d]imidazol-1-yl)quinoline

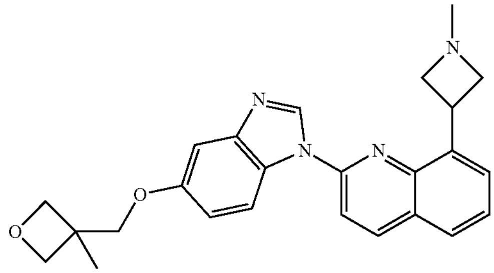 [SMILES: CN1CC(c2cccc3ccc(-n4cnc5cc(OCC6(C)COC6)ccc54)nc23)C1]

Step 1. tert-Butyl 3-(2-chloro-8-quinolyl)azetidine-1-carboxylate

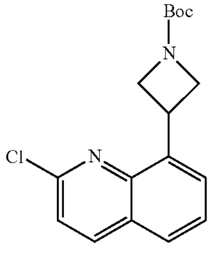 [SMILES: CC(C)(C)OC(=O)N1CC(c2cccc3ccc(Cl)nc23)C1]

A mixture of 8-bromo-2-chloro-quinoline (100 mg, 412.4 μmol, 1 eq), tert-butyl 3-iodoazetidine-1-carboxylate (175.1 mg, 618.6 μmol, 1.5 eq), dichloronickel; 1,2-dimethoxyethane (453.0 μg, 2.1 μmol, 0.005 eq), 4-tert-butyl-2-(4-tert-butyl-2-pyridyl)pyridine (553.4 μg, 2.1 μmol, 0.005 eq) and bis[3,5-difluoro-2-[5-(trifluoromethyl)-2-pyridyl]phenyl] iridium, 4-tert-butyl-2-(4-tert-butyl-2-pyridyl)pyridine, hexafluorophosphate (4.6 mg, 4.1 μmol, 0.01 eq), $Na_2CO_3$ (87.4 mg, 824.7 μmol, 2 eq), and tris(trimethylsilyl)silane (TTMSS, 102.5 mg, 412.4 μmol, 127.2 μL, 1 eq) in DME (3 mL) was degassed and purged with $N_2$ (3×), and then the mixture was stirred at 25° C. for 12 h under $N_2$ atmosphere and a 34 W blue LED. The reaction mixture was added to water (40 mL) and extracted with EtOAc (10 mL, 3×). The combined organic layers were washed with brine (20 mL) dried over $Na_2SO_4$, filtered, and concentrated under reduced pressure. The resulting residue was purified by prep-TLC ($SiO_2$, petroleum ether:ethyl acetate=3:1) to afford the title compound as a yellow oil (240 mg, crude).

Step 2. tert-Butyl 3-[2-[4-[(3-methyloxetan-3-yl)methoxy]-2-nitro-anilino]-8-quinolyl]azetidine-1-carboxylate

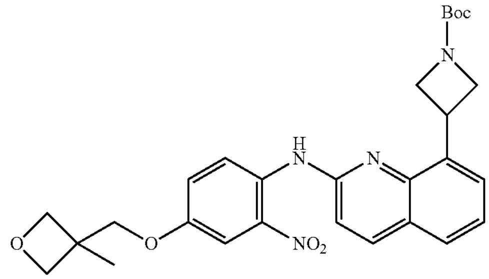 [SMILES: CC1(COc2ccc(Nc3ccc4cccc(C5CN(C(=O)OC(C)(C)C)C5)c4n3)c([N+](=O)[O-])c2)COC1]

A mixture of 4-[(3-methyloxetan-3-yl)methoxy]-2-nitro-aniline (25 mg, 104.9 μmol, 1 eq), tert-butyl 3-(2-chloro-8-quinolyl)azetidine-1-carboxylate (46.8 mg, 146.9 μmol, 1.4 eq), $Cs_2CO_3$ (68.4 mg, 209.9 μmol, 2 eq), BINAP (13.1 mg, 20.9 μmol, 0.2 eq), and $Pd_2(dba)_3$ (9.6 mg, 10.5 μmol, 0.1 eq) in dioxane (2 mL) was degassed and purged with $N_2$ (3×), and then the mixture was stirred at 100° C. for 12 h under $N_2$ atmosphere. The reaction mixture was added to water (10 mL) and extracted with EtOAc (10 mL, 3×). The combined organic layers were washed with brine (20 mL), dried over $Na_2SO_4$, filtered, and concentrated under reduced pressure. The resulting residue was purified by prep-TLC ($SiO_2$, petroleum ether:ethyl acetate=1:1) to afford the title compound as a yellow oil (37 mg, crude).

Step 3. tert-Butyl 3-[2-[2-amino-4-[(3-methyloxetan-3-yl)methoxy]anilino]-8-quinolyl]azetidine-1-carboxylate

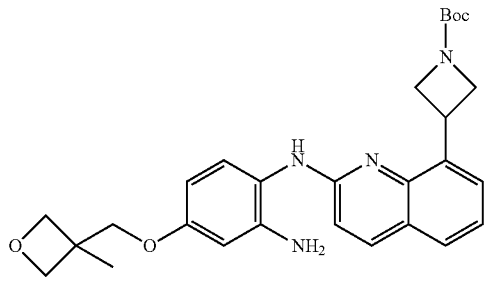 [SMILES: CC1(COc2ccc(Nc3ccc4cccc(C5CN(C(=O)OC(C)(C)C)C5)c4n3)c(N)c2)COC1]

A mixture of tert-butyl 3-[2-[4-[(3-methyloxetan-3-yl)methoxy]-2-nitro-anilino]-8-quinolyl]azetidine-1-carboxylate (470.0 mg, 902.9 μmol, 1 eq) and Pd/C (200 mg, 10% purity) in EtOAc (20 mL) was degassed and purged with $H_2$ (3×), and then the mixture was stirred at 25° C. for 1 h under $H_2$ atmosphere (15 psi). The reaction mixture was filtered and concentrated under reduced pressure to afford the title compound as a yellow solid (420 mg, crude).

Step 4. tert-Butyl 3-[2-[5-[(3-methyloxetan-3-yl)methoxy]benzimidazol-1-yl]-8-quinolyl]azetidine-1-carboxylate

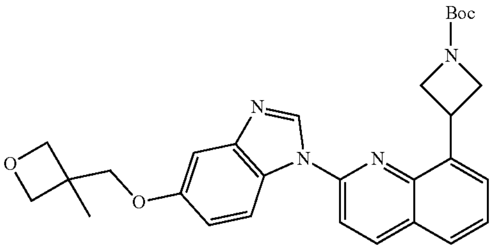 [SMILES: CC1(COc2ccc3c(c2)ncn3-c2ccc3cccc(C4CN(C(=O)OC(C)(C)C)C4)c3n2)COC1]

To a solution of tert-butyl 3-[2-[2-amino-4-[(3-methyloxetan-3-yl)methoxy]anilino]-8-quinolyl]azetidine-1-carboxylate (0.8 g, 1.6 mmol, 1 eq) in trimethylorthoformate (5 mL) was added HCOOH (235.0 mg, 4.9 mmol, 3 eq), and the mixture was stirred at 100° C. for 2 h. The reaction mixture was cooled to 25° C., petroleum ether (50 mL) was added, the mixture was filtered, the filter cake was dried under vacuum to afford the title compound as a yellow solid (270 mg, crude).

Step 5. 8-(Azetidin-3-yl)-2-[5-[(3-methyloxetan-3-yl)methoxy]benzimidazol-1-yl]quinoline

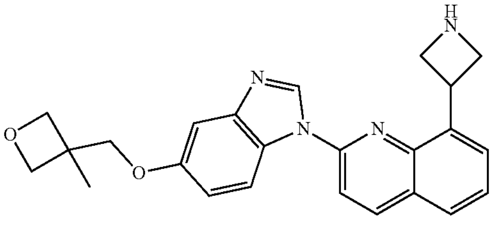 [SMILES: CC1(COc2ccc3c(c2)ncn3-c2ccc3cccc(C4CNC4)c3n2)COC1]

To a solution of tert-butyl 3-[2-[5-[(3-methyloxetan-3-yl)methoxy]benzimidazol-1-yl]-8-quinolyl]azetidine-1-carboxylate (30 mg, 59.9 μmol, 1 eq) in DCM (1.5 mL) was added TFA (92.4 mg, 810.4 μmol, 60.0 μL, 13.5 eq) at 0° C., and the mixture was then stirred at 20° C. for 10 min. The reaction mixture was concentrated under reduced pressure and the resulting residue was dissolved in MeOH (2 mL). Diisopropylethylamine was added to the solution to pH ~8. The reaction mixture was then concentrated under reduced pressure to afford the title compound as a yellow oil (25 mg crude).

Step 6. 8-(1-Methylazetidin-3-yl)-2-[5-[(3-methyloxetan-3-yl)methoxy]benzimidazol-1-yl]quinoline

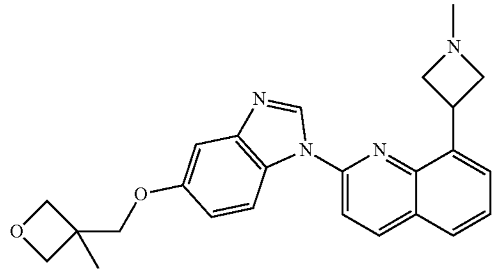 [SMILES: CN1CC(c2cccc3ccc(-n4cnc5cc(OCC6(C)COC6)ccc54)nc23)C1]

To a solution of 8-(azetidin-3-yl)-2-[5-[(3-methyloxetan-3-yl)methoxy]benzimidazol-1-yl]quinoline (25 mg, 62.4 μmol, 1 eq) in MeOH (1 mL) was added AcOH (3.8 mg, 62.4 mol, 3.6 μL, 1 eq) to pH ~5, then HCHO (18.8 mg, 624.3 μmol, 17.2 μL, 10 eq) was added at 0° C., and the resulting mixture was stirred at 25° C. for 30 min. Next, $NaBH_3CN$ (11.8 mg, 187.3 μmol, 3 eq) was added and the mixture was stirred at 25° C. for 12 h. The reaction mixture was filtered, concentrated under reduced pressure, and the resulting residue was purified by prep-HPLC (basic condition; column: Waters Xbridge Prep OBD C18 150*40 mm*10 μm; mobile phase: [water (0.05% $NH_3H_2O$+10 mM $NH_4HCO_3$)-ACN]; B %: 20%-50%, 8 min) to afford the title compound as a white solid (4.0 mg, 9.6 μmol, 15.4% yield, 99.3% purity). $^1H$ NMR (400 MHz, MeOD-$d_4$) δ: 8.92 (s, 1H), 8.47 (dd, J=6.9, 8.7 Hz, 2H), 7.93 (d, J=8.9 Hz, 1H), 7.85 (d, J=8.0 Hz, 1H), 7.74 (br d, J=7.0 Hz, 1H), 7.64-7.56 (m, 1H), 7.33 (d, J=2.3 Hz, 1H), 7.21 (dd, J=2.3, 8.9 Hz, 1H), 4.80-4.63 (m, 3H), 4.51 (d, J=5.9 Hz, 2H), 4.14 (s, 2H), 4.10 (br t, J=7.9 Hz, 2H), 3.39 (br t, J=8.3 Hz, 2H), 2.44 (s, 3H), 1.51 (s, 3H).

Example 16. 2-(5-((3-Methyloxetan-3-yl)methoxy)-1H-benzo[d]imidazol-1-yl)-8-(pyrrolidin-3-yl)quinoline

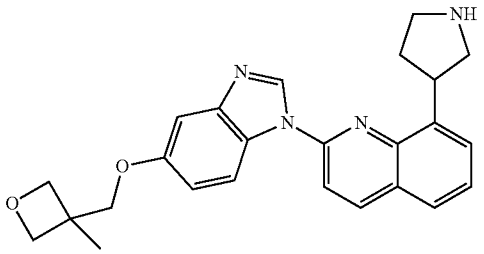 [SMILES: CC1(COc2ccc3c(c2)ncn3-c2ccc3cccc(C4CCNC4)c3n2)COC1]

Step 1. tert-Butyl 4-[2-[5-[(3-methyloxetan-3-yl)methoxy]benzimidazol-1-yl]-8-quinolyl]-2,3-dihydropyrrole-1-carboxylate

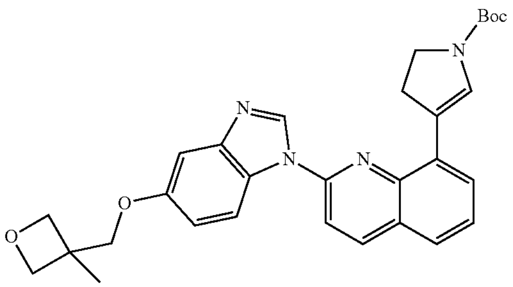 [SMILES: CC1(COc2ccc3c(c2)ncn3-c2ccc3cccc(C4=CN(C(=O)OC(C)(C)C)CC4)c3n2)COC1]

A mixture of [2-[5-[(3-methyloxetan-3-yl)methoxy]benzimidazol-1-yl]-8-quinolyl]trifluoromethanesulfonate (100 mg, 202.7 μmol, 1 eq), tert-butyl 4-(4,4,5,5-tetramethyl-1,3,2-dioxaborolan-2-yl)-2,3-dihydropyrrole-1-carboxylate (89.7 mg, 303.9 mol, 1.5 eq), $Na_2CO_3$ (42.9 mg, 405.3 μmol, 2 eq), Pd(dppf)$Cl_2$ (14.8 mg, 20.3 μmol, 0.1 eq) in dioxane (2 mL), and $H_2O$ (0.2 mL) was degassed and purged with $N_2$ (3×), and then the mixture was stirred at 100° C. for 12 h under $N_2$ atmosphere. The reaction mixture was concentrated and the resulting residue was purified by column chromatography ($SiO_2$, petroleum ether:ethyl acetate=50:1 to 0:1) to afford the title compound as a yellow solid (200 mg, crude).

Step 2. tert-Butyl 3-[2-[5-[(3-methyloxetan-3-yl)methoxy]benzimidazol-1-yl]-8-quinolyl]pyrrolidine-1-carboxylate

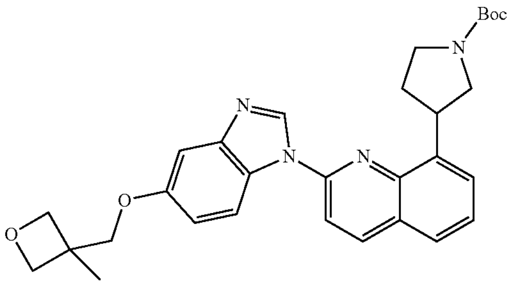 [SMILES: CC1(COc2ccc3c(c2)ncn3-c2ccc3cccc(C4CCN(C(=O)OC(C)(C)C)C4)c3n2)COC1]

A mixture of tert-butyl 4-[2-[5-[(3-methyloxetan-3-yl)methoxy]benzimidazol-1-yl]-8-quinolyl]-2,3-dihydropyrrole-1-carboxylate (150 mg, 292.6 μmol, 1 eq) and Pd/C (20 mg, 97.5 μmol, 10% purity) in EtOAc (10 mL) was degassed and purged with $H_2$ (3×), and then the mixture was stirred at 15° C. for 3 h under $H_2$ atmosphere (15 psi). The reaction mixture was filtered and concentrated under reduced pressure to afford the title compound as a yellow solid (190 mg, crude).

Step 3. 2-[5-[(3-Methyloxetan-3-yl)methoxy]benzimidazol-1-yl]-8-pyrrolidin-3-yl-quinoline

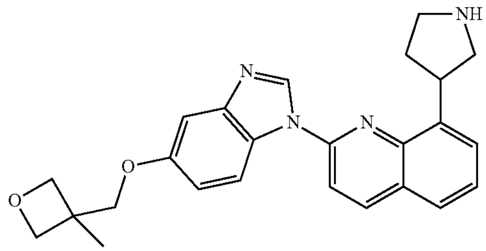 [SMILES: CC1(COc2ccc3c(c2)ncn3-c2ccc3cccc(C4CCNC4)c3n2)COC1]

A mixture of tert-butyl 3-[2-[5-[(3-methyloxetan-3-yl)methoxy]benzimidazol-1-yl]-8-quinolyl]pyrrolidine-1-carboxylate (70 mg, 136.0 μmol, 1 eq) in TFA (0.1 mL) and DCM (1 mL) was stirred at 15° C. for 30 min. The reaction mixture was concentrated under reduced pressure and the resulting residue was dissolved in MeOH (2 mL). Diisopropylethylamine (DIEA) was added to the solution to pH ~8. The reaction mixture was then concentrated under reduced pressure and the resulting residue was purified by prep-HPLC (basic condition; column: Waters X bridge Prep OBD C18 150*40 mm*10 m; mobile phase: [water (0.05% $NH_3H_2O$+10 mM $NH_4HCO_3$)-ACN]; B %: 30%-60%, 8 min) to afford the title compound as a yellow solid (5.3 mg, 12.1 μmol, 8.9% yield, 94.8% purity). $^1H$ NMR (400 MHz, MeOD-$d_4$) δ: 9.00-8.94 (m, 1H), 8.55-8.48 (m, 1H), 8.46-8.39 (m, 1H), 8.03-7.93 (m, 1H), 7.90-7.83 (m, 1H), 7.78 (br d, J=7.1 Hz, 1H), 7.59 (dt, J=3.4, 7.7 Hz, 1H), 7.36-7.29 (m, 1H), 7.24-7.15 (m, 1H), 4.71 (dd, J=2.1, 5.9 Hz, 2H), 4.66-4.56 (m, 1H), 4.48 (dd, J=1.5, 5.9 Hz, 2H), 4.16-4.07 (m, 2H), 3.65 (br dd, J=7.9, 10.9 Hz, 1H), 3.37-3.32 (m, 1H), 3.28-3.21 (m, 1H), 3.13-3.01 (m, 1H), 2.56-2.42 (m, 1H), 2.19-2.06 (m, 1H), 1.48 (d, J=1.8 Hz, 3H)

Example 17. 2-(5-((3-Methyloxetan-3-yl)methoxy)-1H-benzo[d]imidazol-1-yl)-8-(1-methylpyrrolidin-3-yl)quinoline

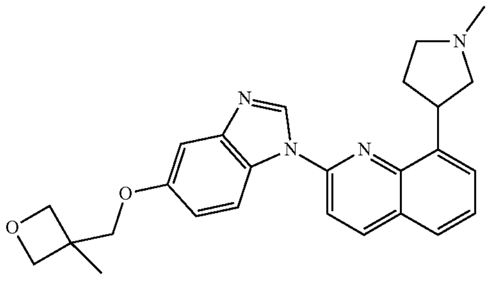 [SMILES: CN1CCC(c2cccc3ccc(-n4cnc5cc(OCC6(C)COC6)ccc54)nc23)C1]

To a solution of 2-[5-[(3-methyloxetan-3-yl)methoxy]benzimidazol-1-yl]-8-pyrrolidin-3-yl-quinoline (Example 16, 56 mg, 135.1 μmol, 1 eq) in MeOH (1 mL) was added AcOH (8.1 mg, 135.1 μmol, 1 eq) until the solution reached pH ~5, then HCHO (40.6 mg, 1.4 mmol, 10 eq) was added at 15° C. and for 30 min. Next, $NaBH_3CN$ (25.5 mg, 405.3 mol, 3 eq) was added and the mixture was stirred at 35° C. for 12 h. The reaction mixture was concentrated and the resulting residue was purified by prep-HPLC (basic condition; column: Phenomenex Gemini-NX C18 75*30 mm*3

μm; mobile phase: [water(0.050% $NH_3H_2O$+10 mM $NH_4HCO_3$)-ACN]; B %: 15%-65%, 8 min) to afford the title compound as a white solid (3 mg, 6.6 μmol, 14.2% yield, 94.7% purity). $^1H$ NMR (400 MHz, MeOD-$d_4$) δ: 9.03 (s, 1H), 8.54 (dd, J=3.1, 8.8 Hz, 2H), 8.02 (d, J=9.0 Hz, 1H), 7.89 (d, J=7.6 Hz, 2H), 7.64 (t, J=7.5 Hz, 1H), 7.39 (s, 1H), 7.25 (br d, J=8.8 Hz, 1H), 4.77 (d, J=5.8 Hz, 2H), 4.53 (d, J=5.9 Hz, 2H), 4.19 (s, 2H), 3.47-3.38 (m, 1H), 3.38 (br s, 1H), 3.12-3.01 (m, 1H), 2.94-2.84 (m, 1H), 2.79 (br t, J=9.1 Hz, 1H), 2.69-2.59 (m, 1H), 2.55 (s, 3H), 2.21-2.09 (m, 1H), 1.53 (s, 3H).

Example 18. 8-(1-Methyl-1H-imidazol-4-yl)-2-(5-((3-methyloxetan-3-yl)methoxy)-1H-benzo[d]imidazol-1-yl)quinoline

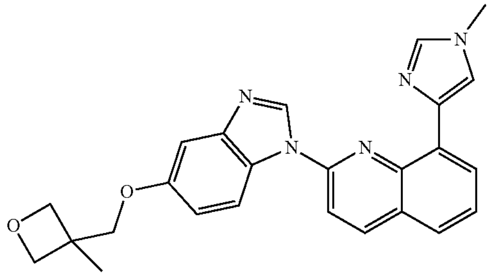 [SMILES: Cn1cnc(-c2cccc3ccc(-n4cnc5cc(OCC6(C)COC6)ccc54)nc23)c1]

Step 1. 2-[5-[(3-Methyloxetan-3-yl)methoxy]benzimidazol-1-yl]-8-(4,4,5,5-tetramethyl-1,3,2-dioxaborolan-2-yl)quinoline

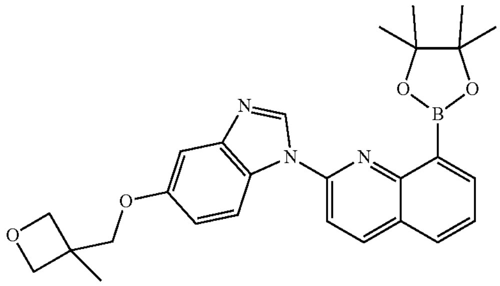 [SMILES: CC1(COc2ccc3c(c2)ncn3-c2ccc3cccc(B4OC(C)(C)C(C)(C)O4)c3n2)COC1]

A mixture of [2-[5-[(3-methyloxetan-3-yl)methoxy]benzimidazol-1-yl]-8-quinolyl]trifluoromethanesulfonate (200 mg, 405.3 μmol, 1 eq), 4,4,5,5-tetramethyl-2-(4,4,5,5-tetramethyl-1,3,2-dioxaborolan-2-yl)-1,3,2-dioxaborolane (113.2 mg, 445.8 μmol, 1.1 eq), KOAc (119.3 mg, 1.2 mmol, 3 eq), and Pd(dppf)$Cl_2$ (29.7 mg, 40.5 μmol, 0.1 eq) in dioxane (2 mL) was degassed and purged with $N_2$ (3×), and then the mixture was stirred at 100° C. for 12 h under $N_2$ atmosphere. The reaction mixture was concentrated to afford the title compound as a yellow oil (190 mg, crude).

Step 2. 8-(1-Methylimidazol-4-yl)-2-[5-[(3-methyloxetan-3-yl)methoxy]benzimidazol-1-yl]quinoline

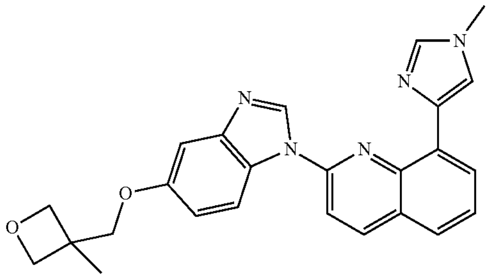 [SMILES: Cn1cnc(-c2cccc3ccc(-n4cnc5cc(OCC6(C)COC6)ccc54)nc23)c1]

A mixture of [2-[5-[(3-methyloxetan-3-yl)methoxy]benzimidazol-1-yl]-8-quinolyl]boronic acid (160 mg, 411.1 μmol, 1 eq), 4-bromo-1-methyl-imidazole (99.3 mg, 616.6 μmol, 1.5 eq), $Na_2CO_3$ (130.7 mg, 1.2 mmol, 3 eq), 4-ditert-butylphosphanyl-N,N-dimethylaniline; dichloropalladium (29.1 mg, 41.1 μmol, 0.1 eq) in dioxane (2 mL), and $H_2O$ (0.2 mL) was degassed and purged with $N_2$ (3×), and then the mixture was stirred at 100° C. for 12 h under $N_2$ atmosphere. The reaction mixture was added to water (20 mL) and extracted with EtOAc (10 mL, 3×). The combined organic layers were washed with brine (20 mL), dried over $Na_2SO_4$, filtered, concentrated under reduced pressure, and the resulting residue was purified by prep-HPLC (basic condition; column: Waters Xbridge Prep OBD C18 150*40 mm*10 m; mobile phase: [water(0.05% $NH_3H_2O$+10 mM $NH_4HCO_3$)-ACN]; B %: 20%-45%, 8 min) to afford the title compound as a white solid (8.5 mg, 19.7 μmol, 4.8% yield, 98.8% purity). $^1H$ NMR (400 MHz, MeOD-$d_4$) δ: 8.95 (s, 1H), 8.56 (d, J=8.9 Hz, 1H), 8.43-8.34 (m, 2H), 8.19 (s, 1H), 7.97 (d, J=8.8 Hz, 1H), 7.90 (d, J=7.3 Hz, 1H), 7.80 (s, 1H), 7.67 (t, J=7.7 Hz, 1H), 7.38 (d, J=2.3 Hz, 1H), 7.13 (dd, J=2.3, 8.9 Hz, 1H), 4.75 (d, J=5.9 Hz, 2H), 4.51 (d, J=5.9 Hz, 2H), 4.16 (s, 2H), 3.82 (s, 3H), 1.51 (s, 3H).

Example 19. 3-(4-cyanophenyl)-N-[(6-methyl-3-pyridyl)methyl]imidazo[1,2-a]pyridine-7-carboxamide

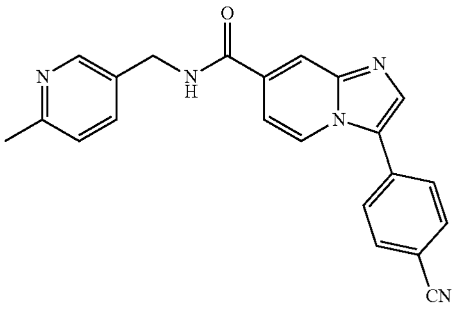

Step 1. Methyl 3-bromoimidazo[1,2-a]pyridine-7-carboxylate

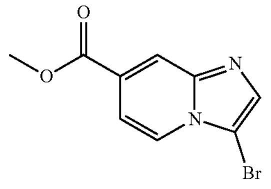

Methyl imidazo[1,2-a]pyridine-7-carboxylate (760 mg, 4.31 mmol, 1 eq) was mixed with NBS (844.60 mg, 4.75 mmol, 1.1 eq) in DMF (10 mL), and then the mixture was stirred at 20° C. for 1 h. The reaction mixture was then quenched by addition water (30 mL) and extracted with EtOAc (150 mL). The combined organic layers were washed with brine (50 mL), dried over $Na_2SO_4$, filtered, and concentrated under reduced pressure to afford the title compound (1.1 g, crude) as a yellow solid.

Step 2: Methyl 3-(4-cyanophenyl)imidazo[1,2-a]pyridine-7-carboxylate

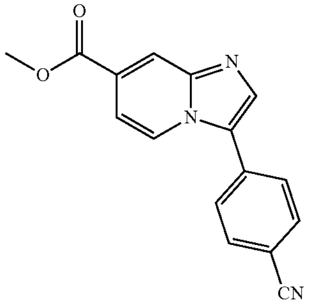 [SMILES: COC(=O)c1ccn2c(-c3ccc(C#N)cc3)cnc2c1]

A mixture of methyl 3-bromoimidazo[1,2-a]pyridine-7-carboxylate (750 mg, 2.94 mmol, 1 eq), (4-cyanophenyl)boronic acid (518.47 mg, 3.53 mmol, 1.2 eq), $Na_2CO_3$ (623.30 mg, 5.88 mmol, 2 eq), Pd(dppf)$Cl_2$ (215.15 mg, 294.04 μmol, 0.1 eq) in dioxane (20 mL) and $H_2O$ (2 mL) was degassed and purged with $N_2$ (3×), and then the mixture was stirred at 90° C. for 12 h under $N_2$ atmosphere. The reaction mixture was then filtered and the filtrate was concentrated under reduced pressure to give a residue. The residue was triturated with MeOH (30 mL) at 25° C. for 30 min, filtered, and the filter cake was concentrated under reduced pressure to afford the title compound (300 mg, crude) as a gray solid.

Step 3. 3-(4-Cyanophenyl)imidazo[1,2-a]pyridine-7-carboxylic acid

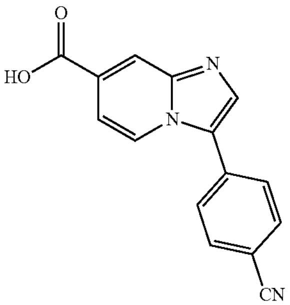 [SMILES: N#Cc1ccc(-c2cnc3cc(C(=O)O)ccn23)cc1]

A mixture of methyl 3-(4-cyanophenyl)imidazo[1,2-a]pyridine-7-carboxylate (280 mg, 1.01 mmol, 1 eq), NaOH (80.79 mg, 2.02 mmol, 2 eq) in MeOH (30 mL), THE (10 mL), and $H_2O$ (5 mL) was prepared, and the mixture was stirred at 25° C. for 24 h. The reaction mixture was concentrated under reduced pressure to remove MeOH and THF, then HCl (12 N; 1 mL) was added. The resulting solution was filtered and the filter cake was concentrated under reduced pressure to afford the title compound (300 mg, crude) as a brown solid.

Step 4. 3-(4-Cyanophenyl)-N-[(6-methyl-3-pyridyl)methyl]imidazo[1,2-a]pyridine-7-carboxamide

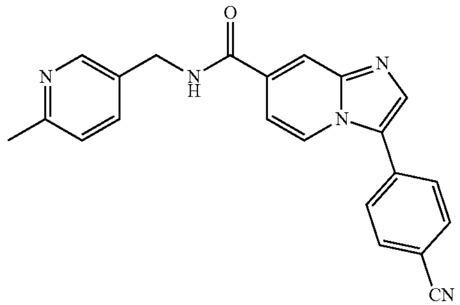

A mixture of 3-(4-cyanophenyl)imidazo[1,2-a]pyridine-7-carboxylic acid (70 mg, 265.91 μmol, 1 eq), (6-methyl-3-pyridyl)methanamine (35.73 mg, 292.50 μmol, 1.1 eq) and DIEA (68.73 mg, 531.81 μmol, 92.63 μL, 2 eq) in DMF (3 mL) was prepared, then HATU (151.66 mg, 398.86 μmol, 1.5 eq) was added and the resulting mixture was stirred at 40° C. for 12 h. The reaction mixture was filtered and the resulting residue was purified by prep-HPLC (basic condition; column: Waters Xbridge Prep OBD C18 150*40 mm*10 um; mobile phase: [water(0.04% NH3H2O+10 mM NH4HCO3)-ACN]; B %: 15%-45%, 1 min) to afford the title compound (62.4 mg, 169.52 mol, 63.75% yield, 99.810% purity) as a white solid. $^1$H NMR (400 MHz, DMSO-$d_6$) δ: 9.35 (t, J=5.8 Hz, 1H), 8.77 (d, J=7.1 Hz, 1H), 8.44 (d, J=1.9 Hz, 1H), 8.28 (s, 1H), 8.13 (s, 1H), 8.05-7.99 (m, 2H), 7.97-7.93 (m, 2H), 7.65 (dd, J=2.2, 7.9 Hz, 1H), 7.46 (dd, J=1.6, 7.3 Hz, 1H), 7.23 (d, J=7.9 Hz, 1H), 4.49 (d, J=5.8 Hz, 2H), 2.45 (s, 3H).

Examples 20-28

Examples 20-28 were prepared according to the procedures described in Example 19, using appropriately substituted starting materials. NMR data for the compounds of Examples 20-28 are shown in Table 3B.

TABLE 3A

| Ex. No. | Compound Name | Structure | Amount | Purity |
|---|---|---|---|---|
| 20 | 3-(4-cyanophenyl)-N-(pyridazin-4-ylmethyl)imidazo[1,2-a]pyridine-7-carboxamide | 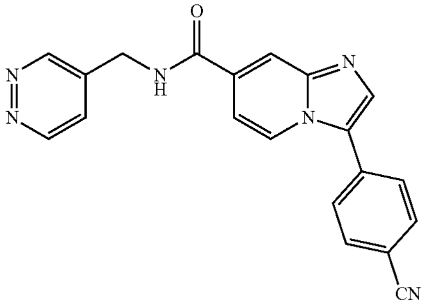 [SMILES: N#Cc1ccc(-c2cnc3cc(C(=O)NCc4ccnnc4)ccn23)cc1] | 45.2 mg | 99.75% |
| 21 | 3-(4-cyanophenyl)-N-(pyrazin-2-ylmethyl)imidazo[1,2-a]pyridine-7-carboxamide | 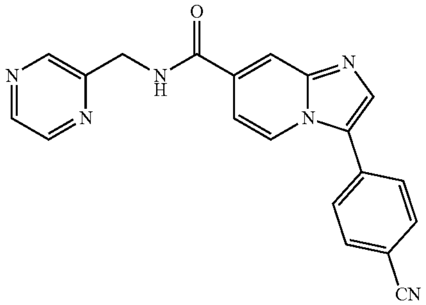 [SMILES: N#Cc1ccc(-c2cnc3cc(C(=O)NCc4cnccn4)ccn23)cc1] | 22.8 mg | 100% |
| 22 | N-((1H-benzo[d]imidazol-2-yl)methyl)-3-(4-cyanophenyl)imidazo[1,2-a]pyridine-7-carboxamide | 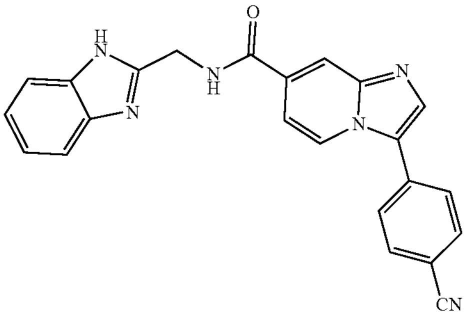 [SMILES: N#Cc1ccc(-c2cnc3cc(C(=O)NCc4nc5ccccc5[nH]4)ccn23)cc1] | 27.0 mg | 100% |
| 23 | 3-(4-cyanophenyl)-N-((1-methyl-1H-benzo[d]imidazol-2-yl)methyl)imidazo[1,2-a]pyridine-7-carboxamide | 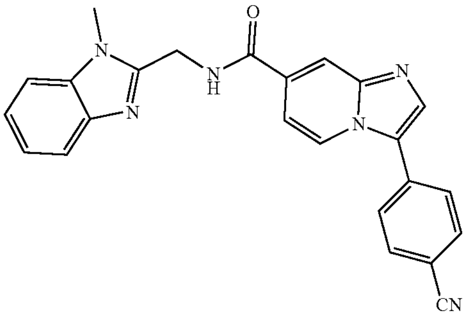 [SMILES: Cn1c(CNC(=O)c2ccn3c(-c4ccc(C#N)cc4)cnc3c2)nc2ccccc21] | 10.4 mg | 98.89% |
| 24 | 3-(4-cyanophenyl)-N-(imidazo[1,2-a]pyridin-2-ylmethyl)imidazo[1,2-a]pyridine-7-carboxamide | 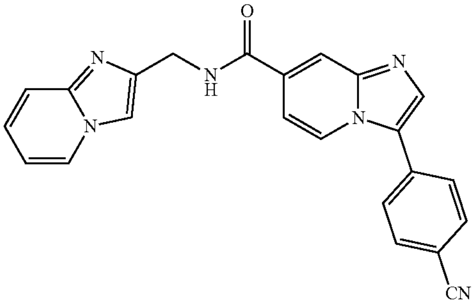 [SMILES: N#Cc1ccc(-c2cnc3cc(C(=O)NCc4cn5ccccc5n4)ccn23)cc1] | 25.5 mg | 99.1% |

TABLE 3A-continued

| Ex. No. | Compound Name | Structure | Amount | Purity |
|---|---|---|---|---|
| 25 | N-((3H-imidazo[4,5-c]pyridin-2-yl)methyl)-3-(4-cyanophenyl)imidazo[1,2-a]pyridine-7-carboxamide | 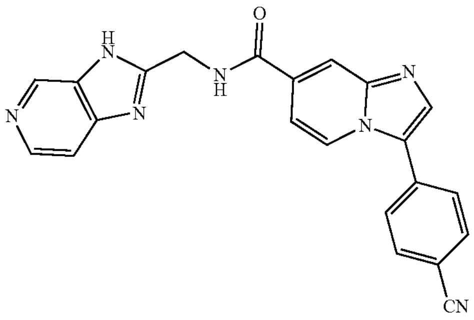 [SMILES: N#Cc1ccc(-c2cnc3cc(C(=O)NCc4nc5ccncc5[nH]4)ccn23)cc1] | 21.5 mg | 100% |
| 26 | N-(benzo[d]oxazol-2-ylmethyl)-3-(4-cyanophenyl)imidazo[1,2-a]pyridine-7-carboxamide | 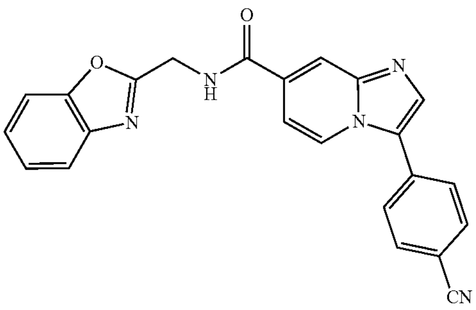 [SMILES: N#Cc1ccc(-c2cnc3cc(C(=O)NCc4nc5ccccc5o4)ccn23)cc1] | 29 mg | 96.7% |
| 27 | 3-(4-cyanophenyl)-N-(furan-2-ylmethyl)imidazo[1,2-a]pyridine-7-carboxamide | 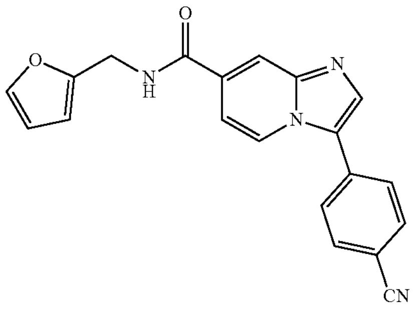 [SMILES: N#Cc1ccc(-c2cnc3cc(C(=O)NCc4ccco4)ccn23)cc1] | 8.0 mg | 93.1% |
| 28 | 4-(7-(1,2,3,4-tetrahydrobenzo[4,5]imidazo[1,2-a]pyrazine-2-carbonyl)imidazo[1,2-a]pyridin-3-yl)benzonitrile | 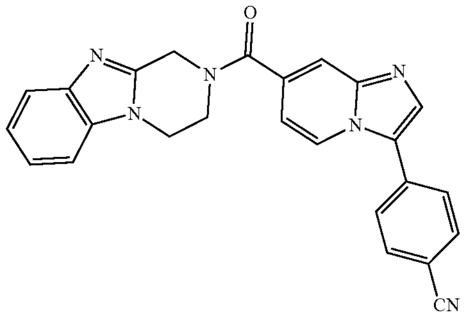 [SMILES: N#Cc1ccc(-c2cnc3cc(C(=O)N4CCn5c(nc6ccccc65)C4)ccn23)cc1] | 9.7 mg | 99.5% |

TABLE 3B

| Ex. No. | 1H-NMR Data |
|---|---|
| 20 | $^1H$ NMR (400 MHz, DMSO-$d_6$) δ: 9.47 (t, J = 5.8 Hz, 1H), 9.28-9.22 (m, 1H), 9.18 (dd, J = 1.2, 5.3 Hz, 1H), 8.82-8.72 (m, 1H), 8.34 (d, J = 0.8 Hz, 1H), 8.15 (s, 1H), 8.07-8.00 (m, 2H), 7.99-7.92 (m, 2H), 7.63 (dd, J = 2.4, 5.3 Hz, 1H), 7.46 (dd, J = 1.9, 7.3 Hz, 1H), 4.59 (d, J = 5.8 Hz, 2H) |

TABLE 3B-continued

| Ex. No. | 1H-NMR Data |
|---|---|
| 21 | $^1$H NMR (400 MHz, DMSO-$d_6$) δ: 9.49 (t, J = 5.8 Hz, 1H), 8.78 (d, J = 7.4 Hz, 1H), 8.70 (d, J = 1.3 Hz, 1H), 8.65-8.60 (m, 1H), 8.57 (d, J = 2.5 Hz, 1H), 8.33 (s, 1H), 8.14 (s, 1H), 8.05-8.02 (m, 2H), 7.98-7.95 (m, 2H), 7.48 (dd, J = 1.8, 7.3 Hz, 1H), 4.67 (d, J = 5.6 Hz, 2H) |
| 22 | $^1$H NMR (400 MHz, DMSO-$d_6$) δ: 4.71-4.77 (m, 2 H) 7.10-7.17 (m, 2 H) 7.42-7.59 (m, 3 H) 7.94-7.99 (m, 2 H) 8.00-8.05 (m, 2 H) 8.12-8.16 (m, 1 H) 8.34-8.38 (m, 1 H) 8.77-8.82 (m, 1 H) 9.46-9.52 (m, 1 H) 12.23-12.44 (m, 1 H) |
| 23 | $^1$H NMR (400 MHz, DMSO-$d_6$) δ: 9.45 (t, J = 5.3 Hz, 1H), 8.78 (d, J = 7.3 Hz, 1H), 8.34 (s, 1H), 8.13 (s, 1H), 8.06-8.00 (m, 2H), 7.98-7.94 (m, 2H), 7.60 (d, J = 8.0 Hz, 1H), 7.55 (d, J = 8.0 Hz, 1H), 7.50 (d, J = 7.5 Hz, 1H), 7.28-7.23 (m, 1H), 7.22-7.17 (m, 1H), 4.83 (d, J = 5.3 Hz, 2H), 3.85 (s, 3H) |
| 24 | $^1$H NMR (400 MHz, DMSO-$d_6$) δ: 9.35 (t, J = 5.7 Hz, 1H), 8.77 (d, J = 7.2 Hz, 1H), 8.50 (d, J = 6.7 Hz, 1H), 8.33 (s, 1H), 8.16-8.11 (m, 1H), 8.05-7.93 (m, 4H), 7.85 (s, 1H), 7.50 (d, J = 9.0 Hz, 2H), 7.29-7.10 (m, 1H), 6.90-6.82 (m, 1H), 4.63 (d, J = 5.6 Hz, 2H) |
| 25 | $^1$H NMR (400 MHz, DMSO-$d_6$) δ ppm 4.91 (d, J = 5.51 Hz, 2 H) 7.59 (dd, J = 7.28, 1.54 Hz, 1 H) 7.94-8.01 (m, 2 H) 8.02-8.08 (m, 2 H) 8.12 (d, J = 6.39 Hz, 1 H) 8.29 (s, 1 H) 8.41 (s, 1 H) 8.59 (d, J = 6.40 Hz, 1 H) 8.86 (d, J = 7.28 Hz, 1 H) 9.39 (s, 1 H) 9.80 (t, J = 5.62 Hz, 1 H) |
| 26 | $^1$H NMR (400 MHz, DMSO-$d_6$) δ: 4.82 (d, J = 5.50 Hz, 2 H) 7.34-7.42 (m, 2 H) 7.48 (dd, J = 7.32, 1.19 Hz, 1 H) 7.69-7.76 (m, 2 H) 7.93-8.07 (m, 4 H) 8.14 (s, 1 H) 8.33 (s, 1 H) 8.79 (d, J = 7.25 Hz, 1 H) 9.62 (br t, J = 5.50 Hz, 1 H) |
| 27 | $^1$H NMR (400 MHz, DMSO-$d_6$) δ: 9.27 (t, J = 5.7 Hz, 1H), 8.76 (d, J = 7.2 Hz, 1H), 8.28 (s, 1H), 8.12 (s, 1H), 8.05-7.91 (m, 4H), 7.63-7.58 (m, 1H), 7.47 (dd, J = 1.8, 7.3 Hz, 1H), 6.42 (dd, J = 1.8, 3.2 Hz, 1H), 6.33 (d, J = 3.1 Hz, 1H), 4.52 (d, J = 5.6 Hz, 2H) |
| 28 | $^1$H NMR (400 MHz, DMSO-$d_6$) δ: 3.87-4.24 (m, 2 H) 4.28 (br d, J = 4.63 Hz, 2 H) 5.04 (br s, 2 H) 7.10-7.28 (m, 3 H) 7.53 (br d, J = 8.16 Hz, 2 H) 7.92-7.98 (m, 3 H) 8.00-8.04 (m, 2 H) 8.10 (s, 1 H) 8.77 (d, J = 7.06 Hz, 1 H) |

Example 29. 3-(4-Cyanophenyl)-N-methyl-N-[(1-methylbenzimidazol-2-yl)methyl]imidazo[1,2-a]pyridine-7-carboxamide

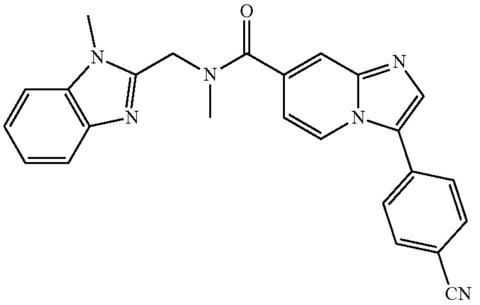 [SMILES: CN(Cc1nc2ccccc2n1C)C(=O)c1ccn2c(-c3ccc(C#N)cc3)cnc2c1]

Step 1. 3-(4-Cyanophenyl)-N-[(1-methylbenzimidazol-2-yl)methyl]imidazo[1,2-a]pyridine-7-carboxamide

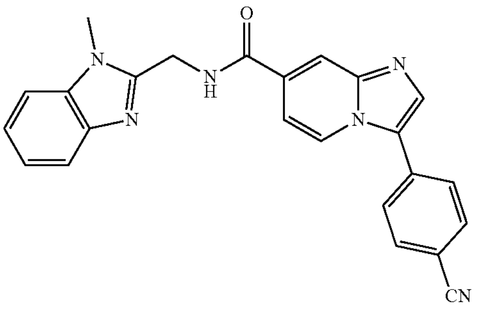 [SMILES: Cn1c(CNC(=O)c2ccn3c(-c4ccc(C#N)cc4)cnc3c2)nc2ccccc21]

A mixture of 3-(4-cyanophenyl)imidazo[1,2-a]pyridine-7-carboxylic acid (100 mg, 379.9 μmol, 1 eq), (1-methylbenzimidazol-2-yl)methanamine (67.4 mg, 417.8 μmol, 1.1 eq) and DIEA (98.2 mg, 759.7 μmol, 132.3 μL, 2 eq) in DMF (2 mL) was prepared, then HATU (216.6 mg, 569.8 μmol, 1.5 eq) was added and the mixture was stirred at 40° C. for 12 h. The reaction mixture was filtered and the filter cake was concentrated under reduced pressure to give a residue. The residue was purified by prep-HPLC (basic condition, column: Waters X bridge Prep OBD C18 150*40 mm*10 um; mobile phase: [ ]; B %: 20%-50%, 8 min) to afford the title compound (80 mg, crude) as a white solid.

Step 2. 3-(4-Cyanophenyl)-N-methyl-N-[(1-methylbenzimidazol-2-yl)methyl]imidazo[1,2-a]pyridine-7-carboxamide

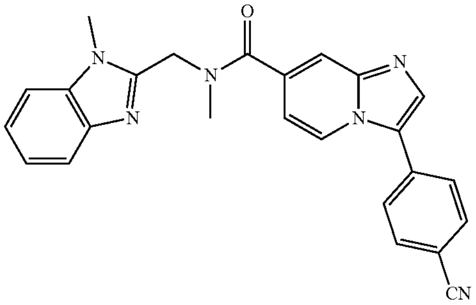 [SMILES: CN(Cc1nc2ccccc2n1C)C(=O)c1ccn2c(-c3ccc(C#N)cc3)cnc2c1]

To a mixture of 3-(4-cyanophenyl)-N-[(1-methylbenzimidazol-2-yl)methyl]imidazo[1,2-a]pyridine-7-carboxamide (80 mg, 196.8 μmol, 1 eq) in DMF (0.5 mL) was added NaH (7.9 mg, 196.8 μmol, 60% purity, 1 eq) at 0° C., and then the mixture was stirred at 0° C. for 0.5 h. Methyl iodide (22.3 mg, 157.5 μmol, 9.80 μL, 0.8 eq) in DMF (0.1 mL) was added to the reaction mixture, then the mixture was stirred at 25° C. for 0.5 h. The reaction was quenched by addition of saturated $NH_4Cl$ (aqueous, 15 mL) at 0° C., then extracted with DCM (60 mL). The combined organic layers were washed with brine (50 mL), dried over $Na_2SO_4$, filtered, and concentrated under reduced pressure to give a residue. The residue was purified by prep-HPLC (basic condition; column: Waters X bridge Prep OBD C18 150*40 mm*10 um; mobile phase: [water(0.05% $NH_3H_2O$ 10 mM $NH_4HCO_3$)-ACN]; B %: 25%-38%, 8 min) to afford the title compound (10 mg, 23.8 μmol, 12.1% yield, 100% purity) as a white solid. $^1$H NMR (400 MHz, DMSO-$d_6$) δ: 8.82-8.61 (m, 1H), 8.35-7.80 (m, 6H), 7.74-7.59 (m, 1H), 7.59-7.47 (m, 1H), 7.32-7.17 (m, 2H), 7.12 (d, J=7.1 Hz, 1H), 5.12-4.72 (m, 2H), 3.95-3.56 (m, 3H), 3.10 (br s, 3H).

Example 30. 3-(4-Cyanophenyl)-N-methyl-N-((6-methylpyridin-3-yl)methyl)imidazo[1,2-a]pyridine-7-carboxamide

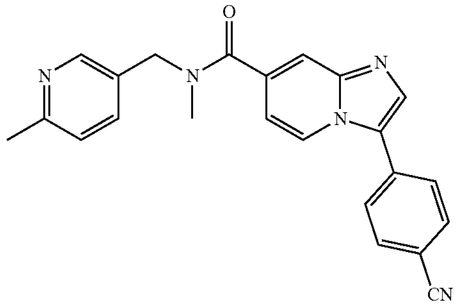 [SMILES: Cc1ccc(CN(C)C(=O)c2ccn3c(-c4ccc(C#N)cc4)cnc3c2)cn1]

The title compound was prepared according to the procedures described in Example 29, substituting (6-methylpyridin-3-yl)methanamine for the (1-methyl-1H-benzo[d]imidazol-2-yl)methanamine. Yield: 32.3 mg; 100% purity. $^1$H NMR (400 MHz, DMSO-$d_6$) δ: 8.72 (d, J=7.1 Hz, 1H), 8.52-8.41 (m, 1H), 8.06 (s, 1H), 8.02-7.97 (m, 2H), 7.96-7.91 (m, 2H), 7.85 (br s, 1H), 7.73-7.56 (m, 1H), 7.27 (br d, J=8.0 Hz, 1H), 7.08 (br d, J=6.8 Hz, 1H), 4.67 (br s, 2H), 2.95 (br s, 3H), 2.46 (s, 3H).

Example 31. 3-(2,5-dimethoxyphenyl)-N-(3-pyridylmethyl)imidazo[1,2-a]pyridine-7-carboxamide

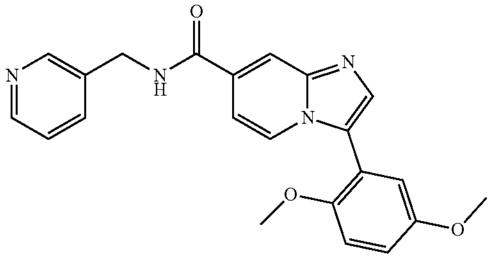 [SMILES: COc1ccc(OC)c(-c2cnc3cc(C(=O)NCc4cccnc4)ccn23)c1]

Step 1 Methyl 3-bromoimidazo[1,2-a]pyridine-7-carboxylate

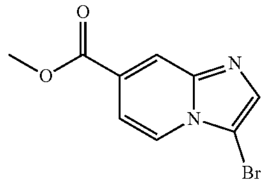

To a mixture of methyl imidazo[1,2-a]pyridine-7-carboxylate (300 mg, 1.70 mmol, 1 eq) in DMF (5 mL) was added NBS (333.39 mg, 1.87 mmol, 1.1 eq) at 20° C., then the reaction mixture was stirred at 20° C. for 1 h. The mixture was added to water (30 mL) and extracted with EtOAc (2 mL, 3×). The organic layer was dried over $Na_2SO_4$ and concentrated to afford the title compound (450 mg, crude) as a yellow solid.

Step 2. Methyl 3-(2,5-dimethoxyphenyl)imidazo[1,2-a]pyridine-7-carboxylate

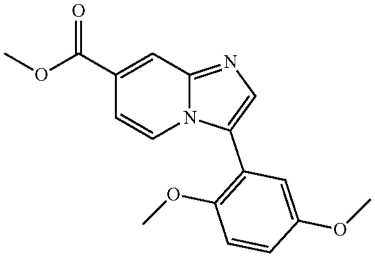

To a mixture of methyl 3-bromoimidazo[1,2-a]pyridine-7-carboxylate (450 mg, 1.76 mmol, 1 eq), (2,5-dimethoxyphenyl)boronic acid (321.06 mg, 1.76 mmol, 1 eq) in dioxane (15 mL), and $H_2O$ (1.5 mL) was added $Na_2CO_3$ (373.98 mg, 3.53 mmol, 2 eq) and Pd(dppf)$Cl_2$ (129.09 mg, 176.42 μmol, 0.1 eq) at 20° C., and the mixture was heated at 100° C. for 12 h under $N_2$. The reaction mixture was then concentrated to give the crude product, which was purified by column chromatography on silica gel (Petroleum ether: Ethyl acetate=10:1-1:1) to afford the title compound (240 mg, 768.44 μmol, 43.56% yield) as a yellow solid.

Step 3. 3-(2,5-Dimethoxyphenyl)imidazo[1,2-a]pyridine-7-carboxylic acid

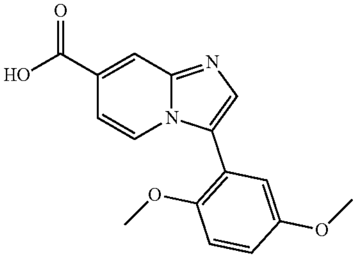 [SMILES: COc1ccc(OC)c(-c2cnc3cc(C(=O)O)ccn23)c1]

To a mixture of methyl 3-(2,5-dimethoxyphenyl)imidazo[1,2-a]pyridine-7-carboxylate (240 mg, 768.44 μmol, 1 eq) in MeOH (2 mL)/$H_2O$ (7 mL) was added NaOH (61.47 mg, 1.54 mmol, 2 eq) at 20° C., then the reaction mixture was stirred at 20° C. for 12 h. The mixture was concentrated to remove MeOH, then the water layer was acidified with HCl (6M) to pH=3, filtered, and the filter cake was dried under vacuum. The title compound (180 mg, crude) was obtained a yellow solid.

Step 4. 3-(2,5-Dimethoxyphenyl)-N-(3-pyridylmethyl)imidazo[1,2-a]pyridine-7-carboxamide

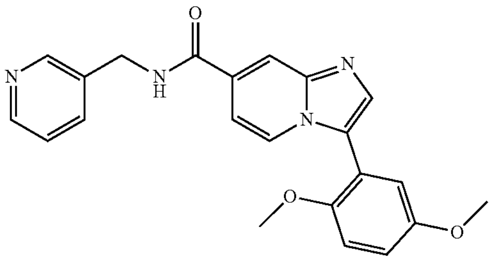 [SMILES: COc1ccc(OC)c(-c2cnc3cc(C(=O)NCc4cccnc4)ccn23)c1]

To a mixture of 3-(2,5-dimethoxyphenyl)imidazo[1,2-a]pyridine-7-carboxylic acid (80 mg, 268.19 μmol, 1 eq) in DMF (2 mL) was added DIEA (69.32 mg, 536.39 μmol, 93.43 μL, 2 eq), 3-pyridylmethanamine (29.00 mg, 268.19 μmol, 27.11 μL, 1 eq), and HATU (122.37 mg, 321.83 μmol, 1.2 eq), and the reaction mixture was stirred at 40° C. for 12 h.

The reaction mixture was then concentrated to give the crude product, which was purified by prep-HPLC (basic condition, column: Waters Xbridge Prep OBD C18 150*40 mm*10 um; mobile phase: [water(0.04%/$NH_3H_2O$+10 mM $NH_4HCO_3$)-ACN]; B %: 15%-45%, 10 min) to afford the title compound (39.5 mg, 100.21 μmol, 37.37% yield, 98.544% purity) as a white solid. $^1H$ NMR (400 MHz, DMSO-$d_6$) δ: 3.74 (s, 3H) 3.78 (s, 3H) 4.54 (d, J=5.75 Hz, 2H) 7.04 (d, J=3.13 Hz, 1H) 7.07-7.12 (m, 1H) 7.16-7.20 (m, 1H) 7.36-7.41 (m, 2H) 7.77 (br d, J=7.88 Hz, 1H) 7.81 (s, 1H) 8.03 (d, J=7.25 Hz, 1H) 8.24 (s, 1H) 8.48 (d, J=3.50 Hz, 1H) 8.59 (d, J=1.63 Hz, 1H) 9.30-9.37 (m, 1H) 9.33 (br t, J=5.82 Hz, 1H).

Example 32. 1-(4-cyanophenyl)-N-(3-pyridylmethyl)benzimidazole-5-carboxamide

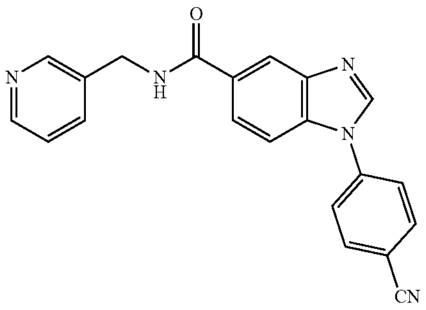 [SMILES: N#Cc1ccc(-n2cnc3cc(C(=O)NCc4cccnc4)ccc32)cc1]

Step 1. Methyl 4-(4-cyanoanilino)-3-nitro-benzoate

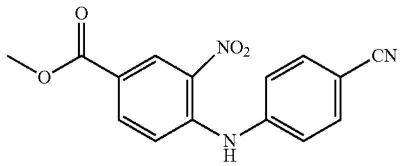 [SMILES: COC(=O)c1ccc(Nc2ccc(C#N)cc2)c([N+](=O)[O-])c1]

To a mixture of methyl 4-fluoro-3-nitrobenzoate (600 mg, 3.01 mmol, 1 eq) and 4-aminobenzonitrile (427.13 mg, 3.62 mmol, 1.2 eq) in DMF (10 mL) was added t-BuOK (676.18 mg, 6.03 mmol, 2 eq) in one portion at 15° C. under $N_2$, and the mixture was stirred at 40° C. for 12 h. The reaction mixture was added to $H_2O$ (10 mL), filtered, and the cake was concentrated under reduced pressure to afford the title compound (850 mg, crude) as a yellow solid. $^1H$ NMR (400 MHz, DMSO-$d_6$) δ: 9.82 (br s, 1H), 8.65-8.59 (m, 1H), 8.08-8.00 (m, 1H), 7.88-7.81 (m, 2H), 7.53-7.44 (m, 3H), 3.90-3.85 (m, 3H).

Step 2. Methyl 3-amino-4-(4-cyanoanilino)benzoate

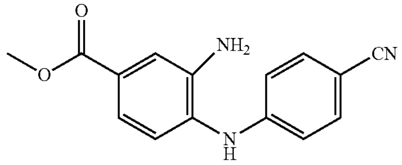 [SMILES: COC(=O)c1ccc(Nc2ccc(C#N)cc2)c(N)c1]

A mixture of methyl 4-(4-cyanoanilino)-3-nitrobenzoate (850 mg, 2.86 mmol, 1 eq), Fe (798.49 mg, 14.30 mmol, 5 eq) and $NH_4Cl$ (1.53 g, 28.59 mmol, 10 eq) in EtOH (10 mL) and $H_2O$ (2 mL) was heated at 80° C. and stirred for 30 min. The reaction mixture was filtered and the filtrate was added to $H_2O$ (20 mL), diluted with ethyl acetate (20 mL), and extracted with ethyl acetate (20 mL, 2×). The combined organic layers were washed with brine (30 mL), dried over $Na_2SO_4$, filtered, and concentrated under reduced pressure to afford the title compound (690 mg, crude) as a light yellow solid.

Step 3. Methyl 1-(4-cyanophenyl)benzimidazole-5-carboxylate

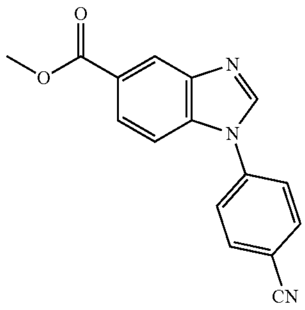

A mixture of methyl 3-amino-4-(4-cyanoanilino)benzoate (690 mg, 2.58 mmol, 1 eq) and HCOOH (372.06 mg, 7.74 mmol, 3 eq) in trimethoxymethane (5 mL) was heated at 100° C. and stirred for 1 h. The reaction mixture was filtered and the cake was concentrated under reduced pressure to afford the title compound (550 mg, crude) as a light yellow solid.

Step 4. 1-(4-Cyanophenyl)benzimidazole-5-carboxylic acid

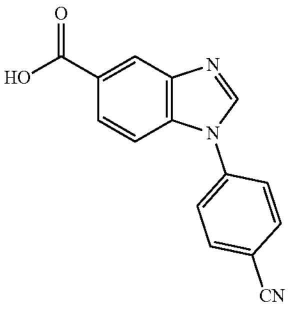 [SMILES: N#Cc1ccc(-n2cnc3cc(C(=O)O)ccc32)cc1]

A mixture of methyl 1-(4-cyanophenyl)benzimidazole-5-carboxylate (200 mg, 721.30 μmol, 1 eq) and NaOH (57.70 mg, 1.44 mmol, 2 eq) in MeOH (1 mL) and $H_2O$ (1 mL) was stirred at 70° C. for 1 h. The reaction mixture was then concentrated to remove MeOH, HCl (12 N, 3 mL) was added, the mixture was filtered, and the cake was concentrated under reduced pressure to afford the title compound (120 mg, crude) as a white solid.

Step 5. 1-(4-Cyanophenyl)-N-(3-pyridylmethyl) benzimidazole-5-carboxamide

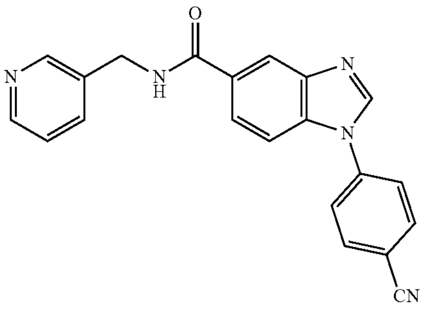 [SMILES: N#Cc1ccc(-n2cnc3cc(C(=O)NCc4cccnc4)ccc32)cc1]

To a mixture of 1-(4-cyanophenyl)benzimidazole-5-carboxylic acid (120 mg, 455.84 μmol, 1 eq), DIEA (88.37 mg, 683.76 μmol, 119.10 μL, 1.5 eq) and 3-pyridylmethanamine (54.22 mg, 501.42 μmol, 50.68 μL, 1.1 eq) in DMF (2 mL) was added HATU (207.99 mg, 547.01 μmol, 1.2 eq) in one portion at 15° C. under $N_2$, and the mixture was heated to 40° C. and stirred for 12 h. The reaction mixture was filtered and the resulting residue was purified by prep-HPLC (FA condition: column: Phenomenex Luna C18 200*40 mm*10 um; mobile phase: [water (0.225% FA)-ACN]; B %: 1%-40%, 12 min) to afford the title compound (76.2 mg, 189.51 μmol, 41.57% yield, 99.331% purity, FA) as a white solid. LCMS m/z 390.1 (M+1). $^1H$ NMR (400 MHz, DMSO-$d_6$) δ: 9.28-9.15 (m, 1H), 8.83-8.77 (m, 1H), 8.66-8.60 (m, 1H), 8.54-8.48 (m, 1H), 8.42-8.38 (m, 1H), 8.19-8.11 (m, 2H), 8.03-7.92 (m, 3H), 7.88-7.78 (m, 2H), 7.49-7.39 (m, 1H), 4.60-4.53 (in, 2H).

Examples 33-34

Examples 33-34 were prepared according to the procedures described for Example 32, using appropriately substituted starting materials. NMR data for the compounds of Examples 20-28 are shown in Table 4B.

TABLE 4A

| Ex. No. | Compound Name | Structure | Amount | Purity |
|---|---|---|---|---|
| 33 | 1-(4-cyanophenyl)-N-(imidazo[1,2-a]pyridin-2-ylmethyl)-1H-benzo[d]imidazole-5-carboxamide | 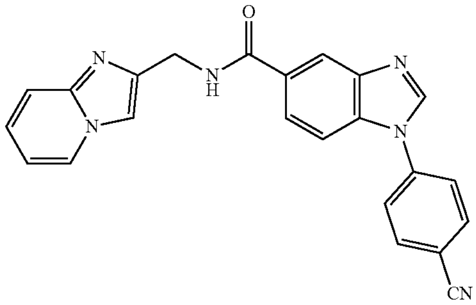 [SMILES: N#Cc1ccc(-n2cnc3cc(C(=O)NCc4cn5ccccc5n4)ccc32)cc1] | 16.1 mg | 100% |

TABLE 4A-continued

| Ex. No. | Compound Name | Structure | Amount | Purity |
| --- | --- | --- | --- | --- |
| 34 | N-((1H-benzo[d]imidazol-2-yl)methyl)-1-(4-cyanophenyl)-1H-benzo[d]imidazole-5-carboxamide | 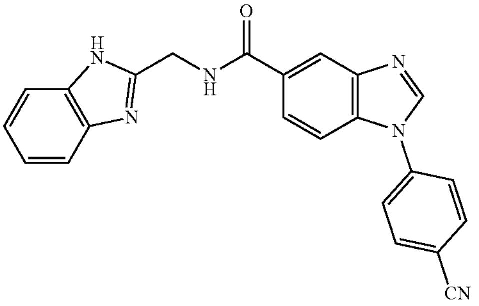 [SMILES: N#Cc1ccc(-n2cnc3cc(C(=O)NCc4nc5ccccc5[nH]4)ccc32)cc1] | 21.2 mg | 98.6% |

TABLE 4B

| Ex. No. | 1H-NMR Data |
| --- | --- |
| 33 | $^1H$ NMR (400 MHz, DMSO-$d_6$) δ: 4.62 (d, J = 5.73 Hz, 2 H) 6.84 (t, J = 6.73 Hz, 1 H) 7.15-7.24 (m, 1 H) 7.48 (d, J = 9.04 Hz, 1 H) 7.76-7.85 (m, 2 H) 7.98 (br d, J = 8.82 Hz, 3 H) 8.14 (d, J = 8.60 Hz, 2 H) 8.42 (s, 1 H) 8.50 (d, J = 6.62 Hz, 1 H) 8.79 (s, 1 H) 9.14 (t, J = 5.62 Hz, 1 H) |
| 34 | $^1H$ NMR (400 MHz, DMSO-$d_6$) δ: 12.28 (br s, 1H), 9.27 (br t, J = 5.4 Hz, 1H), 8.79 (s, 1H), 8.44 (s, 1H), 8.12 (d, J = 8.6 Hz, 2H), 8.01-7.92 (m, 3H), 7.81 (d, J = 8.6 Hz, 1H), 7.54 (br d, J = 6.6 Hz, 1H), 7.43 (br d, J = 6.2 Hz, 1H), 7.13 (br s, 2H), 4.72 (br d, J = 5.7 Hz, 2H) |

Example 35. 3-(4-Cyanophenyl)-N-(3H-imidazo[4,5-b]pyridin-2-ylmethyl)pyrazolo[1,5-a]pyridine-6-carboxamide

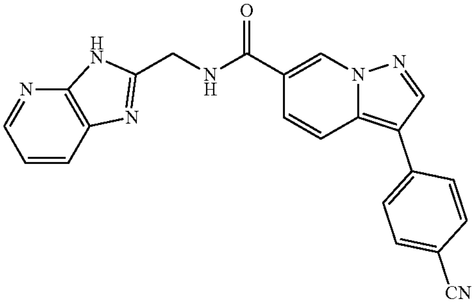 [SMILES: N#Cc1ccc(-c2cnn3cc(C(=O)NCc4nc5cccnc5[nH]4)ccc23)cc1]

Step 1. Methyl pyrazolo[1,5-a]pyridine-6-carboxylate

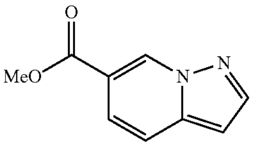 [SMILES: COC(=O)c1ccc2ccnn2c1]

To a solution of 6-bromopyrazolo[1,5-a]pyridine (0.5 g, 2.54 mmol, 1 eq) and $Et_3N$ (1.28 g, 12.69 mmol, 1.77 mL, 5 eq) in MeOH (20 mL) was added Pd(dppf)$Cl_2$ (185.68 mg, 253.77 μmol, 0.1 eq) under $N_2$. The suspension was degassed under vacuum and purged with CO several times. The mixture was stirred under CO (50 psi) at 70° C. for 12 h. The reaction mixture was then filtered and concentrated under reduced pressure to afford the title compound (1 g, crude) as a brown solid.

Step 2. Methyl 3-iodopyrazolo[1,5-a]pyridine-6-carboxylate

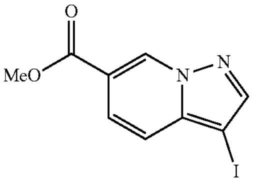 [SMILES: COC(=O)c1ccc2c(I)cnn2c1]

A mixture of methyl pyrazolo[1,5-a]pyridine-6-carboxylate (100 mg, 567.63 μmol, 1 eq) and NIS (140.48 mg, 624.39 μmol, 1.1 eq) in DMF (2 mL) was stirred at 20° C. for 1 h. The reaction was quenched by addition water (10 mL) and extracted with EtOAc (30 mL). The combined organic layers were washed with brine (20 mL), dried over $Na_2SO_4$, filtered, and concentrated under reduced pressure to afford the title compound (180 mg, crude) as a yellow solid.

Step 3. Methyl 3-(4-cyanophenyl)pyrazolo[1,5-a]pyridine-6-carboxylate

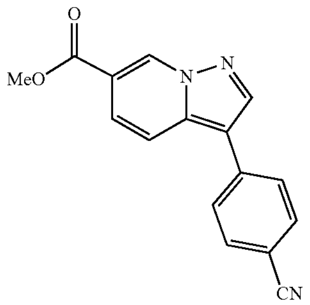 [SMILES: COC(=O)c1ccc2c(-c3ccc(C#N)cc3)cnn2c1]

A mixture of methyl 3-iodopyrazolo[1,5-a]pyridine-6-carboxylate (180 mg, 595.89 μmol, 1 eq), (4-cyanophenyl) boronic acid (105.07 mg, 715.07 μmol, 1.2 eq), $Na_2CO_3$ (126.32 mg, 1.19 mmol, 2 eq), Pd(dppf)$Cl_2$ (43.60 mg, 59.59 μmol, 0.1 eq) in dioxane (5 mL), and $H_2O$ (0.5 mL) was degassed and purged with $N_2$ (3×), and then the mixture was stirred at 90° C. for 12 h under $N_2$ atmosphere. The reaction mixture was filtered and concentrated under reduced pressure to give a residue. The reaction mixture was concentrated under reduced pressure to remove dioxane, then diluted with water (10 mL) and extracted with EtOAc (80 mL). The combined organic layers were washed with brine (30 mL), dried over $Na_2SO_4$, filtered, and concentrated under reduced pressure to afford the title compound (150 mg, crude) as a gray solid.

Step 4. 3-(4-Cyanophenyl)pyrazolo[1,5-a]pyridine-6-carboxylic acid

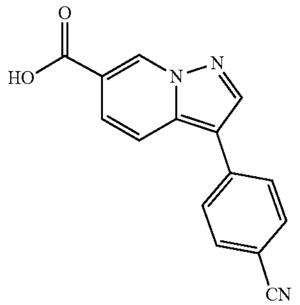 [SMILES: N#Cc1ccc(-c2cnn3cc(C(=O)O)ccc23)cc1]

A mixture of methyl 3-(4-cyanophenyl)pyrazolo[1,5-a] pyridine-6-carboxylate (130 mg, 468.85 μmol, 1 eq), NaOH (37.51 mg, 937.69 μmol, 2 eq) in MeOH (30 mL), $H_2O$ (2 mL), and THE (10 mL) was stirred at 25° C. for 14 h. The reaction mixture was concentrated under reduced pressure to remove MeOH, then HCl (12 N, 1 mL) was added. The solution was filtered and the filter cake was concentrated under reduced pressure to afford the title compound (80 mg, crude) as a gray solid.

Step 5. 3-(4-Cyanophenyl)-N-(3H-imidazo[4,5-b]pyridin-2-ylmethyl)pyrazolo[1,5-a]pyridine-6-carboxamide

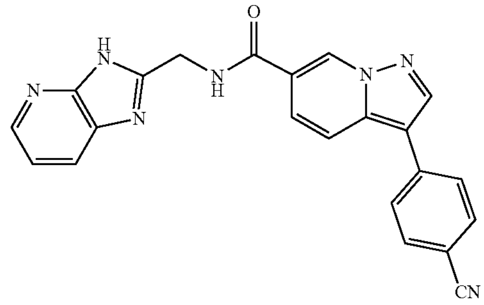 [SMILES: N#Cc1ccc(-c2cnn3cc(C(=O)NCc4nc5cccnc5[nH]4)ccc23)cc1]

To a solution of 3-(4-cyanophenyl)pyrazolo[1,5-a]pyridine-6-carboxylic acid (70 mg, 265.91 μmol, 1 eq), 3H-imidazo[4,5-b]pyridin-2-ylmethanamine (43.34 mg, 292.50 μmol, 1.1 eq) and DIEA (68.73 mg, 531.81 μmol, 92.63 μL, 2 eq) in DMF (2.5 mL), was added HATU (151.66 mg, 398.86 μmol, 1.5 eq) and the resulting mixture was stirred at 40° C. for 12 h. The reaction mixture was filtered to give a residue, which was purified by prep-HPLC (basic condition, column: Waters Xbridge Prep OBD C18 150*40 mm*10 um; mobile phase: [water(0.04% NH3H2O+10 mM $NH_4HCO_3$)-ACN]; B %: 15%-45%, 8 min) to afford the title compound (19.9 mg, 50.39 μmol, 18.95% yield, 99.618% purity) as a white solid. $^1H$ NMR (400 MHz, DMSO-$d_6$) δ: 9.42 (s, 2H), 8.74 (s, 1H), 8.27 (br s, 1H), 8.19 (d, J=9.4 Hz, 1H), 8.22-8.14 (m, 1H), 8.01-7.96 (m, 2H), 7.95-7.85 (m, 4H), 7.20 (dd, J=4.7, 7.9 Hz, 1H), 4.78 (br s, 2H).

Example 36. 3-(4-cyanophenyl)-N-(3-pyridylmethyl)imidazo[1,2-a]pyrimidine-7-carboxamide

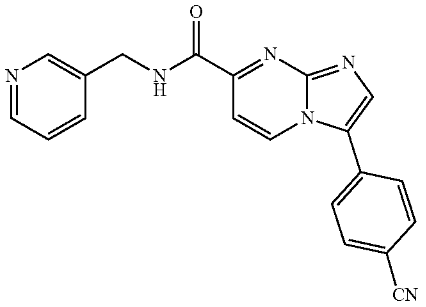 [SMILES: N#Cc1ccc(-c2cnc3nc(C(=O)NCc4cccnc4)ccn23)cc1]

Step 1. Ethyl imidazo[1,2-a]pyrimidine-7-carboxylate

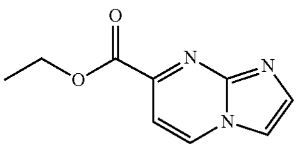

A solution of 2-bromo-1,1-diethoxyethane (1.03 g, 5.22 mmol, 786 μL, 8 eq) and HBr (330 mg, 1.96 mmol, 222 μL, 48% purity, 3 eq) in EtOH (3 mL) was heated at 90° C. for 2 h. The solution was cooled to 25° C. and solid $NaHCO_3$ (274 mg, 3.27 mmol, 5 eq) was added in small portions, follow by methyl 2-aminopyrimidine-4-carboxylate (100 mg, 653 μmol, 1 eq). The mixture was then stirred at 70° C. for 12 h, then the mixture was stirred at 90° C. for 12 h. Nine batches were worked together, the reaction mixture was added into saturated $NaHCO_3$ (aq., 100 mL), then extracted with EtOAc (100 mL, 3×). The combined organic phase was washed with brine (50 mL), then dried over $Na_2SO_4$, filtered, and filtrate was concentrated under reduced pressure to give a residue, which was purified by prep-TLC (Ethyl acetate:Methanol=5:1) to afford the title compound (75 mg, crude) as a yellow solid. $^1$H NMR (400 MHz, DMSO-$d_6$) δ: 1.37 (t, J=7.17 Hz, 3H) 4.39 (q, J=7.06 Hz, 2H) 7.60 (d, J=7.06 Hz, 1H) 7.99 (d, J=1.32 Hz, 1H) 8.15 (d, J=1.32 Hz, 1H) 9.15 (d, J=7.06 Hz, 1H).

Step 2. Ethyl 3-bromoimidazo[1,2-a]pyrimidine-7-carboxylate

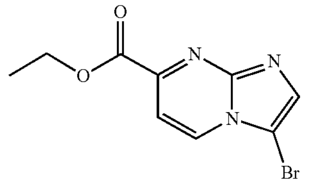

To a solution of ethyl imidazo[1,2-a]pyrimidine-7-carboxylate (45 mg, 235 μmol, 1 eq) in DMF (3 mL) was added NBS (41.9 mg, 235 μmol, 1 eq) in one portion at 0° C., and the resulting mixture was stirred at 0° C. for 1 h. The reaction mixture was added into $H_2O$ (30 mL), then extracted with EtOAc (30 mL, 3×). The combined organic phase was washed with brine (30 mL), then dried over $Na_2SO_4$, filtered, and filtrate was concentrated under reduced pressure to afford the title compound (68 mg, crude) as a yellow solid.

Step 3. 3-(4-Cyanophenyl)imidazo[1,2-a]pyrimidine-7-carboxylic acid

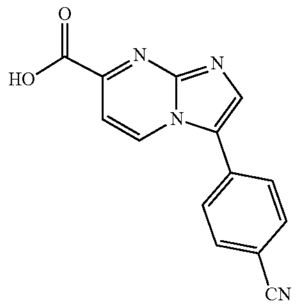 [SMILES: N#Cc1ccc(-c2cnc3nc(C(=O)O)ccn23)cc1]

A mixture of ethyl 3-bromoimidazo[1,2-a]pyrimidine-7-carboxylate (68 mg, 251.78 μmol, 1 eq), (4-cyanophenyl) boronic acid (44.4 mg, 302 μmol, 1.2 eq), $Na_2CO_3$ (53.4 mg, 504 μmol, 2 eq), Pd(dppf)$Cl_2$ (18.4 mg, 25.2 μmol, 0.1 eq) in dioxane (4 mL), and $H_2O$ (0.4 mL) was degassed and purged with $N_2$ (3×), and then the mixture was stirred at 90° C. for 5 h under $N_2$ atmosphere. The reaction mixture was added into $H_2O$ (20 mL), then extracted with EtOAc (20 mL, 2×). The combined organic phase was washed with $H_2O$ (20 mL), then HCl (3N) was added to the water phase to pH=5, then extracted with EtOAc (20 mL, 2×), dried over $Na_2SO_4$, filtered, and the filtrate was concentrated under reduced pressure to afford the title compound (67 mg, crude) as a yellow solid.

Step 4. 3-(4-Cyanophenyl)-N-(3-pyridylmethyl)imidazo[1,2-a]pyrimidine-7-carboxamide

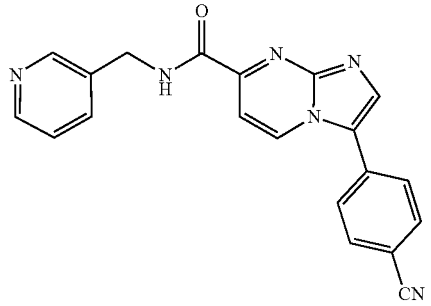 [SMILES: N#Cc1ccc(-c2cnc3nc(C(=O)NCc4cccnc4)ccn23)cc1]

To a solution of 3-(4-cyanophenyl)imidazo[1,2-a]pyrimidine-7-carboxylic acid (57 mg, 216 μmol, 1 eq) and 3-pyridylmethanamine (25.7 mg, 237 μmol, 24 μL, 1.1 eq) in DMF (2 mL) was added DIEA (83.6 mg, 647 μmol, 113 μL, 3 eq) and HATU (164 mg, 431 μmol, 2 eq) in one portion at 25° C., and the resulting mixture was stirred at 40° C. for 3 h. The mixture was filtered and the filtrate was concentrated to give a crude product, which was purified by prep-HPLC (basic condition column: Waters Xbridge Prep OBD C18 150*40 mm*10 um; mobile phase: [water (0.040% $NH_3H_2O$+10 mM $NH_4HCO_3$)-ACN]; B %: 15%-40%, 8 min) to afford the title compound (5.9 mg, 16.25 μmol, 7.53% yield, 97.578% purity) as a white solid. $^1$H NMR (400 MHz, DMSO-$d_6$) δ: 4.54 (d, J=6.39 Hz, 2H) 7.36 (dd, J=7.61, 4.52 Hz, 1H) 7.68 (d, J=7.06 Hz, 1H) 7.73-7.80 (m, 1H) 7.94-8.08 (m, 4H) 8.36 (s, 1H) 8.46 (dd, J=4.74, 1.43 Hz, 1H) 8.58 (d, J=1.54 Hz, 1H) 9.28 (d, J=7.06 Hz, 1H) 9.71-9.86 (m, 1H).

Example 37. 3-(4-Cyanophenyl)-N-(3-pyridylmethyl)pyrazolo[1,5-a]pyridine-6-carboxamide

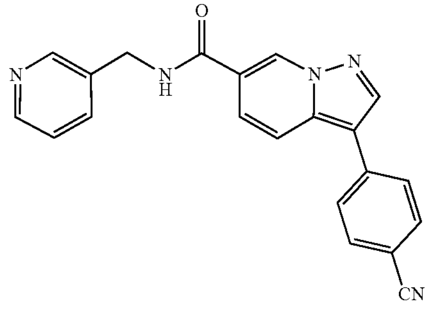 [SMILES: N#Cc1ccc(-c2cnn3cc(C(=O)NCc4cccnc4)ccc23)cc1]

Step 1. N-(3-Pyridylmethyl)pyrazolo[1,5-a]pyridine-6-carboxamide

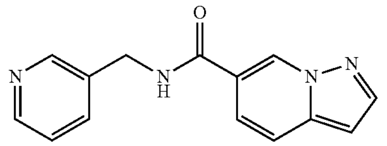 [SMILES: O=C(NCc1cccnc1)c1ccc2ccnn2c1]

A mixture of pyrazolo[1,5-a]pyridine-6-carboxylic acid (0.1 g, 616.73 μmol, 1 eq), 3-pyridylmethanamine (73.36 mg, 678.40 μmol, 68.56 μL, 1.1 eq) 3-pyridylmethanamine (73.36 mg, 678.40 μmol, 68.56 μL, 1.1 eq), DIEA (159.42 mg, 1.23 mmol, 214.85 μL, 2 eq) and HATU (351.75 mg, 925.10 μmol, 1.5 eq) in DMF (3 mL) was stirred at 40° C. for 12 h. The reaction was quenched by addition water (30 mL) then extracted with EtOAc (200 mL). The combined organic layers were washed with brine (50 mL), dried over $Na_2SO_4$, filtered, and concentrated under reduced pressure to afford the title compound (160 mg, crude) as a brown oil.

Step 2. 3-Iodo-N-(3-pyridylmethyl)pyrazolo[1,5-a]pyridine-6-carboxamide

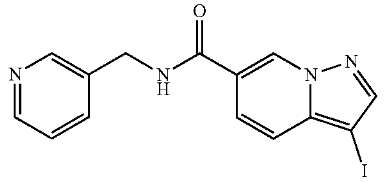 [SMILES: O=C(NCc1cccnc1)c1ccc2c(I)cnn2c1]

A mixture of N-(3-pyridylmethyl)pyrazolo[1,5-a]pyridine-6-carboxamide (160 mg, 634.24 μmol, 1 eq) and NIS (156.96 mg, 697.66 μmol, 1.1 eq) in DMF (5 mL) was stirred at 20° C. for 1 h. The reaction mixture was quenched by addition water (25 mL) and extracted with EtOAc (160 mL). The combined organic layers were washed with brine (90 mL), dried over $Na_2SO_4$, filtered, and concentrated under reduced pressure to afford the title compound (240 mg, crude) as a yellow solid.

Step 3. 3-(4-Cyanophenyl)-N-(3-pyridylmethyl)pyrazolo[1,5-a]pyridine-6-carboxamide

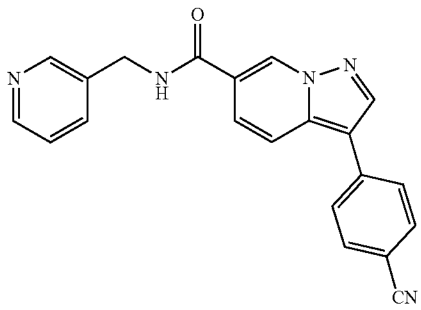 [SMILES: N#Cc1ccc(-c2cnn3cc(C(=O)NCc4cccnc4)ccc23)cc1]

A mixture of 3-iodo-N-(3-pyridylmethyl)pyrazolo[1,5-a]pyridine-6-carboxamide (210 mg, 555.31 μmol, 1 eq), (4-cyanophenyl)boronic acid (97.92 mg, 666.37 μmol, 1.2 eq), $Na_2CO_3$ (117.71 mg, 1.11 mmol, 2 eq), Pd(dppf)$Cl_2$ (40.63 mg, 55.53 μmol, 0.1 eq) in dioxane (5 mL) and $H_2O$ (0.5 mL) was degassed and purged with $N_2$ (3×), and then the mixture was stirred at 90° C. for 12 h under $N_2$ atmosphere. The reaction mixture was filtered and concentrated under reduced pressure to give a residue, which was purified by prep-HPLC (basic condition column: Waters Xbridge 150*25 mm*5 um; mobile phase: [water(0.04% $NH_3H_2O$+10 mM $NH_4HCO_3$)-ACN]; B %: 27%-57%, 10 min) to afford the title compound (90.3 mg, 252.33 μmol, 45.44% yield, 98.746% purity) as a light yellow solid. $^1$H NMR (400 MHz, DMSO-$d_6$) δ: 9.35 (s, 1H), 8.72 (s, 1H), 8.60 (d, J=1.4 Hz, 1H), 8.48 (d, J=3.6 Hz, 1H), 8.16 (d, J=9.4 Hz, 1H), 7.98-7.94 (m, 2H), 7.93-7.88 (m, 2H), 7.85 (dd, J=1.1, 9.4 Hz, 1H), 7.78 (br d, J=7.9 Hz, 1H), 7.38 (dd, J=4.9, 7.8 Hz, 1H), 7.21 (br s, 1H), 4.55 (d, J=5.6 Hz, 2H).

Example 38. 4-[7-[(3-Methyloxetan-3-yl)methoxy]imidazo[1,2-a]pyridin-3-yl]benzonitrile

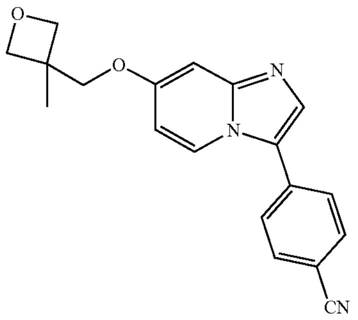 [SMILES: CC1(COc2ccn3c(-c4ccc(C#N)cc4)cnc3c2)COC1]

A mixture of 7-[(3-methyloxetan-3-yl)methoxy]imidazo[1,2-a]pyridine (0.1 g, 458.2 mol, 1 eq), 4-bromobenzonitrile (100.1 mg, 549.8 μmol, 1.2 eq), $Cs_2CO_3$ (447.9 mg, 1.4 mmol, 3 eq), [2-(2-aminophenyl)phenyl]chloropalladium; bis(1-adamantyl)butylphosphane (30.6 mg, 45.8 μmol, 0.1 eq) in DMF (3 mL) was degassed and purged with $N_2$ (3×), and then the mixture was stirred at 100° C. for 12 h under $N_2$ atmosphere. The reaction mixture was filtered and concentrated under reduced pressure to give a residue, which was purified by prep-HPLC (basic condition; column: Waters Xbridge Prep OBD C18 150*40 mm*10 um; mobile phase: [water (0.04% $NH_3H_2O$+10 mM $NH_4HCO_3$)-ACN]; B %: 25%-55%, 8 min) to afford the title compound (8.7 mg, 25.2 μmol, 5.5% yield, 92.3% purity) as a yellow solid which was confirmed by $^1$H-NMR and QC LCMS. $^1$H NMR (400 MHz, DMSO-$d_6$) δ: 8.58 (d, J=7.5 Hz, 1H), 8.02-7.92 (m, 2H), 7.91-7.81 (m, 3H), 7.16 (d, J=2.4 Hz, 1H), 6.78 (dd, J=2.5, 7.6 Hz, 1H), 4.53 (d, J=5.9 Hz, 2H), 4.35 (d, J=5.9 Hz, 2H), 4.20 (s, 2H), 1.41 (s, 3H).

Examples 39-40

Examples 39-40 were prepared according to the procedures described for Example 38, using appropriately substituted starting materials. NMR data for the compounds of Examples 39-40 are shown in Table 5B.

TABLE 5A

| Ex. No. | Compound Name | Structure | Amount | Purity |
|---|---|---|---|---|
| 39 | 2-(2,6-dimethoxy-4-(7-((3-methyloxetan-3-yl)methoxy)imidazo[1,2-a]pyridin-3-yl)phenyl)-5-ethyl-1,3,4-oxadiazole | 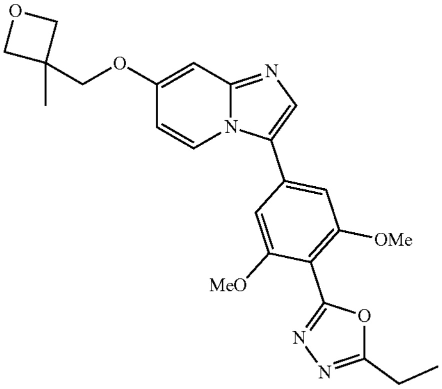 [SMILES: CCc1nnc(-c2c(OC)cc(-c3cnc4cc(OCC5(C)COC5)ccn34)cc2OC)o1] | 29.5 mg | 97.963% |
| 40 | 2,6-dimethoxy-4-(7-((3-methyloxetan-3-yl)methoxy)imidazo[1,2-a]pyridin-3-yl)benzonitrile | 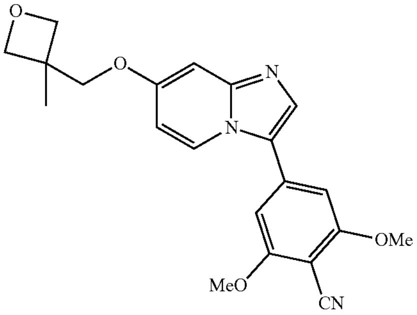 [SMILES: COc1cc(-c2cnc3cc(OCC4(C)COC4)ccn23)cc(OC)c1C#N] | | 98.384% |

TABLE 5B

| Ex. No. | 1H-NMR Data |
|---|---|
| 39 | $^1$H NMR (400 MHz, MeOD-$d_4$) δ: 8.69 (d, J = 7.6 Hz, 1H), 7.98 (br s, 1H), 7.33 (br s, 1H), 7.09 (s, 3H), 4.71 (d, J = 6.0 Hz, 2H), 4.53 (d, J = 6.0 Hz, 2H), 4.32 (s, 2H), 3.92 (s, 6H), 3.01 (q, J = 7.6 Hz, 2H), 1.51 (s, 3H), 1.44 (t, J = 7.6 Hz, 3H) |
| 40 | $^1$H NMR (400 MHz, DMSO-$d_6$) δ: 8.68 (d, J = 7.5 Hz, 1H), 7.87 (s, 1H), 7.16 (d, J = 2.0 Hz, 1H), 7.01 (s, 2H), 6.75 (dd, J = 2.4, 7.6 Hz, 1H), 4.53 (d, J = 5.9 Hz, 2H), 4.35 (d, J = 5.8 Hz, 2H), 4.20 (s, 2H), 4.00 (s, 6H), 1.41 (s, 3H) |

Example 41. 4-[7-[2-(6-Methyl-3-pyridyl)ethoxy]imidazo[1,2-a]pyridin-3-yl]benzonitrile

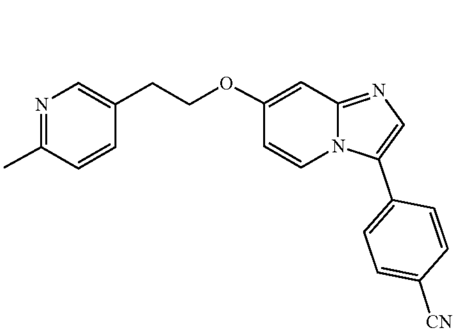 [SMILES: Cc1ccc(CCOc2ccn3c(-c4ccc(C#N)cc4)cnc3c2)cn1]

Step 1. Diethyl 2-(6-methyl-3-pyridyl)propanedioate

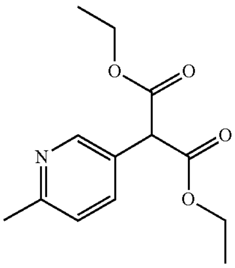 [SMILES: CCOC(=O)C(C(=O)OCC)c1ccc(C)nc1]

A mixture of 5-bromo-2-methylpyridine (5 g, 29.1 mmol, 1 eq), diethyl propanedioate (11.6 g, 72.7 mmol, 11.0 mL, 2.5 eq), $Pd(OAc)_2$ (653 mg, 2.91 mmol, 0.1 eq), $K_3PO_4$ (18.5 g, 87.2 mmol, 3 eq), and ditert-butyl-(2-phenylphenyl)

phosphane (867 mg, 2.91 mmol, 0.1 eq) in toluene (30 mL) was degassed and purged with $N_2$ (3×), and then the mixture was stirred at 100° C. for 48 h under $N_2$ atmosphere. The reaction mixture was filtered and concentrated under reduced pressure to give a residue, which was purified by column chromatography ($SiO_2$, Petroleum ether/Ethyl acetate=1/0 to 8/1) to afford the title compound (5 g, crude) as a yellow oil.

Step 2. 2-(6-Methyl-3-pyridyl)acetic acid

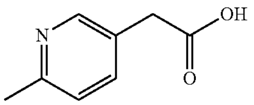

A mixture of diethyl 2-(6-methyl-3-pyridyl)propanedioate (5 g, 19.9 mmol, 1 eq) in HCl (6 N, 30 mL) was stirred at 100° C. for 4 h. The mixture was concentrated to give a crude product, which was added into $H_2O$ (20 mL), then extracted with EtOAc (30 mL, 2×), and the water phase was lyophilized to afford the title compound (3.7 g, crude) as a yellow solid. $^1H$ NMR (400 MHz, DMSO-$d_6$) δ: 2.75 (s, 3H) 3.90 (s, 2H) 7.89 (d, J=8.25 Hz, 1H) 8.39 (dd, J=8.25, 1.75 Hz, 1H) 8.70 (d, J=1.38 Hz, 1H).

Step 3. 2-(6-Methyl-3-pyridyl) ethanol

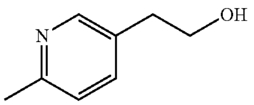

To a solution of 2-(6-methyl-3-pyridyl)acetic acid (2 g, 13.2 mmol, 1 eq) in THE (30 mL) was added $BH_3$·THF (1 M, 46.3 mL, 3.5 eq) dropwise at 0° C., and the resulting mixture was stirred at 0° C. for 30 min, followed by stirring at 25° C. for 2 h. The reaction was quenched with methanol (50 mL) at 0° C., then the mixture was stirred at 25° C. for 12 h. The mixture was filtered and the filtrate was concentrated to give a crude product, which was purified by column chromatography ($SiO_2$, Petroleum ether/Ethyl acetate=1:0 to 1:4, 5% TEA) to afford the title compound (1.17 g, crude) as a yellow oil.

Step 4. 4-[2-(6-Methyl-3-pyridyl)ethoxy]pyridin-2-amine

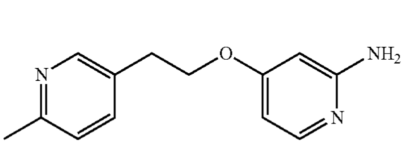 [SMILES: Cc1ccc(CCOc2ccnc(N)c2)cn1]

To a solution of 2-aminopyridin-4-ol (0.6 g, 5.45 mmol, 1 eq), 2-(6-methyl-3-pyridyl)ethanol (449 mg, 3.27 mmol, 0.6 eq) and $PPh_3$ (1.43 g, 5.45 mmol, 1 eq) in DCM (60 mL), was added DIAD (1.10 g, 5.45 mmol, 1.06 mL, 1 eq) at 0° C. under $N_2$, and the resulting mixture was stirred at 25° C. for 12 h under $N_2$. The mixture was filtered and the filtrate was concentrated to give a crude product, which was purified by column chromatography ($SiO_2$, Petroleum ether/Ethyl acetate/Methanol=1:0:0 to 0:10:1.5% TEA) to afford the title compound (390 mg, crude) as a yellow solid.

Step 5. 7-[2-(6-Methyl-3-pyridyl)ethoxy]imidazo[1,2-a]pyridine

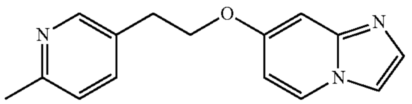 [SMILES: Cc1ccc(CCOc2ccn3ccnc3c2)cn1]

To a mixture of 4-[2-(6-methyl-3-pyridyl)ethoxy]pyridin-2-amine (97 mg, 423 μmol, 1 eq) in EtOH (4 mL) was added $NaHCO_3$ (142 mg, 1.69 mmol, 65.8 μL, 4 eq) and 2-chloroacetaldehyde (415 mg, 2.12 mmol, 340 μL, 5 eq) in one portion at 25° C., and the resulting mixture was stirred at 70° C. for 2 h. Four batches were worked together and concentrated under reduced pressure to remove EtOH, then extracted with EtOAc (50 mL, 2×). The combined organic phase was washed with saturated $NH_4Cl$ (aq., 50 mL) and brine (50 mL), then dried over $Na_2SO_4$, filtered, and the filtrate was concentrated under reduced pressure to give a residue, which was purified by column ($SiO_2$, Petroleum ether/Ethyl acetate/Methanol=1:0:0 to 0:10:1, 5% TEA) to afford the title compound (380 mg, crude) as a yellow oil.

Step 6. 4-[7-[2-(6-Methyl-3-pyridyl)ethoxy]imidazo[1,2-a]pyridin-3-yl]benzonitrile

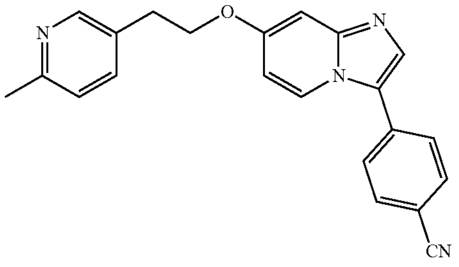 [SMILES: Cc1ccc(CCOc2ccn3c(-c4ccc(C#N)cc4)cnc3c2)cn1]

To a solution of 4-bromobenzonitrile (201 mg, 1.11 mmol, 1.4 eq), 7-[2-(6-methyl-3-pyridyl)ethoxy]imidazo[1,2-a]pyridine (200 mg, 790 μmol, 1 eq), and $Cs_2CO_3$ (772 mg, 2.37 mmol, 3 eq) in DMAC (5 mL) was added Pd(dppf)$Cl_2$·$CH_2Cl_2$ (32.2 mg, 39.5 μmol, 0.05 eq), in one portion at 25° C. under $N_2$, and the resulting mixture was stirred at 100° C. for 12 h. The reaction mixture was added into saturated $NH_4Cl$ (aq., 50 mL), then extracted with EtOAc (50 mL, 2×). The combined organic phase was washed with brine (50 mL), then dried over $Na_2SO_4$, filtered, and filtrate was concentrated under reduced pressure to give a residue, which was purified by prep-TLC (Ethyl acetate:Methanol:$NH_3$·$H_2O$=100:10:4) to give a crude product. The crude was purified by prep-HPLC (basic condition, column: Waters Xbridge Prep OBD C18 150*40 mm*40 um; mobile phase: [water(0.05% $NH_3H_2O$+10 mM $NH_4HCO_3$)-ACN]; B %: 30%-60%, 8 min) to afford the title compound (73.8 mg, 207.72 μmol, 26.31% yield, 99.753% purity) as a gray solid. $^1H$ NMR (400 MHz, DMSO-$d_6$) δ: 2.43 (s, 3H) 3.06 (t, J=6.44 Hz, 2H) 4.32 (t, J=6.50 Hz, 2H) 6.68 (dd, J=7.63, 2.50 Hz, 1H) 7.10 (d, J=2.50 Hz, 1H) 7.19 (d, J=7.88 Hz, 1H) 7.65 (dd, J=7.94, 2.31 Hz, 1H) 7.78-7.87 (m, 3H) 7.90-7.97 (m, 2H) 8.41 (d, J=2.00 Hz, 1H) 8.52 (d, J=7.63 Hz, 1H).

Example 42. 2-[2,6-Dimethoxy-4-[7-[(6-methyl-3-pyridyl)methoxy]imidazo[1,2-a]pyridin-3-yl]phenyl]-5-ethyl-1,3,4-oxadiazole

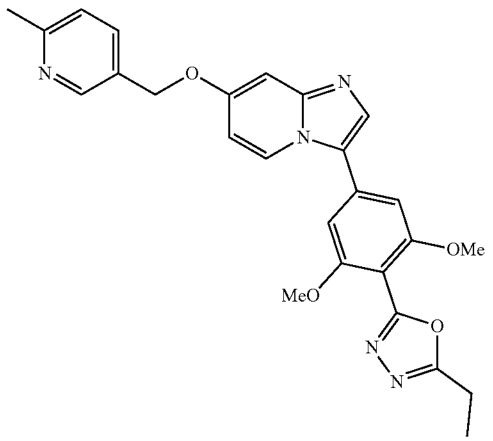 [SMILES: CCc1nnc(-c2c(OC)cc(-c3cnc4cc(OCc5ccc(C)nc5)ccn34)cc2OC)o1]

Step 1. 4-[(6-Methyl-3-pyridyl)methoxy]pyridin-2-amine

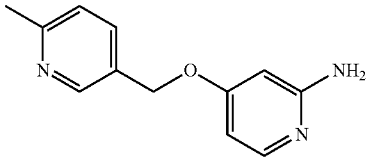 [SMILES: Cc1ccc(COc2ccnc(N)c2)cn1]

To a solution of 2-aminopyridin-4-ol (3 g, 27.24 mmol, 1 eq), (6-methyl-3-pyridyl)methanol (2.01 g, 16.35 mmol, 0.6 eq) and $PPh_3$ (7.15 g, 27.24 mmol, 1 eq) in DCM (50 mL) was added DIAD (5.51 g, 27.24 mmol, 5.30 mL, 1 eq) at 0° C. under $N_2$, and the resulting mixture was stirred at 20° C. for 12 h. The mixture was filtered and the filtrate was concentrated to give a crude product, which was purified by column chromatography ($SiO_2$, Petroleum ether/Ethyl acetate/Methanol=50:1:0 to 0:10:1) to afford the title compound (1.8 g, 8.36 mmol, 30.69% yield) as a light yellow solid.

Step 2. 7-[(6-Methyl-3-pyridyl)methoxy]imidazo[1,2-a]pyridine

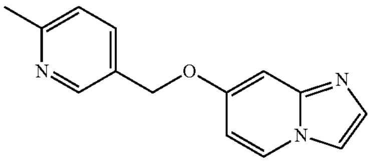 [SMILES: Cc1ccc(COc2ccn3ccnc3c2)cn1]

To a mixture of 4-[(6-methyl-3-pyridyl)methoxy]pyridin-2-amine (500 mg, 2.32 mmol, 1 eq) in EtOH (5 mL) was added $NaHCO_3$ (779.58 mg, 9.28 mmol, 360.92 μL, 4 eq) and 2-chloroacetaldehyde (910.57 mg, 11.60 mmol, 746.37 μL, 5 eq) in at 20° C., and the resulting mixture was stirred at 70° C. for 4 h. The reaction mixture was concentrated under reduced pressure to remove EtOH and then extracted with EtOAc (50 mL, 2×). The combined organic phase was washed with saturated $NH_4Cl$ (aq., 15 mL) and brine (50 mL), then dried over $Na_2SO_4$, filtered, and the filtrate was concentrated under reduced pressure to afford the title compound (500 mg, crude) as a yellow solid.

Step 3. 2-[2,6-Dimethoxy-4-[7-[(6-methyl-3-pyridyl)methoxy]imidazo[1,2-a]pyridin-3-yl]phenyl]-5-ethyl-1,3,4-oxadiazole

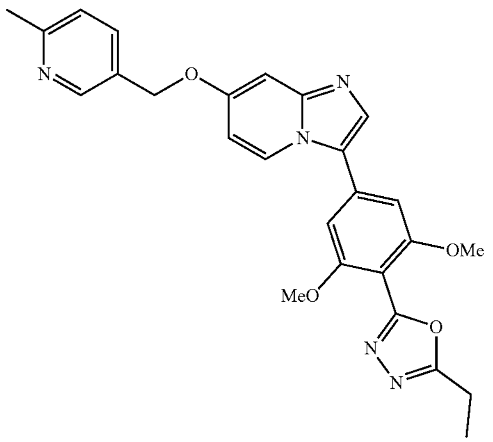 [SMILES: CCc1nnc(-c2c(OC)cc(-c3cnc4cc(OCc5ccc(C)nc5)ccn34)cc2OC)o1]

To a solution of 7-[(6-methyl-3-pyridyl)methoxy]imidazo[1,2-a]pyridine (300 mg, 1.25 mmol, 1 eq), 2-(4-bromo-2,6-dimethoxy-phenyl)-5-ethyl-1,3,4-oxadiazole (392.62 mg, 1.25 mmol, 1 eq), and $Cs_2CO_3$ (817.03 mg, 2.51 mmol, 2 eq) in DMA (1 mL) was added $Pd(dppf)Cl_2 \cdot CH_2Cl_2$ (102.39 mg, 125.38 μmol, 0.1 eq) under $N_2$, and the resulting mixture was stirred at 100° C. for 3 h. The reaction mixture was then concentrated to give the crude product, which was purified by prep-HPLC (basic condition; column: Phenomenex Gemini-NX C18 75*30 mm*3 um; mobile phase: [water (0.05% $NH_3H_2O$+10 mM $NH_4HCO_3$)-ACN]; B %: 20%-50%, 8 min) to afford the title compound (43.4 mg, 88.99 μmol, 7.10% yield, 96.681% purity) as a pink solid. $^1H$ NMR (400 MHz, DMSO-$d_6$) δ: 8.68 (d, J=7.6 Hz, 1H), 8.61 (s, 1H), 7.82 (s, 2H), 7.33 (d, J=7.9 Hz, 1H), 7.22 (br d, J=1.3 Hz, 1H), 7.02 (s, 2H), 6.77 (dd, J=1.9, 7.4 Hz, 1H), 5.26 (s, 2H), 3.86 (s, 6H), 2.94 (q, J=7.5 Hz, 2H), 2.50 (br s, 3H), 1.32 (t, J=7.5 Hz, 3H).

Example 43. 4-[5-(1-Ethylpyrazol-4-yl)benzimidazol-1-yl]benzonitrile

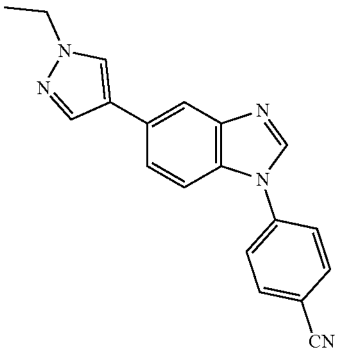 [SMILES: CCn1cc(-c2ccc3c(c2)ncn3-c2ccc(C#N)cc2)cn1]

Step 1. 4-(4-Bromo-2-nitroanilino)benzonitrile

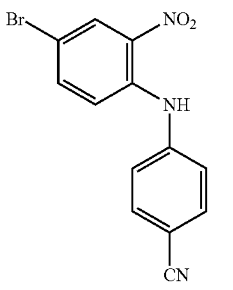 [SMILES: N#Cc1ccc(Nc2ccc(Br)cc2[N+](=O)[O-])cc1]

To a solution of 4-bromo-1-fluoro-2-nitrobenzene (300 mg, 1.4 mmol, 167.6 μL, 1 eq) and t-BuOK (306.0 mg, 2.7 mmol, 2 eq) in DMSO (3 mL) was added 4-aminobenzonitrile (161.1 mg, 1.4 mmol, 1 eq), and the resulting mixture was stirred at 80° C. for 2 h. The mixture was then partitioned between water (5 mL) and ethyl acetate (5 mL, 3×). The organic phase was separated, washed with brine (5 mL), dried over $Na_2SO_4$, filtered, and concentrated under reduced pressure to afford the title compound (400 mg, crude) as brown oil.

Step 2. 4-(2-Amino-4-bromoanilino)benzonitrile

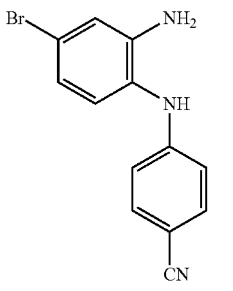 [SMILES: N#Cc1ccc(Nc2ccc(Br)cc2N)cc1]

To a solution of 4-(4-bromo-2-nitroanilino)benzonitrile (300 mg, 943.0 μmol, 1 eq) and $NH_4Cl$ (252.2 mg, 4.7 mmol, 5 eq) in EtOH (4 mL) and $H_2O$ (0.5 mL) was added Fe (263.3 mg, 4.7 mmol, 5 eq), and the resulting mixture was stirred at 80° C. for 2 h. The reaction mixture was filtered and the filtrate was concentrated to afford the title compound (200 mg, 694.1 μmol, 73.6% yield) as a pink solid.

Step 3. 4-(5-Bromobenzimidazol-1-yl)benzonitrile

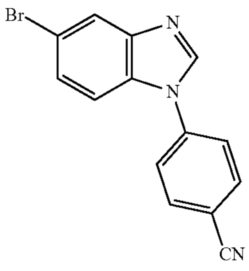 [SMILES: N#Cc1ccc(-n2cnc3cc(Br)ccc32)cc1]

To a solution of 4-(2-amino-4-bromoanilino)benzonitrile (200 mg, 694.1 μmol, 1 eq) in trimethylorthoformate (2 mL) was added HCOOH (100.0 mg, 2.1 mmol, 3 eq), and the resulting mixture was stirred at 100° C. for 2 h. The reaction mixture was concentrated under reduced pressure to give a residue, which was purified by prep-TLC ($SiO_2$, Petroleum ether/Ethyl acetate=1:1) to afford the title compound (40 mg, 134.2 μmol, 19.3% yield) as a pink solid.

Step 4. 4-[5-(1-Ethylpyrazol-4-yl)benzimidazol-1-yl]benzonitrile

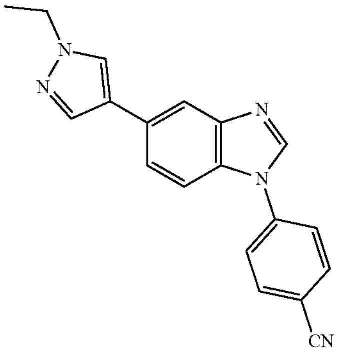 [SMILES: CCn1cc(-c2ccc3c(c2)ncn3-c2ccc(C#N)cc2)cn1]

To a solution of 4-(5-bromobenzimidazol-1-yl)benzonitrile (40 mg, 134.2 μmol, 1 eq), 1-ethyl-4-(4,4,5,5-tetramethyl-1,3,2-dioxaborolan-2-yl)pyrazole (32.8 mg, 147.6 μmol, 1.1 eq) and $Na_2CO_3$ (28.4 mg, 268.3 μmol, 2 eq) in dioxane (1 mL) and $H_2O$ (0.2 mL) was added $Pd(dppf)Cl_2$ (9.8 mg, 13.4 μmol, 0.1 eq) under $N_2$, and the resulting mixture was stirred at 100° C. for 12 h. The mixture was partitioned between water (5 mL) and ethyl acetate (5 mL, 3×). The organic phase was separated, washed with brine (5 mL), dried over $Na_2SO_4$, filtered, and concentrated under reduced pressure to give the crude product, which was purified by prep-HPLC (basic condition, column: Phenomenex Gemini-NX C18 75*30 mm*3 um; mobile phase: [water(0.05% $NH_3H_2O$+10 mM $NH_4HCO_3$)-ACN]; B %: 15%-45%, 8 min) to afford the title compound (12.4 mg, 39.2 μmol, 29.2% yield, 99.1% purity) as a white solid. $^1H$ NMR (400 MHz, MeOD-$d_4$) δ: 8.55 (s, 1H), 8.08 (s, 1H), 8.02 (d, J=8.5 Hz, 2H), 7.94 (s, 1H), 7.92-7.87 (m, 3H), 7.77-7.59 (m, 2H), 4.25 (q, J=7.3 Hz, 2H), 1.53 (t, J=7.3 Hz, 3H).

Example 44. 4-(5-(1-Cyclopropyl-1H-pyrazol-4-yl)-1H-benzo[d]imidazol-1-yl)benzonitrile

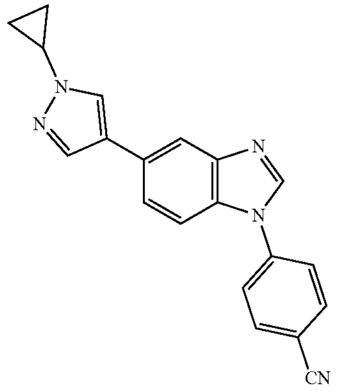 [SMILES: N#Cc1ccc(-n2cnc3cc(-c4cnn(C5CC5)c4)ccc32)cc1]

The title compound was prepared according to the procedures described in Example 43, using appropriately substituted starting materials. Yield: 19.3 mg; 95.5% purity. $^1H$ NMR (400 MHz, DMSO-$d_6$) δ: 8.69 (s, 1H), 8.33 (s, 1H), 8.14 (br d, J=7.9 Hz, 2H), 8.04 (br s, 1H), 7.98 (br d, J=9.5 Hz, 3H), 7.72 (br d, J=8.3 Hz, 1H), 7.63 (br d, J=8.3 Hz, 1H), 3.76 (br s, 1H), 1.19-0.89 (m, 4H).

Example 45. 4-[7-(1-Ethylpyrazol-4-yl) imidazo[1,2-a]pyridin-3-yl]benzonitrile

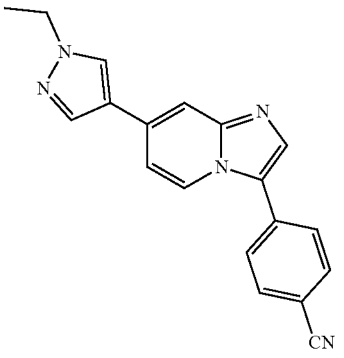 [SMILES: CCn1cc(-c2ccn3c(-c4ccc(C#N)cc4)cnc3c2)cn1]

Step 1. 7-(1-Ethylpyrazol-4-yl)imidazo[1,2-a]pyridine

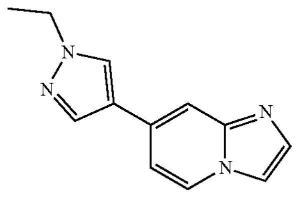 [SMILES: CCn1cc(-c2ccn3ccnc3c2)cn1]

A mixture of 7-bromoimidazo[1,2-a]pyridine (150 mg, 761.3 μmol, 1 eq), 1-ethyl-4-(4,4,5,5-tetramethyl-1,3,2-dioxaborolan-2-yl)pyrazole (169.1 mg, 761.3 μmol, 1 eq), $Na_2CO_3$ (161.4 mg, 1.5 mmol, 2 eq), Pd(dppf)$Cl_2$ (55.7 mg, 76.1 μmol, 0.1 eq) in dioxane (5 mL) and $H_2O$ (0.5 mL) was degassed and purged with $N_2$ (3×), then the mixture was stirred at 90° C. for 12 h under $N_2$ atmosphere. The reaction mixture was diluted with water (30 mL) and extracted with EtOAc (150 mL). The combined organic layers were washed with brine (50 mL), dried over $Na_2SO_4$, filtered, and concentrated under reduced pressure to afford the title compound (160 mg, crude) as a brown oil.

Step 2. 4-[7-(1-Ethylpyrazol-4-yl)imidazo[1,2-a]pyridin-3-yl]benzonitrile

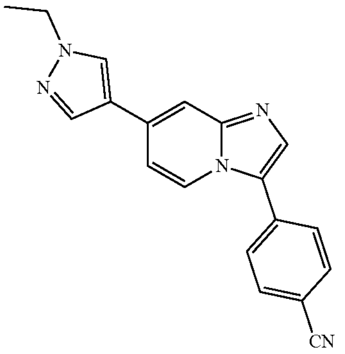 [SMILES: CCn1cc(-c2ccn3c(-c4ccc(C#N)cc4)cnc3c2)cn1]

To a solution of 7-(1-ethylpyrazol-4-yl)imidazo[1,2-a]pyridine (160 mg, 753.8 μmol, 1 eq), 4-bromobenzonitrile (164.7 mg, 904.6 μmol, 1.2 eq), and $Cs_2CO_3$ (736.8 mg, 2.3 mmol, 3 eq) in DMA (5 mL) was added Pd(dppf)$Cl_2$·$CH_2Cl_2$ (30.8 mg, 37.7 μmol, 0.05 eq), and the resulting mixture was stirred at 100° C. for 12 h. The reaction mixture was filtered and concentrated under reduced pressure to give a residue, which was triturated with EtOAc (15 mL) at 25° C. for 20 min to afford the title compound (60.6 mg, 191.7 μmol, 25.4% yield, 99.1% purity) as a yellow solid. $^1H$ NMR (400 MHz, DMSO-$d_6$) δ: 8.63 (d, J=7.3 Hz, 1H), 8.41 (s, 1H), 8.07 (s, 1H), 7.97-7.85 (m, 6H), 7.25 (dd, J=1.5, 7.1 Hz, 1H), 4.14 (q, J=7.3 Hz, 2H), 1.39 (t, J=7.3 Hz, 3H).

Examples 46-47

Examples 46-47 were prepared according to the procedures described in Example 45, using appropriately substituted starting materials. NMR data for the compounds of Examples 46-47 are shown in Table 6B.

TABLE 6A

| Ex. No. | Compound Name | Structure | Amount | Purity |
|---|---|---|---|---|
| 46 | 5-(7-(1-ethyl-1H-pyrazol-4-yl)imidazo[1,2-a]pyridin-3-yl)picolinonitrile | 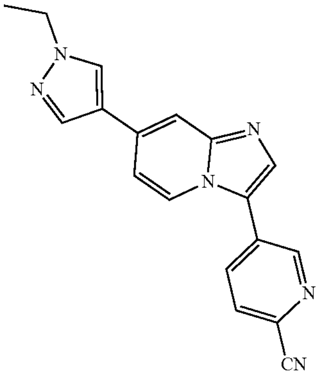 [SMILES: CCn1cc(-c2ccn3c(-c4ccc(C#N)nc4)cnc3c2)cn1] | 37.6 mg | 100% |
| 47 | 4-(7-(1-ethyl-1H-pyrazol-4-yl)imidazo[1,2-a]pyridin-3-yl)-2-methylbenzonitrile | 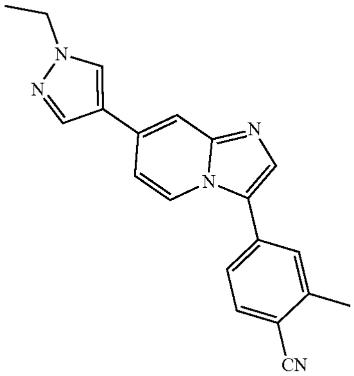 [SMILES: CCn1cc(-c2ccn3c(-c4ccc(C#N)c(C)c4)cnc3c2)cn1] | 13.1 mg | 97.3% |

TABLE 6B

| Ex. No. | 1H-NMR Data |
|---|---|
| 46 | $^1$H NMR (400 MHz, MeOD-$d_4$) δ: 9.07 (d, J = 2.0 Hz, 1H), 8.66 (d, J = 7.3 Hz, 1H), 8.34 (dd, J = 2.3, 8.1 Hz, 1H), 8.28 (s, 1H), 8.07-8.00 (m, 2H), 7.96 (s, 1H), 7.83 (s, 1H), 7.36 (dd, J = 1.5, 7.3 Hz, 1H), 4.28 (q, J = 7.3 Hz, 2H), 1.54 (t, J = 7.3 Hz, 3H) |
| 47 | $^1$H NMR (400 MHz, MeOD-$d_4$) δ: 8.60 (d, J = 7.3 Hz, 1H), 8.26 (s, 1H), 8.03 (s, 1H), 7.86-7.73 (m, 4H), 7.68 (d, J = 8.0 Hz, 1H), 7.32 (dd, J = 1.6, 7.3 Hz, 1H), 4.27 (q, J = 7.3 Hz, 2H), 2.65 (s, 3H), 1.54 (t, J = 7.3 Hz, 3H) |

Example 48. 4-[7-(4-Cyclopropylimidazol-1-yl)imidazo[1,2-a]pyridin-3-yl]benzonitrile

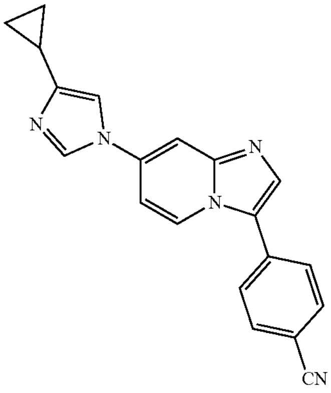 [SMILES: N#Cc1ccc(-c2cnc3cc(-n4cnc(C5CC5)c4)ccn23)cc1]

Step 1. 7-Bromoimidazo[1,2-a]pyridine

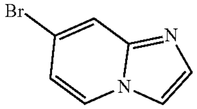

A mixture of 4-bromopyridin-2-amine (25 g, 144.5 mmol, 1 eq), 2-chloroacetaldehyde (70.9 g, 361.3 mmol, 58.1 mL, 40% purity, 2.5 eq), and $NaHCO_3$ (24.3 g, 289.0 mmol, 11.2 mL, 2 eq) in EtOH (500 mL) was stirred at 80° C. for 12 h. The reaction mixture was concentrated under reduced pressure to remove EtOH, and the resulting residue was purified by column chromatography ($SiO_2$, Petroleum ether:Ethyl acetate=1:0 to 0:1) to afford the title compound (33 g, crude) as a brown oil.

Step 2. 7-(4-Cyclopropylimidazol-1-yl)imidazo[1,2-a]pyridine

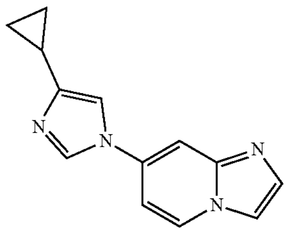 [SMILES: c1cn2ccc(-n3cnc(C4CC4)c3)cc2n1]

To a solution of 7-bromoimidazo[1,2-a]pyridine (120 mg, 609.0 μmol, 1 eq), 4-cyclopropyl-1H-imidazole (65.9 mg, 609.0 μmol, 1 eq), and $Cs_2CO_3$ (396.9 mg, 1.2 mmol, 2 eq) in DMF (1 mL) was added CuI (11.6 mg, 60.9 μmol, 0.1 eq). The sealed tube was heated at 150° C. for 3 h under microwave. The mixture was then partitioned between water (5 mL) and of ethyl acetate (5 mL, 3×). The organic phase was separated, washed with brine (5 mL), dried over $Na_2SO_4$, filtered, and concentrated under reduced pressure to give the crude product, which was purified by prep-TLC ($SiO_2$, Ethyl acetate:MeOH=10:1) to afford the title compound (80 mg, 356.7 μmol, 58.6% yield) as a yellow solid.

Step 3. 4-[7-(4-Cyclopropylimidazol-1-yl)imidazo[1,2-a]pyridin-3-yl]benzonitrile

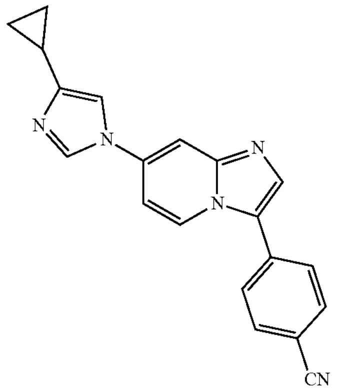 [SMILES: N#Cc1ccc(-c2cnc3cc(-n4cnc(C5CC5)c4)ccn23)cc1]

To a solution of 7-(4-cyclopropylimidazol-1-yl)imidazo[1,2-a]pyridine (80 mg, 356.7 mol, 1 eq), 4-bromobenzonitrile (64.9 mg, 356.7 μmol, 1 eq), and $Cs_2CO_3$ (348.7 mg, 1.1 mmol, 3 eq) in DMA (2 mL) was added $Pd(dppf)Cl_2 \cdot CH_2Cl_2$ (29.1 mg, 35.7 μmol, 0.1 eq) under $N_2$, and the resulting mixture was stirred at 100° C. for 12 h. The mixture was then partitioned between water (5 mL) and ethyl acetate (5 mL, 3×). The organic phase was separated, washed with brine (5 mL), dried over $Na_2SO_4$, filtered, and concentrated under reduced pressure to give the crude product, which was purified by prep-HPLC (basic condition, column: Phenomenex Gemini-NX C18 75*30 mm*3 um; mobile phase: [water(0.050% $NH_3H_2O$+10 mM $NH_4HCO_3$)-ACN]; B %: 15%-45%, 8 min) to afford the title compound (9.1 mg, 25.7 μmol, 7.2% yield, 91.9% purity) as a brown solid. $^1H$ NMR (400 MHz, DMSO-$d_6$) δ: 8.82-8.73 (m, 1H), 8.41-8.34 (m, 1H), 8.06-7.97 (m, 4H), 7.96-7.90 (m, 2H), 7.78-7.73 (m, 1H), 7.49-7.43 (m, 1H), 1.93-1.80 (m, 1H), 0.89-0.78 (m, 2H), 0.78-0.67 (m, 2H).

Examples 49-50

Examples 49-50 were prepared according to the procedures described in Example 48, using appropriately substituted starting materials. NMR data for the compounds of Examples 49-50 are shown in Table 7B.

TABLE 7A

| Ex. No. | Compound Name | Structure | Amount | Purity |
|---|---|---|---|---|
| 49 | 4-(7-(1-cyclopropyl-1H-pyrazol-4-yl)imidazo[1,2-a]pyridin-3-yl)benzonitrile | 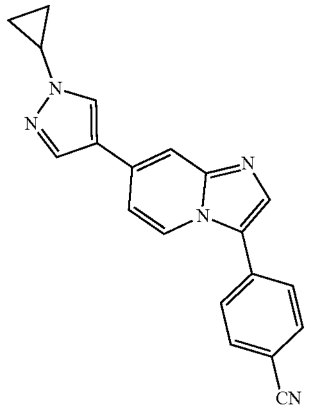 [SMILES: N#Cc1ccc(-c2cnc3cc(-c4cnn(C5CC5)c4)ccn23)cc1] | 71 mg | 98.5% |

TABLE 7A-continued

| Ex. No. | Compound Name | Structure | Amount | Purity |
|---|---|---|---|---|
| 50 | 4-(7-(1-(oxetan-3-yl)-1H-pyrazol-4-yl)imidazo[1,2-a]pyridin-3-yl)benzonitrile | 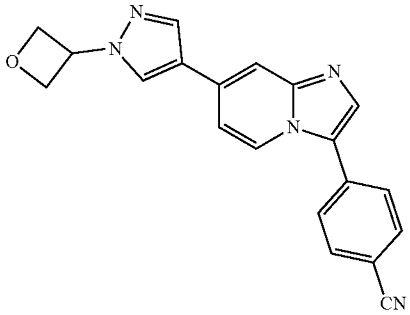 [SMILES: N#Cc1ccc(-c2cnc3cc(-c4cnn(C5COC5)c4)ccn23)cc1] | 14.4 mg | 99.3% |

TABLE 7B

| Ex. No. | 1H-NMR Data |
|---|---|
| 49 | $^1$H NMR (400 MHz, DMSO-$d_6$) δ: 8.68 (d, J = 7.3 Hz, 1H), 8.52 (s, 1H), 8.12 (s, 1H), 8.03-7.89 (m, 6H), 7.32 (dd, J = 1.4, 7.3 Hz, 1H), 3.78 (tt, J = 3.8, 7.3 Hz, 1H), 1.15-0.98 (m, 4H) |
| 50 | $^1$H NMR (400 MHz, DMSO-$d_6$) δ: 8.76-8.61 (m, 2H), 8.30 (s, 1H), 8.02-7.96 (m, 4H), 7.96-7.91 (m, 2H), 7.34 (dd, J = 1.8, 7.3 Hz, 1H), 5.62 (quin, J = 6.9 Hz, 1H), 4.97 (quin, J = 6.6 Hz, 4H) |

Example 51. 2-[2,6-Dimethoxy-4-[7-(1-methylpyrazol-4-yl)imidazo[1,2-a]pyridin-3-yl]phenyl]-5-ethyl-1,3,4-oxadiazole

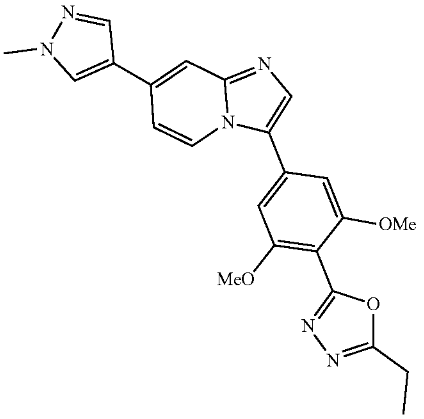 [SMILES: CCc1nnc(-c2c(OC)cc(-c3cnc4cc(-c5cnn(C)c5)ccn34)cc2OC)o1]

Step 1. Methyl 2,6-dimethoxy-4-[7-(1-methylpyrazol-4-yl)imidazo[1,2-a]pyridine-3-yl]benzoate

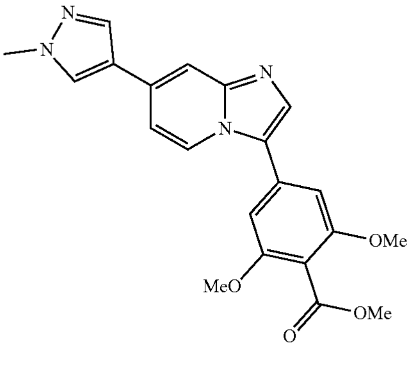 [SMILES: COC(=O)c1c(OC)cc(-c2cnc3cc(-c4cnn(C)c4)ccn23)cc1OC]

To a solution of 7-(1-methylpyrazol-4-yl)imidazo[1,2-a]pyridine (920 mg, 4.6 mmol, 1 eq), methyl 4-bromo-2,6-dimethoxy-benzoate (1.5 g, 5.6 mmol, 1.2 eq), and $Cs_2CO_3$ (4.5 g, 13.9 mmol, 3 eq) in DMA (30 mL) was added $Pd(dppf)Cl_2 \cdot CH_2Cl_2$ (189.5 mg, 232.1 μmol, 0.05 eq), in one portion at 25° C. under $N_2$, and the resulting mixture was stirred at 100° C. for 12 h. The reaction mixture was added into saturated $NH_4Cl$ (aq. 50 mL), then extracted with EtOAc (50 mL, 3×). The combined organic phase was washed with brine (50 mL), then dried over $Na_2SO_4$, filtered, and the filtrate was concentrated under reduced pressure to give a residue, which was purified by column chromatography ($SiO_2$, Petroleum ether:Ethyl acetate:Methanol=10:1:0 to 0:10:1) to afford the title compound (1.4 g, crude) as a brown solid.

Step 2. 2,6-Dimethoxy-4-(7-(1-methyl-1H-pyrazol-4-yl)imidazo[1,2-a]pyridin-3-yl)benzoic acid

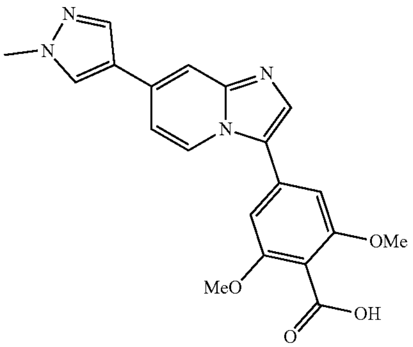 [SMILES: COc1cc(-c2cnc3cc(-c4cnn(C)c4)ccn23)cc(OC)c1C(=O)O]

A mixture of methyl 2,6-dimethoxy-4-[7-(1-methylpyrazol-4-yl)imidazo[1,2-a]pyridine-3-yl]benzoate (380 mg, 968.4 μmol, 1 eq), NaOH (2 M, 2.9 mL, 6 eq) in MeOH (4 mL) was stirred at 70° C. for 12 h. The reaction mixture was concentrated under reduced pressure to remove MeOH, then HCl (3 N) was added to the solution to pH=5. The mixture was filtered and the filter cake was concentrated under reduced pressure to afford the title compound (360 mg, crude) as a yellow solid.

Step 3. 2,6-Dimethoxy-4-[7-(1-methylpyrazol-4-yl) imidazo[1,2-a]pyridin-3-yl]-N'-propanoyl-benzohydrazide

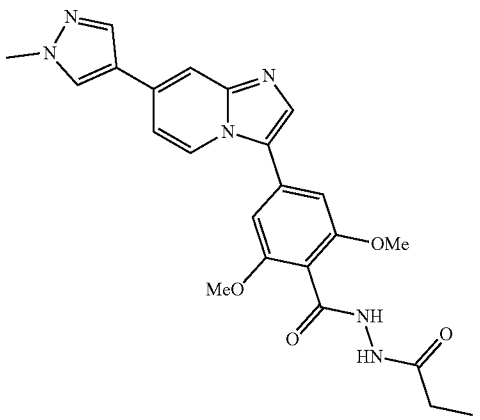 [SMILES: CCC(=O)NNC(=O)c1c(OC)cc(-c2cnc3cc(-c4cnn(C)c4)ccn23)cc1OC]

To a solution of 2,6-dimethoxy-4-[7-(1-methylpyrazol-4-yl)imidazo[1,2-a]pyridin-3-yl]benzoic acid (200 mg, 528.6 μmol, 1 eq), propanehydrazide (186.3 mg, 2.1 mmol, 4 eq), and DIEA (204.9 mg, 1.6 mmol, 276.2 μL, 3 eq) in DMF (5 mL), was added HATU (301.5 mg, 792.8 μmol, 1.5 eq) in one portion at 20° C., and the resulting mixture was stirred at 40° C. for 12 h. The reaction mixture was added into saturated $NH_4Cl$ (aq. 50 mL), then extracted with EtOAc (50 mL, 3×). The combined organic phase was washed with brine (50 mL), then dried over $Na_2SO_4$, filtered, and filtrate was concentrated under reduced pressure to afford the title compound (180 mg, crude) as a yellow oil.

Step 4. 2-[2,6-Dimethoxy-4-[7-(1-methylpyrazol-4-yl)imidazo[1,2-a]pyridin-3-yl]phenyl]-5-ethyl-1,3,4-oxadiazole

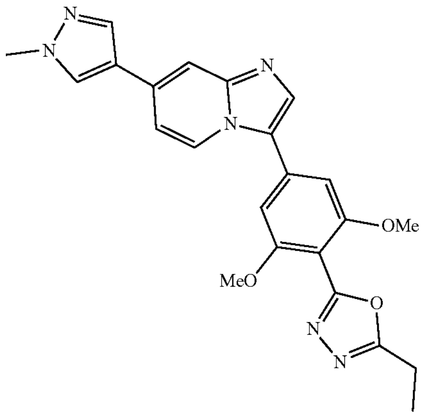 [SMILES: CCc1nnc(-c2c(OC)cc(-c3cnc4cc(-c5cnn(C)c5)ccn34)cc2OC)o1]

A mixture of 2,6-dimethoxy-4-[7-(1-methylpyrazol-4-yl) imidazo[1,2-a]pyridine-3-yl]-N'-propanoylbenzohydrazide (100 mg, 222.9 μmol, 1 eq) and 1-methoxy-N-triethylammoniosulfonylmethanimidate (79.7 mg, 334.5 μmol, 1.5 eq) in THF (4 mL) was stirred at 70° C. for 2 h. The mixture was concentrated to give a crude product, which was purified by prep-HPLC (basic condition column: Waters X bridge Prep OBD C18 150*40 mm*10 um; mobile phase: [water (0.050% $NH_3H_2O$+10 mM $NH_4HCO_3$)-ACN]; B %: 25%-38%, 8 min) to afford the title compound (10.6 mg, 24.6 μmol, 11.0% yield, 100% purity) as a white solid. $^1H$ NMR (400 MHz, MeOD-$d_4$) δ: 1.42 (t, J=7.57 Hz, 3H) 2.98 (d, J=7.51 Hz, 2H) 3.90 (s, 6H) 3.97 (s, 3H) 6.92-7.09 (m, 2H) 7.23-7.36 (m, 1H) 7.70-7.94 (m, 1H) 7.97-8.10 (m, 1H) 8.19 (br s, 1H) 8.52-9.06 (m, 1H).

Example 52. 4-[6-(1-Ethylpyrazol-4-yl)pyrazolo[1,5-a]pyridin-3-yl]benzonitrile

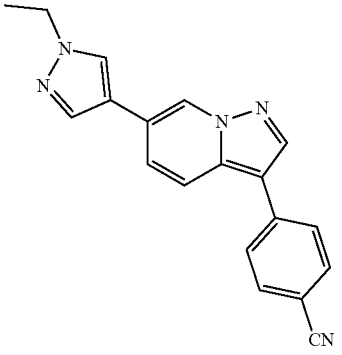 [SMILES: CCn1cc(-c2ccc3c(-c4ccc(C#N)cc4)cnn3c2)cn1]

Step 1. 6-(1-Ethylpyrazol-4-yl)pyrazolo[1,5-a]pyridine

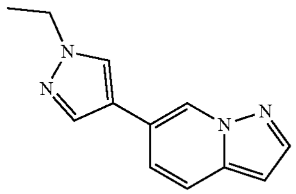 [SMILES: CCn1cc(-c2ccc3ccnn3c2)cn1]

A mixture of 6-bromopyrazolo[1,5-a]pyridine (0.2 g, 1.0 mmol, 55.9 μL, 1 eq), 1-ethyl-4-(4,4,5,5-tetramethyl-1,3,2-dioxaborolan-2-yl)pyrazole (270.5 mg, 1.2 mmol, 1.2 eq), $Na_2CO_3$ (215.2 mg, 2.0 mmol, 2 eq), Pd(dppf)$Cl_2$ (74.3 mg, 101.5 μmol, 0.1 eq) in dioxane (3 mL) and $H_2O$ (0.3 mL) was degassed and purged with $N_2$ (3×), and then the mixture was stirred at 90° C. for 12 h under $N_2$ atmosphere. The reaction mixture was filtered and the filtrate was concentrated under reduced pressure to afford the title compound (0.2 g, crude) as a brown oil.

Step 2. 6-(1-Ethylpyrazol-4-yl)-3-iodo-pyrazolo[1,5-a]pyridine

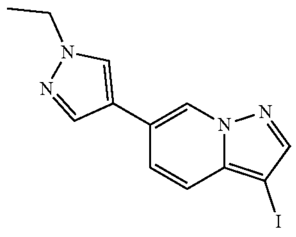 [SMILES: CCn1cc(-c2ccc3c(I)cnn3c2)cn1]

A mixture of 6-(1-ethylpyrazol-4-yl)pyrazolo[1,5-a]pyridine (160 mg, 753.8 μmol, 1 eq) and NIS (186.6 mg, 829.2 μmol, 1.1 eq) in DMF (3 mL) was stirred at 25° C. for 1 h. The reaction was quenched by addition water (20 mL) then extracted with EtOAc (90 mL). The combined organic layers were washed with brine (50 mL), dried over $Na_2SO_4$, filtered, and concentrated under reduced pressure to give a residue, which was purified by column chromatography ($SiO_2$, Petroleum ether:Ethyl acetate=1:0 to 4:1) to afford the title compound (0.2 g, crude) as a yellow solid.

Step 3. 4-[6-(1-Ethylpyrazol-4-yl)pyrazolo[1,5-a]pyridin-3-yl]benzonitrile

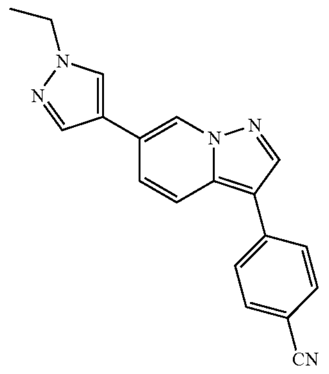 [SMILES: CCn1cc(-c2ccc3c(-c4ccc(C#N)cc4)cnn3c2)cn1]

A mixture of 6-(1-ethylpyrazol-4-yl)-3-iodo-pyrazolo[1,5-a]pyridine (0.1 g, 295.7 mol, 1 eq), (4-cyanophenyl) boronic acid (52.2 mg, 354.9 μmol, 1.2 eq), $Na_2CO_3$ (62.7 mg, 591.5 μmol, 2 eq), Pd(dppf)$Cl_2$ (21.6 mg, 29.6 μmol, 0.1 eq) in dioxane (3 mL) and $H_2O$ (0.3 mL) was degassed and purged with $N_2$ (3×), and then the mixture was stirred at 90° C. for 12 h under $N_2$ atmosphere. The reaction mixture was filtered and concentrated under reduced pressure to give a residue, which was purified by prep-HPLC (FA condition, column: Phenomenex Luna C18 100*30 mm*5 um; mobile phase: [water(0.2% FA)-ACN]; B %: 30%-60%, 9 min) to afford the title compound (17 mg, 51.7 μmol, 17.5n yield, 95.3% purity) as a yellow solid. $^1H$ NMR (400 MHz, DMSO-$d_6$) δ: 9.14 (s, 1H), 8.57 (s, 1H), 8.41 (s, 1H), 8.17-8.03 (m, 2H), 8.01-7.83 (m, 4H), 7.72 (br d, J=9.1 Hz, 1H), 4.18 (q, J=7.3 Hz, 2H), 1.44 (t, J=7.3 Hz, 3H).

Examples 53-54

Examples 53-54 were prepared according to the procedures described in Example 52, using appropriately substituted starting materials. NMR data for the compounds of Examples 53-54 are shown in Table 8B.

TABLE 8A

| Ex. No. | Compound Name | Structure | Amount | Purity |
|---|---|---|---|---|
| 53 | 2-(4-(6-(1-cyclopropyl-1H-pyrazol-4-yl)pyrazolo[1,5-a]pyridin-3-yl)-2,6-dimethoxyphenyl)-5-ethyl-1,3,4-oxadiazole | 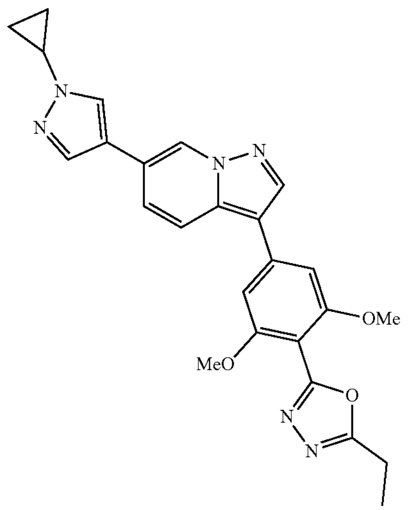 [SMILES: CCc1nnc(-c2c(OC)cc(-c3cnn4cc(-c5cnn(C6CC6)c5)ccc34)cc2OC)o1] | 2.0 mg | 94.9% |
| 54 | 4-(6-(1-cyclopropyl-1H-pyrazol-4-yl)pyrazolo[1,5-a]pyridin-3-yl)benzonitrile | 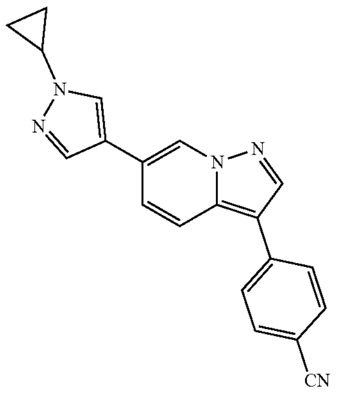 [SMILES: N#Cc1ccc(-c2cnn3cc(-c4cnn(C5CC5)c4)ccc23)cc1] | 6.3 mg | 98.0% |

TABLE 8B

| Ex. No. | 1H-NMR Data |
|---|---|
| 53 | $^1$H NMR (400 MHz, DMSO-$d_6$) δ: 9.12 (s, 1H), 8.54 (s, 1H), 8.43 (s, 1H), 8.12 (d, J = 9.3 Hz, 1H), 8.06 (s, 1H), 7.68 (dd, J = 1.4, 9.3 Hz, 1H), 7.05 (s, 2H), 3.91-3.85 (m, 6H), 3.77 (tt, J = 3.8, 7.4 Hz, 1H), 2.93 (d, J = 7.5 Hz, 2H), 1.31 (t, J = 7.6 Hz, 3H), 1.10 (br d, J = 3.8 Hz, 2H), 1.05-0.97 (m, 2H) |
| 54 | $^1$H NMR (400 MHz, DMSO-$d_6$) δ: 9.12 (s, 1H), 8.54 (s, 1H), 8.43 (s, 1H), 8.12-8.04 (m, 2H), 7.97-7.92 (m, 2H), 7.90-7.85 (m, 2H), 7.71 (dd, J = 1.1, 9.3 Hz, 1H), 3.76 (td, J = 3.6, 7.3 Hz, 1H), 1.09 (br d, J = 3.9 Hz, 2H), 1.04-0.97 (m, 2H) |

Example 55. 2-[4-[7-(1-Cyclopropylpyrazol-4-yl)imidazo[1,2-a]pyridin-3-yl]-2,6-dimethoxy-phenyl]-5-ethyl-1,3,4-oxadiazole

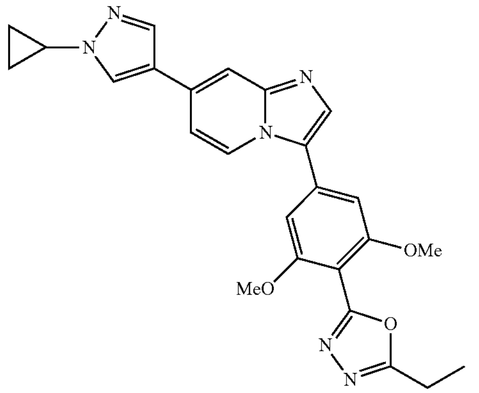 [SMILES: CCc1nnc(-c2c(OC)cc(-c3cnc4cc(-c5cnn(C6CC6)c5)ccn34)cc2OC)o1]

Step 1. Methyl 4-bromo-2,6-dimethoxybenzoate

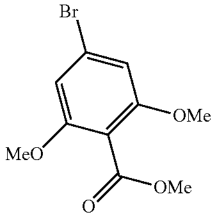 [SMILES: COC(=O)c1c(OC)cc(Br)cc1OC]

To a solution of methyl 4-bromo-2,6-difluorobenzoate (2 g, 7.9 mmol, 1 eq) in MeOH (20 mL) was added sodium methanolate (3.2 g, 17.5 mmol, 30% purity, 2.2 eq), and the resulting mixture was stirred at 80° C. for 12 h. The reaction mixture was concentrated under reduced pressure to remove MeOH, then the reaction mixture was added to water (20 mL) and extracted with EtOAc (10 mL, 3×). The combined organic layers were washed with brine (20 mL), dried over $Na_2SO_4$, filtered, and concentrated under reduced pressure to afford the title compound (1.5 g, crude) as a white solid.

Step 2. 4-Bromo-2,6-dimethoxybenzoic acid

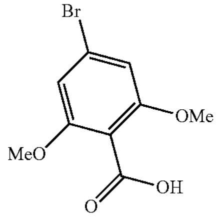 [SMILES: COc1cc(Br)cc(OC)c1C(=O)O]

A mixture of methyl 4-bromo-2,6-dimethoxybenzoate (200 mg, 727.0 μmol, 1 eq), NaOH (58.2 mg, 1.5 mmol, 2 eq) in MeOH (20 mL), and $H_2O$ (5 mL) was stirred at 70° C. for 12 h. The reaction mixture was concentrated under reduced pressure to remove MeOH, then HCl (12 N, 0.5 mL) was added to the solution. The mixture was filtered and the filter cake was concentrated under reduced pressure to afford the title compound (100 mg, crude) as a white solid.

Step 3. 4-Bromo-2,6-dimethoxy-N'-propanoylbenzohydrazide

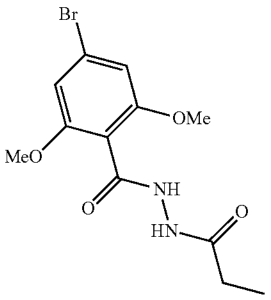 [SMILES: CCC(=O)NNC(=O)c1c(OC)cc(Br)cc1OC]

To a solution of 4-bromo-2,6-dimethoxybenzoic acid (1 g, 3.8 mmol, 1 eq) and propanehydrazide (371.2 mg, 4.2 mmol, 1.1 eq), and 4-bromo-2,6-dimethoxy-benzoic acid (1 g, 3.8 mmol, 1 eq) in DMF (20 mL), was added HATU (2.2 g, 5.8 mmol, 1.5 eq) and DIEA (990.1 mg, 7.7 mmol, 1.3 mL, 2 eq), and the resulting mixture was stirred at 40° C. for 12 h. The reaction mixture was added to water (20 mL) and extracted with EtOAc (10 mL, 3×). The combined organic layers were washed with brine (20 mL), dried over $Na_2SO_4$, filtered, and concentrated under reduced pressure to afford the title compound (280 mg, crude) as a white solid.

Step 4. 2-(4-Bromo-2,6-difluorophenyl)-5-ethyl-1,3,4-oxadiazole

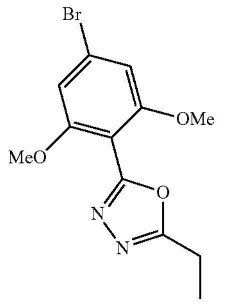 [SMILES: CCc1nnc(-c2c(OC)cc(Br)cc2OC)o1]

To a solution of 4-bromo-2,6-difluoro-N'-propanoyl-benzohydrazide (300 mg, 976.9 mol, 1 eq) in THE (3 mL) was added methoxycarbonyl (triethylammonio)sulfonylazanide (Burgess reagent, 698.4 mg, 2.9 mmol, 3 eq), and the resulting mixture was stirred at 70° C. for 12 h. The mixture was partitioned between water (5 mL) and ethyl acetate (5 mL, 3×). The organic phase was separated, washed with brine (5 mL), dried over $Na_2SO_4$, filtered, and concentrated under reduced pressure to afford the title compound (200 mg, crude) as a yellow oil.

Step 5. 2-[4-[7-(1-Cyclopropylpyrazol-4-yl)imidazo[1,2-a]pyridin-3-yl]-2,6-dimethoxyphenyl]-5-ethyl-1,3,4-oxadiazole

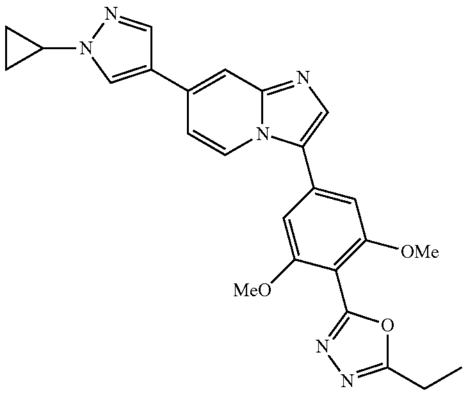 [SMILES: CCc1nnc(-c2c(OC)cc(-c3cnc4cc(-c5cnn(C6CC6)c5)ccn34)cc2OC)o1]

A mixture of 2-(4-bromo-2,6-dimethoxyphenyl)-5-ethyl-1,3,4-oxadiazole (70 mg, 223.5 μmol, 1 eq), 7-(1-cyclopropylpyrazol-4-yl)imidazo[1,2-a]pyridine (50.1 mg, 223.5 mol, 1 eq), $Cs_2CO_3$ (218.5 mg, 670.6 μmol, 3 eq), and Pd(dppf)$Cl_2$·$CH_2Cl_2$ (18.3 mg, 22.4 mol, 0.1 eq) in DMA (1 mL) was degassed and purged with $N_2$ (3×), and then the mixture was stirred at 100° C. for 12 h under $N_2$ atmosphere. The resulting residue was purified by prep-HPLC (basic condition; column: Phenomenex Gemini-NX C18 75*30 mm*3 um; mobile phase: [water(0.05% $NH_3H_2O$+10 mM $NH_4HCO_3$)-ACN]; B %: 20%-50%, 8 min) to afford the title compound (16.2 mg, 35.5 μmol, 15.9% yield, 100% purity) as a pink solid. $^1$H NMR (400 MHz, METHANOL-$d_4$) δ: 8.65 (br d, J=7.0 Hz, 1H), 8.29 (s, 1H), 8.01 (s, 1H), 7.82 (br d, J=16.8 Hz, 2H), 7.32 (br d, J=7.3 Hz, 1H), 7.05 (s, 2H), 3.92 (s, 6H), 3.81-3.70 (m, 1H), 3.00 (q, J=7.6 Hz, 2H), 1.44 (t, J=7.6 Hz, 3H), 1.23-1.07 (m, 4H).

Example 55A. 4-(7-(1-cyclopropyl-1H-pyrazol-4-yl)imidazo[1,2-a]pyridin-3-yl)-2,6-dimethoxybenzohydrazide

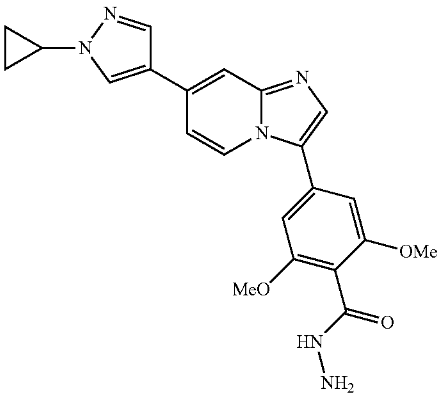 [SMILES: COc1cc(-c2cnc3cc(-c4cnn(C5CC5)c4)ccn23)cc(OC)c1C(=O)NN]

Figure 17:
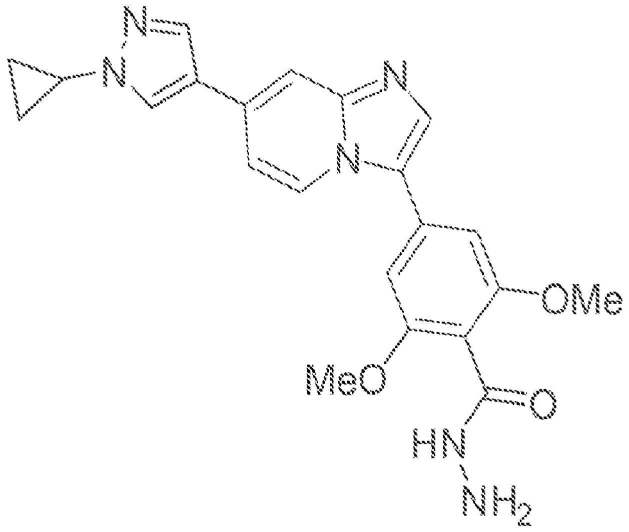
FIG. 17 contains chemical structure and intro $IC_{50}$ values for compound 55A.

The title compound was prepared according to the methods and procedures similar to those described in Example 55. The testing results are provided in FIG. 17.

Examples 56-60

Examples 56-60 were prepared according to the procedures described in Example 55, using appropriately substituted starting materials. NMR data for the compounds of Examples 56-60 are shown in Table 9B.

TABLE 9A
| Ex. No. | Compound Name | Structure | Amount | Purity |
|---|---|---|---|---|
| 56 | 2-(4-(7-(1-ethyl-1H-pyrazol-4-yl)imidazo[1,2-a]pyridin-3-yl)phenyl)-5-methyl-1,3,4-oxadiazole | 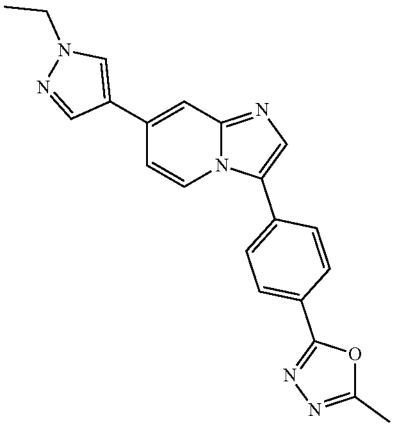 [SMILES: CCn1cc(-c2ccn3c(-c4ccc(-c5nnc(C)o5)cc4)cnc3c2)cn1] | 29.1 mg | 92.3% |
| 57 | 2-ethyl-5-(2-methoxy-4-(7-(1-methyl-1H-pyrazol-4-yl)imidazo[1,2-a]pyridin-3-yl)phenyl)-1,3,4-oxadiazole | 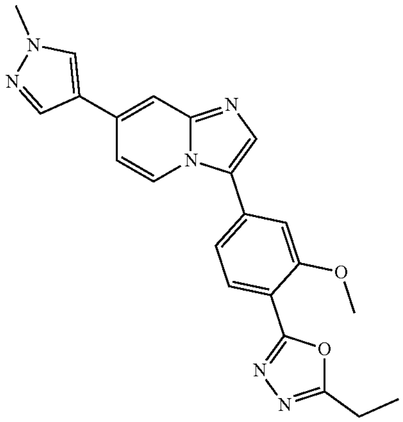 [SMILES: CCc1nnc(-c2ccc(-c3cnc4cc(-c5cnn(C)c5)ccn34)cc2OC)o1] | 18.9 mg | 100% |
| 58 | 2-(2,6-difluoro-4-(7-(1-methyl-1H-pyrazol-4-yl)imidazo[1,2-a]pyridin-3-yl)phenyl)-5-ethyl-1,3,4-oxadiazole | 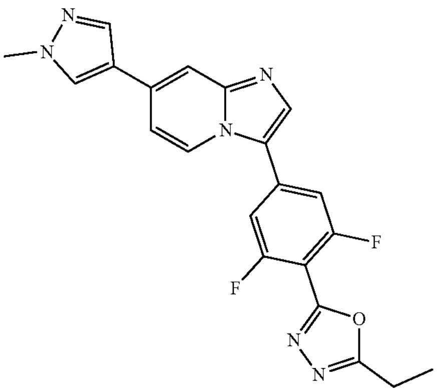 [SMILES: CCc1nnc(-c2c(F)cc(-c3cnc4cc(-c5cnn(C)c5)ccn34)cc2F)o1] | 4.1 mg | 95.5% |

TABLE 9A-continued

| Ex. No. | Compound Name | Structure | Amount | Purity |
|---|---|---|---|---|
| 59 | 2-(2,6-dichloro-4-(7-(1-methyl-1H-pyrazol-4-yl)imidazo[1,2-a]pyridin-3-yl)phenyl)-5-ethyl-1,3,4-oxadiazole | 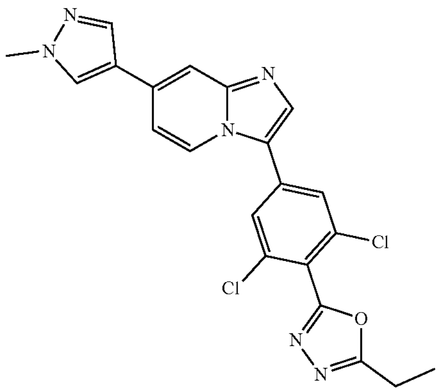 [SMILES: CCc1nnc(-c2c(Cl)cc(-c3cnc4cc(-c5cnn(C)c5)ccn34)cc2Cl)o1] | 16.8 mg | 92.1% |
| 60 | 2-cyclopropyl-5-(2,6-dimethoxy-4-(7-(1-methyl-1H-pyrazol-4-yl)imidazo[1,2-a]pyridin-3-yl)phenyl)-1,3,4-oxadiazole | 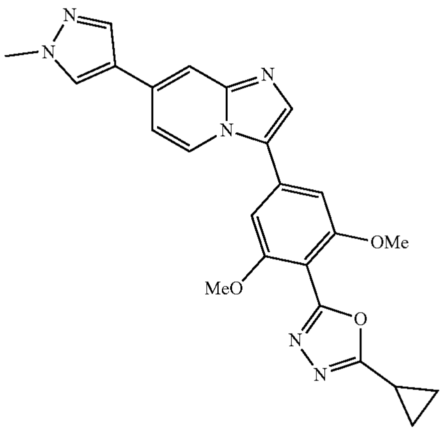 [SMILES: COc1cc(-c2cnc3cc(-c4cnn(C)c4)ccn23)cc(OC)c1-c1nnc(C2CC2)o1] | 12 mg | 100% |

TABLE 9B

| Ex. No. | 1H-NMR Data |
|---|---|
| 56 | $^1$H NMR (400 MHz, DMSO-$d_6$) δ: 8.75 (d, J = 7.3 Hz, 1H), 8.55 (s, 1H), 8.23-8.08 (m, 4H), 8.03-7.89 (m, 3H), 7.50-7.42 (m, 1H), 4.21 (q, J-7.3 Hz, 2H), 2.64 (s, 3H), 1.45 (t, J = 7.3 Hz, 3H) |
| 57 | $^1$H NMR (400 MHz, MeOD-$d_4$) δ: 8.64 (d, J = 7.3 Hz, 1H), 8.19 (s, 1H), 8.06 (d, J = 8.0 Hz, 1H), 8.01 (s, 1H), 7.85 (s, 1H), 7.79 (s, 1H), 7.50-7.40 (m, 2H), 7.31 (br d, J = 6.9 Hz, 1H), 4.07 (s, 3H), 3.98 (s, 3H), 3.03 (q, J = 7.6 Hz, 2H), 1.47 (t, J = 7.6 Hz, 3H) |
| 58 | $^1$H NMR (400 MHz, MeOD-$d_4$) δ: 8.72 (d, J = 7.3 Hz, 1H), 8.22 (s, 1H), 8.04 (s, 1H), 7.96 (s, 1H), 7.82 (s, 1H), 7.65 (d, J = 9.6 Hz, 2H), 7.37 (dd, J = 1.3, 7.3 Hz, 1H), 3.99 (s, 3H), 3.07 (q, J = 7.6 Hz, 2H), 1.47 (t, J = 7.6 Hz, 3H) |
| 59 | $^1$H NMR (400 MHz, MeOD-$d_4$) δ: 8.71-8.64 (m, 1H), 8.25-8.21 (m, 1H), 8.08-8.03 (m, 1H), 8.00-7.98 (m, 2H), 7.96-7.94 (m, 1H), 7.85-7.80 (m, 1H), 7.42-7.34 (m, 1H), 4.02-3.96 (m, 3H), 3.13-3.02 (m, 2H), 1.52-1.42 (m, 3H) |
| 60 | $^1$H NMR (400 MHz, MeOD-$d_4$) δ: 8.60 (br d, J = 6.9 Hz, 1H), 8.15 (s, 1H), 7.98 (s, 1H), 7.82 (br s, 1H), 7.74 (br s, 1H), 7.27 (br d, J = 7.0 Hz, 1H), 6.99 (s, 2H), 3.96 (s, 3H), 3.90 (s, 6H), 2.34-2.21 (m, 1H), 1.31-1.22 (m, 2H), 1.15 (br dd, J = 2.4, 4.1 Hz, 2H) |

Example 61. 3-[2,6-Dimethoxy-4-[7-(1-methylpyrazol-4-yl)imidazo[1,2-a]pyridin-3-yl]phenyl]-5-ethyl-1,2,4-oxadiazole

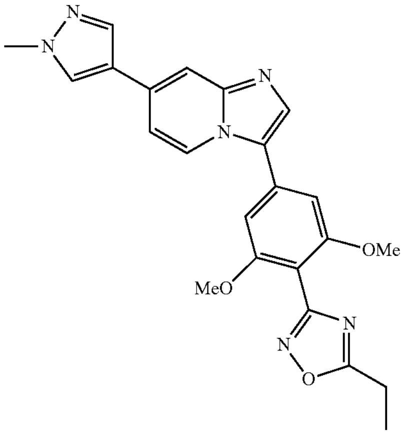 [SMILES: CCc1nc(-c2c(OC)cc(-c3cnc4cc(-c5cnn(C)c5)ccn34)cc2OC)no1]

Step 1. 4-Bromo-2,6-dimethoxybenzonitrile

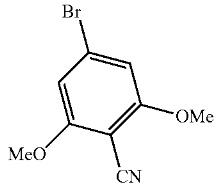 [SMILES: COc1cc(Br)cc(OC)c1C#N]

A mixture of 4-bromo-2,6-difluorobenzonitrile (1 g, 4.6 mmol, 1 eq) and NaOMe (1 g, 18.5 mmol, 4.0 eq) in MeOH (10 mL) was stirred at 25° C. for 2 h. The reaction mixture was filtered and concentrated under reduced pressure to afford the title compound (1 g, crude) as a white solid.

Step 2. 4-Bromo-N'-hydroxy-2,6-dimethoxybenzamidine

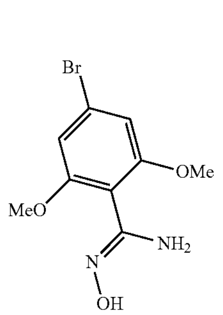 [SMILES: COc1cc(Br)cc(OC)c1/C(N)=N/O]

A mixture of 4-bromo-2,6-dimethoxybenzonitrile (0.8 g, 3.3 mmol, 1 eq), $NH_2OH$ HCl (298.6 mg, 4.3 mmol, 1.3 eq), and $NaHCO_3$ (416.4 mg, 4.9 mmol, 192.8 μL, 1.5 eq) in EtOH (3 mL), was stirred at 80° C. for 12 h. The mixture was filtered and the filtrate was concentrated to afford the title compound (1 g, crude) as a white solid.

Step 3. 3-(4-Bromo-2,6-dimethoxyphenyl)-5-ethyl-1,2,4-oxadiazole

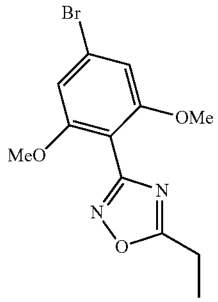 [SMILES: CCc1nc(-c2c(OC)cc(Br)cc2OC)no1]

A mixture of 4-bromo-N'-hydroxy-2,6-dimethoxybenzamidine (900 mg, 3.3 mmol, 1 eq), ethyl propanoate (501.2 mg, 4.9 mmol, 563.1 μL, 1.5 eq), and NaOH (196.3 mg, 4.9 mmol, 1.5 eq) in DMSO (15 mL) was stirred at 30° C. for 2 h. The mixture was filtered and the filter cake was dried to afford the title compound (900 mg, crude) as a white solid.

Step 4. 3-[2,6-Dimethoxy-4-[7-(1-methylpyrazol-4-yl)imidazo[1,2-a]pyridin-3-yl]phenyl]-5-ethyl-1,2,4-oxadiazole

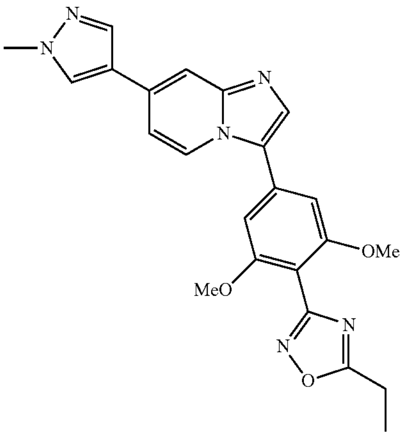 [SMILES: CCc1nc(-c2c(OC)cc(-c3cnc4cc(-c5cnn(C)c5)ccn34)cc2OC)no1]

To a solution of 7-(1-methylpyrazol-4-yl)imidazo[1,2-a]pyridine (100 mg, 504.5 mol, 1 eq), 3-(4-bromo-2,6-dimethoxyphenyl)-5-ethyl-1,2,4-oxadiazole (165.9 mg, 529.7 mol, 1.0 eq) and Pd(dppf)$Cl_2$·$CH_2Cl_2$ (20.6 mg, 25.2 μmol, 0.05 eq) in DMA (5 mL) was added $Cs_2CO_3$ (493.1 mg, 1.5 mmol, 3 eq), in one portion at 20° C. under $N_2$, and the resulting mixture was stirred at 100° C. for 12 h. The reaction mixture was added into saturated $NH_4Cl$ (aq., 50 mL) then extracted with EtOAc (50 mL, 3 mL). The combined organic phase was washed with brine (50 mL), then dried over $Na_2SO_4$, filtered, and the filtrate was concentrated under reduced pressure to give a residue, which was purified by prep-HPLC (basic condition, column: Phenomenex Gemini-NX C18 75*30 mm*3 um; mobile phase: [water (0.04% $NH_3H_2O$+10 mM $NH_4HCO_3$)-ACN]; B %: 15%-40%, 10 min) to afford the title compound (31.7 mg, 73.4 μmol, 14.6% yield, 99.6% purity) as a white solid. $^1H$ NMR (400 MHz, DMSO-$d_6$) δ: 1.33 (t, J=7.61 Hz, 3H) 3.02

(q, J=7.50 Hz, 2H) 3.82 (s, 6H) 3.89 (s, 3H) 7.04 (s, 2H) 7.25 (dd, J=7.17, 1.21 Hz, 1H) 7.88 (s, 2H) 8.09 (s, 1H) 8.36 (s, 1H) 8.73 (d, J=7.28 Hz, 1H).

Example 62. 3-(4-(7-(1-Ethyl-1H-pyrazol-4-yl)imidazo[1,2-a]pyridin-3-yl)phenyl)-5-methyl-1,2,4-oxadiazole

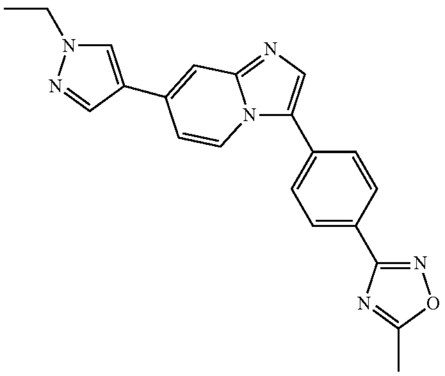 [SMILES: CCn1cc(-c2ccn3c(-c4ccc(-c5noc(C)n5)cc4)cnc3c2)cn1]

The title compound was prepared according to the procedures described in Example 61, using appropriately substituted starting materials. Yield: 29.1 mg; 92.3% purity. $^1H$ NMR (400 MHz, DMSO-$d_6$) δ: 8.67 (d, J=7.2 Hz, 1H), 8.44 (s, 1H), 8.21-8.06 (m, 3H), 7.90 (d, J=8.8 Hz, 4H), 7.28 (br d, J=6.1 Hz, 1H), 4.19 (q, J=7.2 Hz, 2H), 2.70 (s, 3H), 1.44 (t, J=7.3 Hz, 3H).

Example 63. 4-[6-(1-Ethylpyrazol-4-yl)pyrazolo[1,5-a]pyrimidin-3-yl]benzonitrile

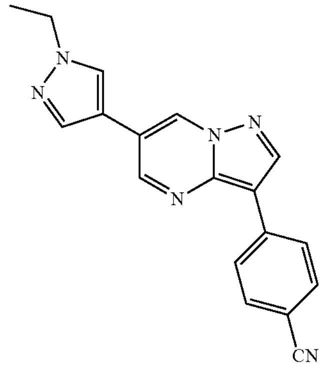 [SMILES: CCn1cc(-c2cnc3c(-c4ccc(C#N)cc4)cnn3c2)cn1]

Step 1. 6-(1-Ethylpyrazol-4-yl)pyrazolo[1,5-a]pyrimidine

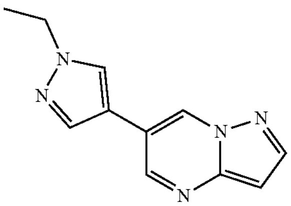 [SMILES: CCn1cc(-c2cnc3ccnn3c2)cn1]

A mixture of 6-bromopyrazolo[1,5-a]pyrimidine (400 mg, 2.0 mmol, 1 eq), 1-ethyl-4-(4,4,5,5-tetramethyl-1,3,2-dioxaborolan-2-yl)pyrazole (448.6 mg, 2.0 mmol, 1 eq), Pd(dppf)$Cl_2$ (147.8 mg, 202.0 μmol, 0.1 eq), $Na_2CO_3$ (428.2 mg, 4.0 mmol, 2 eq) in dioxane (3 mL) and $H_2O$ (0.3 mL) was degassed and purged with $N_2$ (3×), and then the mixture was stirred at 100° C. for 12 h under $N_2$ atmosphere. The reaction mixture was added to water (50 mL) and extracted with EtOAc (20 mL, 3×). The combined organic layers were washed with brine (20 mL), dried over $Na_2SO_4$, filtered, and concentrated under reduced pressure to give a residue. The residue was purified by column chromatography ($SiO_2$, Petroleum ether:Ethyl acetate=50:1 to 0:1) to afford the title compound (250 mg, crude) as a yellow solid.

Step 2. 3-Bromo-6-(1-ethylpyrazol-4-yl)pyrazolo[1,5-a]pyrimidine

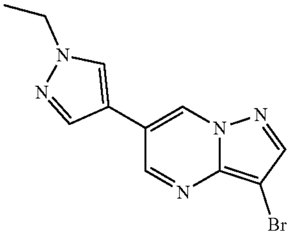 [SMILES: CCn1cc(-c2cnc3c(Br)cnn3c2)cn1]

To a solution of 6-(1-ethylpyrazol-4-yl)pyrazolo[1,5-a]pyrimidine (240 mg, 1.1 mmol, 1 eq) in DCM (2 mL) was added NBS (210.3 mg, 1.2 mmol, 1.0 eq) at 0° C., and the resulting mixture was stirred at 0° C. for 1 h. The reaction mixture was added to water (20 mL) and extracted with DCM (10 mL, 3×). The combined organic layers were washed with brine (20 mL) dried over $Na_2SO_4$, filtered, and concentrated under reduced pressure to afford the title compound (320 mg, crude) as a yellow solid.

Step 3. 4-[6-(1-Ethylpyrazol-4-yl)pyrazolo[1,5-a]pyrimidin-3-yl]benzonitrile

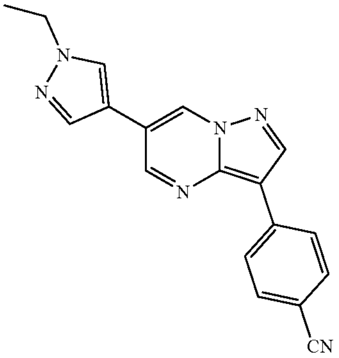 [SMILES: CCn1cc(-c2cnc3c(-c4ccc(C#N)cc4)cnn3c2)cn1]

A mixture of 3-bromo-6-(1-ethylpyrazol-4-yl)pyrazolo[1,5-a]pyrimidine (100 mg, 342.3 μmol, 1 eq), (4-cyanophenyl)boronic acid (55.3 mg, 376.5 μmol, 1.1 eq), Pd(dppf)$Cl_2$ (25.1 mg, 34.2 μmol, 0.1 eq), $Na_2CO_3$ (108.8 mg, 1.0 mmol, 3 eq) in dioxane (2 mL) and $H_2O$ (0.2 mL) was degassed and purged with $N_2$ (3×), and then the mixture was stirred at 100° C. for 3 h under $N_2$ atmosphere. The reaction mixture was concentrated to give the crude product, which was purified by prep-HPLC (basic condition; column: Phenomenex Gemini-NX C18 75*30 mm*3 um; mobile phase: [water (0.05% $NH_3H_2O$+10 mM $NH_4HCO_3$)-ACN]; B %: 25%-55%, 8 min) to afford the title compound (12.2 mg, 36.7 μmol, 10.7% yield, 94.4% purity) as a green solid. $^1H$ NMR (400 MHz, DMSO-$d_6$) δ: 9.53 (d, J=2.1 Hz, 1H), 9.07 (d, J=2.1 Hz, 1H), 8.90 (s, 1H), 8.46 (s, 1H), 8.39 (d, J=8.4 Hz, 2H), 8.14 (s, 1H), 7.91 (d, J=8.5 Hz, 2H), 4.21 (q, J=7.3 Hz, 2H), 1.44 (t, J=7.3 Hz, 3H).

Example 64. 4-[6-(1-Cyclopropylpyrazol-4-yl)pyrazolo[1,5-a]pyrimidin-3-yl]benzonitrile

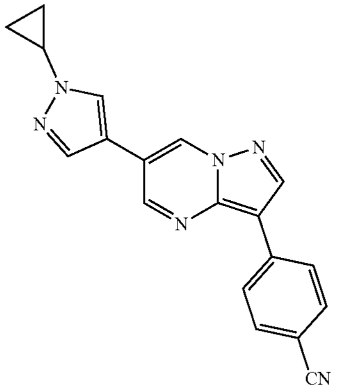 [SMILES: N#Cc1ccc(-c2cnn3cc(-c4cnn(C5CC5)c4)cnc23)cc1]

Step 1. 6-(1-Cyclopropylpyrazol-4-yl)pyrazolo[1,5-a]pyrimidine

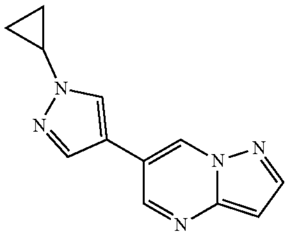 [SMILES: c1cc2ncc(-c3cnn(C4CC4)c3)cn2n1]

To a solution of 6-bromopyrazolo[1,5-a]pyrimidine (200 mg, 1.0 mmol, 1 eq), 1-cyclopropyl-4-(4,4,5,5-tetramethyl-1,3,2-dioxaborolan-2-yl)pyrazole (260.1 mg, 1.1 mmol, 1.1 eq) and $Na_2CO_3$ (321.2 mg, 3.0 mmol, 3 eq) in dioxane (2 mL) and $H_2O$ (0.4 mL) was added Pd(dppf)$Cl_2$ (73.9 mg, 101.0 μmol, 0.1 eq) under $N_2$, and the resulting mixture was stirred at 100° C. for 12 h. The mixture was partitioned between water (5 mL) and ethyl acetate (5 mL, 3×). The organic phase was separated, washed with brine (5 mL), dried over $Na_2SO_4$, filtered, and concentrated under reduced pressure to give the crude product, which was purified by prep-TLC ($SiO_2$, Petroleum ether:Ethyl acetate=0:1) to afford the title compound (120 mg, 532.74 μmol, 52.75% yield) as a yellow solid.

Step 2. 6-(1-Cyclopropylpyrazol-4-yl)-3-iodo-pyrazolo[1,5-a]pyrimidine

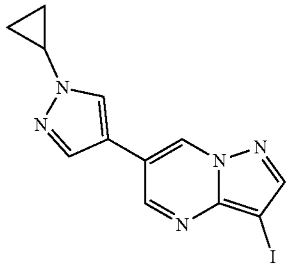 [SMILES: Ic1cnn2cc(-c3cnn(C4CC4)c3)cnc12]

To a solution of 6-(1-cyclopropylpyrazol-4-yl)pyrazolo[1,5-a]pyrimidine (120 mg, 532.7 μmol, 1 eq) in DMF (2 mL) was added NIS (239.7 mg, 1.1 mmol, 2 eq), and the resulting mixture was stirred at 20° C. for 1 h. The mixture was partitioned between water (5 mL) and ethyl acetate (5 mL, 3×). The organic phase was separated, washed with brine (5 mL), dried over $Na_2SO_4$, filtered, and concentrated under reduced pressure to afford the title compound (180 mg, crude) as a yellow solid.

Step 3. 4-[6-(1-Cyclopropylpyrazol-4-yl)pyrazolo[1,5-a]pyrimidin-3-yl]benzonitrile

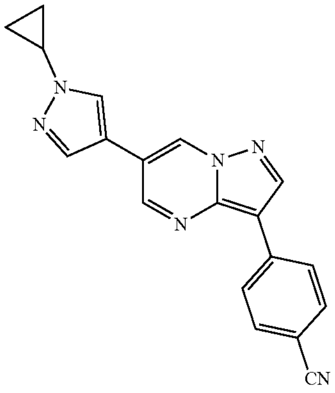 [SMILES: N#Cc1ccc(-c2cnn3cc(-c4cnn(C5CC5)c4)cnc23)cc1]

To a solution of 6-(1-cyclopropylpyrazol-4-yl)-3-iodo-pyrazolo[1,5-a]pyrimidine (180 mg, 512.6 μmol, 1 eq), (4-cyanophenyl)boronic acid (75.3 mg, 512.6 μmol, 1 eq) and $Na_2CO_3$ (162.9 mg, 1.5 mmol, 3 eq) in dioxane (2 mL) and $H_2O$ (0.4 mL) was added Pd(dppf)$Cl_2$ (37.5 mg, 51.3 μmol, 0.1 eq) under $N_2$, and the resulting mixture was stirred at 100° C. for 12 h. The mixture was partitioned between water (5 mL) and ethyl acetate (5 mL, 3×). The organic phase was separated, washed with brine (5 mL), dried over $Na_2SO_4$, filtered, and concentrated under reduced pressure to give the crude product, which was purified by prep-HPLC (basic condition; column: Phenomenex Gemini-NX C18 75*30 mm*3 um; mobile phase: [water(0.05% $NH_3H_2O$+10 mM $NH_4HCO_3$)-ACN]; B %: 20%-50%, 8 min) to afford the title compound (3.9 mg, 11.2 μmol, 2.18% yield, 93.3% purity) as a yellow solid. $^1H$ NMR (400 MHz, DMSO-$d_6$) δ: 9.55-9.49 (m, 1H), 9.52 (d, J=2.0 Hz, 1H), 9.08 (d, J=2.0 Hz, 1H), 8.90 (s, 1H), 8.51 (s, 1H), 8.38 (d, J=8.4 Hz, 2H), 8.13 (s, 1H), 7.91 (d, J=8.4 Hz, 2H), 3.87-3.70 (m, 1H), 1.11-1.01 (m, 4H).

Example 65. 6-(1-Cyclopropylpyrazol-4-yl)-3-[4-(1-ethyltriazol-4-yl)-3,5-dimethoxy-phenyl]pyrazolo[1,5-a]pyridine

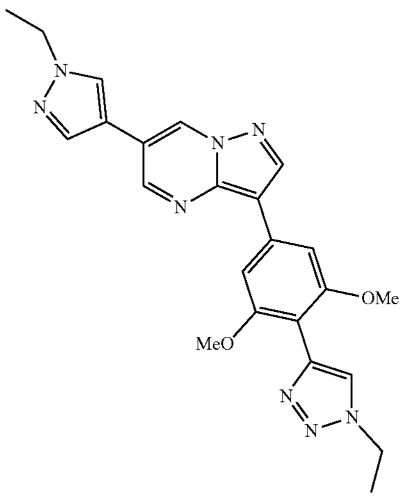 [SMILES: CCn1cc(-c2cnc3c(-c4cc(OC)c(-c5cn(CC)nn5)c(OC)c4)cnn3c2)cn1]

Step 1. 5-Bromo-2-ethynyl-1,3-dimethoxybenzene

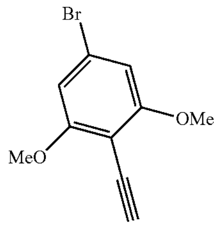

To a solution of 4-bromo-2,6-dimethoxybenzaldehyde (4 g, 16.32 mmol, 1 eq) in MeOH (10 mL) was added $K_2CO_3$ (6.77 g, 48.97 mmol, 3 eq) and 1-diazo-1-dimethoxyphosphorylpropan-2-one (4.70 g, 24.48 mmol, 1.5 eq), and the resulting mixture was stirred at 20° C. for 12 h. The residue was purified by column chromatography ($SiO_2$, Petroleum ether/Ethyl acetate=100/1 to 20/1) to afford the title compound (2.5 g, crude) as a white solid.

Step 2. 4-(4-Bromo-2,6-dimethoxyphenyl)-1-ethyltriazole

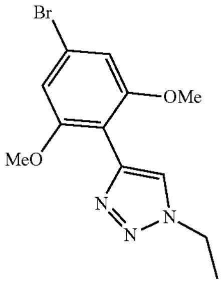 [SMILES: CCn1cc(-c2c(OC)cc(Br)cc2OC)nn1]

To a solution of 5-bromo-2-ethynyl-1,3-dimethoxybenzene (1 g, 4.15 mmol, 1 eq) in $H_2O$ (10 mL) was added $NaN_3$ (539.32 mg, 8.30 mmol, 2 eq) and CuI (158.00 mg, 829.60 μmol, 0.2 eq), sodium (2R)-2-[(2R)-3,4-dihydroxy-5-oxo-2H-furan-2-yl]-2-hydroxyethanolate (821.74 mg, 4.15 mmol, 1 eq), and iodoethane (323.47 mg, 2.07 mmol, 165.88 μL, 0.5 eq), and the resulting mixture was stirred at 80° C. for 0.5 h. The reaction mixture was added to water (20 mL) and extracted with EtOAc (10 mL, 3×). The combined organic layers were washed with brine (20 mL), dried over $Na_2SO_4$, filtered, and concentrated under reduced pressure to give a residue, which was purified by column chromatography ($SiO_2$, Petroleum ether/Ethyl acetate=50/1 to 0/1) to afford the title compound (150 mg, crude) as a white solid.

Step 3. 4-[2,6-Dimethoxy-4-(4,4,5,5-tetramethyl-1,3,2-dioxaborolan-2-yl)phenyl]-1-ethyltriazole

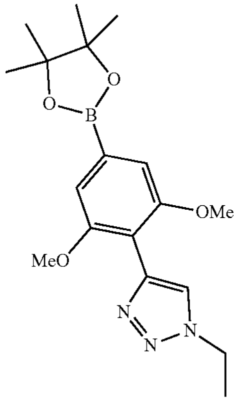 [SMILES: CCn1cc(-c2c(OC)cc(B3OC(C)(C)C(C)(C)O3)cc2OC)nn1]

A mixture of 4-(4-bromo-2,6-dimethoxyphenyl)-1-ethyltriazole (150 mg, 480.52 μmol, 1 eq), 4,4,5,5-tetramethyl-2-(4,4,5,5-tetramethyl-1,3,2-dioxaborolan-2-yl)-1,3,2-dioxaborolane (146.43 mg, 576.62 μmol, 1.2 eq), KOAc (94.32 mg, 961.04 μmol, 2 eq), and Pd(dppf)$Cl_2$ (35.16 mg, 48.05 μmol, 0.1 eq) in dioxane (1 mL) was degassed and purged with $N_2$ (3×), and then the mixture was stirred at 90° C. for 3 h. The reaction mixture was concentrated to afford the title compound (170 mg, crude) as black oil was used into the next step without further purification.

Step 4. 6-(1-Cyclopropylpyrazol-4-yl)-3-[4-(1-ethyltriazol-4-yl)-3,5-dimethoxyphenyl]pyrazolo[1,5-a]pyridine

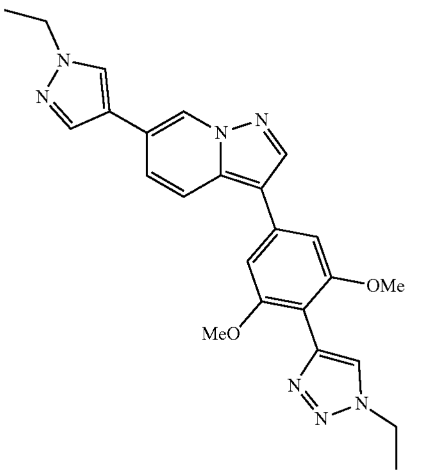 [SMILES: CCn1cc(-c2ccc3c(-c4cc(OC)c(-c5cn(CC)nn5)c(OC)c4)cnn3c2)cn1]

To a solution of 4-[2,6-dimethoxy-4-(4,4,5,5-tetramethyl-1,3,2-dioxaborolan-2-yl)phenyl]-1-ethyltriazole (150 mg, 417.56 μmol, 1 eq), 6-(1-cyclopropylpyrazol-4-yl)-3-iodopyrazolo[1,5-a]pyridine (160.83 mg, 459.32 μmol, 1.1 eq), and Pd(dppf)$Cl_2$ (30.55 mg, 41.76 μmol, 0.1 eq) in dioxane (2 mL) and $H_2O$ (0.2 mL) was added $Na_2CO_3$ (88.51 mg, 835.13 μmol, 2 eq) under $N_2$, and the resulting mixture was stirred at 90° C. for 4 h. The reaction mixture was concentrated to give the crude product, which was purified by prep-HPLC (basic condition; column: Phenomenex Gemini-NX C18 75*30 mm*3 um; mobile phase: [water (0.05%/$NH_3H_2O$)-ACN]; B %: 25%-55%, 12 min) to afford the title compound (2.1 mg, 4.61 μmol, 2.91% yield, 100% purity) as a gray solid. $^1$H NMR (400 MHz, DMSO-$d_6$) δ: 9.11 (s, 1H), 8.48 (s, 1H), 8.43 (s, 1H), 8.09-8.05 (m, 2H), 7.65 (br d, J=9.3 Hz, 2H), 7.00 (s, 2H), 4.48-4.40 (m, 2H), 3.83 (s, 6H), 3.78 (br d, J=3.8 Hz, 1H), 1.51 (t, J=7.3 Hz, 3H), 1.13-1.08 (m, 2H), 1.03 (br d, J=5.0 Hz, 2H).

Example 66. 4-[7-(1-Cyclopropyltriazol-4-yl)imidazo[1,2-a]pyridin-3-yl]benzonitrile

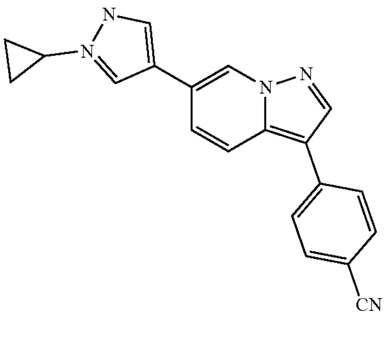

Step 1. 2-Imidazo[1,2-a]pyridin-7-ylethynyl(trimethyl)silane

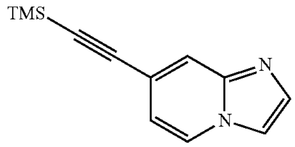 [SMILES: C[Si](C)(C)C#Cc1ccn2ccnc2c1]

To a solution of 7-bromoimidazo[1,2-a]pyridine (2 g, 10.15 mmol, 1 eq), ethynyl(trimethyl)silane (2.99 g, 30.45 mmol, 4.22 mL, 3 eq) and TEA (4.11 g, 40.60 mmol, 5.65 mL, 4 eq) in DMF (40 mL) was added Pd$(PPh_3)_2Cl_2$ (712.47 mg, 1.02 mmol, 0.1 eq) and CuI (193.32 mg, 1.02 mmol, 0.1 eq) under $N_2$, and the resulting mixture was stirred at 70° C. for 12 h. The mixture was partitioned between water (50 mL) and ethyl acetate (50 mL, 3×). The organic phase was separated, washed with brine (100 mL), dried over $Na_2SO_4$, filtered, and concentrated under reduced pressure to give the crude product, which was purified by column chromatography ($SiO_2$, Petroleum ether/Ethyl acetate=1:0 to 2:1) to afford the title compound (1.4 g, 6.53 mmol, 64.35% yield) as a brown oil.

Step 2. 7-Ethynylimidazo[1,2-a]pyridine

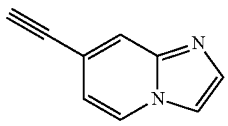

To a solution of 2-imidazo[1,2-a]pyridin-7-ylethynyl(trimethyl)silane (800 mg, 3.73 mmol, 1 eq) in MeOH (10 mL) was added $K_2CO_3$ (1.55 g, 11.20 mmol, 3 eq), and the resulting mixture was stirred at 20° C. for 0.5 h. The reaction mixture was concentrated under reduced pressure to give a residue, which was partitioned between water (5 mL) and ethyl acetate (5 mL, 3×). The organic phase was separated, washed with brine (5 mL), dried over $Na_2SO_4$, filtered, and concentrated under reduced pressure to afford the title compound (200 mg, crude) as a yellow solid.

Step 3. 7-(1H-Triazol-4-yl)imidazo[1,2-a]pyridine

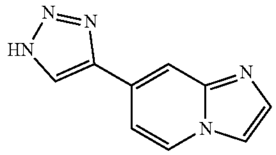 [SMILES: c1cn2ccc(-c3c[nH]nn3)cc2n1]

To a solution of 7-ethynylimidazo[1,2-a]pyridine (170 mg, 1.20 mmol, 1 eq) and $TMSN_3$ (275.55 mg, 2.39 mmol, 314.55 μL, 2 eq) in DMF (1.8 mL) and MeOH (0.2 mL) was added CuI (11.39 mg, 59.79 μmol, 0.05 eq) under $N_2$, and the resulting mixture was stirred at 100° C. for 12 h. The reaction mixture was concentrated under reduced pressure to give a residue, which was purified by reversed-phase HPLC (column: C18 20-35 um 100 Å 40 g; mobile phase: [water- ACN]; B %: 0%-20% at 30 mL/min) to afford the title compound (150 mg, 810.00 μmol, 67.73% yield) as a yellow solid.

Step 4. 7-(1-Cyclopropyltriazol-4-yl)imidazo[1,2-a] pyridine

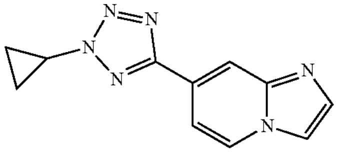 [SMILES: c1cn2ccc(-c3nnn(C4CC4)n3)cc2n1]

To solution of 7-(1H-triazol-4-yl)imidazo[1,2-a]pyridine (120 mg, 648.00 μmol, 1 eq) and cyclopropylboronic acid (278.31 mg, 3.24 mmol, 6.49 μL, 5 eq) in pyridine (512.57 mg, 6.48 mmol, 523.03 μL, 10 eq) was added $Cu(OAc)_2$ (353.10 mg, 1.94 mmol, 3 eq) and DIEA (837.50 mg, 6.48 mmol, 1.13 mL, 10 eq), and the resulting mixture was stirred at 100° C. for 6 h. The mixture was partitioned between water (5 mL) and ethyl acetate (5 mL, 3×). The organic phase was separated, washed with brine (5 mL), dried over $Na_2SO_4$, filtered, and concentrated under reduced pressure to give the crude product, which was purified by prep-HPLC (basic condition; column: Waters Xbridge Prep OBD C18 150*40 mm*10 um; mobile phase: [water (0.05% $NH_3H_2O$+10 mM $NH_4HCO_3$)-ACN]; B %: 15%-45%, 8 min) to afford the title compound (15 mg, 66.59 μmol, 10.28% yield) as a green solid.

Step 5. 4-[7-(1-Cyclopropyltriazol-4-yl)imidazo[1,2-a]pyridin-3-yl]benzonitrile

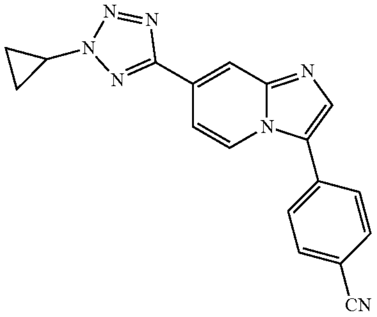 [SMILES: N#Cc1ccc(-c2cnc3cc(-c4nnn(C5CC5)n4)ccn23)cc1]

To a solution of 7-(1-cyclopropyltriazol-4-yl)imidazo[1,2-a]pyridine (15 mg, 66.59 μmol, 1 eq), 4-bromobenzonitrile (12.12 mg, 66.59 μmol, 1 eq), and $Cs_2CO_3$ (43.39 mg, 133.19 μmol, 2 eq) in DMA (0.5 mL) was added Pd(dppf) $Cl_2 \cdot CH_2Cl_2$ (5.44 mg, 6.66 μmol, 0.1 eq) under $N_2$, and the resulting mixture was stirred at 100° C. for 4 h. The reaction mixture was concentrated to give the crude product, which was purified by prep-HPLC (basic condition; column: Phenomenex Gemini-NX C18 75*30 mm*3 um; mobile phase: [water(0.05% $NH_3H_2O$+10 mM $NH_4HCO_3$)-ACN]; B %: 28%-58%, 8 min) to afford the title compound (9 mg, 27.17 μmol, 40.80% yield, 98.526% purity) as a gray solid. $^1H$ NMR (400 MHz, DMSO-$d_6$) δ: 8.76 (d, J=7.1 Hz, 1H), 8.49 (s, 1H), 8.19 (s, 1H), 8.06-7.98 (m, 3H), 7.98-7.91 (m, 2H), 7.48 (br d, J=7.3 Hz, 1H), 4.21 (td, J=3.7, 7.4 Hz, 1H), 1.28 (br d, J=3.1 Hz, 2H), 1.20-1.08 (m, 2H).

Example 67. 4-[7-(2-Ethyltetrazol-5-yl)imidazo[1,2-a]pyridin-3-yl]benzonitrile

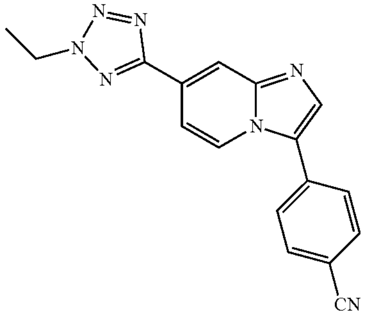 [SMILES: CCn1nnc(-c2ccn3c(-c4ccc(C#N)cc4)cnc3c2)n1]

Step 1. Imidazo[1,2-a]pyridine-7-carbonitrile

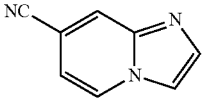 [SMILES: N#Cc1ccn2ccnc2c1]

A mixture of 2-aminopyridine-4-carbonitrile (5 g, 41.9 mmol, 1 eq), 2-chloroacetaldehyde (20.6 g, 104.9 mmol, 16.9 mL, 40% purity, 2.5 eq) and $NaHCO_3$ (7.1 g, 83.9 mmol, 3.3 mL, 2 eq), in EtOH (60 mL) was stirred at 80° C. for 12 h. The reaction mixture was concentrated under reduced pressure to remove EtOH, and the resulting residue was purified by column chromatography ($SiO_2$, Petroleum ether:Ethyl acetate=1:0 to 0:1) to afford the title compound (7 g, crude) as a brown oil.

Step 2. 7-(2H-Tetrazol-5-yl)imidazo[1,2-a]pyridine

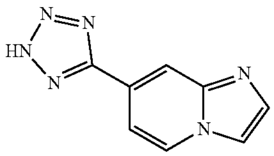 [SMILES: c1cn2ccc(-c3nn[nH]n3)cc2n1]

A mixture of imidazo[1,2-a]pyridine-7-carbonitrile (1 g, 6.9 mmol, 1 eq), azidosodium (454.2 mg, 6.9 mmol, 1 eq), and $NH_4Cl$ (411.1 mg, 7.7 mmol, 1.1 eq) in DMF (5 mL) was stirred at 80° C. for 12 h to afford the crude product (1.3 g, crude) as a black oil, which was used in the next step without further purification.

Step 3. 7-(2-Ethyltetrazol-5-yl)imidazo[1,2-a]pyridine

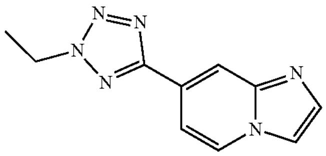 [SMILES: CCn1nnc(-c2ccn3ccnc3c2)n1]

To a solution of 7-(2H-tetrazol-5-yl)imidazo[1,2-a]pyridine (150 mg, 805.7 μmol, 1 eq) in DMF (2 mL) was added NaH (48.3 mg, 1.2 mmol, 60% purity, 1.5 eq) at 0° C., and the resulting mixture was stirred at 0° C. for 0.5 h. Iodoethane (125.7 mg, 805.7 μmol, 64.4 μL, 1 eq) was added and the mixture was stirred at 15° C. for 0.5 h. The reaction mixture was added to water (20 mL) and extracted with EtOAc (10 mL, 3×). The combined organic layers were washed with brine (20 mL), dried over $Na_2SO_4$, filtered, and concentrated under reduced pressure to afford the title compound (170 mg, crude) as black oil.

Step 4. 4-[7-(2-Ethyltetrazol-5-yl)imidazo[1,2-a]pyridin-3-yl]benzonitrile

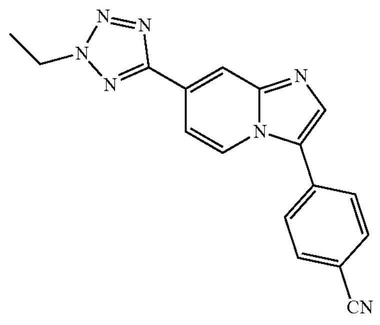 [SMILES: CCn1nnc(-c2ccn3c(-c4ccc(C#N)cc4)cnc3c2)n1]

A mixture of 7-(2-ethyltetrazol-5-yl)imidazo[1,2-a]pyridine (170 mg, 793.6 μmol, 1 eq), 4-bromobenzonitrile (144.4 mg, 793.6 μmol, 1 eq), $Cs_2CO_3$ (517.1 mg, 1.6 mmol, 2 eq), and $Pd(dppf)Cl_2·CH_2Cl_2$ (64.8 mg, 79.4 μmol, 0.1 eq) in DMA (2 mL) was degassed and purged with $N_2$ (3×), and then the mixture was stirred at 100° C. for 12 h under $N_2$ atmosphere.

The reaction mixture was concentrated to give the crude product, which was purified by prep-HPLC (basic condition; column: Waters X bridge Prep OBD C18 150*40 mm*10 um; mobile phase: [water(0.05% $NH_3H_2O$+10 mM $NH_4HCO_3$)-ACN]; B %: 30%-60%, 8 min) to afford the title compound (16.4 mg, 52.0 μmol, 6.6% yield, 100% purity) as a brown solid. $^1H$ NMR (400 MHz, DMSO-$d_6$) δ: 8.88 (br d, J=7.1 Hz, 1H), 8.32 (s, 1H), 8.14 (br s, 1H), 8.08-8.02 (m, 2H), 8.02-7.95 (m, 2H), 7.62 (br d, J=7.3 Hz, 1H), 4.83 (q, J=7.3 Hz, 2H), 1.69-1.55 (m, 3H).

Example 68. 3-[3,5-Dimethoxy-4-(2,2,2-trifluoroethylcarbamoyl)phenyl]-N-[(6-methyl-3-pyridyl)methyl]imidazo[1,2-a]pyridine-7-carboxamide

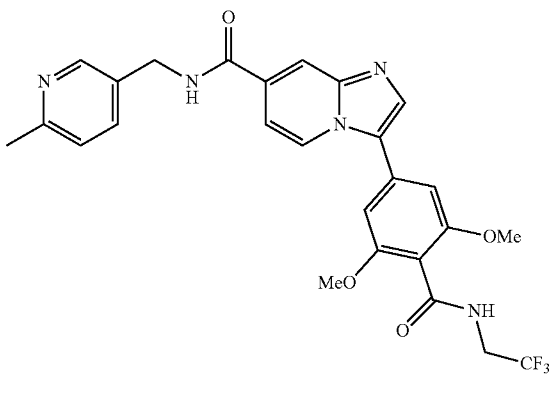 [SMILES: COc1cc(-c2cnc3cc(C(=O)NCc4ccc(C)nc4)ccn23)cc(OC)c1C(=O)NCC(F)(F)F]

Step 1. Methyl 4-bromo-2,6-dimethoxybenzoate

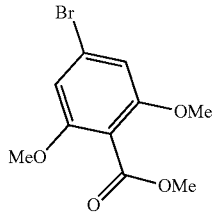 [SMILES: COC(=O)c1c(OC)cc(Br)cc1OC]

A mixture of methyl 4-bromo-2,6-difluorobenzoate (5 g, 19.92 mmol, 1 eq) and NaOMe (5.38 g, 99.59 mmol, 5 eq) in MeOH (80 mL) was stirred at 80° C. for 12 h. The reaction mixture was concentrated under reduced pressure to remove MeOH, then diluted with water (100 mL) and extracted with EtOAc (300 mL). The combined organic layers were washed with brine (50 mL), dried over $Na_2SO_4$, filtered, and concentrated under reduced pressure to afford the title compound (8 g, crude) as a white solid.

Step 2. 4-Bromo-2,6-dimethoxybenzoic acid

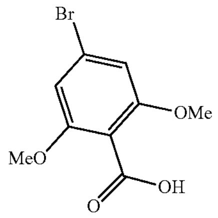 [SMILES: COc1cc(Br)cc(OC)c1C(=O)O]

A mixture of methyl 4-bromo-2,6-dimethoxybenzoate (2 g, 7.27 mmol, 1 eq), NaOH (872.42 mg, 21.81 mmol, 3 eq) in MeOH (50 mL), THE (20 mL), and $H_2O$ (10 mL) was stirred at 70° C. for 12 h. The reaction mixture was concentrated under reduced pressure to remove MeOH and THF, then HCl (12 N, 0.5 mL) was added. The mixture was filtered and the filter cake was concentrated under reduced pressure to afford the title compound (1.8 g, crude) as a white solid.

Step 3. 4-Bromo-2,6-dimethoxy-N-(2,2,2-trifluoroethyl)benzamide

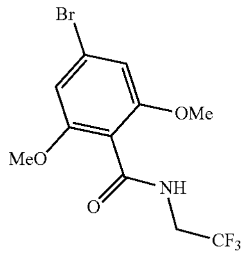 [SMILES: COc1cc(Br)cc(OC)c1C(=O)NCC(F)(F)F]

To a solution of 4-bromo-2,6-dimethoxybenzoic acid (0.8 g, 3.06 mmol, 1 eq), 2,2,2-trifluoroethanamine (333.89 mg, 3.37 mmol, 264.99 μL, 1.1 eq) in DMF (15 mL) was added DIEA (792.07 mg, 6.13 mmol, 1.07 mL, 2 eq) and HATU (1.75 g, 4.60 mmol, 1.5 eq), and the resulting mixture was stirred at 25° C. for 12 h. The reaction mixture was diluted with water (50 mL) and extracted with EtOAc (200 mL). The combined organic layers were washed with brine (50 mL), dried over $Na_2SO_4$, filtered, and concentrated under reduced pressure to give a residue, which was purified by column chromatography ($SiO_2$, Petroleum ether/Ethyl acetate=1/0 to 8/1) to afford the title compound (0.4 g, crude) as white solid.

Step 4. Methyl 3-[3,5-dimethoxy-4-(2, 2,2-trifluoro-ethylcarbamoyl)phenyl]-imidazo-[1,2-a]pyridine-7-carboxylate

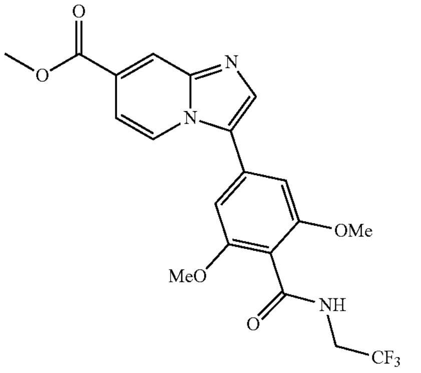 [SMILES: COC(=O)c1ccn2c(-c3cc(OC)c(C(=O)NCC(F)(F)F)c(OC)c3)cnc2c1]

To a solution of methyl imidazo[1,2-a]pyridine-7-carboxylate (0.20 g, 1.14 mmol, 1 eq), 4-bromo-2,6-dimethoxy-N-(2,2,2-trifluoroethyl)benzamide (388.38 mg, 1.14 mmol, 1 eq) and $Cs_2CO_3$ (1.11 g, 3.41 mmol, 3 eq) in DMAC (6 mL) was added Pd(dppf)$Cl_2$ (46.35 mg, 56.76 μmol, 0.05 eq), and the resulting mixture was stirred at 100° C. for 12 h. The reaction mixture was diluted with water (60 mL) and extracted with EtOAc (200 mL). The combined organic layers were washed with brine (100 mL), dried over $Na_2SO_4$, filtered, and concentrated under reduced pressure to give a residue, which was purified by prep-TLC ($SiO_2$, ethyl acetate:methanol=10:1) to afford the title compound (350 mg, crude) as a yellow solid.

Step 6. 3-[3,5-Dimethoxy-4-(2,2,2-trifluoroethylcarbamoyl)phenyl]imidazo-[1,2-a]pyridine-7-carboxylic acid

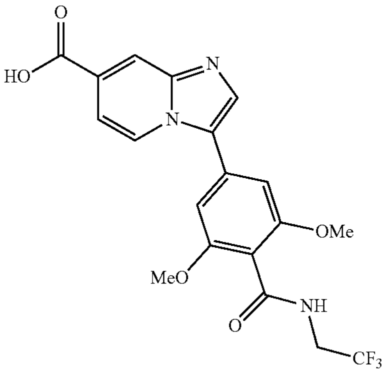 [SMILES: COc1cc(-c2cnc3cc(C(=O)O)ccn23)cc(OC)c1C(=O)NCC(F)(F)F]

A mixture of methyl 3-[3,5-dimethoxy-4-(2,2,2-trifluoroethylcarbamoyl)phenyl]imidazo-[1,2-a]pyridine-7-carboxylate (350 mg, 800.24 μmol, 1 eq), NaOH (64.02 mg, 1.60 mmol, 2 eq), in MeOH (15 mL) and $H_2O$ (5 mL) stirred at 50° C. for 2 h. The reaction mixture was concentrated under reduced pressure to remove MeOH, then HCl (12 N, 0.2 mL) was added to the solution. The mixture was filtered and the filter cake was concentrated under reduced pressure to afford the title compound (150 mg, crude) as a brown solid.

Step 7. 3-[3,5-Dimethoxy-4-(2,2,2-trifluoroethylcarbamoyl)phenyl]-N-[(6-methyl-3-pyridyl)methyl]imidazo[1,2-a]pyridine-7-carboxamide

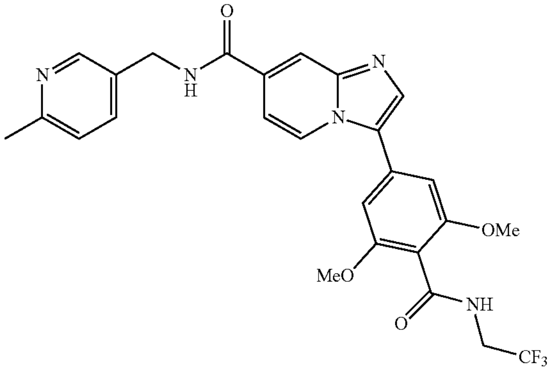 [SMILES: COc1cc(-c2cnc3cc(C(=O)NCc4ccc(C)nc4)ccn23)cc(OC)c1C(=O)NCC(F)(F)F]

To a solution of 3-[3,5-dimethoxy-4-(2,2,2-trifluoroethylcarbamoyl)phenyl]imidazo[1,2-a]pyridine-7-carboxylic acid (80 mg, 188.97 μmol, 1 eq), (6-methyl-3-pyridyl)methanamine (23.09 mg, 188.97 μmol, 1 eq), and DIEA (48.85 mg, 377.95 μmol, 65.83 μL, 2 eq) in DMF (2 mL) was added HATU (93.41 mg, 245.66 μmol, 1.3 eq), and the resulting mixture was stirred at 40° C. for 12 h. The reaction mixture was filtered to give a residue, which was purified by prep-HPLC (column: Waters Xbridge Prep OBD C18 150*40 mm*10 um; mobile phase: [water(0.05% NH3H2O+10 mM NH4HCO3)-ACN]; B %: 15%-45%, 8 min) to afford the title compound (62.7 mg, 118.26 μmol, 62.58% yield, 99.496% purity) as a white solid. $^1$H NMR (400 MHz, MeOD-$d_4$) δ: 8.66 (d, J=7.1 Hz, 1H), 8.71-8.59 (m, 1H), 8.47 (s, 1H), 8.18 (s, 1H), 7.92 (s, 1H), 7.79 (dd, J=2.1, 8.1 Hz, 1H), 7.47 (dd, J=1.5, 7.3 Hz, 1H), 7.32 (d, J=7.9 Hz, 1H), 6.96 (s, 2H), 4.63 (s, 2H), 4.08 (q, J=9.3 Hz, 2H), 3.91 (s, 6H), 2.54 (s, 3H).

Biological Assays

The following general materials and methods were used in Examples A-D.

Gene Expression Analysis

A single cell sub-clone of Ocy454 cells (Wein et al, *Journal of Bone and Mineral Research: The Official Journal of the American Society for Bone and Mineral Research*, 2015, 30(3):400-11) was used for all experiments. Cells were passaged in alpha-MEM supplemented with heat inactivated 10% fetal bovine serum and 1% antibiotic-antimycotic (Gibco™) at 33° C. with 5% $CO_2$. Cells were seeded at 50,000 cells/mL and allowed to reach confluency at 33° C. in 2-3 days. Then, cells were transferred from 33° C. to 37° C. to inactivate the temperature sensitive T antigen and facilitate osteocytic differentiation. Cells were then treated with compounds from 10 mM DMSO stocks for four hours at indicated doses in experimental duplicates. Total RNA was collected from cultured cells using QIAshredder (QIAGEN) and PureLink RNA mini kit (Invitrogen™) following the manufacturer's instructions. Lysis buffer with 2-mercaptoethanol was added to cold PBS washed cells and collected into QIAshredder, then centrifuged at 15,000 g for 3 minutes. The flow-through was collected into a new tube and RNA isolation was carried out with PureLink RNA mini kit. For qRT-PCR, cDNA was prepared with 750 ng RNA using the Primescript RT kit (Takara Inc.) and analyzed with PerfeCa® SYBR® Green FAstMix® ROX (Quanta bio) in the StepOnePlus™ Real-time PCR System (Applied Biosystems) using specific primers designed for each targeted gene. Relative expression was calculated using the $2^{-\Delta\Delta CT}$ method by normalizing to β-actin housekeeping gene expression, and presented as fold increase relative to β-actin. Primers used were β-actin (CCTCTATGCCAACACAGTGC (SEQ ID NO. 1) and ACATCTGCTGGAAGGTGGAC (SEQ ID NO. 2)), SOST (GCCTCATCTGCCTACTTGTG (SEQ ID NO. 3) and CTGTGGCATCATTCCTGAAG (SEQ ID NO. 4)), and RANKL (GCTGGGCCAAGATCTCTAAC (SEQ ID NO. 5) and GTAGGTACGCTTCCCGATGT (SEQ ID NO. 6)). Data are represented as maximal RANKL fold induction versus DMSO (vehicle) control.

Western Blotting

Immunoblotting was performed as previously described (see e.g., Wein et al, *Nature Communications,* 2016, 7:13176; and Sato et al, *Nature Communications,* 2020, 11(1):3282). Whole cell lysates were prepared using TNT (Tris-NaCl-Tween buffer, 20 mM Tris-HCl pH 8, 200 mM NaCl, 0.5% Triton X-100 containing protease inhibitor (PI), 1 mM NaF, 1 mM DTT, 1 mM vanadate). Adherent cells were washed with ice cold PBS, then scraped into TNT buffer on ice. Material was then transferred into Eppendorf tubes kept on ice, vortexed at top speed for 30 seconds, then centrifuged at top speed for 6 minutes at 4° C. For subcellular fractionation, cells were initially resuspended in hypotonic lysis buffer (20 mM HEPES, 10 mM KCl, 1 mM $MgCl_2$, 0.1% Triton X-100, 5% glycerol supplemented with DTT, protease inhibitors, and phosphatase inhibitors) for 5 minutes on ice. Nuclear pellets were spun down at 5,000 rpm for 5 minutes, and the supernatant was saved as the cytoplasmic lysate. Thereafter, the nuclear pellet was washed once in 1 mL hypotonic lysis buffer. The nuclear pellet was then resuspended in hypertonic lysis buffer (20 mM HEPES, 400 mM NaCl, 1 mM EDTA, 0.1% Triton X-100, 5% glycerol supplemented with DTT, protease inhibitors, and phosphatase inhibitors), followed by vortexing twice for 30 seconds. Debris was spun down at 14,000 rpm for 5 minutes, and the supernatant was saved as the nuclear lysate. For immunoblotting, lysates or immunoprecipitates were separated by SDS-PAGE and proteins were transferred to nitrocellulose. Membranes were blocked with 5% milk in tris-buffered saline plus 0.05% Tween-20 (TBST) and incubated with primary antibody overnight at 4° C. The next day, membranes were washed, incubated with appropriate HRP-coupled secondary antibodies, and signals detected with ECL Western Blotting Substrate (Pierce), ECL Plus Western Blotting Substrate (Pierce), or SuperSignal West Femto Maximum Sensitivity Substrate (Thermo scientific). The primary antibodies phospho-HDAC4/5/7 (S246/S259/S155) (Cell Signaling Technology, 3443) and total HDAC5 (Assay Biotech, C0225).

Example A. In Vitro SIK2 Kinase Assay

Assays were performed in base reaction buffer (20 mM Hepes (pH 7.5), 10 mM $MgCl_2$, 1 mM EGTA, 0.02% Brij35, 0.02 mg/mL BSA, 0.1 mM $Na_3VO_4$, 2 mM DTT, 1% DMSO). Compounds were dissolved in 100% DMSO in a 10 mM stock. Serial dilution was conducted by Integra Viaflo Assist in DMSO. Recombinant SIK2 was used at a concentration of 2.5 nM. The substrate used was pAMARA at a concentration of 0.2 mg/mL. Kinase assays were supplemented with 2 mM $Mn^{2+}$, and 1 μM ATP was added. Assays were performed for 20 minutes at room temperature, after which time $^{33}$P-ATP (10 μCi/μL) was added followed by incubation for another 120 minutes at room temperature. Thereafter, radioactivity incorporated into the pEY peptide substrate was detected by filter-binding method. Kinase activity data were expressed as the percent remaining kinase activity in test samples compared to DMSO reactions. $IC_{50}$ values and curve fits were obtained using Prism (GraphPad Software).

Example B. NanoBRET Cell-Based Target Engagement Assays

Assays were performed at Reaction Biology Corporation (Malvern, PA) in HEK293 cells from ATCC in 384 well plate format using Promega's NanoBRET TE intracellular kinase assay platform. HEK293 cells transiently expressing NanoLuc-SIK2 fusion vector were seeded into 384 well plates. Cells were pre-treated with the NanoBRET Tracer K-4 and then treated with compounds for 60 minutes in 10 point dose response format. The BRET signal was measured on an Envision 2104 Multilabel Reader. IC50 values were calculated and $IC_{50}$ curves were plotted using the GraphPad Prism 4 program on a sigmoidal dose response equation.

Example C. CRTC2 Nuclear Translocation

PathHunter® Nuclear Translocation cell lines are engineered to co-express two fusion proteins: a) Enzyme Donor (ED) tagged target protein; b) an Enzyme Acceptor (EA) tagged TAZ domain, derived from the CBP/P300 transcription factor, that localizes to the nucleus. Activation of the signaling pathway induces translocation of the ED-tagged target protein into the nucleus, which will force complementation of the two enzyme fragments, and result in the formation of a functional enzyme that will hydrolyze substrate and generate a chemiluminescent signal. U2OS CRTC2 (TORC2) translocation assays were performed in 384 well plates at Eurofins DiscoverX (Freemont, CA). Cells were treated with compounds for 90 minutes in experimental duplicates in 5 point dose response format (4-fold serial dilutions with a maximum dose of 10 μM) followed by colorimetric readout on an Envision 2104 Multilabel Reader. In all experiments, forskolin was used as a positive control and maximal CRTC2 nuclear translocation induced by each compound is expressed as a percentage of the signal stimulated by forskolin.

The compounds provided herein were tested in one or more of the assays described in Examples A-C and representative data are shown in Table A.

TABLE A

| Ex. No. | SIK2 IC$_{50}$ (M) | SIK3 IC$_{50}$ (M) | SIK1 IC$_{50}$ (M) | SIK2 NanoBRET (M) | CRTC2 Efficacy (% of forskolin) | RANKL Fold Induction |
|---|---|---|---|---|---|---|
| 1 | 3.073E−08 | NA | NA | NA | NA | 3.08 |
| 2 | 4.21E−08 | 3.87E−08 | 6.25E−07 | NA | 162 | 1.43 |
| 3 | 9.79E−10 | 2.24E−09 | 1.84E−08 | 8.86E−09 | 88.5 | 57.08 |
| 6 | 5.746E−09 | NA | NA | NA | 127.8 | NA |
| 7 | 8.35E−09 | 1.153E−08 | 1.379E−07 | 4.318E−08 | 89 | 30.37 |
| 8 | 1.16E−08 | 3.077E−08 | 5.006E−08 | NA | 64.4 | 17.47 |
| 9 | 2.464E−08 | NA | NA | NA | NA | 9.69 |
| 10 | 2.108E−09 | 3.71E−09 | 3.777E−08 | NA | 75.8 | 58.64 |
| 11 | 2.266E−08 | NA | NA | NA | NA | 1.38 |
| 12 | 4.903E−09 | 1.19E−08 | 1.398E−07 | 9.249E−07 | 37.6 | 62.52 |
| 13 | 4.19E−09 | NA | NA | NA | 140.6 | NA |
| 14 | 1.61E−08 | 6.077E−09 | 1.088E−07 | NA | 94.2 | 1.26 |
| 15 | 1.91E−09 | 1.119E−09 | 4.369E−09 | NA | 63.5 | 88.34 |
| 16 | 3.386E−09 | 4.435E−09 | 1.665E−08 | NA | NA | 27.76 |
| 17 | 1.037E−09 | 1.537E−08 | 5.331E−08 | NA | NA | 12.73 |
| 18 | 1.854E−07 | NA | NA | NA | NA | 7.49 |
| 19 | 4.02E−08 | 5.01E−07 | 8.93E−07 | NA | 27 | 1.04 |
| 20 | 1.09E−07 | NA | NA | NA | 9.4 | NA |
| 21 | 1.18E−07 | NA | NA | NA | 9.9 | NA |
| 22 | 5.58E−09 | 4.97E−07 | 1.30E−05 | 1.17E−07 | 12.9 | 1.19 |
| 23 | 1.43E−08 | 8.61E−07 | NI | NA | 19.8 | NA |
| 24 | 1.14E−08 | 8.35E−07 | 1.25E−05 | 4.21E−08 | 21.2 | 2.24 |
| 25 | 9.74E−09 | 1.19E−06 | 5.45E−06 | NA | 1.6 | 1.10 |
| 26 | 8.30E−08 | NI | NA | NA | 1.3 | 0.55 |
| 27 | 1.32E−07 | NA | NA | NA | 5.3 | NA |
| 28 | 5.97E−07 | 8.09E−06 | NA | NA | 3.4 | 1.25 |
| 29 | 6.08E−07 | 8.34E−06 | NA | NA | 2.8 | 1.48 |
| 30 | 1.70E−06 | NA | NA | NA | 1.7 | NA |
| 31 | 2.63E−08 | 7.61E−08 | 4.09E−07 | 4.02E−06 | 31.2 | 0.90 |
| 32 | 1.48E−07 | 3.38E−07 | NA | NA | 10.6 | NA |
| 33 | 1.42E−08 | 2.55E−06 | 5.42E−06 | 4.48E−08 | 21.7 | 0.92 |
| 34 | 2.00E−08 | NA | NA | NA | 14 | NA |
| 35 | 7.55E−09 | 1.03E−07 | 2.09E−06 | 9.32E−08 | 8.9 | 0.39 |
| 36 | 5.30E−06 | NA | NA | NA | 2.5 | NA |
| 37 | 3.25E−08 | 3.10E−07 | 7.75E−07 | 1.16E−07 | 40.6 | 1.17 |
| 38 | 2.11E−07 | NA | NA | NA | 10.1 | 0.37 |
| 39 | 1.36E−07 | 8.365E−08 | 2.676E−06 | NA | NA | NA |
| 40 | 9.869E−09 | NA | NA | NA | NA | NA |
| 41 | 4.11E−09 | 1.26E−08 | 2.33E−07 | NA | 44.2 | 2.61 |
| 42 | 3.697E−08 | 4.704E−08 | 1.175E−06 | NA | NA | NA |
| 43 | 5.893E−09 | NA | NA | NA | NA | 7.09 |
| 44 | 2.34E−09 | NA | NA | NA | NA | 3.07 |
| 45 | 5.79E−10 | 2.21E−09 | 3.83E−09 | NA | 85 | 9.41 |
| 46 | 1.397E−08 | NA | NA | NA | NA | 3.44 |
| 47 | 8.546E−10 | 4.162E−09 | 8.341E−09 | NA | NA | 17.43 |
| 48 | 7.65E−09 | NA | NA | NA | NA | NA |
| 49 | 1.01E−10 | 1.43E−09 | 2.16E−09 | 1.36E−09 | 92.2 | 6.31 |
| 50 | 2.341E−09 | NA | NA | NA | NA | 15.84 |
| 51 | 4.12E−10 | 1.18E−09 | 6.49E−09 | 1.13E−09 | 86.5 | 9.79 |
| 52 | 1.11E−09 | 1.639E−09 | 4.77E−09 | NA | 77 | 19.99 |
| 53 | 1.768E−09 | 2.62E−09 | 1.743E−08 | NA | NA | NA |
| 54 | 2.24E−09 | NA | NA | NA | NA | 9.07 |
| 55 | 1.48E−09 | 2.664E−09 | 1.598E−08 | NA | NA | 22.80 |
| 56 | 5.33E−07 | 6.17E−07 | 3.12E−06 | NA | 4.9 | 2.18 |
| 57 | 8.763E−09 | 1.102E−08 | 9.075E−08 | 9.083E−08 | NA | 13.68 |
| 58 | 1.083E−06 | NA | NA | NA | NA | 1.26 |
| 59 | 2.70E−07 | NA | NA | NA | NA | NA |
| 60 | 1.49E−09 | 1.643E−09 | 4.447E−09 | NA | NA | 307.25 |
| 61 | 3.07E−09 | 8.25E−09 | 3.78E−08 | NA | 76.9 | 19.00 |
| 62 | 2.53E−07 | 1.09E−06 | 1.13E−06 | NA | 8.6 | NA |
| 63 | 3.397E−09 | NA | NA | NA | NA | 0.89 |
| 64 | 8.80E−09 | NA | NA | NA | NA | 0.47 |
| 65 | 2.368E−08 | NA | NA | NA | NA | NA |
| 66 | 3.703E−08 | NA | NA | NA | NA | NA |
| 67 | 2.27E−07 | NA | NA | NA | NA | 0.47 |
| 68 | 1.24E−08 | 8.67E−09 | 9.47E−08 | NA | 12 | 2.88 |

NA = not available
NI = no inhibition

Example D. Representative Cellular Data

Figure 4A:
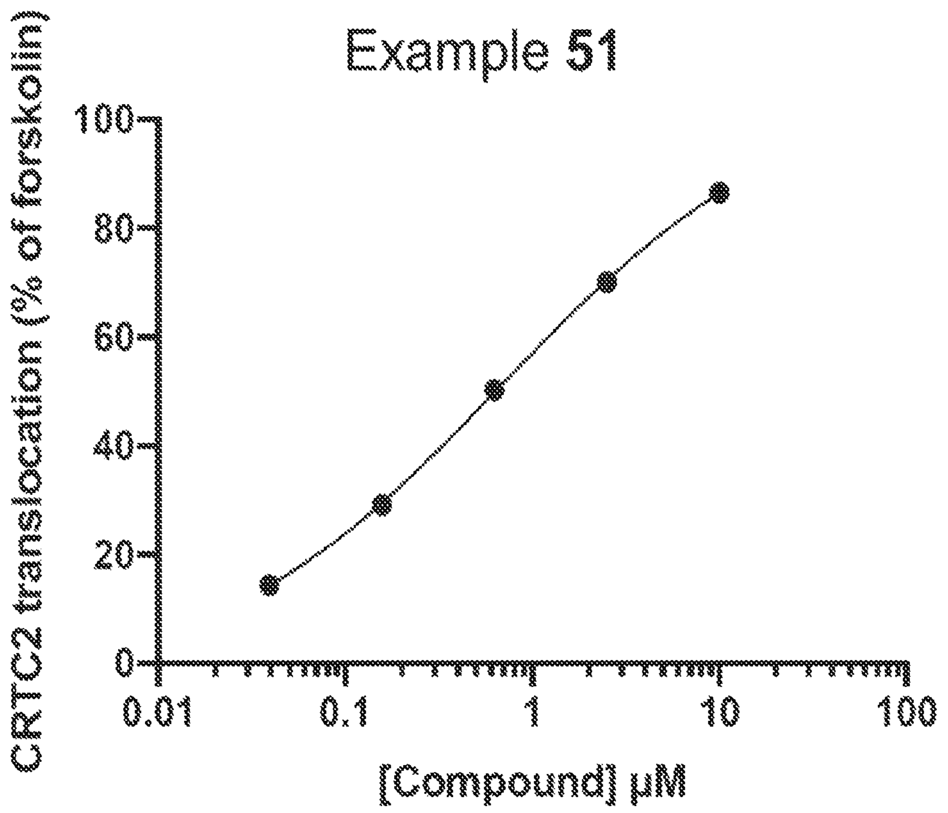
FIG. 4A shows nuclear CRTC2 translocation (presented as percent of the positive control (forskolin) signal) in U2OS CRTC2 (TORC2) PathHunter cells treated with the indicated doses of the compound of Example 51.

U2OS CRTC2 (TORC2) PathHunter cells were treated with the indicated doses of the compound of Example 51 for 90 minutes followed by measurement of nuclear CRTC2 translocation. Representative data are shown in FIG. 4A and presented as percent of the positive control (forskolin) signal.

Figure 4B:
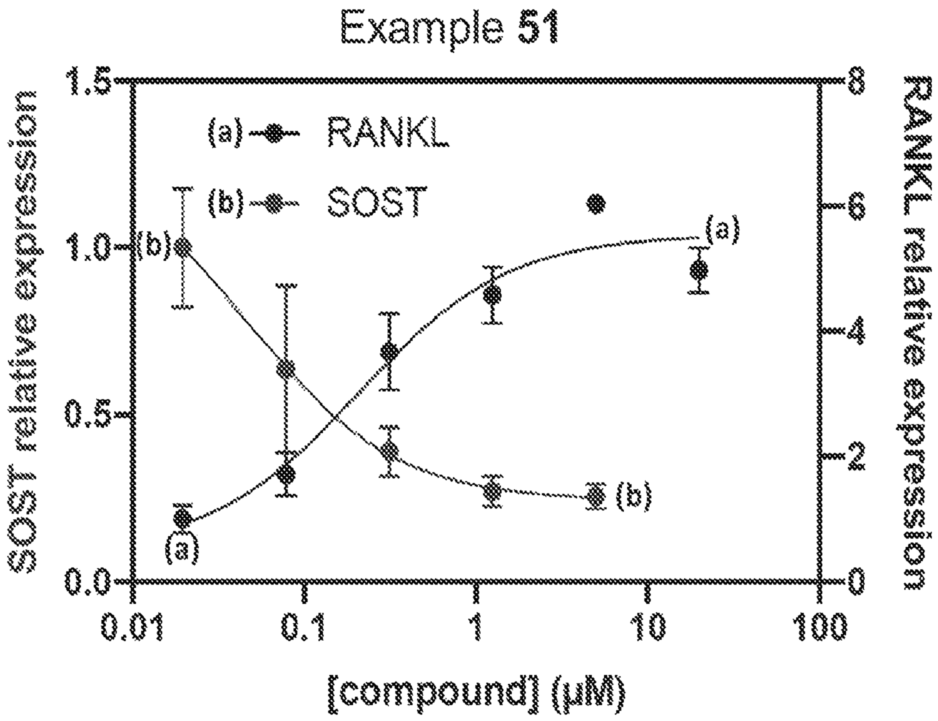
FIG. 4B shows SOST and RANKL expression measured by RT-qPCR in Ocy454 cells treated with the indicated doses of the compound of Example 51.

Ocy454 cells were treated with the indicated doses of the compound of Example 51 for 4 hours followed by RNA isolation and measurement of SOST and RANKL expression by RT-qPCR (normalized to the housekeeping gene β-actin). As shown in FIG. 4B, treatment with the compound of Example 51 reduces SOST and stimulates RANKL expression.

Figure 4C:
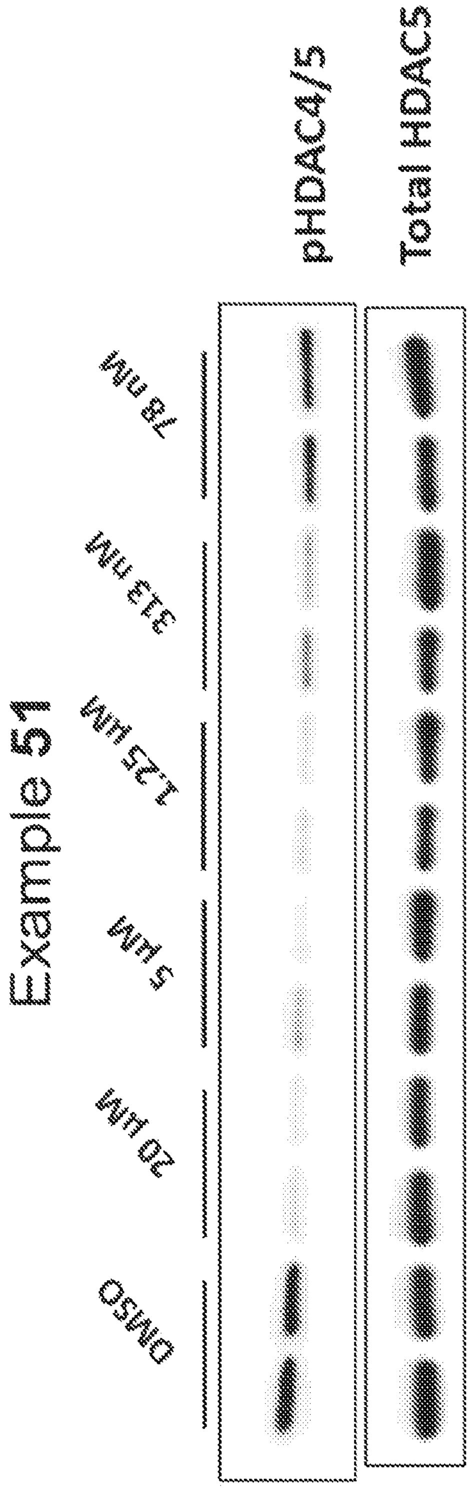
FIG. 4C shows HDAC4/5 phosphorylation in Ocy454 cells treated with the indicated doses of the compound of Example 51.

Ocy454 cells were treated with the indicated doses of the compound of Example 51 for 2 hours followed by protein isolation and immunoblotting. As shown in FIG. 4C, treatment with the compound of Example 51 reduces levels of HDAC4/5 phosphorylation without affecting total HDAC5 protein levels. These data demonstrate PTH-like effects of the small molecule SIK2/3 inhibitor, 2-[2,6-dimethoxy-4-[7-(1-methylpyrazol-4-yl)imidazo[1,2-a]pyridin-3-yl]phenyl]-5-ethyl-1,3,4-oxadiazole, (Example 51) in physiologically-relevant bone cell culture models.

Example E. Cell-Based Data

Figure 5A:
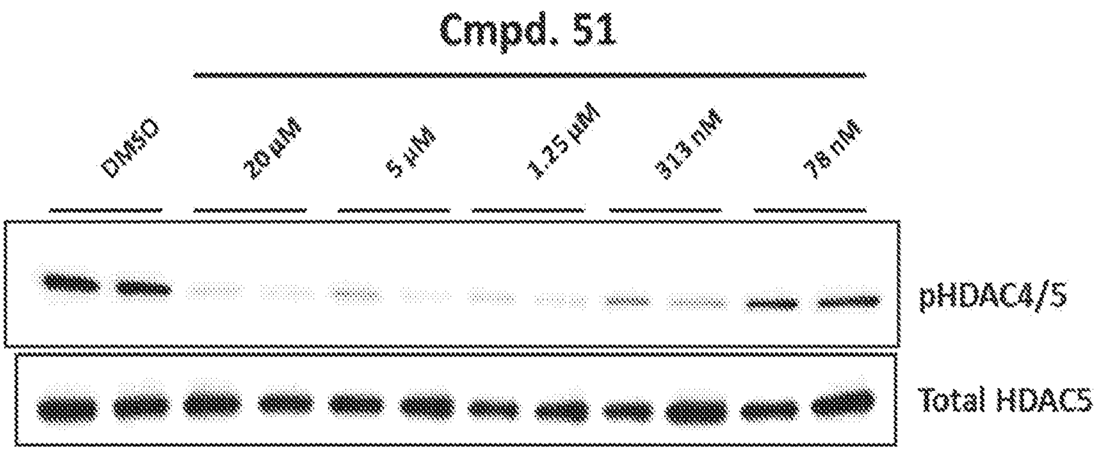
FIG. 5A shows results of the following experiment: Ocy454 cells grown at 37° C. for 7 days were treated with the indicated doses of SK-124 for 2 hours followed by immunoblotting for phosphorylated HDAC4/5 (S246/S259, top) and total HDAC5 (bottom). Cmpd. 51 treatment reduced phosphorylated HDAC4/5 levels without affecting total protein levels of these SIK substrates.
Figure 5B:
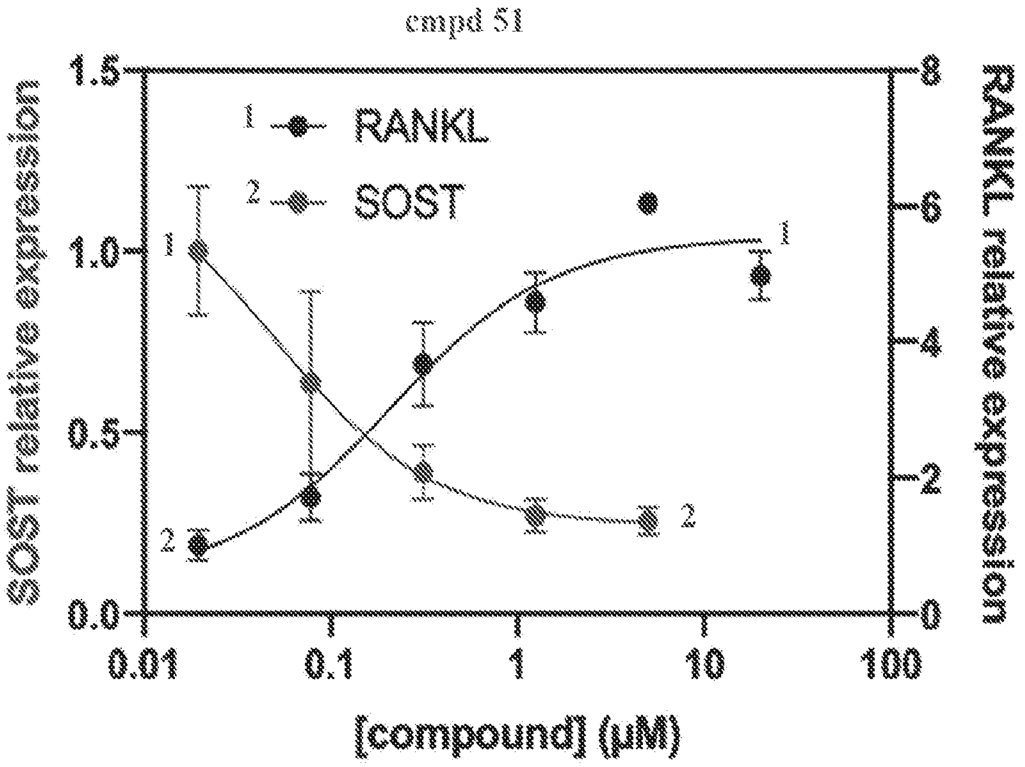
FIG. 5B shows results of the following experiment: Ocy454 cells grown at 37° C. for 14 days were treated with the indicated doses of cmpd. 51 for 4 hours followed by RT-qPCR for SOST (blue, left axis) and RANKL (black, right axis). The compound increased RANKL and suppressed SOST expression.

Cell-based assays were performed to assess the effects of cmpd. 51 in physiologically-relevant bone cell culture models. As shown in FIG. 5A, treatment of Ocy454 cells with cmpd. 51 leads to dose-dependent reduction of phosphorylation of the known SIK2/3 substrate HDAC4/5. Changes in SIK substrate phosphorylation lead to downstream gene expression changes. As shown in FIG. 5B, cmpd. 51 treatment of Ocy454 cells leads to induction of RANKL and suppression of SOST expression.

Figure 6A:
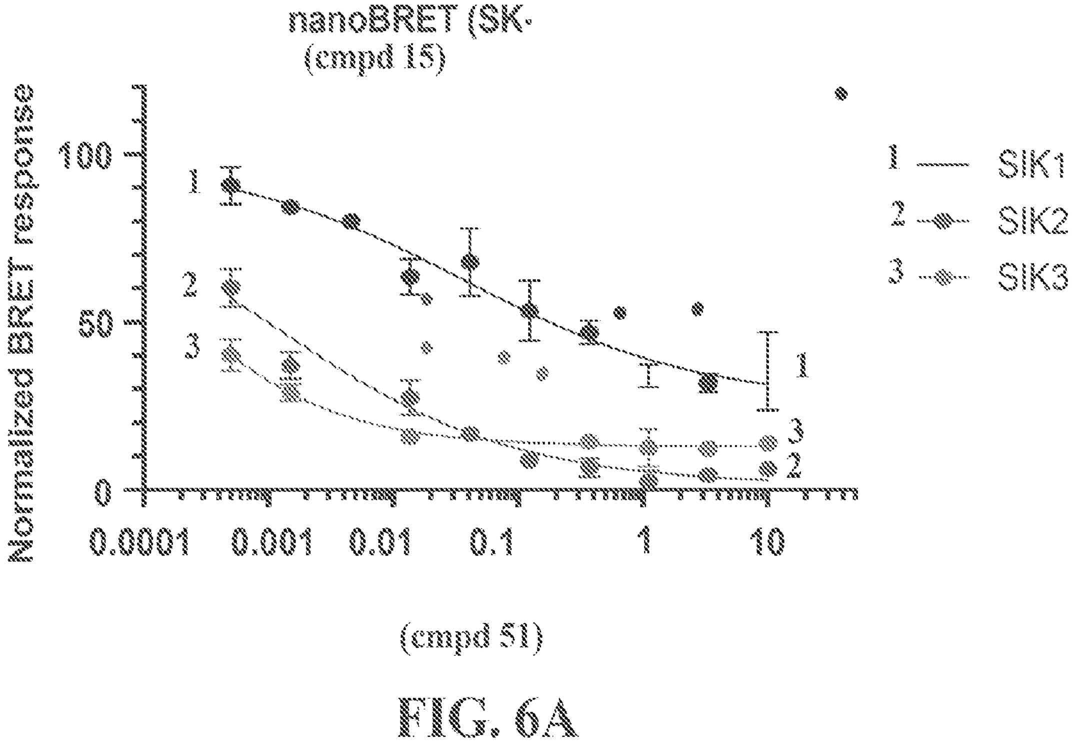
FIG. 6A shows results of the following experiment: SIK isoform nanoBRET assays were performed at Reaction Biology in HEK293T cells in response to cmpd. 51.
Figure 6B:
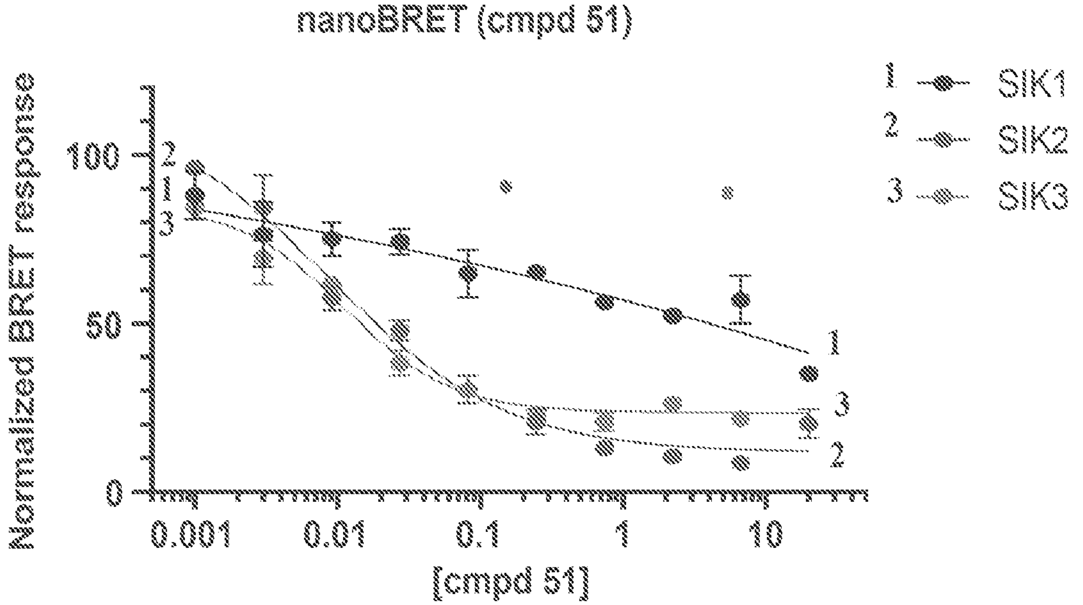
FIG. 6B shows results of the following experiment: SIK isoform nanoBRET assays were performed at Reaction Biology in HEK293T cells in response to cmpd. 55.
Figure 6C:
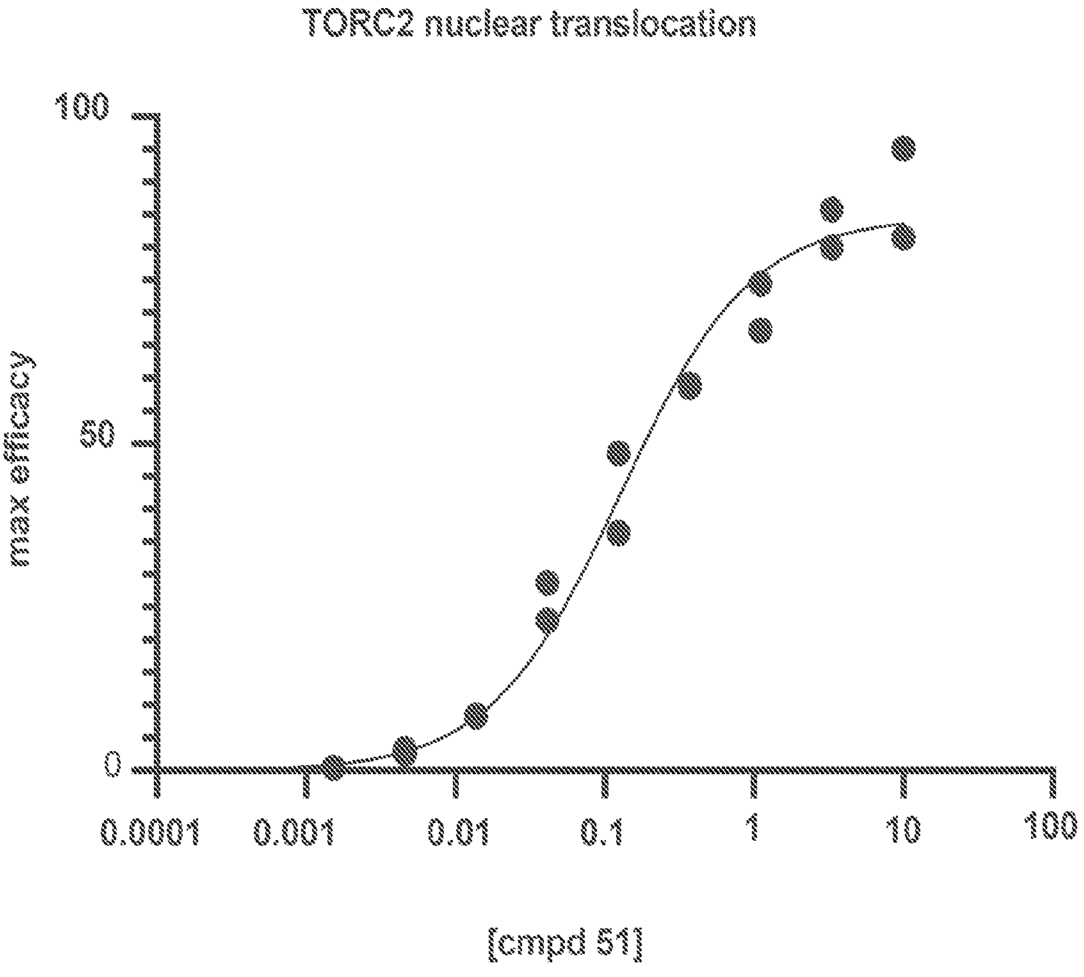
FIG. 6C shows results of CRTC2 (TORC2) nuclear translocation assays that were performed at EuroFins in response to cmpd. 51.

Additional cell-based assays with third party contract research organizations were performed in order to confirm cellular effects of cmpd. 51 and its analogs. As shown in FIGS. 6A and 6B, nanoBRET target engagement assays in HEK293T cells demonstrated selective SIK2/SIK3 engagement for cmpd. 51 and cmpd. 55 in this assay. In these assays, the $IC_{50}$ of cmpd. 51 was calculated to be 1.13 nM for SIK2, 0.51 nM for SIK3, and 32.2 nM for SIK1. The $IC_{50}$ of cmpd. 55 was calculated to be 12.2 nM for SIK2, 4.48 nM for SIK3, and 2.1 μM for SIK1. In addition to direct target engagement, the ability of cmpd. 51 to promote nuclear translocation of CRTC2 (also known as TORC2) was also measured. This assay was performed because SIK2 and SIK3 phosphorylate CRTC2 and promote its cytoplasmic retention. Therefore, SIK2/SIK3 inhibition should lead to reduced CRTC2 phosphorylation and the nuclear translocation of this protein. Indeed, CRTC2 caused robust nuclear translocation in response to increasing doses of cmpd. 51 (FIG. 6C, $EC_{50}$ 147 nM). These results show that cmpd. 51 potently inhibits SIK2 and SIK3 in cells. These data prompted testing of the effects of cmpd. 51 in vivo on bone mass.

Example F. In Vivo Data

Figure 7:
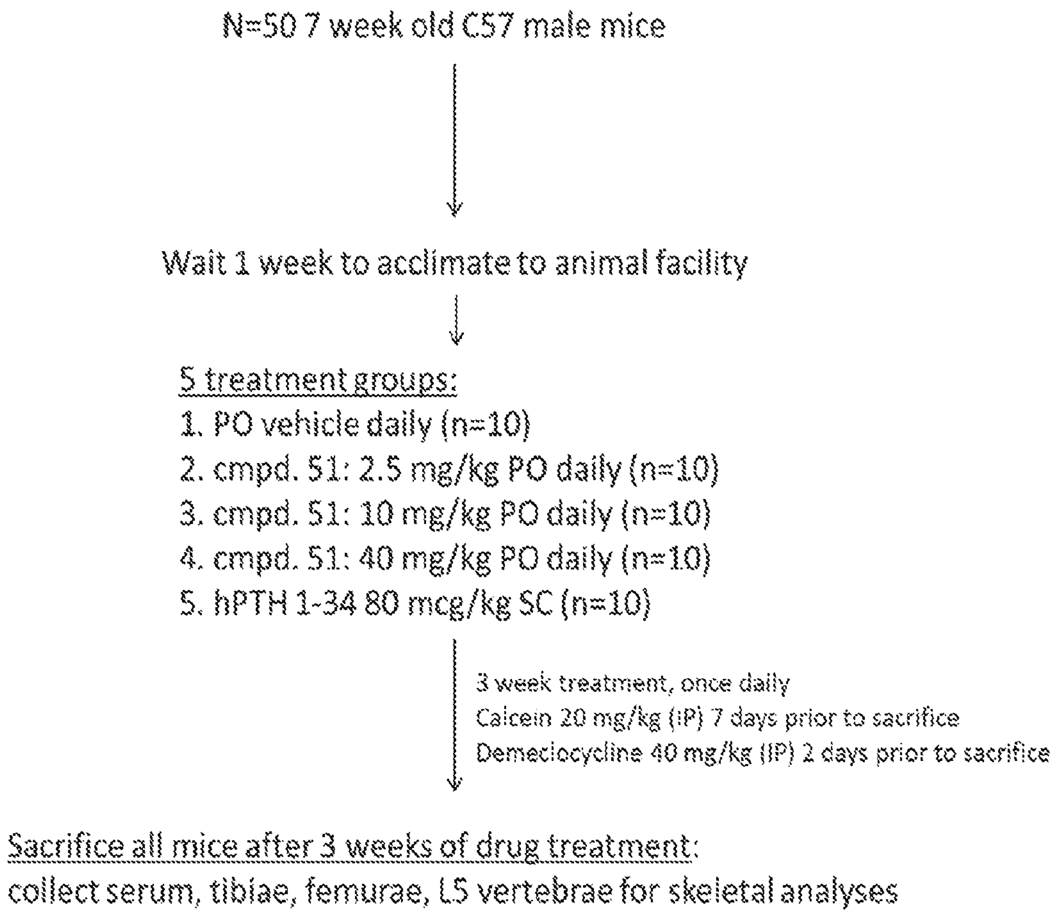
FIG. 7 contains a flow chart showing in vivo study design to test the effects of cmpd. 51 on bone and mineral metabolism endpoints. For oral gavage, cmpd. 51 was dissolved in vehicle solution of 15% hydroxy-propyl beta-cyclodextrin in sterile water.
Figure 8A:
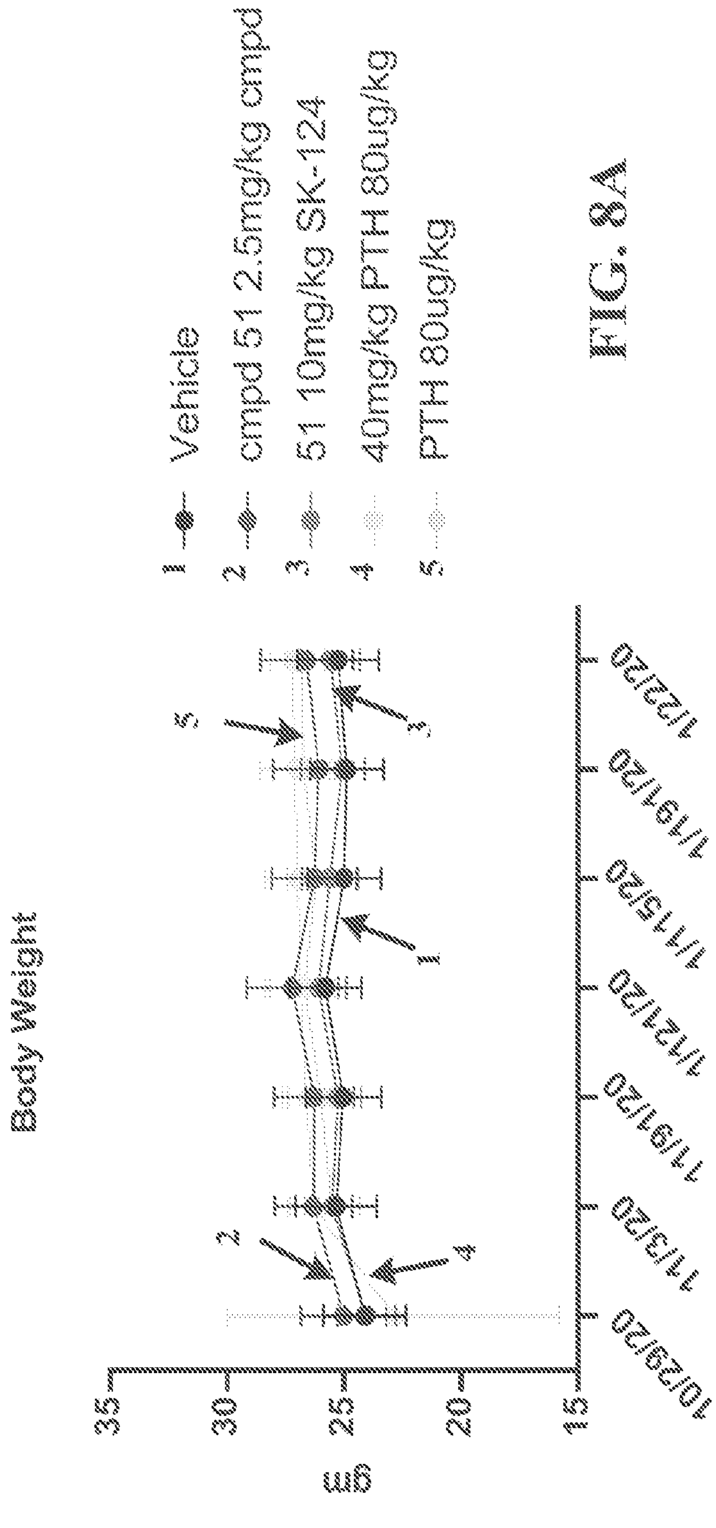
FIG. 8A shows results of the following experiment: mice in the indicated treatment groups were weighed twice per week. No differences in body weight were noted between the different treatment groups.
Figure 8B:
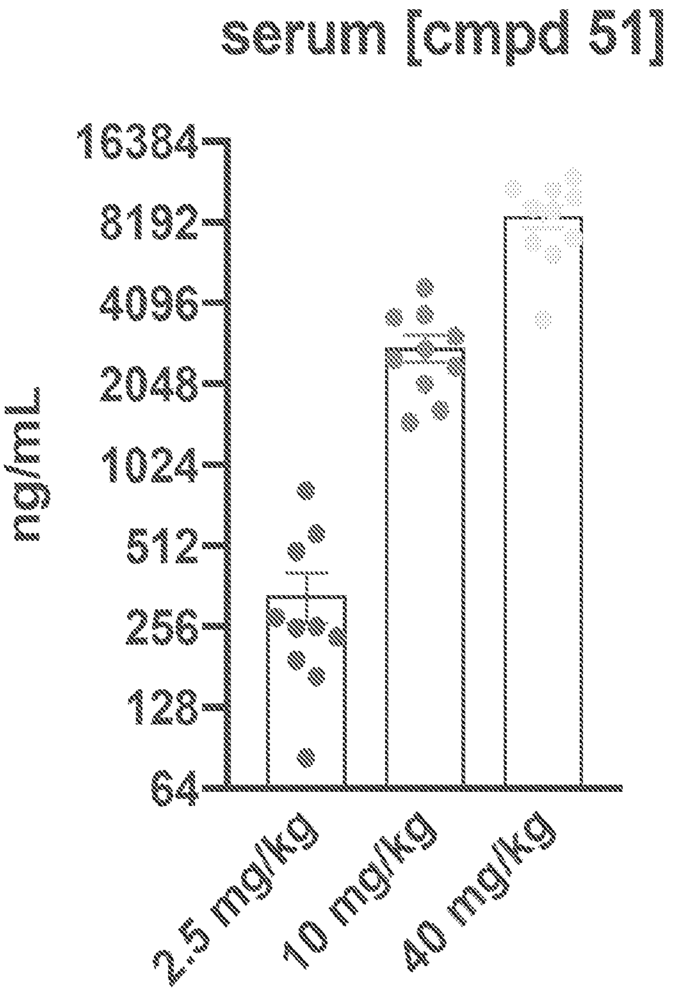
FIG. 8B shows results of the following experiment: serum was collected 2 hours after oral gavage on study day 13 and cmpd. 51 levels were measured by mass spectrometry. Dose-dependent increases in cmpd. 51 levels were observed in the 3 treatment groups.
Figure 9A:
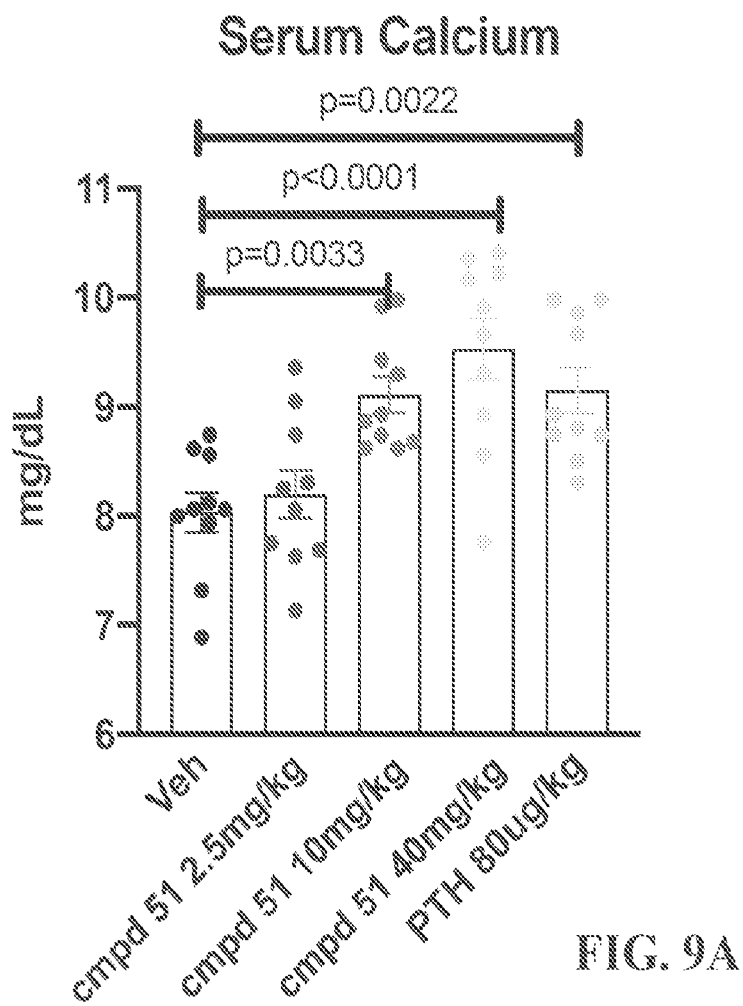
FIG. 9A shows results of the following experiment: serum was collected after 21 days of treatment with cmpd. 51 (2 hours after the final dose) and the indicated parameter was analyzed. Cmpd. 51 treatment increased serum calcium. and 1,25-vitamin D while suppressing PTH levels. SK-124 treatment does not affect serum phosphorus or BUN levels.
Figure 9B:
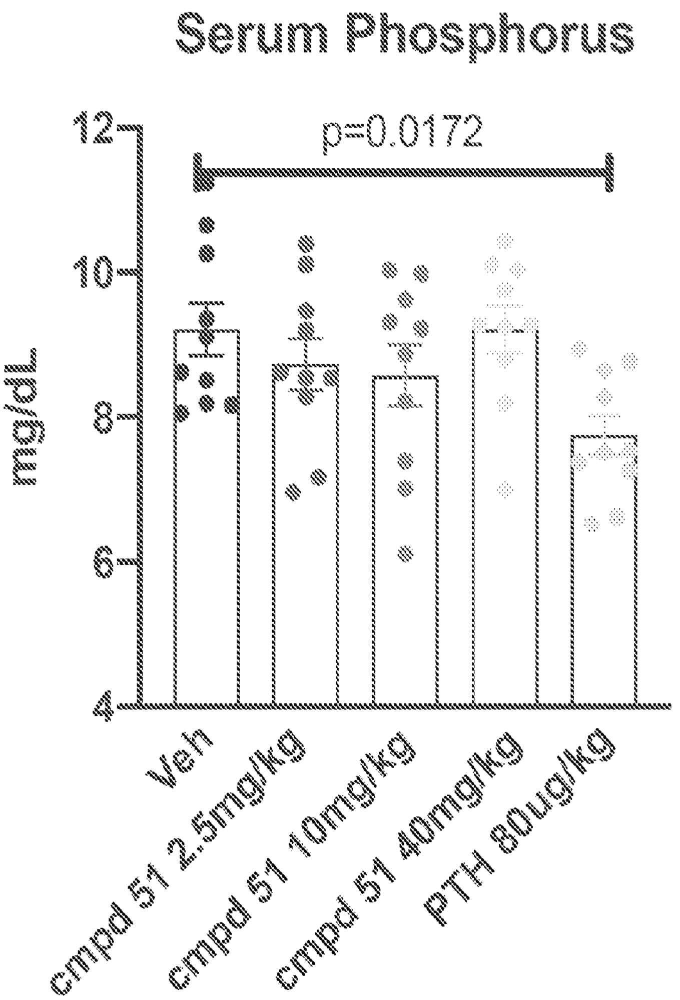
FIG. 9B shows results of the following experiment: serum was collected after 21 days of treatment with cmpd. 51 (2 hours after the final dose) and the indicated parameter was analyzed. Cmpd. 51 treatment did not affect serum phosphorus levels.
Figure 9C:
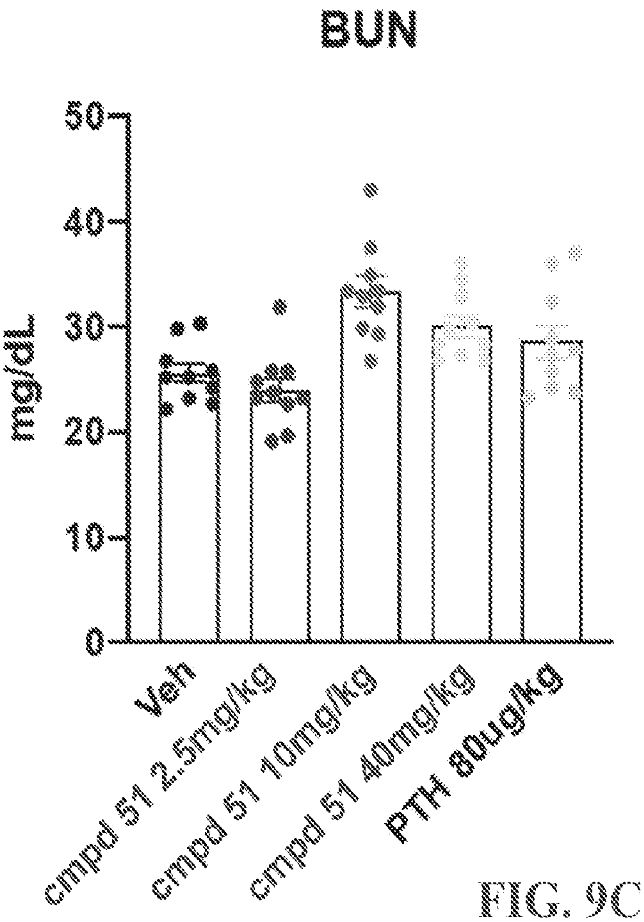
FIG. 9C shows results of the following experiment: serum was collected after 21 days of treatment with cmpd. 51 (2 hours after the final dose) and the indicated parameter was analyzed. Cmpd. 51 treatment did not affect serum BUN levels.
Figure 9D:
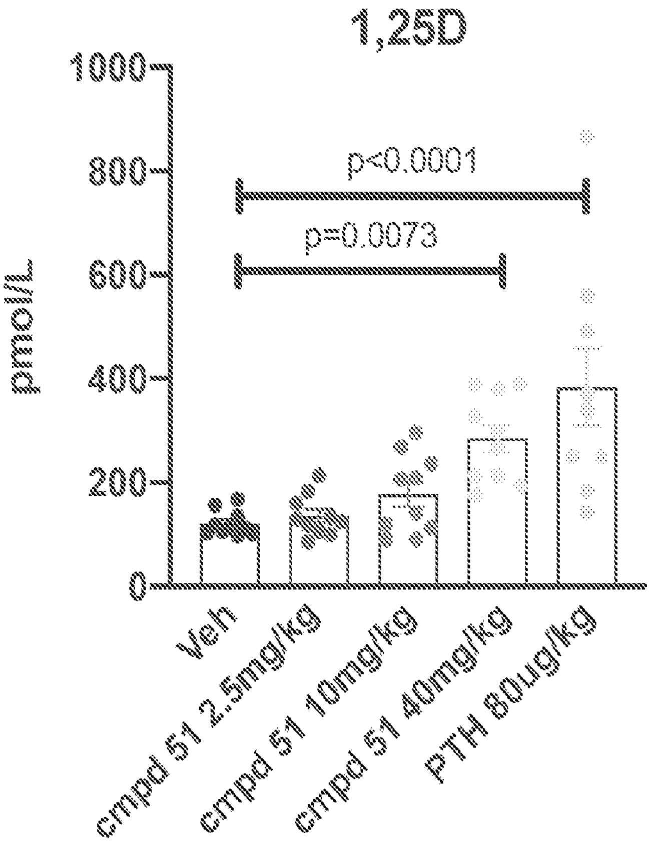
FIG. 9D shows results of the following experiment: serum was collected after 21 days of treatment with cmpd. 51 (2 hours after the final dose) and the indicated parameter was analyzed. Cmpd. 51 treatment increased serum 1,25-vitamin D.
Figure 9E:
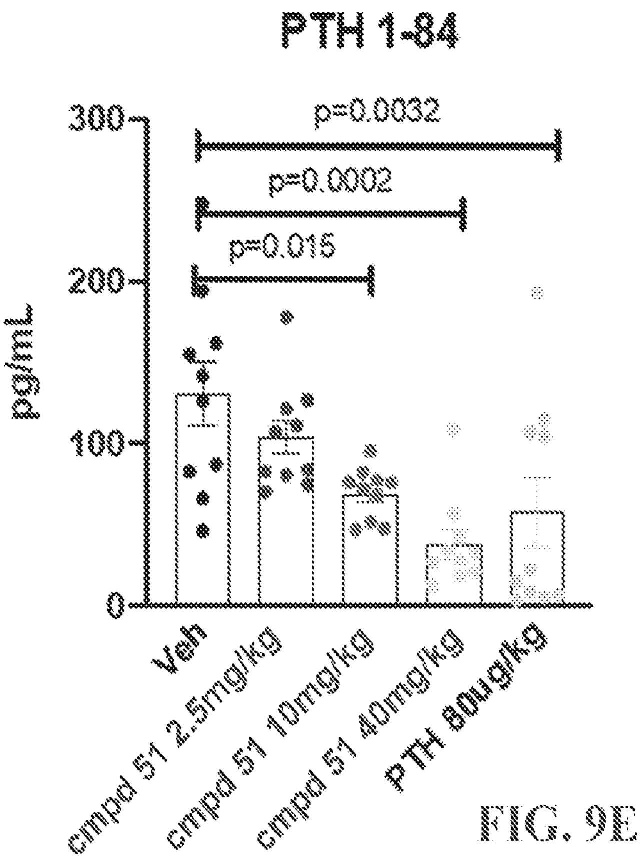
FIG. 9E shows results of the following experiment: serum was collected after 21 days of treatment with cmpd. 51 (2 hours after the final dose) and the indicated parameter was analyzed. Cmpd. 51 treatment suppressed PTH levels.

Based on the initial mouse pharmacokinetic study, there is excellent oral availability after a single cmpd. 51 dose of 10 mg/kg with a maximum serum concentration of 11 μM. Here (as shown in FIG. 7), eugonadal 8 week old male mice (n=10/group) were treated for 3 weeks with three different doses of SK-124 by once daily (7 days per week) oral gavage. In addition, one group of mice with oral vehicle solution (negative control) and another group of mice were treated with once daily subcutaneous hPTH(1-34) (80 μg/kg) injections (positive control). As shown in FIG. 8A, mice tolerated cmpd. 51 treatment well without obvious health concerns or weight loss. Serum was collected 2 hours after oral gavage on treatment day 13 to measure cmpd. 51 drug levels (FIG. 8B). Serum cmpd. 51 was detectable in all treatment groups, and cmpd. 51 serum levels increased in a dose-dependent manner in the 3 treatment groups.

Figure 10A:
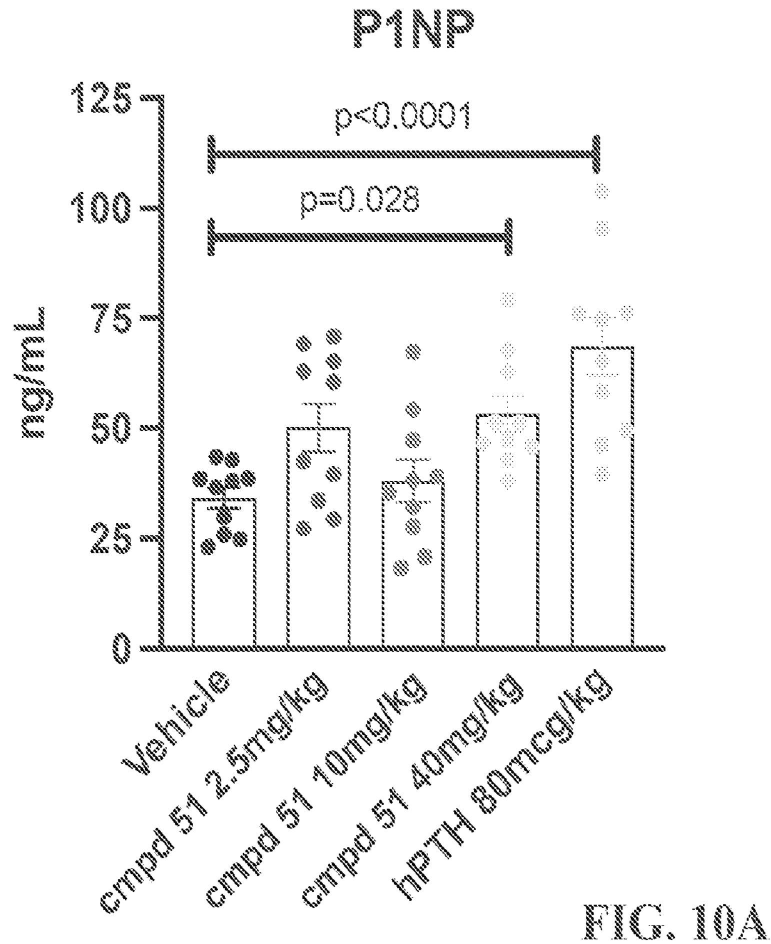
FIG. 10A shows results of the following experiment: P1NP (bone formation marker) was measured in serum collected as in FIGS. 9A-9E. Cmpd. 51 treatment showed PTH-like effects by increasing this marker of bone remodeling in the 40 mg/kg treatment group.
Figure 10B:
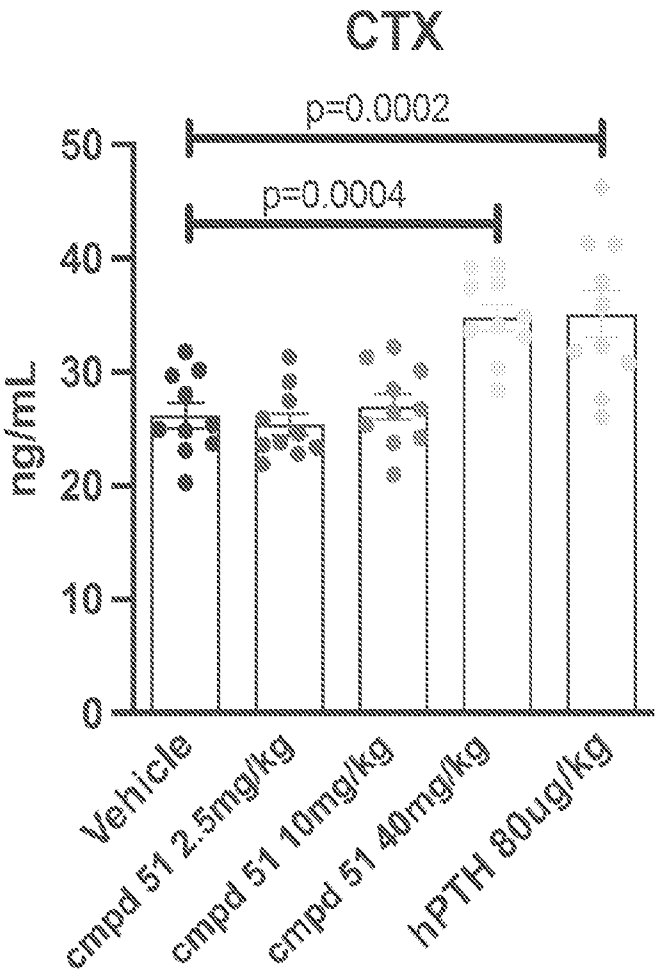
FIG. 10B shows results of the following experiment: CTX (bone resorption marker) was measured in serum collected as in FIGS. 9A-9E. Cmpd. 51 treatment showed PTH-like effects by increasing this marker of bone remodeling in the 40 mg/kg treatment group.

Serum mineral metabolism parameters were measured in mice in all 5 treatment groups after 21 days of treatment (serum was collected 2 hours after the final treatment dose). As shown in FIG. 9, cmpd. 51 treatment in vivo led to parathyroid hormone (PTH)-like effects including increased calcium, increased 1,25-vitamin D levels, and reduced serum PTH levels. In contrast, cmpd. 51 treatment did not alter serum levels of phosphorus or BUN. Taken together, these mineral metabolism changes demonstrate a PTH-like effect of cmpd. 51 treatment and support further investigation into the skeletal effects of this compound. Serum bone turnover markers (P1NP, a marker of bone formation; CTX, a marker of bone resorption) were next measured on samples collected after 21 days of treatment. As shown in FIG. 10, oral cmpd. 51 (40 mg/kg) treatment increased P1NP and CTX compared to vehicle in a manner similar to that of once daily subcutaneous PTH treatment.

Figure 11A:
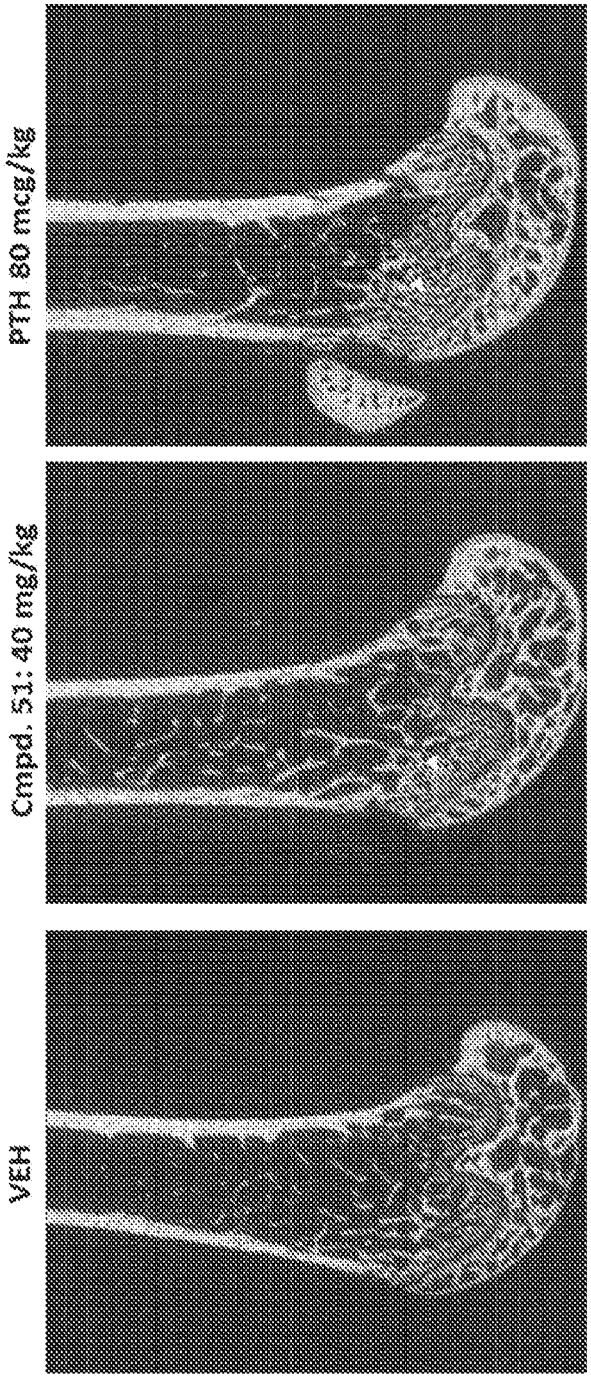
FIG. 11A shows data of the femurs of mice treated for 3 weeks as indicated (VEH, cmpd. 51 at 40 mg/kg, and PTH 80 mcg/kg). Representative images from microCT scans are shown, arrowheads demonstrate increased trabecular bone in the primary spongiosa region of the distal femur.
Figure 11B:
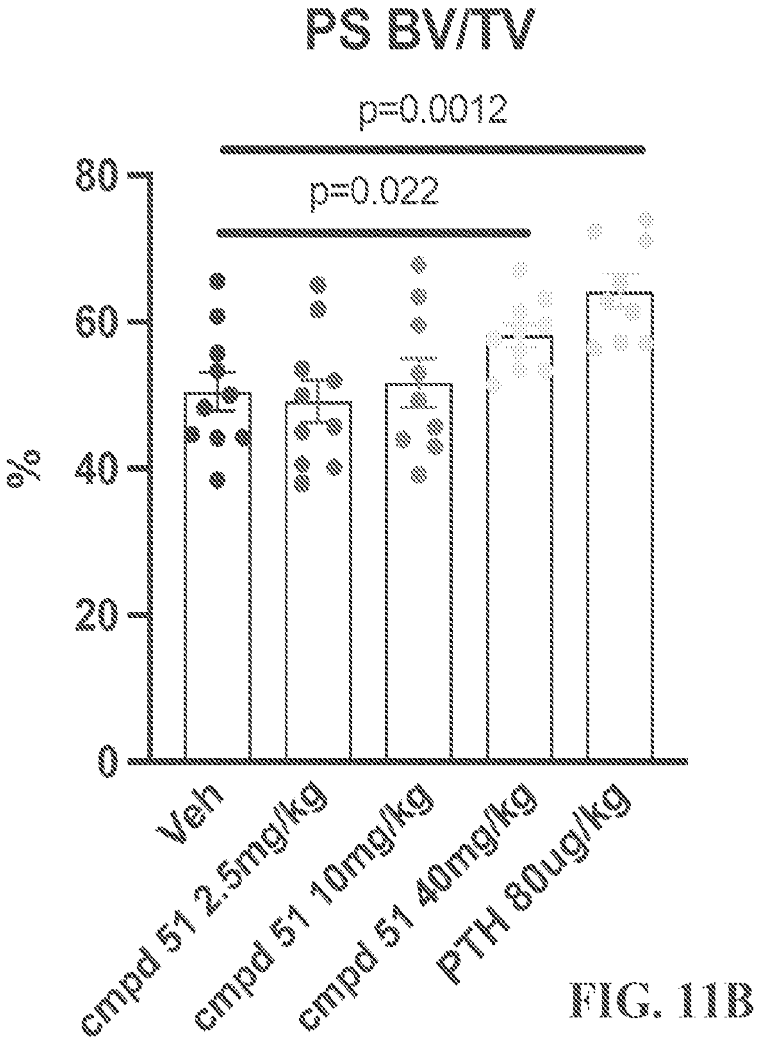
FIG. 11B shows analysis of trabecular bone in the primary spongiosa (PS) of the distal femur. The analysis demonstrates that cmpd. 51 treatment increased bone volume fraction (BV/TV) at this skeletal site.
Figure 11C:
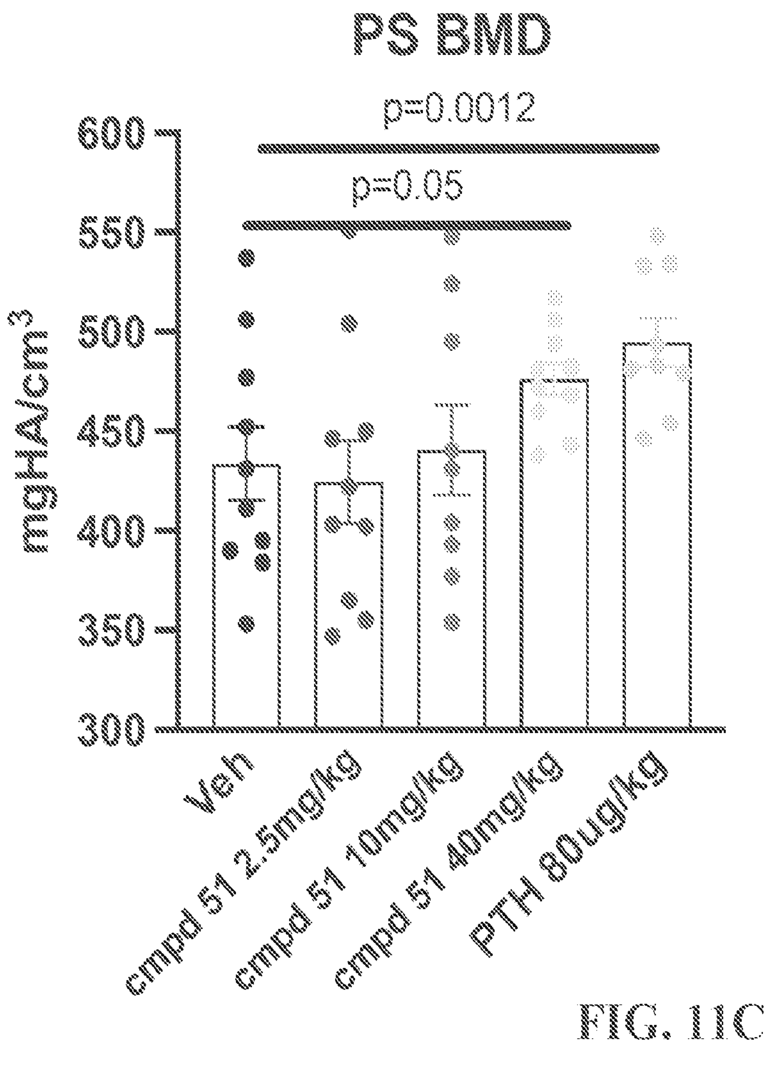
FIG. 11C shows analysis of trabecular bone in the primary spongiosa (PS) of the distal femur. The analysis demonstrates that cmpd. 51 treatment increased bone mineral density (BMD) at this skeletal site.
Figure 11D:
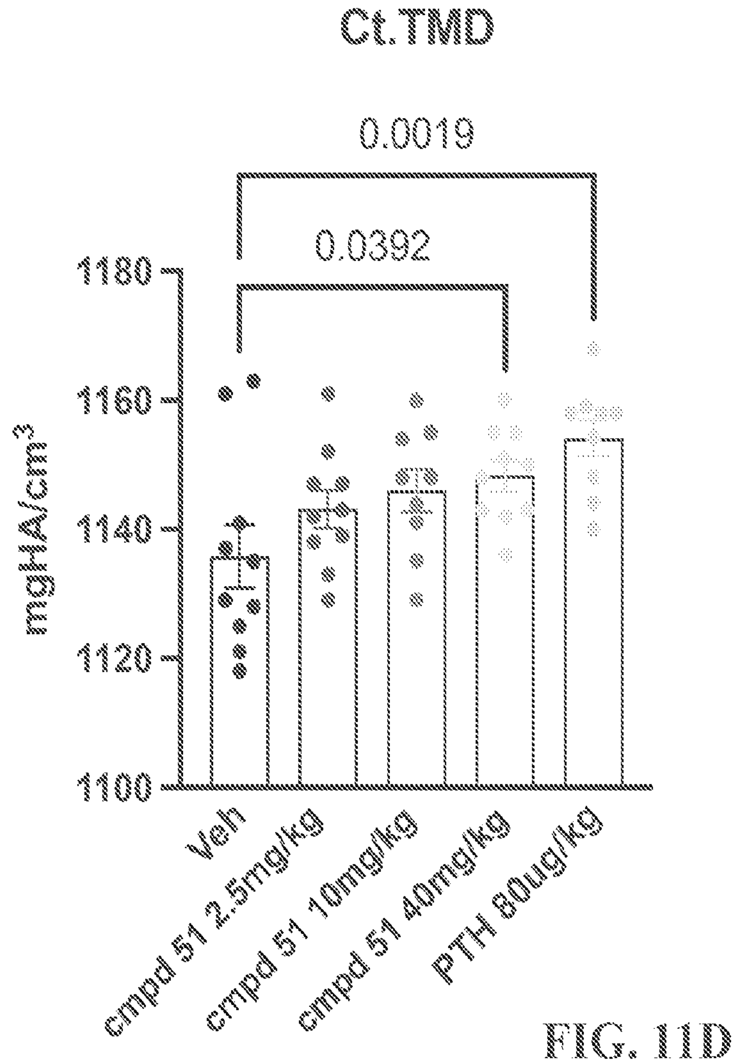
FIG. 11D shows analysis of midshaft cortical bone tissue mineral density (TMD). The analysis revealed gains in bone mass in response to cmpd. 51 at this skeletal site.
Figure 12:
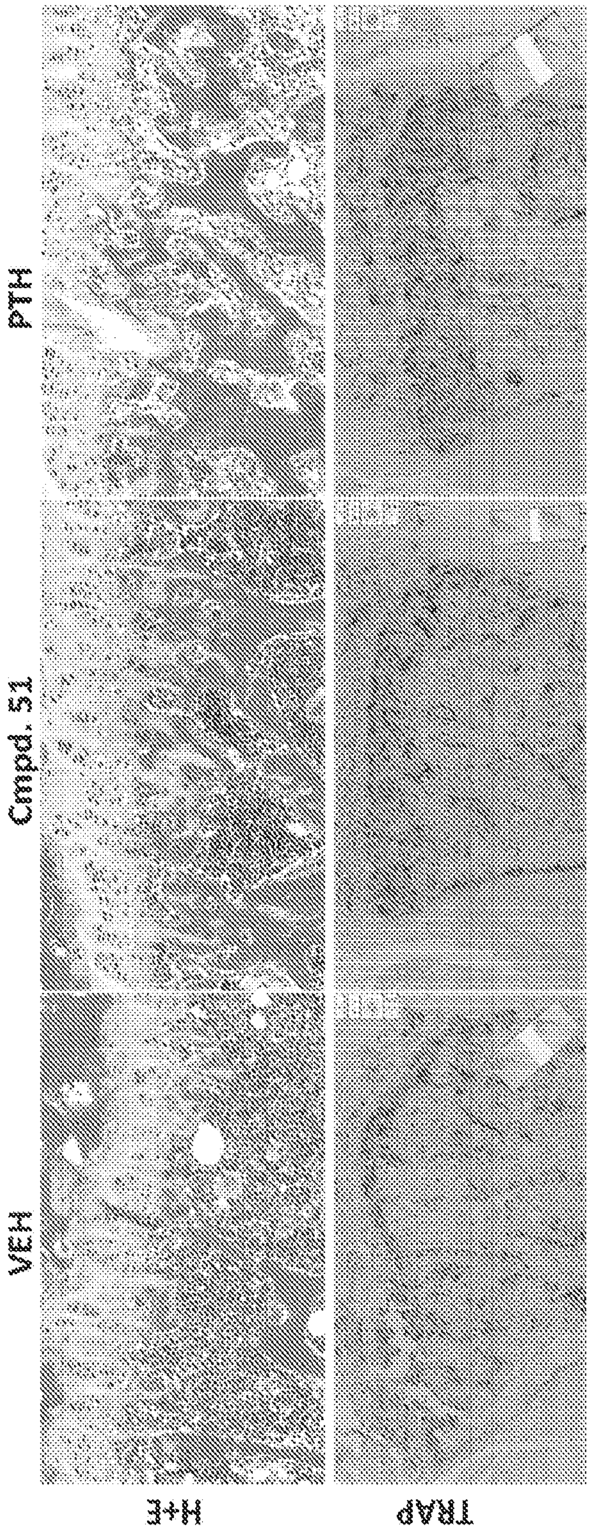
FIG. 12 contains images showing results of the following experiment: tibiae from experimental mice were decalcified for paraffin-embedded sections. The top row shows hematoxylin and eosin stains which demonstrate increased trabecular bone and increased osteoblasts in cmpd. 51 (40 mg/kg) and PTH-treated mice. The bottom row shows TRAP stained images which demonstrate increased osteoclasts (dark) on trabecular surfaces in response to cmpd. 51 and PTH treatments.
Figure 13A:
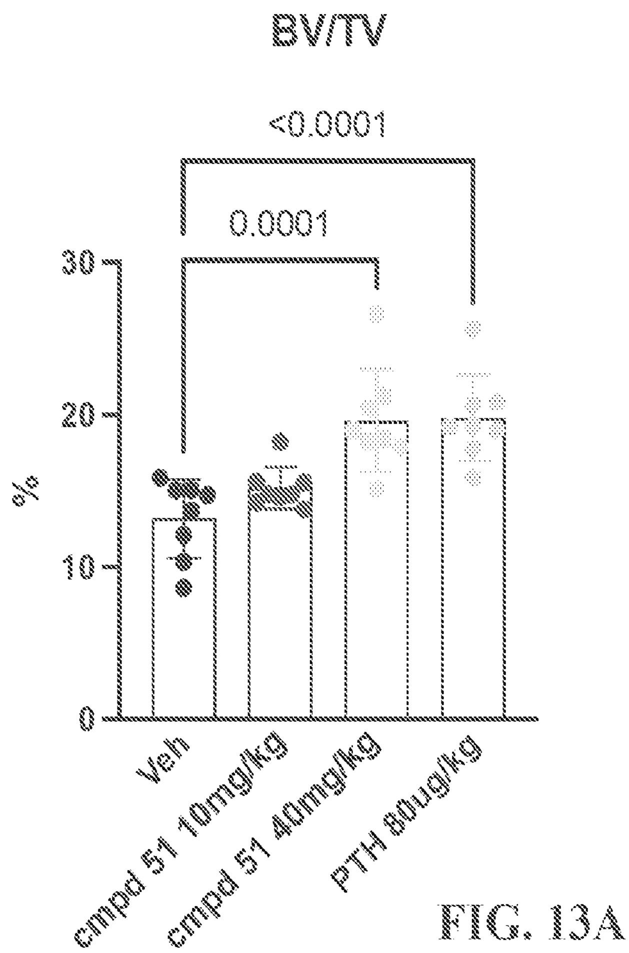
FIG. 13A shows histomorphometry results of the distal femur metaphysis. cmpd. 51 and PTH treatment increased bone volume fraction (BV/TV).
Figure 13B:
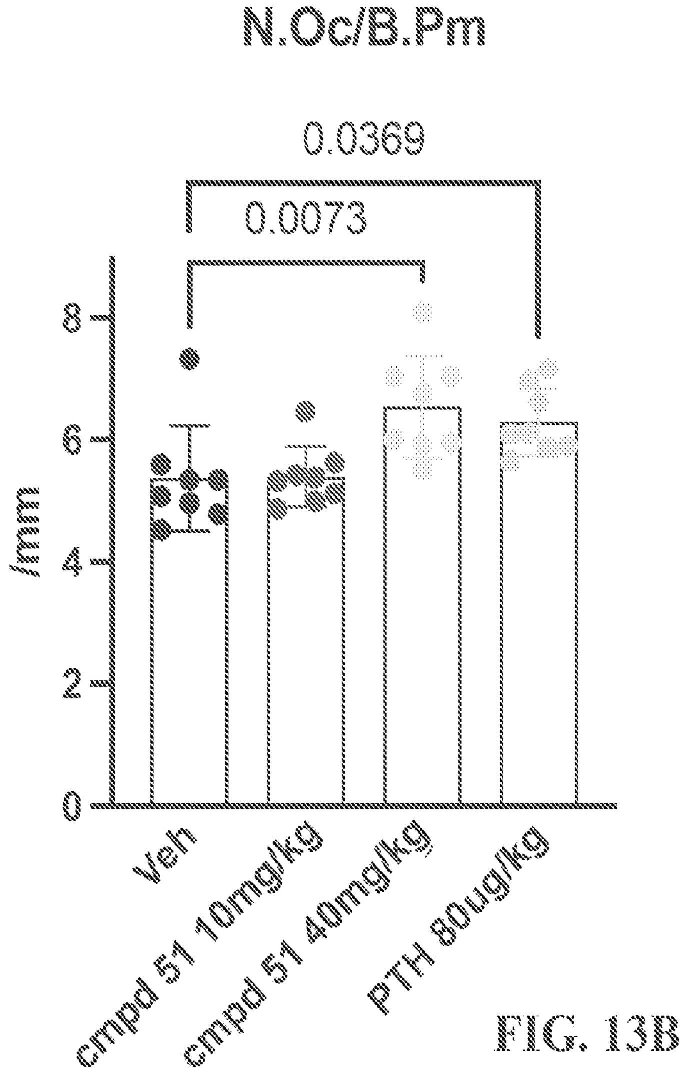
FIG. 13B shows histomorphometry results of the distal femur metaphysis. cmpd. 51 and PTH treatment increased osteoclast numbers in the primary spongiosa (N.Oc/B.Pm).
Figure 13C:
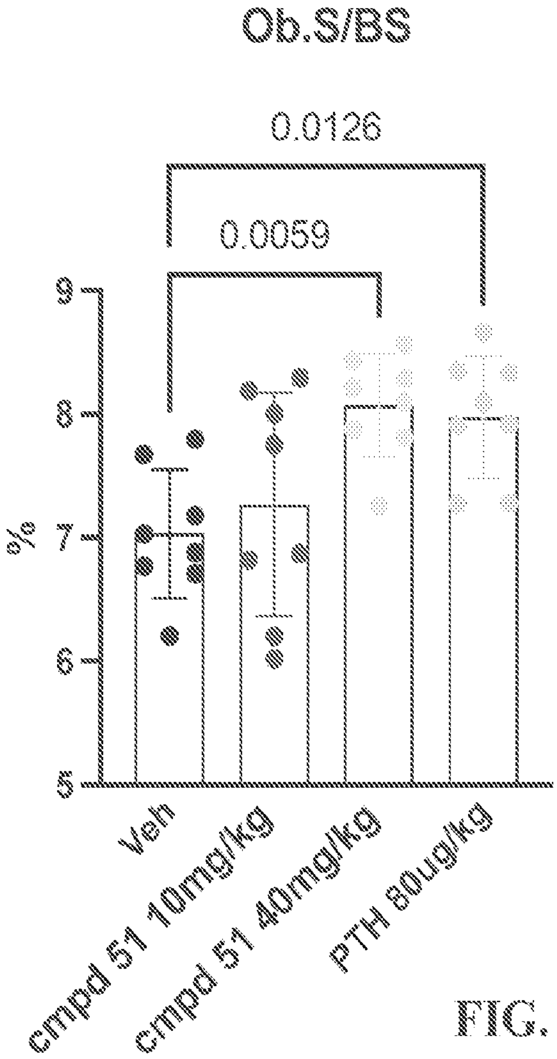
FIG. 13C shows histomorphometry results of the distal femur metaphysis. cmpd. 51 and PTH treatment increased osteoblast surfaces (Ob.S.BS).
Figure 13D:
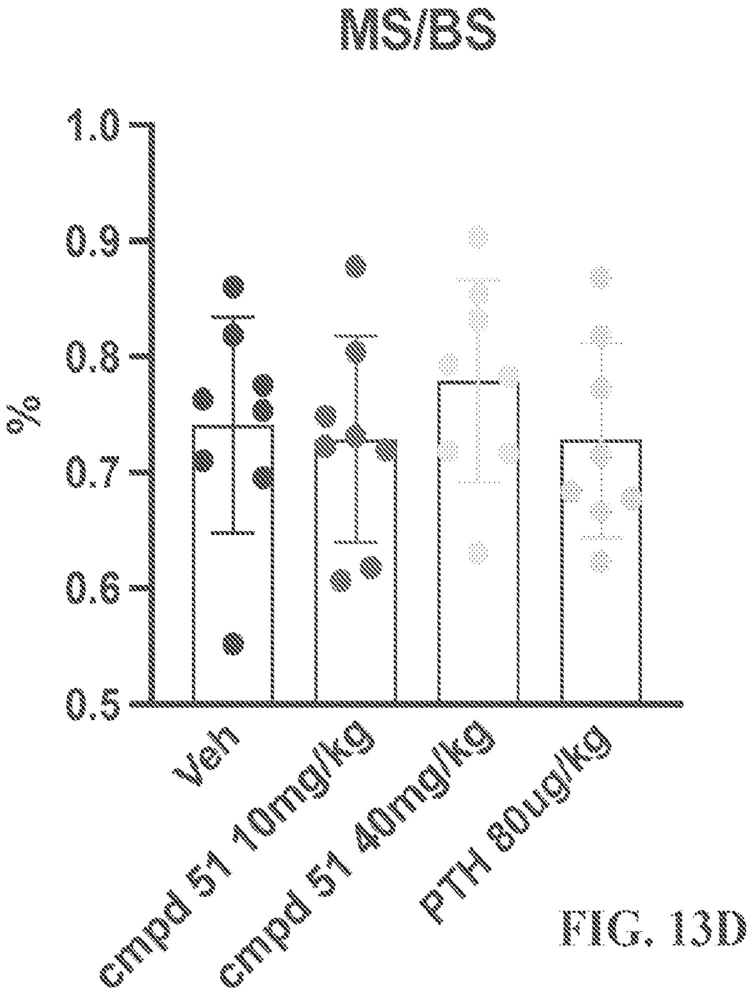
FIG. 13D shows histomorphometry results of the distal femur metaphysis. Neither cmpd. 51 nor PTH treatment increased the mineralizing surface (MS/BS) at this skeletal site.
Figure 13E:
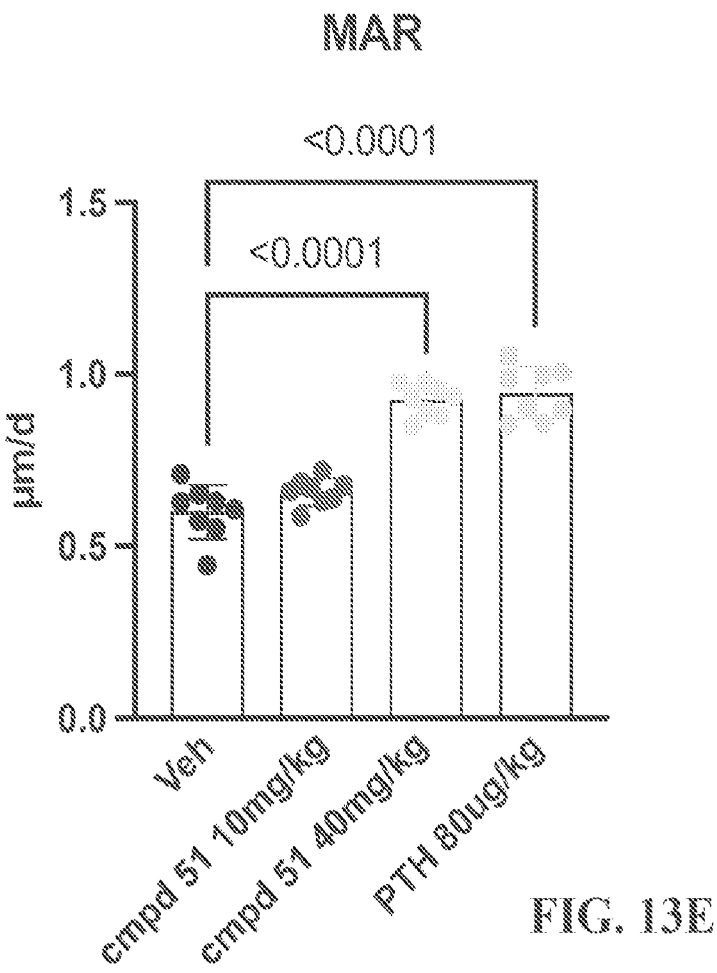
FIG. 13E shows histomorphometry results of the distal femur metaphysis. cmpd. 51 and PTH treatment increased matrix apposition rate (MAR).
Figure 13F:
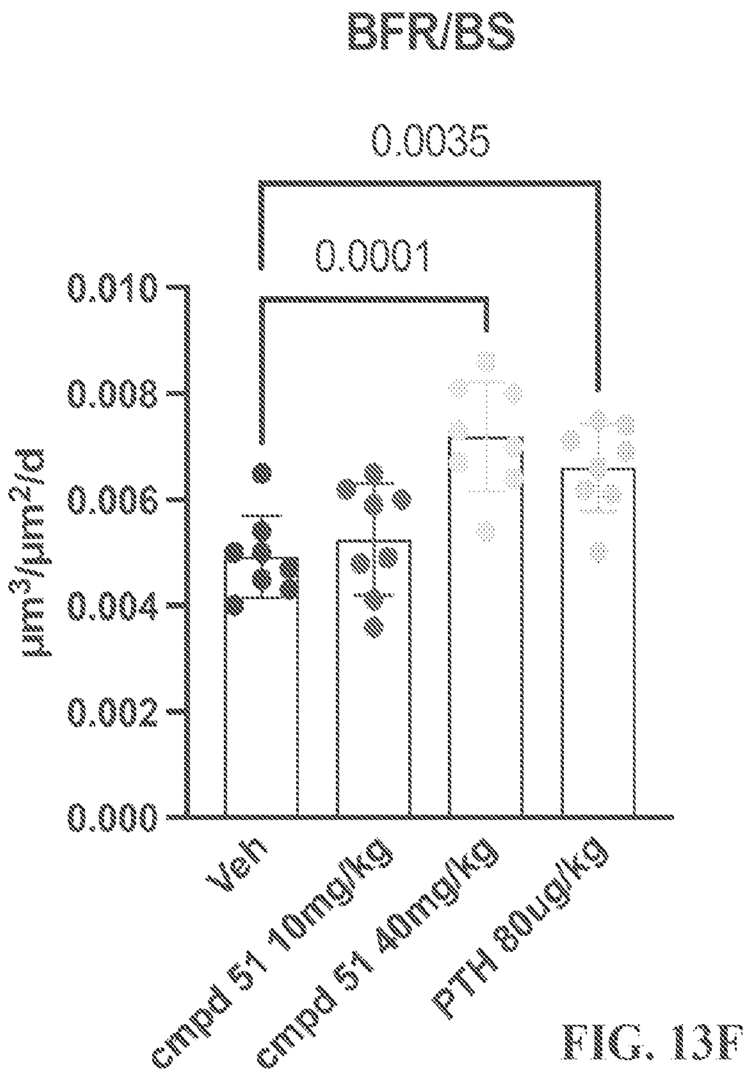
FIG. 13F shows histomorphometry results of the distal femur metaphysis. cmpd. 51 and PTH treatment increased the bone formation rate (BFR/BS).
Figure 14:
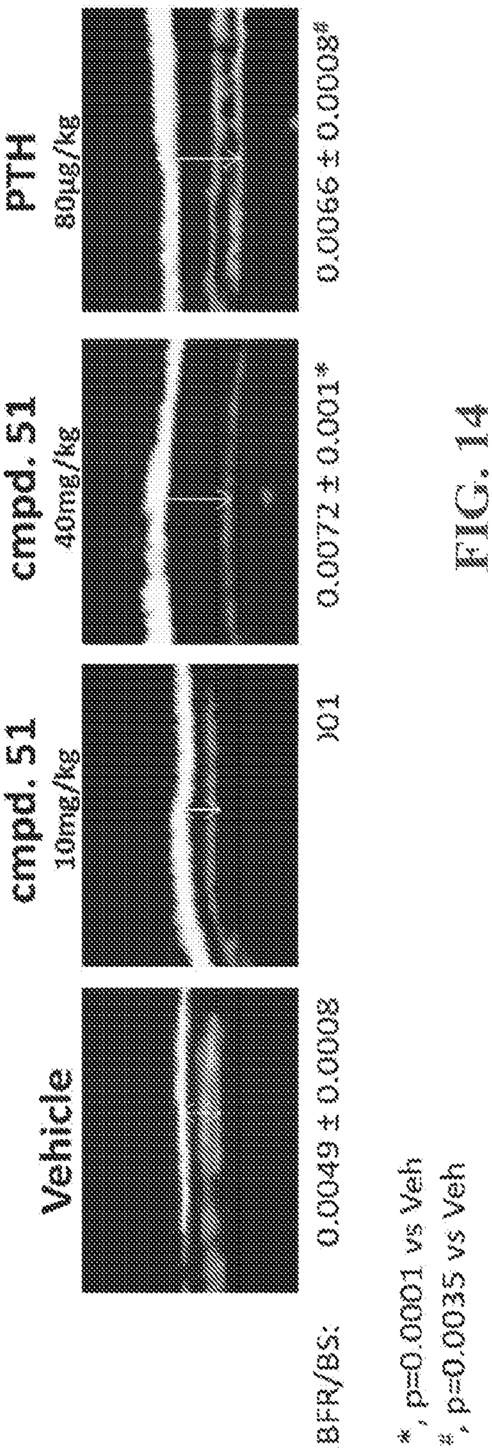
FIG. 14 contains representative images demonstrating increased distance between calcein/demeclocycline dye fronts in mice treated with cmpd. 51 (40 mg/kg) and PTH.

Next, the effects of three weeks of cmpd. 51 treatment on bone mass in the femur were assessed using microCT. As shown in FIGS. 11A and 111B, cmpd. 51 (40 mg/kg) treatment increased primary spongiosa bone volume fraction (BV/TV) and bone mineral density (BMD) in a manner similar to that of subcutaneous PTH injections. Cmpd. 51 treatment also increased cortical bone tissue mineral density (TIMD) as seen in FIG. 7C. Positive effects of cmpd. 51 treatment on bone mass prompted additional exploration of the responsible underlying cellular and molecular mechanisms. As shown in FIG. 12, decalcified paraffin-embedded sections from the tibia demonstrate increased trabecular bone mass, increased osteoblasts, and increased TRAP-positive osteoclasts in mice treated with cmpd. 51 (40 mg/kg). Non-decalcified plastic embedded sections of the femur were obtained and trabecular bone in the distal metaphysis was analyzed by static and dynamic histomorphometry to quantify effects of cmpd. 51 at the level of bone cell composition and activity. cmpd. 51 treatment increased trabecular bone mass, osteoclast numbers, osteoblast numbers, and bone formation rate (FIGS. 13 and 14).

Figure 15A:
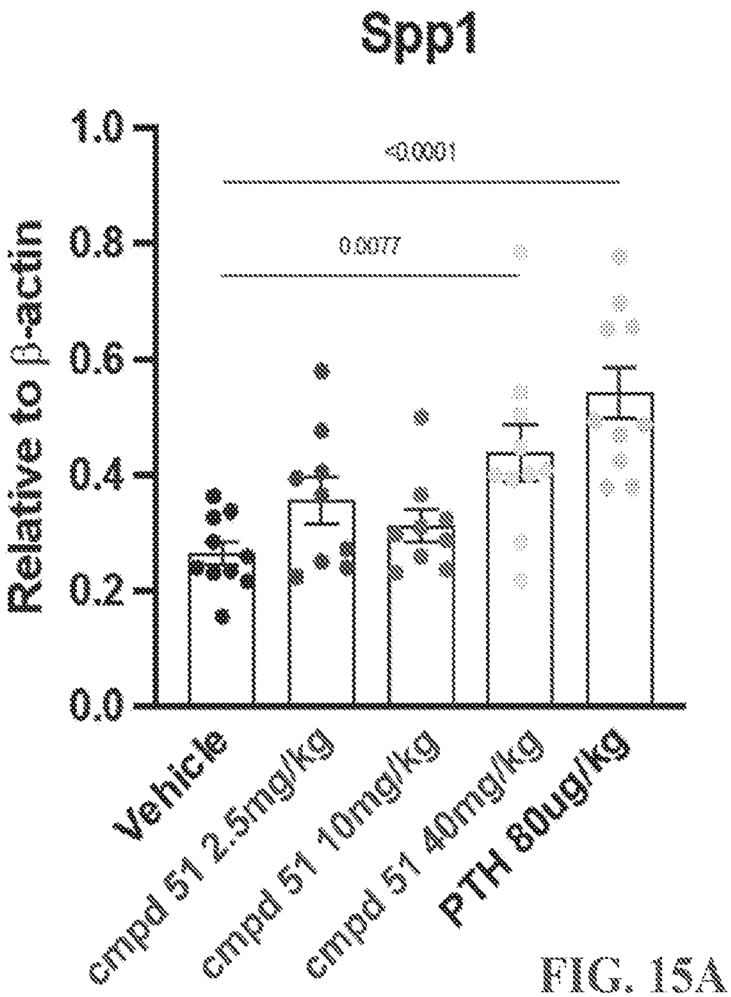
FIG. 15A shows results of the following experiment: cortical bone RNA was isolated from mice after 3 weeks of compound treatment followed by RT-qPCR. Spp1 (osteopontin) is a well-established osteoblast marker gene whose expression was increased by cmpd. 51 and PTH treatment.
Figure 15B:
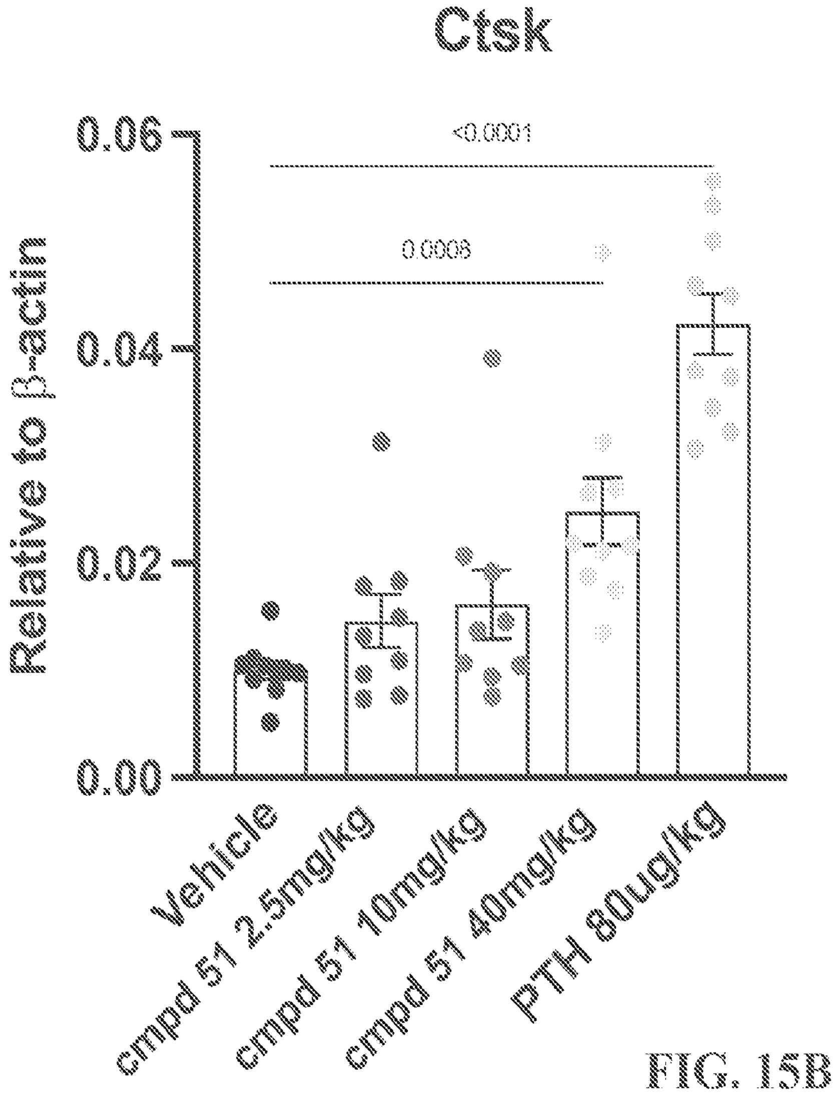
FIG. 15B shows results of the following experiment: cortical bone RNA was isolated from mice after 3 weeks of compound treatment followed by RT-qPCR. Ctsk (cathepsin K) is a well-established osteoclast marker gene whose expression was increased by cmpd. 51 and PTH treatment.
Figure 16A:
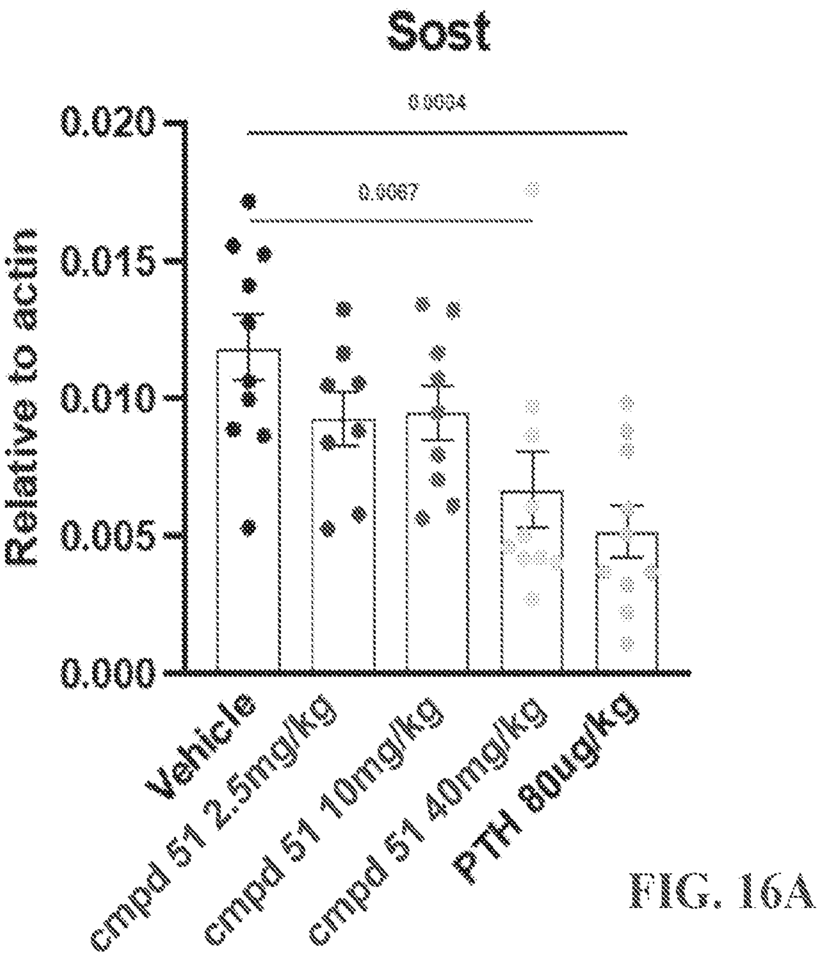
FIG. 16A shows that Sost mRNA was measured in cortical bone by RT-qPCR. Cmpd. 51 and PTH both reduced sclerostin gene expression.
Figure 16B:
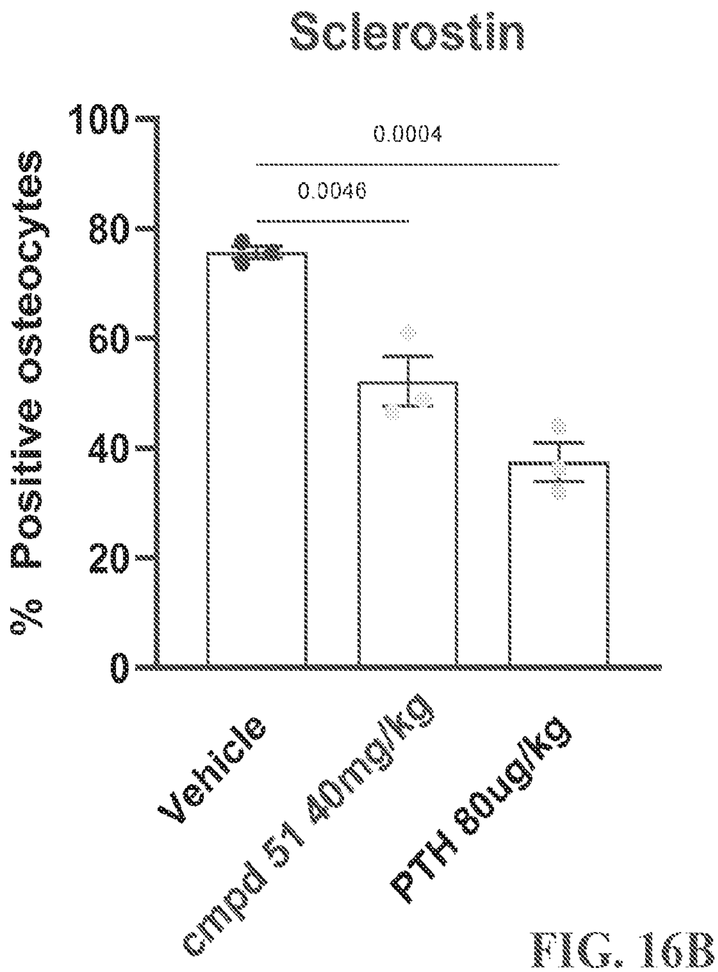
FIG. 16B shows that sclerostin protein was assessed in bone sections by immunohistochemistry. The bar graph shows quantification of sclerostin positive osteocytes in the indicated treatment groups.
Figure 16C:
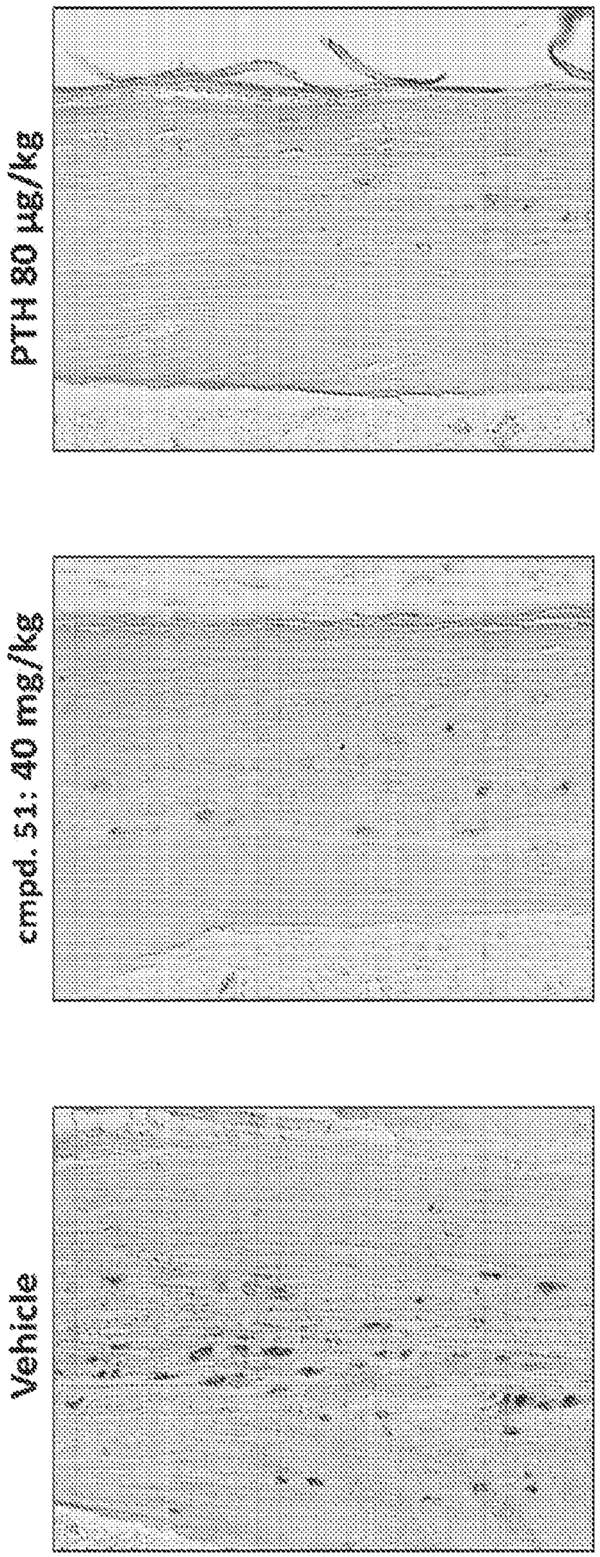
FIG. 16C shows that sclerostin protein was assessed in bone sections by immunohistochemistry. The images show sclerostin-positive (dark) osteocytes.

Having established that oral cmpd. 51 treatment increases bone mass and bone formation, molecular correlates to these cellular changes were assessed. For this, cortical bone RNA isolated from mice following three weeks of cmpd. 51 treatment were analyzed and subjected to RT-qPCR for well-established bone cell marker genes. Consistent with the histology and histomorphometry results, cmpd. 51 treatment increases the expression of Spp1 and Ctsk (FIG. 15). Previous studies demonstrated that SIK2 and SIK3 play a key role in regulating expression of sclerostin, an osteocyte-derived inhibitor of bone formation. Therefore, sclerostin (encoded by the Sost gene) expression in bone in response to cmpd. 51 treatment was also assessed by RT-qPCR and immunohistochemistry. Consistent with the previous studies with non-specific pan-SIK inhibitors and with SIK2/SIK3 gene deletion, cmpd. 51 treatment reduced sclerostin gene expression (FIG. 16A) and protein levels (FIG. 16B, C) in vivo. Cmpd. 55A (FIG. 17) was also identified. Initial in vitro testing of this compound showed remarkably potent SIK2 inhibition ($IC_{50}$<100 pM).

In summary, oral administration of the potent/selective SIK2/3 inhibitor cmpd. 51 increases bone formation and bone mass without obvious toxicities. These in vivo efficacy data support the use of the compounds within the present claims, e.g., for treatment of osteoporosis and related musculoskeletal indications.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure

What is claimed is:

1. A compound of Formula I:

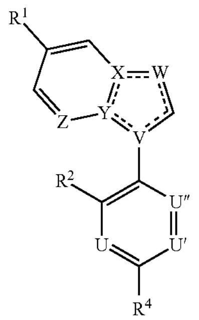

I or a pharmaceutically acceptable salt thereof, wherein:

V, X, and Z are each C, and W and Y are each N; or

V, Y, and Z are each C, and W and X are each N; or

V and Y are each C, and W, X, and Z are each N;

U is $CR^3$ or N;

U' is $CR^5$ or N;

U" is $CR^6$ or N;

$R^1$ is selected from 5 membered heteroaryl, $OR^{a1}$, $C(O)NR^{c1}R^{d1}$, and $NR^{c1}C(O)R^{b1}$, wherein the 5 membered heteroaryl is optionally substituted with 1 or 2 independently selected $R^{1A}$ substituents;

$R^{a1}$, $R^{b1}$, $R^{c1}$, and $R^{d1}$ are each independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 4-10 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, and (5-10 membered heteroaryl)-$C_{1-6}$ alkyl, wherein the $C_{1-6}$ alkyl, $C_{2-6}$ alkenyl, $C_{2-6}$ alkynyl, $C_{6-10}$ aryl, $C_{3-10}$ cycloalkyl, 4-10 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, and (5-10 membered heteroaryl)-$C_{1-6}$ alkyl are each optionally substituted with 1, 2, 3, or 4 independently selected $R^{1A}$ substituents;

or $R^{c1}$ and $R^{d1}$, together with the nitrogen to which they are attached, come together to form a 10-14 membered heterocycloalkyl or 10-14 membered heteroaryl group, wherein the 10-14 membered heterocycloalkyl and 10-14 membered heteroaryl group are each optionally substituted with 1, 2, 3, or 4 independently selected $R^{1A}$ substituents;

each $R^{1A}$ is independently selected from halo, $C_{1-6}$ alkyl, $C_{2-6}$ alkenyl, $C_{2-6}$ alkynyl, $C_{1-6}$ haloalkyl, $C_{1-6}$ alkoxy, $C_{6-10}$ aryl, $C_{3-10}$ cycloalkyl, 4-10 membered heterocycloalkyl, 5-10 membered heteroaryl, $NO_2$, CN, wherein the $C_{1-6}$ alkyl, $C_{2-6}$ alkenyl, and $C_{2-6}$ alkynyl are each optionally substituted with $C_{1-4}$ alkoxy;

$R^2$ is selected from H, halo, $C_{1-6}$ alkyl, $C_{2-6}$ alkenyl, $C_{2-6}$ alkynyl, $C_{1-6}$ haloalkyl, and $C_{1-6}$ alkoxy;

$R^3$ is selected from H, halo, $C_{1-6}$ alkyl, $C_{2-6}$ alkenyl, $C_{2-6}$ alkynyl, $C_{1-6}$ haloalkyl, and $C_{1-6}$ alkoxy;

$R^4$ is selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 4-10 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, (5-10 membered heteroaryl)-$C_{1-6}$ alkyl, $NO_2$, CN, $OR^{a4}$, $C(O)R^{b4}$, $C(O)NR^{c4}R^{d4}$, $C(O)N(R^{c4})NR^{c4}R^{d4}$, $NR^{c4}C(O)R^{b4}$, $C(O)OR^{a4}$, $OC(O)R^{b4}$, $OC(O)NR^{c4}R^{d4}$, and $NR^{c4}C(O)OR^{a4}$, wherein the $C_{6-10}$ aryl, $C_{3-10}$ cycloalkyl, 4-10 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, and (5-10 membered heteroaryl)-$C_{1-6}$ alkyl are each optionally substituted with 1, 2, 3, or 4 independently selected $R^{4A}$ substituents;

$R^{a4}$, $R^{b4}$, $R^{c4}$, and $R^{d4}$ are each independently selected from H, $C_{1-6}$ alkyl, $C_{2-6}$ alkenyl, $C_2$-6 alkynyl, $C_{1-6}$ haloalkyl, and $C_{1-6}$ alkoxy;

each $R^{4A}$ is independently selected from $C_{1-6}$ alkyl, $C_{2-6}$ alkenyl, $C_{2-6}$ alkynyl, $C_{1-6}$ haloalkyl, and $C_{1-6}$ alkoxy;

$R^5$ is selected from H, halo, $C_{1-6}$ alkyl, $C_{2-6}$ alkenyl, $C_{2-6}$ alkynyl, $C_{1-6}$ haloalkyl, and $C_{1-6}$ alkoxy;

or $R^4$ and $R^5$, together with the carbon atoms to which they are attached, come together to form a 5-6 membered aryl ring which is optionally substituted with 1, 2, 3, or 4 independently selected $R^7$ substituents;

$R^6$ is selected from H, $C_{1-6}$ alkyl, $C_{2-6}$ alkenyl, $C_{2-6}$ alkynyl, $C_{1-6}$ haloalkyl, and $C_{1-6}$ alkoxy;

each $R^7$ is independently selected from $C_{6-10}$ aryl, $C_{3-10}$ cycloalkyl, 4-14 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, (5-10 membered heteroaryl)-$C_{1-6}$ alkyl, $NO_2$, CN, and $OR^{a7}$, wherein the $C_{6-10}$ aryl, $C_{3-10}$ cycloalkyl, 4-14 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, (5-10 membered heteroaryl)-$C_{1-6}$ alkyl are each optionally substituted with 1, 2, 3, or 4 independently selected $R^{7A}$ substituents;

each $R^{a7}$ is independently selected from $C_{6-10}$ aryl, $C_{3-10}$ cycloalkyl, 4-10 membered heterocycloalkyl, 5-10 membered heteroaryl, $C_{6-10}$ aryl-$C_{1-6}$ alkyl-, $C_{3-10}$ cycloalkyl-$C_{1-6}$ alkyl-, (4-10 membered heterocycloalkyl)-$C_{1-6}$ alkyl, and (5-10 membered heteroaryl)-$C_{1-6}$ alkyl; and each $R^{7A}$ is independently selected from $C_{1-6}$ alkyl, $C_{2-6}$ alkenyl, $C_{2-6}$ alkynyl, $C_{1-6}$ haloalkyl, $C_{1-6}$ alkoxy, amino, $C_{1-6}$ alkylamino, di($C_{1-6}$ alkyl) amino, phenyl, $C_{3-6}$ cycloalkyl, 4-6 membered heterocycloalkyl, 5-6 membered heteroaryl, and wherein the $C_{1-6}$ alkyl, $C_{2-6}$ alkenyl, and $C_{2-6}$ alkynyl are each optionally substituted with amino or $C_{1-4}$ alkoxy.

2. The compound of claim 1, or a pharmaceutically acceptable salt thereof, wherein:

$R^{a1}$, $R^{b1}$, $R^{c1}$, and $R^{d1}$ are each independently selected from H, 4-10 membered heterocycloalkyl, (4-10 membered heterocycloalkyl)-$C_{1-6}$ alkyl, and (5-10 membered heteroaryl)-$C_{1-6}$ alkyl, wherein the 4-10 membered heterocycloalkyl, (4-10 membered heterocycloalkyl)-$C_{1-6}$ alkyl, and (5-10 membered heteroaryl)-$C_{1-6}$ alkyl are each optionally substituted with 1 or 2 independently selected $R^{1A}$ substituents; or $R^{c1}$ and $R^{d1}$, together with the nitrogen to which they are attached, come together to form a 10-14 membered heterocycloalkyl or 10-14 membered heteroaryl group.

3. The compound of claim 1, or a pharmaceutically acceptable salt thereof, wherein:

each $R^{1A}$ is independently selected from $C_{1-6}$ alkyl, $C_{3-10}$ cycloalkyl, 4-10 membered heterocycloalkyl, and CN, wherein each $C_{1-6}$ alkyl is optionally substituted with $C_{1-4}$ alkoxy.

4. The compound of claim 1, or a pharmaceutically acceptable salt thereof, wherein:

$R^2$ is selected from H and $C_{1-6}$ alkoxy;

$R^3$ is selected from H, halo, and $C_{1-6}$ alkoxy;

$R^4$ is selected from H, 5-10 membered heteroaryl, CN, and C(O)NR$^{c4}$R$^{d4}$, wherein the 5-10 membered heteroaryl is optionally substituted with 1, 2, 3, or 4 independently selected $R^{4A}$ substituents;

$R^5$ is selected from H, halo, $C_{1-6}$ alkyl, and $C_{1-6}$ alkoxy; and $R^6$ is selected from H and $C_{1-6}$ alkoxy.

5. The compound of claim 1, or a pharmaceutically acceptable salt thereof, wherein:

$R^4$ and $R^5$ together with the carbon atoms to which they are attached, come together to form a 6-membered aryl ring which is optionally substituted with 1 or 2 independently selected $R^7$ substituents.

6. The compound of claim 1, or a pharmaceutically acceptable salt thereof, wherein:

each $R^7$ is independently selected from $C_{3-10}$ cycloalkyl, 4-14 membered heterocycloalkyl, 5-10 membered heteroaryl, and OR$^{a7}$, wherein the $C_{3-10}$ cycloalkyl, 4-14 membered heterocycloalkyl, and 5-10 membered heteroaryl are each optionally substituted with 1 or 2 independently selected RA substituents.

7. The compound of claim 1, or a pharmaceutically acceptable salt thereof, wherein:

$R^{a1}$, $R^{b1}$, $R^{c1}$, and $R^{d1}$ are each independently selected from H, 4-10 membered heterocycloalkyl, (4-10 membered heterocycloalkyl)-$C_{1-6}$ alkyl, and (5-10 membered heteroaryl)-$C_{1-6}$ alkyl, wherein the 4-10 membered heterocycloalkyl, (4-10 membered heterocycloalkyl)-$C_{1-6}$ alkyl, and (5-10 membered heteroaryl)-$C_{1-6}$ alkyl are each optionally substituted with 1 or 2 independently selected $R^{1A}$ substituents;

or $R^{c1}$ and $R^{d1}$, together with the nitrogen to which they are attached, come together to form a 10-14 membered heterocycloalkyl or 10-14 membered heteroaryl group;

each $R^{1A}$ is independently selected from $C_{1-6}$ alkyl, $C_{3-10}$ cycloalkyl, 4-10 membered heterocycloalkyl, and CN, wherein each $C_{1-6}$ alkyl is optionally substituted with $C_{1-4}$ alkoxy;

$R^2$ is H or $C_{1-6}$ alkoxy;

U is CR$^3$ or N;

U' is CR$^5$ or N;

U" is CR$^6$ or N;

$R^3$ is selected from H, halo, and $C_{1-6}$ alkoxy;

$R^4$ is selected from H, 5-10 membered heteroaryl, CN, and C(O)NR$^{c4}$R$^{d4}$, wherein the 5-10 membered heteroaryl is optionally substituted with 1, 2, 3, or 4 independently selected $R^{4A}$ substituents;

$R^{c4}$ and $R^{d4}$ are each independently selected from H, $C_{1-6}$ alkyl, and $C_{1-6}$ haloalkyl;

each $R^{4A}$ is an independently selected $C_{1-6}$ alkyl group;

$R^5$ is selected from H, halo, $C_{1-6}$ alkyl, and $C_{1-6}$ alkoxy;

or $R^4$ and $R^5$ together with the carbon atoms to which they are attached, come together to form a 5-6 membered aryl ring which is optionally substituted with 1, 2, 3, or 4 independently selected $R^7$ substituents;

$R^6$ is selected from H and $C_{1-6}$ alkoxy;

each $R^7$ is independently selected from $C_{3-10}$ cycloalkyl, 4-14 membered heterocycloalkyl, 5-10 membered heteroaryl, and OR$^{a7}$, wherein the $C_{3-10}$ cycloalkyl, 4-14 membered heterocycloalkyl, and 5-10 membered heteroaryl are each optionally substituted with 1 or 2 independently selected $R^{7A}$ substituents;

each $R^{a7}$ is an independently selected 4-10 membered heterocycloalkyl group; and each $R^{7A}$ is independently selected from $C_{1-6}$ alkyl, amino, $C_{3-6}$ cyclopropyl and 4-6 membered heterocycloalkyl, wherein each $C_{1-6}$ alkyl is optionally substituted with amino or $C_{1-4}$ alkoxy.

8. The compound of claim 1, or a pharmaceutically acceptable salt thereof, wherein:

$R^{a1}$, $R^{b1}$, $R^{c1}$, and $R^{d1}$ are each independently selected from H, 4-10 membered heterocycloalkyl, (4-10 membered heterocycloalkyl)-$C_{1-6}$ alkyl, and (5-10 membered heteroaryl)-$C_{1-6}$ alkyl, wherein the 4-10 membered heterocycloalkyl, (4-10 membered heterocycloalkyl)-$C_{1-6}$ alkyl, and (5-10 membered heteroaryl)-$C_{1-6}$ alkyl are each optionally substituted with 1 or 2 independently selected $R^{1A}$ substituents;

or $R^{c1}$ and $R^{d1}$, together with the nitrogen to which they are attached, come together to form a 10-14 membered heterocycloalkyl or 10-14 membered heteroaryl group;

each $R^{1A}$ is independently selected from $C_{1-6}$ alkyl, $C_{3-6}$ cycloalkyl, 4-6 membered heterocycloalkyl, and CN, wherein each $C_{1-6}$ alkyl is optionally substituted with $C_{1-4}$ alkoxy;

$R^2$ is H or $C_{1-6}$ alkoxy;

U is CR$^3$ or N;

U' is CR$^5$ or N;

U" is CR$^6$ or N;

$R^3$ is selected from H, halo, and $C_{1-6}$ alkoxy;

$R^4$ is selected from H, 5-6 membered heteroaryl, CN, and C(O)NR$^{c4}$R$^{d4}$, wherein the 5-6 membered heteroaryl is optionally substituted with 1 or 2 independently selected $R^{4A}$ substituents;

$R^{c4}$ and $R^{d4}$ are each independently selected from H, $C_{1-6}$ alkyl, and $C_{1-6}$ haloalkyl;

each $R^{4A}$ is an independently selected $C_{1-6}$ alkyl group;

$R^5$ is selected from H, halo, $C_{1-6}$ alkyl, and $C_{1-6}$ alkoxy;

or $R^4$ and $R^5$ together with the carbon atoms to which they are attached, come together to form a 6-membered aryl ring which is optionally substituted with 1 or 2 independently selected $R^7$ substituents;

each $R^7$ is independently selected from $C_{3-10}$ cycloalkyl, 4-14 membered heterocycloalkyl, 5-10 membered heteroaryl, and OR$^{a7}$, wherein the $C_{3-10}$ cycloalkyl, 4-14 membered heterocycloalkyl, and 5-10 membered heteroaryl are each optionally substituted with 1 or 2 independently selected $R^{7A}$ substituents;

each $R^{a7}$ is an independently selected 4-10 membered heterocycloalkyl group; and each $R^{7A}$ is independently selected from $C_{1-6}$ alkyl, amino, $C_{3-6}$ cyclopropyl and 4-6 membered heterocycloalkyl, wherein each $C_{1-6}$ alkyl is optionally substituted with amino or $C_{1-4}$ alkoxy.

9. The compound of claim 1, or a pharmaceutically acceptable salt thereof, wherein:

$R^{a1}$, $R^{b1}$, $R^{c1}$, and $R^{d1}$ are each independently selected from H, methyl, pyrazolyl, pyridinylmethyl, pyridinylethyl, imidazo [1,2-a]pyridinylmethyl, benzoimidazolylmethyl, imidazo [4,5-c]pyridinylmethyl, benzoxazolylmethyl, oxetanylmethyl, oxetanylethyl, thietanyl-(1,1-dioxide) methyl, 2-oxaspiro [3.3]heptanyl, and 2-oxaspiro [3.5]nonanyl, wherein the methyl, pyrazolyl, pyridinylmethyl, pyridinylethyl, imidazo [1,2-a] pyridinylmethyl, benzoimidazolylmethyl, imidazo [4,5-c]pyridinylmethyl, benzoxazolylmethyl, oxetanylmethyl, oxetanylethyl, thietanyl-(1,1-dioxide) methyl, 2-oxaspiro [3.3]heptanyl, and 2-oxaspiro [3.5]nonanyl are each optionally substituted with 1 or 2 independently selected $R^{1A}$ substituents;

or $R^{c1}$ and $R^{d1}$, together with the nitrogen to which they are attached, come together to form 1,2,3,4-tetrahydrobenzo [4,5]imidazo [1,2-a] pyrazinyl;

each $R^{1A}$ is independently selected from methyl, ethyl, methoxymethyl, and CN;

$R^2$ is H or $C_{1-6}$ alkoxy;

U is $CR^3$ or N;

U' is $CR^5$ or N;

U" is $CR^6$ or N;

$R^3$ is selected from H, halo, and $C_{1-6}$ alkoxy;

$R^4$ is selected from H, 5-6 membered heteroaryl, CN, and $C(O)NR^{c4}R^{d4}$, wherein the 5-6 membered heteroaryl is optionally substituted with 1 or 2 independently selected $R^{4A}$ substituents;

$R^{c4}$ and $R^{d4}$ are each independently selected from H, $C_{1-6}$ alkyl, and $C_{1-6}$ haloalkyl;

each $R^{4A}$ is an independently selected $C_{1-6}$ alkyl group;

$R^5$ is selected from H, halo, $C_{1-6}$ alkyl, and $C_{1-6}$ alkoxy;

or $R^4$ and $R^5$ together with the carbon atoms to which they are attached, come together to form a 6-membered aryl ring which is optionally substituted with 1 or 2 independently selected $R^7$ substituents;

each $R^7$ is independently selected from bicyclo[1.1.1]pentanyl, azetidinyl, pyrrolidinyl, piperidinyl, morpholinyl, imidazolyl, azaspiro [3.3]heptanyl, diazaspiro [3.5]nonanyl, oxadiazaspiro[5.5]undecanyl, diazaspiro [4.4]nonanyl, and azetidinyloxy, wherein the bicyclo [1.1.1]pentanyl, azetidinyl, pyrrolidinyl, piperidinyl, morpholinyl, imidazolyl, azaspiro [3.3]heptanyl, diazaspiro [3.5]nonanyl, oxadiazaspiro[5.5]undecanyl, and diazaspiro [4.4]nonanyl are each optionally substituted with 1 or 2 $R^{7A}$ substituents; and each $R^{7A}$ is independently selected from methyl, methoxyethyl, aminomethyl, amino, cyclopropyl, and oxetanyl.

10. The compound of claim 1, wherein the compound of Formula I is a compound of Formula II:

II

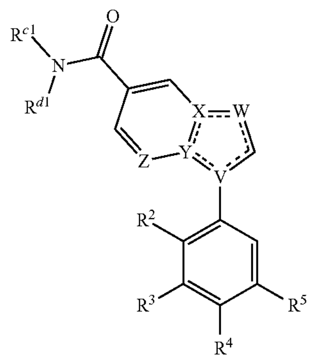

or a pharmaceutically acceptable salt thereof.

11. The compound of claim 1, wherein the compound of Formula I is a compound of Formula III:

III

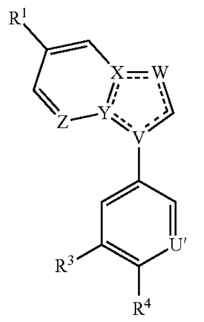

or a pharmaceutically acceptable salt thereof.

12. The compound of claim 1, wherein the compound of Formula I is a compound of Formula IV:

IV

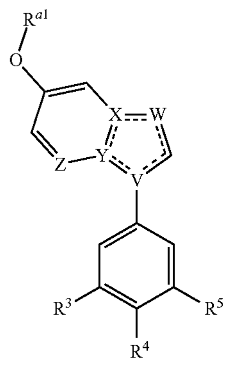

or a pharmaceutically acceptable salt thereof.

13. The compound of claim 1, wherein the compound of Formula I is a compound of Formula V:
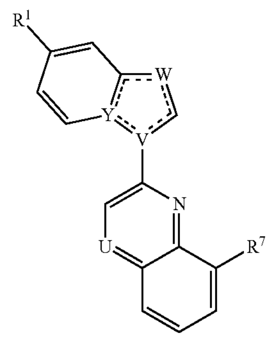
V
or a pharmaceutically acceptable salt thereof.
14. The compound of claim 1, which is selected from:
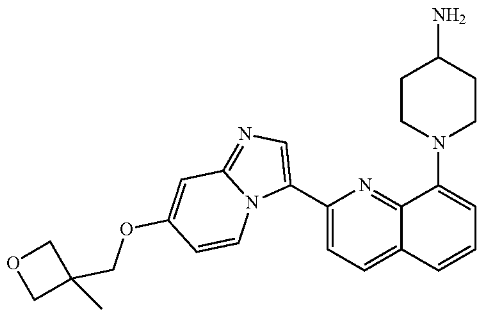 [SMILES: CC1(COc2ccn3c(-c4ccc5cccc(N6CCC(N)CC6)c5n4)cnc3c2)COC1]
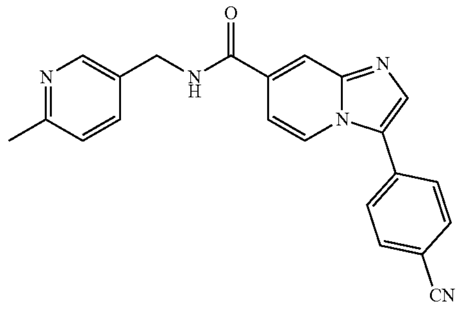
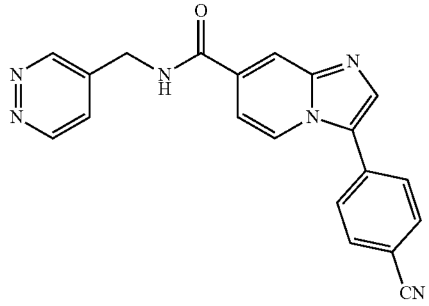
-continued
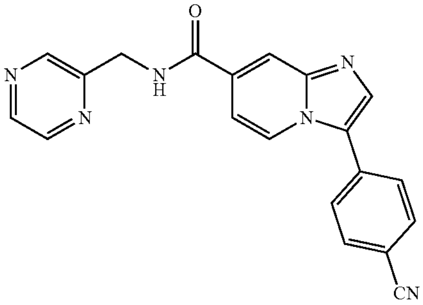
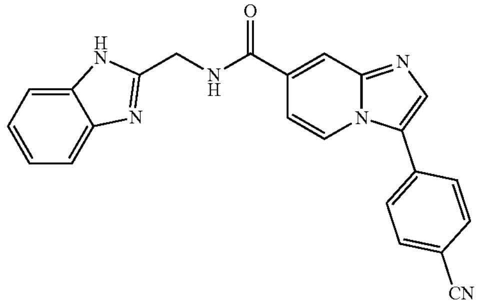
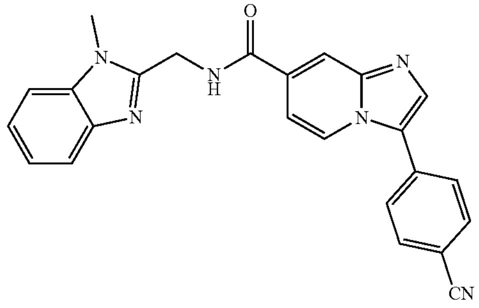
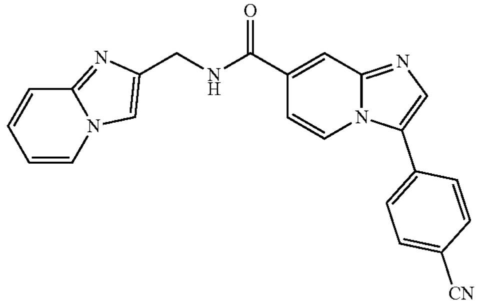
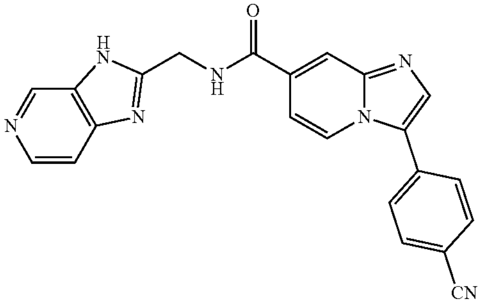

-continued
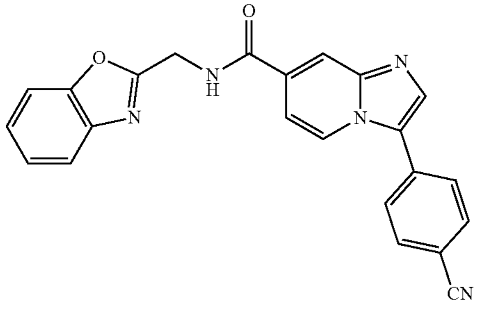
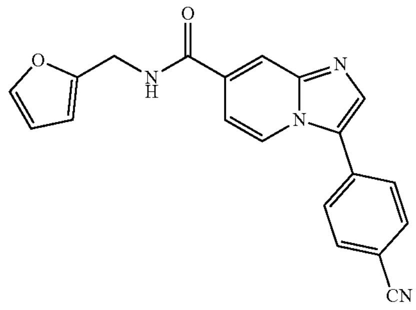
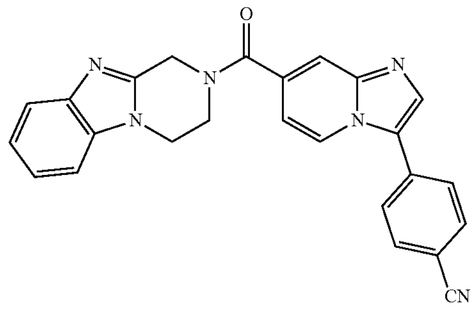
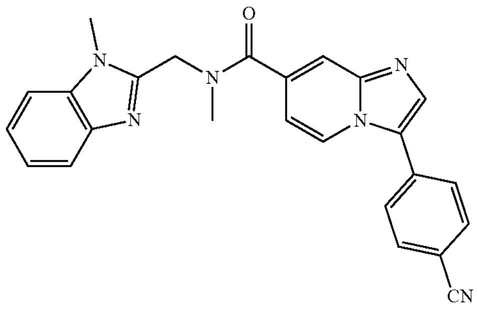
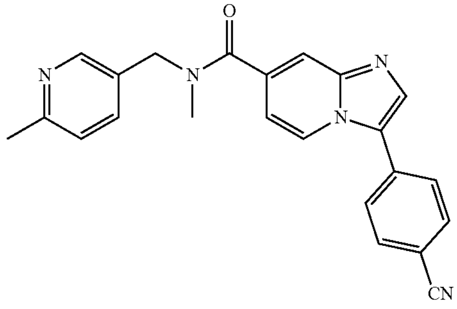
-continued
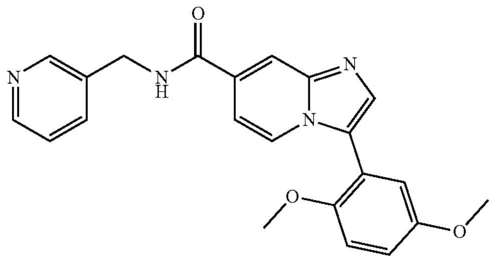
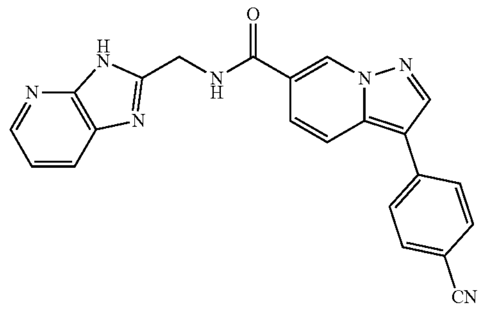
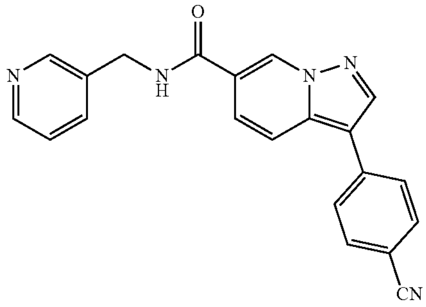
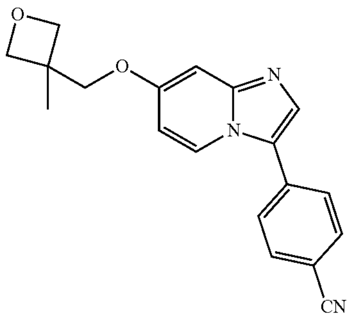
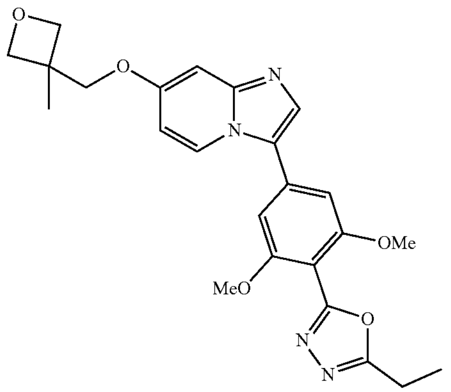

-continued
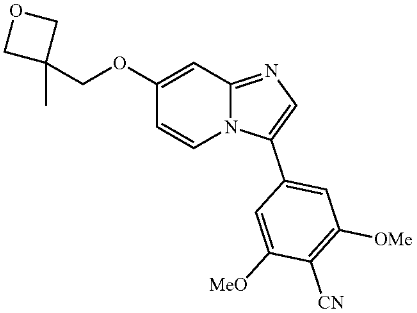
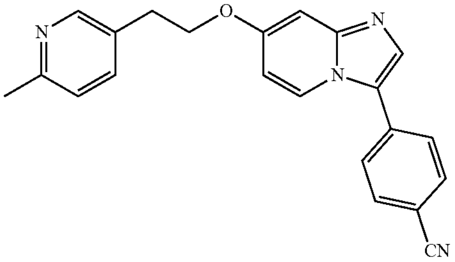
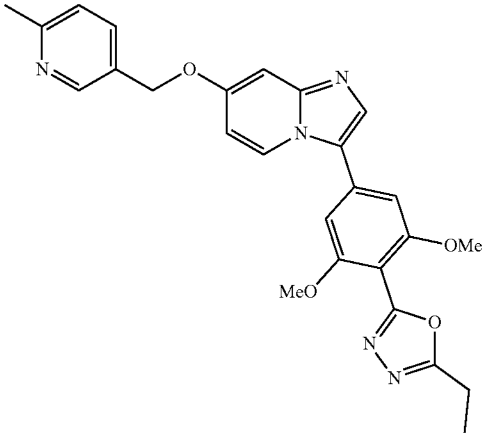
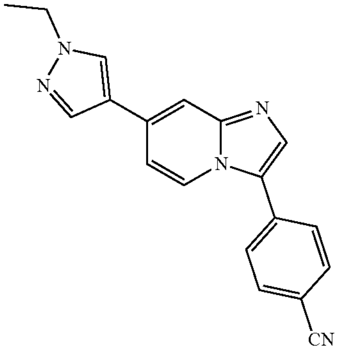
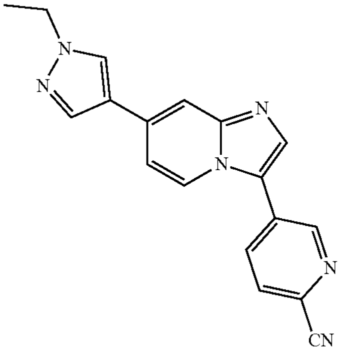
-continued
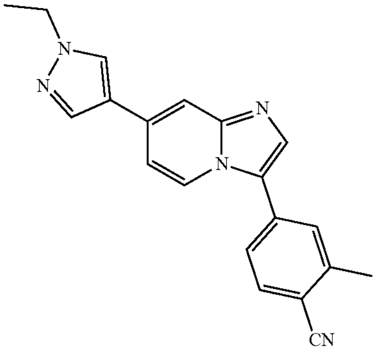
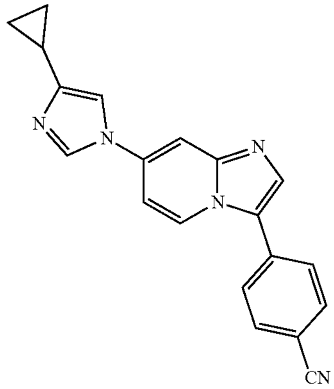
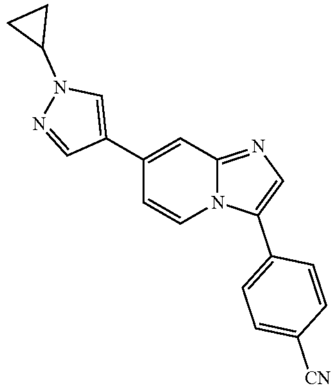
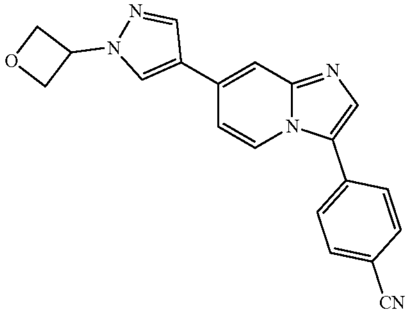

-continued
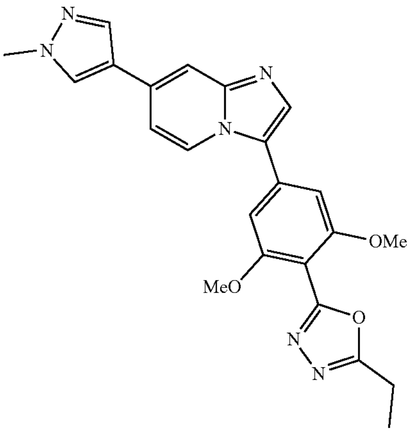
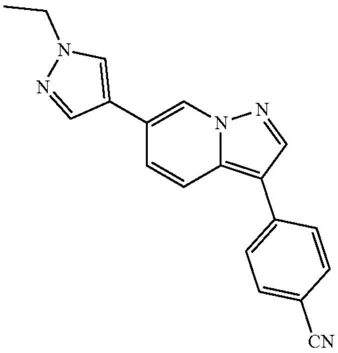
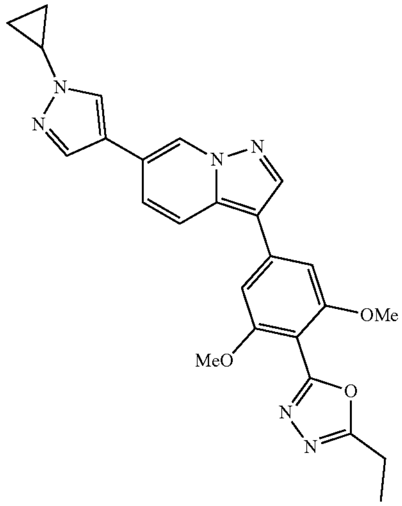
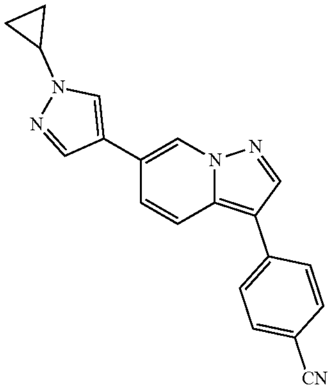
-continued
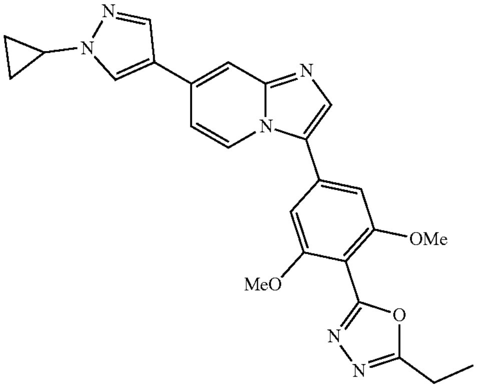
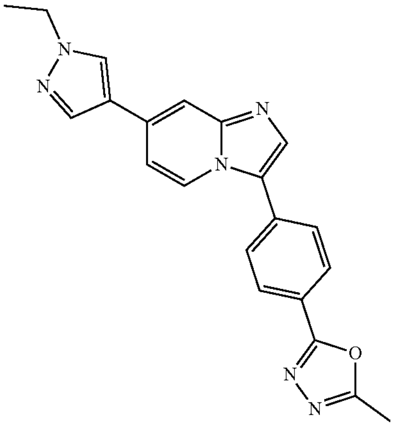
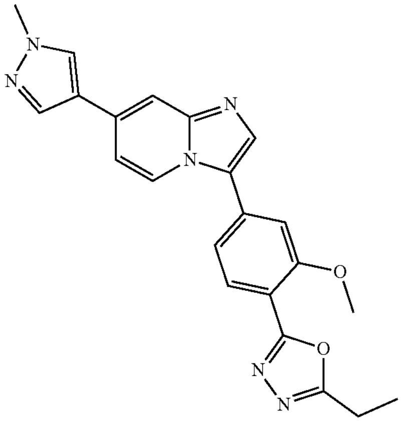
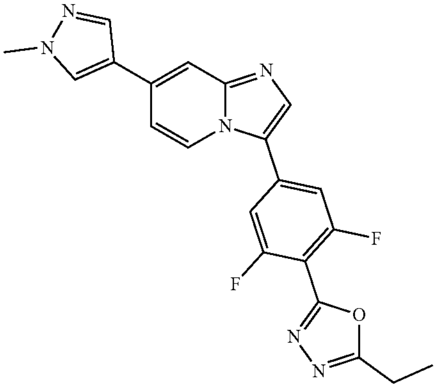

-continued
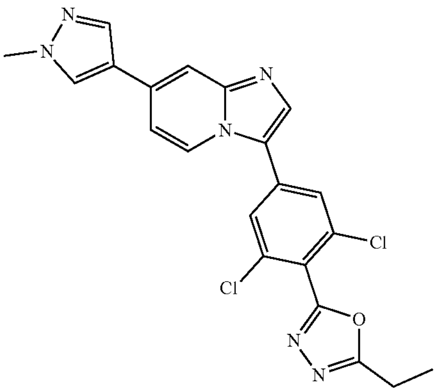
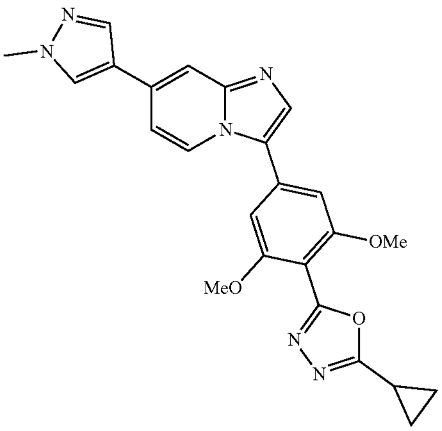
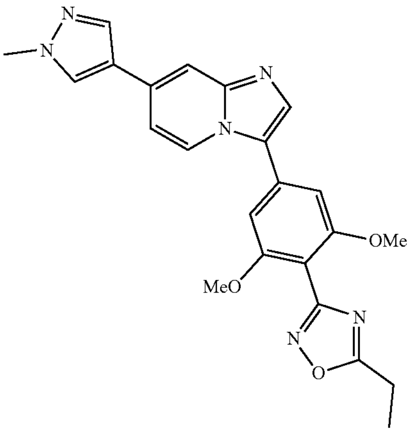
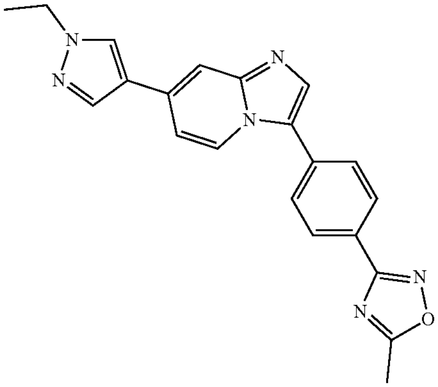
-continued
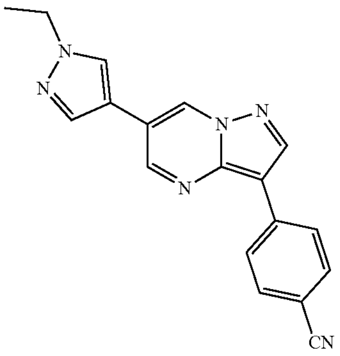
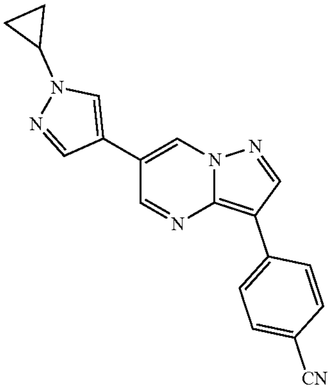
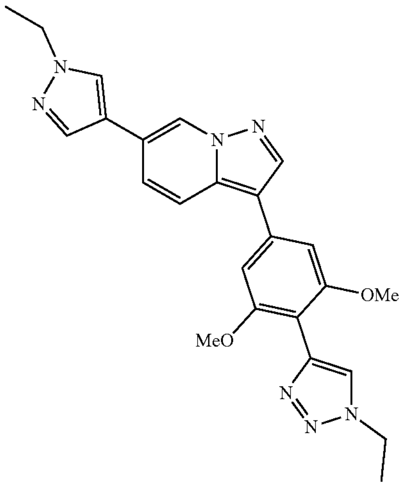
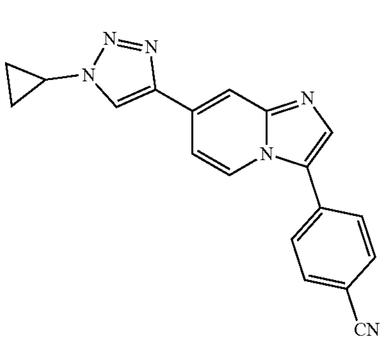

-continued

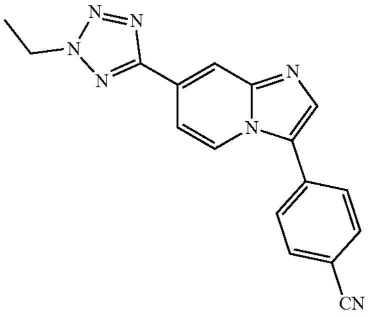

and

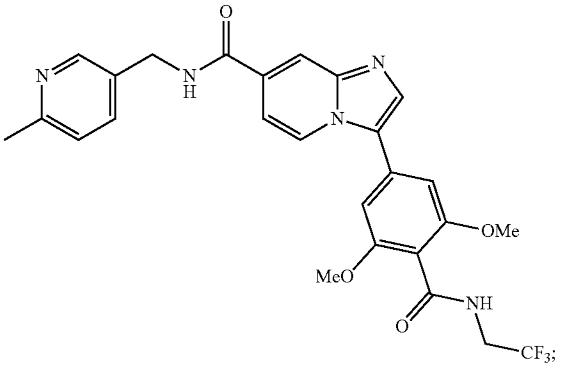

or a pharmaceutically acceptable salt thereof.

15. The compound of claim 1, wherein the compound is:

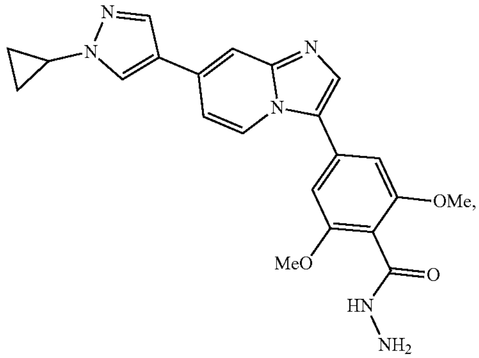 [SMILES: COc1cc(-c2cnc3cc(-c4cnn(C5CC5)c4)ccn23)cc(OC)c1C(=O)NN]

or a pharmaceutically acceptable salt thereof.

16. A pharmaceutical composition comprising a compound of claim 1, or a pharmaceutically acceptable salt thereof, and a pharmaceutically acceptable carrier.

17. A method of inhibiting an activity of a salt inducible kinase (SIK), the method comprising contacting the salt inducible kinase (SIK) with a compound of claim 1, or a pharmaceutically acceptable salt thereof.

18. A compound, which is selected from:

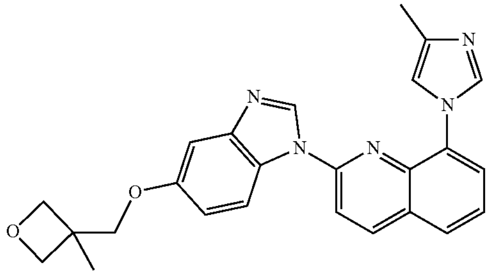

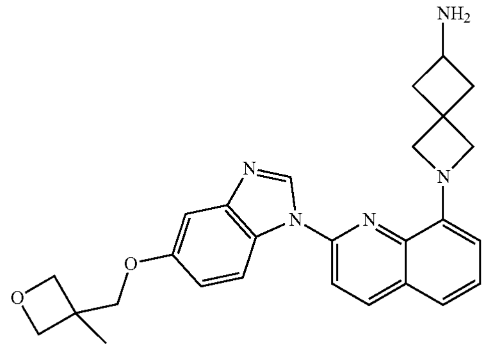

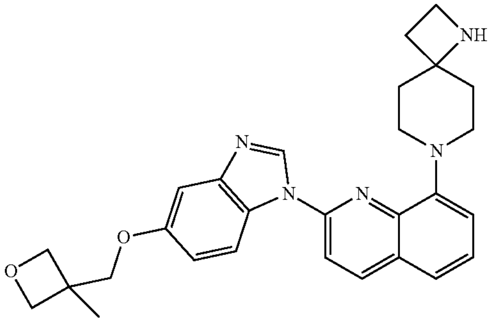

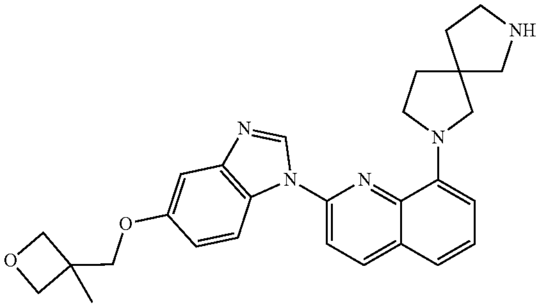

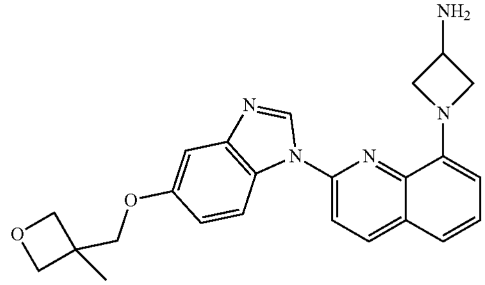

-continued
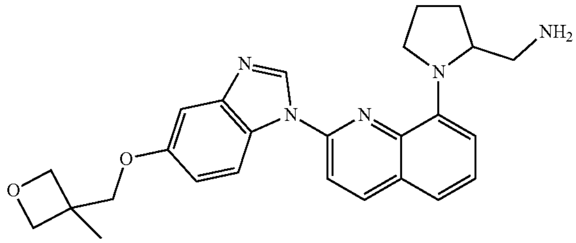
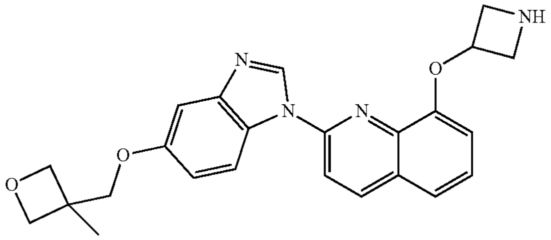
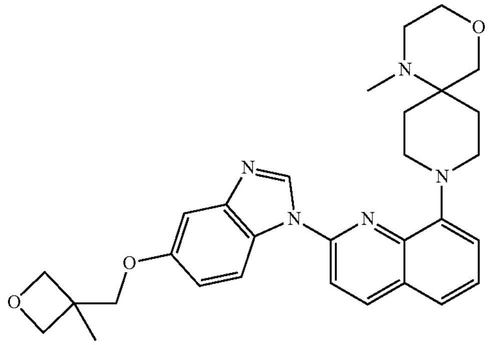
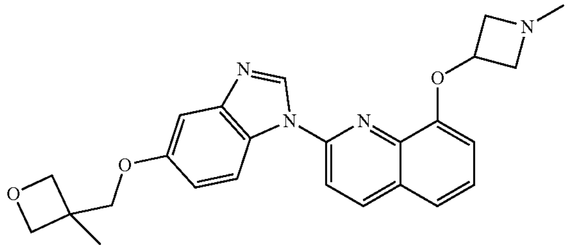
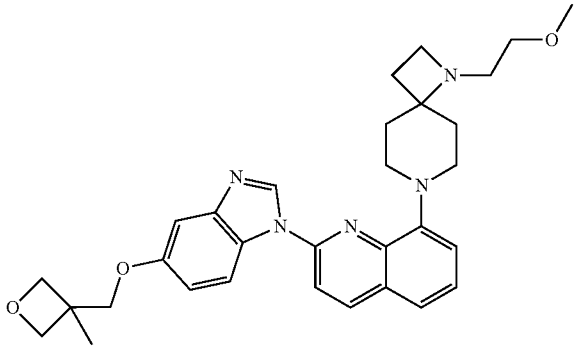
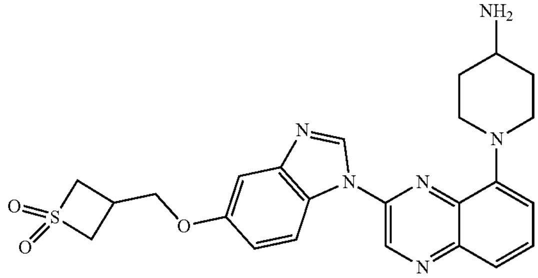
-continued
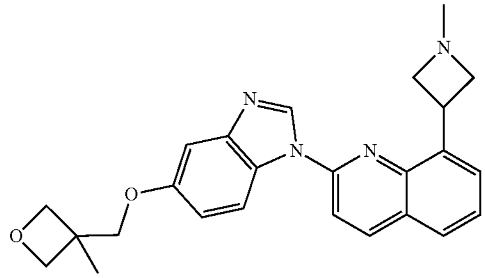
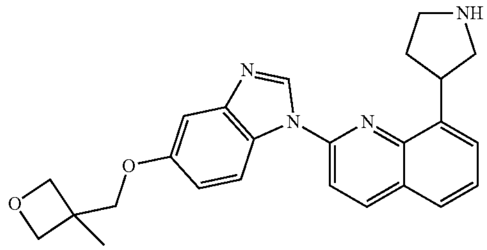
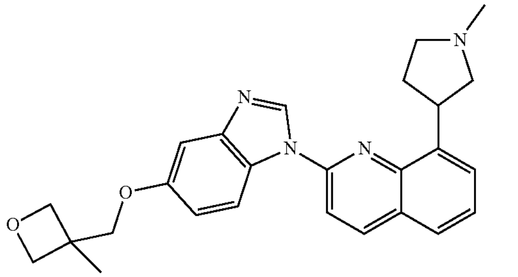
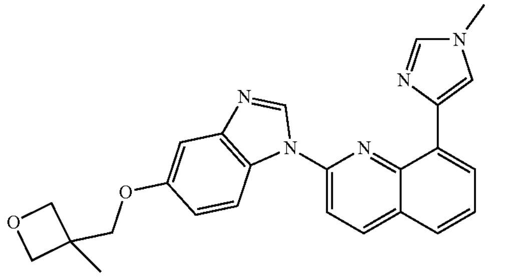
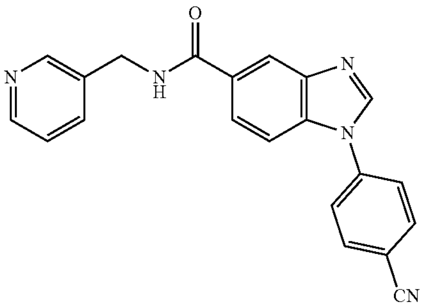

-continued

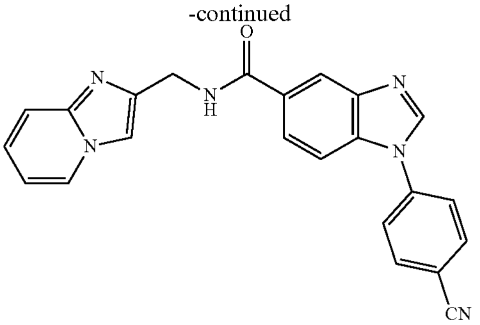

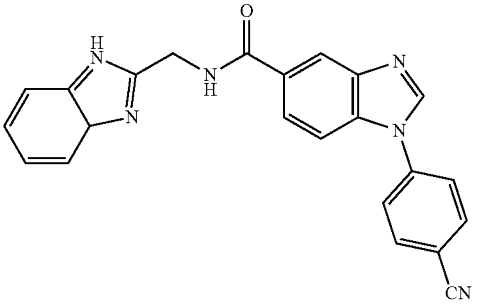

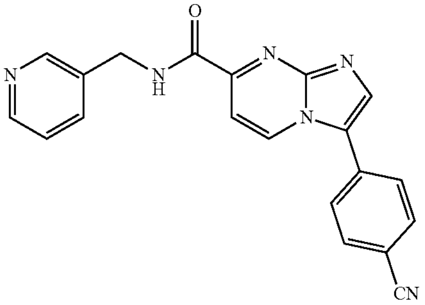

-continued

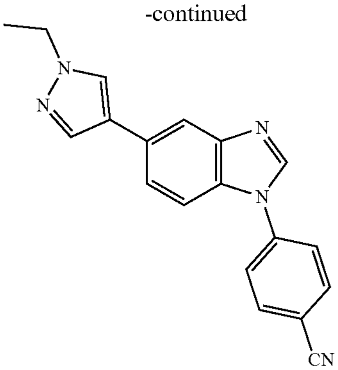

and

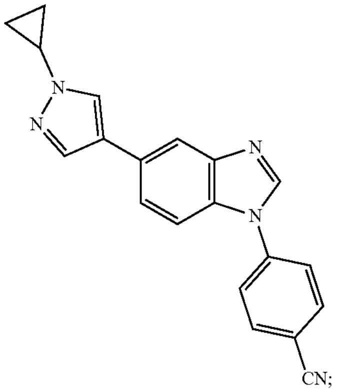 [SMILES: N#Cc1ccc(-n2cnc3cc(-c4cnn(C5CC5)c4)ccc32)cc1]

or a pharmaceutically acceptable salt thereof.

19. A pharmaceutical composition comprising a compound of claim 18, or a pharmaceutically acceptable salt thereof, and a pharmaceutically acceptable carrier.

20. A method of inhibiting an activity of a salt inducible kinase (SIK), the method comprising contacting the salt inducible kinase (SIK) with a compound of claim 18, or a pharmaceutically acceptable salt thereof.

* * * * *